United States Patent
Masada et al.

(10) Patent No.: US 8,642,770 B2
(45) Date of Patent: Feb. 4, 2014

(54) INDOLE DERIVATIVE

(75) Inventors: Shinichi Masada, Kanagawa (JP); Yoshito Terao, Kanagawa (JP); Toshiki Murata, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 13/520,373

(22) PCT Filed: Jan. 5, 2011

(86) PCT No.: PCT/JP2011/050056
§ 371 (c)(1),
(2), (4) Date: Sep. 19, 2012

(87) PCT Pub. No.: WO2011/083804
PCT Pub. Date: Jul. 14, 2011

(65) Prior Publication Data
US 2013/0018073 A1  Jan. 17, 2013

(30) Foreign Application Priority Data
Jan. 6, 2010  (JP) .................................. 2010-001296

(51) Int. Cl.
| C07D 401/00 | (2006.01) |
| C07D 411/02 | (2006.01) |
| C07D 209/16 | (2006.01) |
| A61K 31/445 | (2006.01) |
| A61K 31/405 | (2006.01) |

(52) U.S. Cl.
USPC ........... 546/201; 548/468; 548/504; 514/323; 514/414; 514/415

(58) Field of Classification Search
None
See application file for complete search history.

(56) References Cited

U.S. PATENT DOCUMENTS

| 2003/0212070 A1 | 11/2003 | Schwink et al. |
| 2004/0077628 A1 | 4/2004 | Ishihara et al. |
| 2005/0209213 A1 | 9/2005 | Ishihara et al. |
| 2008/0293801 A1 | 11/2008 | Friesen et al. |
| 2011/0015225 A1 | 1/2011 | Murata et al. |
| 2012/0035213 A1 | 2/2012 | Murata et al. |

FOREIGN PATENT DOCUMENTS

| JP | 2005-505530 A | 2/2005 |
| JP | 2007-511500 A | 5/2007 |
| JP | 2008-088120 A | 4/2008 |
| WO | WO 01/21577 A2 | 3/2001 |
| WO | WO 2009/123194 A1 | 10/2009 |
| WO | WO 2010/092154 A1 | 8/2010 |

*Primary Examiner* — Nyeemah A Grazier
(74) *Attorney, Agent, or Firm* — Foley & Lardner LLP

(57) ABSTRACT

The present invention provides an indole derivative having a melanin-concentrating hormone receptor antagonistic action, which is useful as an agent for the prophylaxis or treatment of obesity and the like.

The present invention relates to a compound represented by the formula (I):

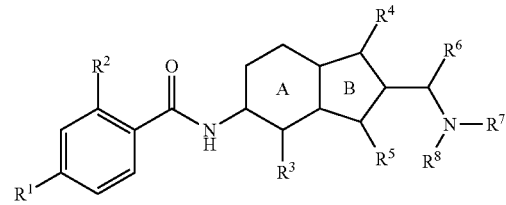

(I)

wherein each symbol is as defined in the specification, or a salt thereof.

16 Claims, No Drawings

INDOLE DERIVATIVE

TECHNICAL FIELD

The present invention relates to an indole derivative having melanin-concentrating hormone (hereinafter sometimes abbreviated as MCH) receptor antagonistic action, and useful as an agent for the prophylaxis or treatment of obesity and the like.

BACKGROUND OF THE INVENTION

MCH is a hypothalamus-derived hormone known to have an appetite increasing action. Furthermore, it has been reported that MCH knockout mouse behaves normally but shows a significantly decreased food ingestion amount and a lighter body weight as compared to normal mouse (non-patent document 1 (Nature, vol. 396, page 670, 1998)). Furthermore, MCH receptor-1-deficient mice have been reported to show a lean phenotype (non-patent document 2 (Proc. Natl. Acad. Sci. USA, vol. 99, page 3240, 2002)). Therefrom MCH receptor (particularly MCH receptor 1) antagonists are expected to be superior appetite suppressants or anti-obesity agents.

As compounds having a MCH receptor antagonistic action, the following compounds are known.

1) Patent document 1 (WO01/21577) discloses a melanin-concentrating hormone antagonist comprising a compound represented by the formula:

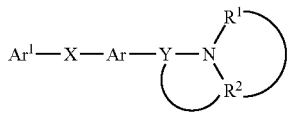

wherein
$Ar^1$ is a cyclic group optionally having substituent(s);
X is a spacer with a main chain having an atom number of 1 to 6;
Y is a bond or a spacer with a main chain having an atom number of 1 to 6;
Ar is a monocyclic aromatic ring optionally condensed with a 4- to 8-membered nonaromatic ring and further optionally having substituent(s);
$R^1$ and $R^2$ are the same or different and each is a hydrogen atom or a hydrocarbon group optionally having substituent(s), $R^1$ and $R^2$ may form, together with the adjacent nitrogen atom, nitrogen-containing heterocycle optionally having substituent(s), $R^2$ forms a spiro ring together with Ar, or $R^2$ may form, together with the adjacent nitrogen atom and Y, a nitrogen-containing heterocycle optionally having substituent(s),
or a salt thereof.

2) Patent document 2 (WO01/82925) discloses a melanin-concentrating hormone antagonist comprising a compound represented by the formula:

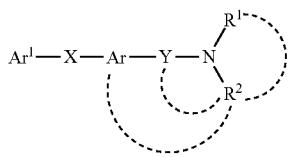

wherein
$Ar^1$ is a cyclic group optionally having substituent(s);
X and Y are the same or different and each is a spacer with a main chain having an atom number of 1 to 6;
Ar is a condensed polycyclic aromatic ring optionally having substituent(s);
$R^1$ and $R^2$ are the same or different and each is a hydrogen atom or a hydrocarbon group optionally having substituent(s), $R^1$ and $R^2$ may form, together with the adjacent nitrogen atom, nitrogen-containing heterocycle optionally having substituent(s), $R^2$ may form, together with the adjacent nitrogen atom and Y, nitrogen-containing heterocycle optionally having substituent(s), or $R^2$ may form, together with the adjacent nitrogen atom, Y and Ar, a nitrogen-containing fused ring optionally having substituent(s),
or a salt thereof.

3) Patent document 3 (WO03/035624) discloses a compound represented by the formula:

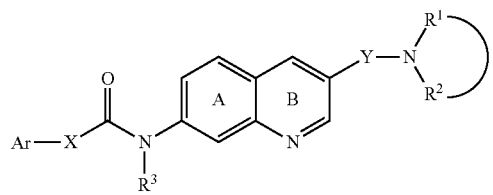

wherein
Ar is a cyclic group optionally having substituent(s);
X is a bond or a spacer with a main chain having an atom number of 1 to 6;
$R^1$ and $R^2$ are the same or different and each is a hydrogen atom or a hydrocarbon group optionally having substituent(s),
$R^1$ and $R^2$ may form, together with the adjacent nitrogen atom, nitrogen-containing heterocycle optionally having substituent(s);
Y is a divalent hydrocarbon group optionally having substituent(s) (excluding CO);
$R^3$ is a hydrogen atom or a hydrocarbon group optionally having substituent(s); and
ring A and ring B may further have substituent(s), and when ring B further has substituent(s), the substituent(s) may be bonded to $R^1$ to form a ring,
or a salt thereof or a prodrug thereof.

4) Patent document 4 (JP-A-2008-68120) discloses a compound represented by the formula:

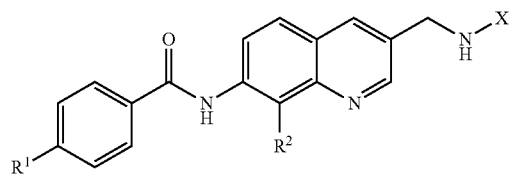

wherein
$R^1$ is an optionally substituted $C_{1-6}$ alkoxy group;
$R^2$ is a hydrogen atom, a methyl group or a halogen atom;
X is a $C_{4-7}$ hydrocarbon group substituted by a hydroxy group or an oxo group,
or a salt thereof.

5) Patent document 5 (WO2009/123194) discloses a compound represented by the formula:

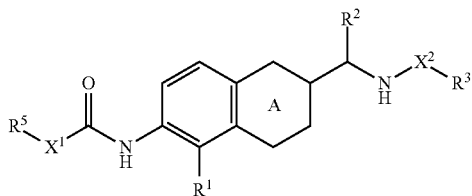

wherein
ring A is a 6-membered ring further optionally substituted;
$R^1$ is a hydrogen atom, a halogen atom or a $C_{1-6}$ alkyl group;
$R^2$ is a hydrogen atom or a $C_{1-6}$ alkyl group;
$R^3$ is a group represented by the formula: —Y—S(O)$_{m1}$—R$^{4a}$
wherein Y is a bond or NH; m1 is an integer of 1 or 2; and $R^{4a}$ is a $C_{1-6}$ alkyl group optionally substituted by 1 to 3 halogen atoms, or a cyclic group represented by the formula:

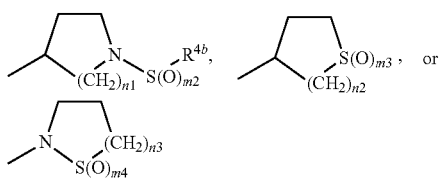

wherein m2, m3, m4, n1, n2 and n3 are independently an integer of 1 or 2; and $R^{4b}$ is a $C_{1-6}$ alkyl group optionally substituted by 1 to 3 halogen atoms (the ring moiety of the cyclic group is optionally further substituted);
$R^5$ is a 5- or 6-membered cyclic group optionally further substituted;
$X^1$ is a bond or a $C_{1-6}$ alkylene group; and
$X^2$ is a bond or a $C_{1-6}$ alkylene group,
or a salt thereof.
6) Patent document 6 (WO2010/087454) discloses a compound represented by the formula:

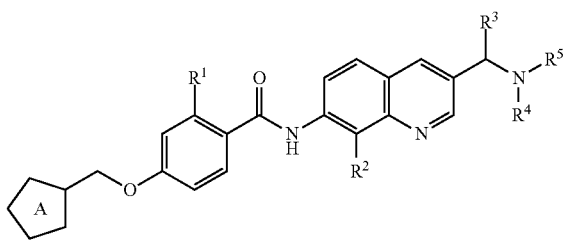

wherein
ring A is a tetrahydrofuran ring optionally further substituted;
$R^1$ is a hydrogen atom or a halogen atom;
$R^2$ is a hydrogen atom, a halogen atom or a $C_{1-6}$ alkyl group;
$R^3$ is a hydrogen atom or a $C_{1-6}$ alkyl group; and
$R^4$ and $R^5$
(1) are each independently a hydrogen atom, an optionally substituted $C_{1-6}$ alkyl group, an optionally substituted $C_{3-10}$ cycloalkyl group, or an optionally substituted 5- or 6-membered heterocyclic group, or
(2) may form, together with the adjacent nitrogen atom, substituted 4- to 6-membered nitrogen-containing heterocycle, provided that
when one of $R^4$ and $R^5$ is a hydrogen atom, then the other is not a group represented by the formula: —X$^1$—R$^{41}$
wherein
$X^1$ is a bond or a $C_{1-6}$ alkylene group; and
$R^{A1}$ is a group represented by the formula: —Y—S(O)$_{m1}$—R$^{B1}$
wherein Y is a bond or NH; m1 is an integer of 1 or 2; and $R^{B1}$ is a $C_{1-6}$ alkyl group optionally substituted by 1 to 3 halogen atoms, or a cyclic group represented by the formula:

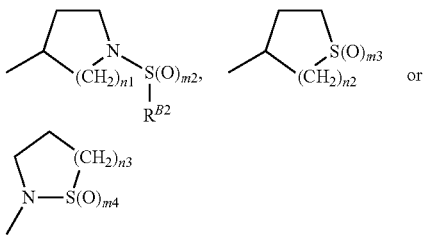

wherein m2, m3, m4, n1, n2 and n3 are each independently an integer of 1 or 2; and $R^{B2}$ is a $C_{1-6}$ alkyl group optionally substituted by 1 to 3 halogen atoms,
(the ring moiety of the cyclic group is optionally further substituted),
or a salt thereof.

DOCUMENT LIST

Patent Documents patent document 1: WO01/21577
patent document 2: WO01/82925
patent document 3: WO03/035624
patent document 4: JP-A-2008-88120
patent document 5: WO2009/123194
patent document 6: WO2010/087454

Non-Patent Documents non-patent document 1: Nature, vol. 396, page 670, 1998
non-patent document 2: Proc. Natl. Acad. Sci. USA, vol. 99, page 3240, 2002

SUMMARY OF THE INVENTION

Problems to be Solved by the Invention

The development of a compound having an MCH receptor antagonistic action and low toxicity, which is useful as an agent for the prophylaxis or treatment of obesity and the like is desired.

Means of Solving the Problems

The present inventors have conducted intensive studies of a compound having an MCH receptor antagonistic action and low toxicity [particularly, cardiotoxicity (e.g., human ether-a-go-go related gene (hereinafter sometimes to be abbreviated as hERG) inhibitory activity), phospholipidosis (hereinafter sometimes to be abbreviated as PLsis) inducing potential and the like, which sometimes pose problems in drug discovery], and found that a compound represented by the following formula (I) or a salt thereof has a superior MCH receptor antagonistic action and shows low toxicity such as cardiotoxicity (e.g., hERG inhibitory activity), PLsis inducing potential and the like as compared to conventional MCH receptor antagonists, which resulted in the completion of the present invention.

Accordingly, the present invention relates to the following.

[1] A compound represented by the formula

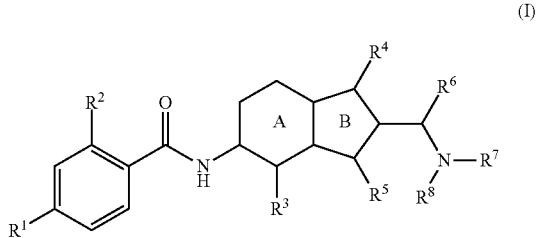

(I)

wherein
ring AB is an indole ring;
$R^1$ is an optionally substituted $C_{1-6}$ alkoxy group, an optionally substituted $C_{1-6}$ alkyl group, an optionally substituted $C_{2-6}$ alkenyl group, or an optionally substituted $C_{2-6}$ alkynyl group;
$R^2$ is a hydrogen atom or a fluorine atom;
$R^3$ is a hydrogen atom, a halogen atom or a $C_{1-6}$ alkyl group;
$R^4$ and $R^5$ are each independently a hydrogen atom or a methyl group;
$R^6$ is a hydrogen atom or a methyl group; and
(1) $R^7$ is a hydrogen atom or a $C_{1-6}$ alkyl group; and
$R^8$ is an optionally substituted $C_{1-6}$ alkyl group, an optionally substituted $C_{3-10}$ cycloalkyl group, or an optionally substituted 4- to 7-membered saturated heterocyclic group; or
(2) $R^7$ and $R^8$ optionally form, together with the adjacent nitrogen atom, an optionally substituted 4- to 7-membered nitrogen-containing heterocycle,
or a salt thereof (hereinafter sometimes to be abbreviated as "compound (I)").

[2] The compound of the above-mentioned [1], wherein $R^1$ is
(a) a $C_{1-6}$ alkoxy group optionally substituted by 1 to 3 substituents selected from a $C_{3-10}$ cycloalkyl group and a 5- or 6-membered oxygen-containing heterocyclic group, or
(b) a $C_{2-6}$ alkynyl group optionally substituted by 1 to 3 substituents selected from a $C_{3-10}$ cycloalkyl group optionally substituted by 1 to 3 hydroxy groups,
or a salt thereof.

[3] The compound of the above-mentioned [1] or [2], wherein $R^3$ is a hydrogen atom, a fluorine atom or a methyl group, or a salt thereof.

[4] The compound of any of the above-mentioned [1] to [3], wherein $R^7$ is a hydrogen atom; and
$R^8$ is
(a) a $C_{1-6}$ alkyl group optionally substituted by 1 to 3 substituents selected from a hydroxy group, a $C_{1-6}$ alkoxy group and a 5- or 6-membered oxygen-containing heterocyclic group, or
(b) a $C_{3-10}$ cycloalkyl group optionally substituted by 1 to 3 substituents selected from a hydroxy group and a $C_{1-6}$ alkyl group,
or a salt thereof.

[5] The compound of any of the above-mentioned [1] to [4], wherein $R^7$ and $R^8$ form, together with the adjacent nitrogen atom, a 4- to 6-membered nitrogen-containing heterocycle optionally substituted by 1 to 3 substituents selected from a hydroxy group and a $C_{1-6}$ alkyl group,
or a salt thereof.

[6] The compound of any of the above-mentioned [1] to [5], wherein $R^1$ is
(a) a $C_{1-6}$ alkoxy group optionally substituted by 1 to 3 substituents selected from a $C_{3-10}$ cycloalkyl group and a 5- or 6-membered oxygen-containing heterocyclic group, or
(b) a $C_{2-6}$ alkynyl group optionally substituted by 1 to 3 substituents selected from a $C_{3-10}$ cycloalkyl group optionally substituted by 1 to 3 hydroxy groups;
$R^3$ is a hydrogen atom, a fluorine atom or a methyl group;
$R^7$ is a hydrogen atom; and
$R^8$ is
(a) a $C_{1-6}$ alkyl group optionally substituted by 1 to 3 substituents selected from a hydroxy group, a $C_{1-6}$ alkoxy group and a 5- or 6-membered oxygen-containing heterocyclic group, or
(b) a $C_{3-10}$ cycloalkyl group optionally substituted by 1 to 3 substituents selected from a hydroxy group and a $C_{1-6}$ alkyl group,
or a salt thereof.

[7] The compound of any of the above-mentioned [1] to [6], wherein $R^1$ is
(a) a $C_{1-6}$ alkoxy group optionally substituted by 1 to 3 substituents selected from a $C_{3-10}$ cycloalkyl group and a 5- or 6-membered oxygen-containing heterocyclic group, or
(b) a $C_{2-6}$ alkynyl group optionally substituted by 1 to 3 substituents selected from a $C_{3-10}$ cycloalkyl group optionally substituted by 1 to 3 hydroxy groups;
$R^3$ is a hydrogen atom, a fluorine atom or a methyl group; and
$R^7$ and $R^8$ form, together with the adjacent nitrogen atom, a 4- to 6-membered nitrogen-containing heterocycle optionally substituted by 1 to 3 substituents selected from a hydroxy group and a $C_{1-6}$ alkyl group,
or a salt thereof.

[8] N-(1-methyl-2-{[(tetrahydro-2H-pyran-4-ylmethyl)amino]methyl}-1H-indol-5-yl)-4-[(2S)-tetrahydrofuran-2-ylmethoxy]benzamide or a salt thereof. (Example 17)

[9] 4-(cyclopropylmethoxy)-N-(2-{[(2-hydroxy-2-methylpropyl)amino]methyl}-1,4-dimethyl-1H-indol-5-yl)benzamide or a salt thereof. (Example 50)

[10] N-(1,4-dimethyl-2-{[(tetrahydro-2H-pyran-4-ylmethyl)amino]methyl}-1H-indol-5-yl)-4-[(2S)-tetrahydrofuran-2-ylmethoxy]benzamide or a salt thereof. (Example 55)

[11] A prodrug of the compound of any of the above-mentioned [1] to [10], or a salt thereof.

[12] A medicament comprising the compound of any of the above-mentioned [1] to [10], or a salt thereof or a prodrug thereof.

[13] The medicament of the above-mentioned [12], which is a melanin-concentrating hormone receptor antagonist.

[14] The medicament of the above-mentioned [12], which is an anorexigenic agent.

[15] The medicament of the above-mentioned [12], which is a prophylactic or therapeutic agent for obesity.

[16] A method of preventing or treating obesity in a mammal, comprising administering an effective amount of the compound of any of the above-mentioned [1] to [10] or a salt thereof or a prodrug thereof to the mammal.

[17] Use of the compound of any of the above-mentioned [1] to [10] or a salt thereof or a prodrug thereof for the production of a prophylactic or therapeutic agent for obesity.

[18] A medicament comprising the compound of any of the above-mentioned [1] to [10] or a salt thereof or a prodrug thereof,
and other pharmaceutically active ingredient.

Effect of the Invention

Compound (I) has a high MCH receptor antagonistic action, and low toxicity such as cardiotoxicity (e.g., hERG inhibitory activity), PLsis inducing potential and the like, as compared to conventional MCH receptor antagonists. Therefore, compound (I) is highly useful as an agent for the prophylaxis or treatment of obesity and the like.

DETAILED DESCRIPTION OF THE INVENTION

The definitions of the symbols and terms used in the present invention are described in detail in the following.

The "halogen atom" means, unless otherwise specified, a fluorine atom, a chlorine atom, a bromine atom or an iodine atom.

The "$C_{1-6}$ alkoxy group" means, unless otherwise specified, methoxy, ethoxy, propoxy, isopropoxy, butoxy, isobutoxy, sec-butoxy, tert-butoxy and the like. Of these, methoxy and isopropoxy are preferable.

The "optionally substituted $C_{1-6}$ alkoxy group" is a $C_{1-6}$ alkoxy group optionally substituted by 1 to 3 substituents selected from the following substituent group (hereinafter to be abbreviated as substituent group A). When the number of the substituents is two or more, the respective substituents may be the same or different.

Substituent Group A:
(1) a halogen atom;
(2) a hydroxy group;
(3) a $C_{1-6}$ alkoxy group;
(4) a $C_{3-10}$ cycloalkyl group optionally substituted by 1 to 3 $C_{1-6}$ alkyl groups;
(5) a 4- to 6-membered (e.g., 5- or 6-membered) oxygen-containing heterocyclic group optionally substituted by 1 to 3 $C_{1-6}$ alkyl groups
[e.g., a 4- to 6-membered (e.g., 5- or 6-membered) oxygen-containing heterocyclic group containing at least one oxygen atom as a ring-constituting atom besides carbon atom, and optionally further containing 1 to 3 hetero atoms selected from an oxygen atom, a sulfur atom and a nitrogen atom (e.g., oxetanyl (e.g., oxetan-3-yl), furyl (e.g., furan-2-yl, furan-3-yl), oxazolyl (e.g., oxazol-2-yl, oxazol-4-yl, oxazol-5-yl), isoxazolyl, oxadiazolyl (e.g., 1,2,4-oxadiazol-5-yl, 1,3,4-oxadiazol-2-yl), tetrahydrofuryl (e.g., tetrahydrofuran-2-yl, tetrahydrofuran-3-yl), pyranyl (e.g., 2H-pyranyl), tetrahydropyranyl (e.g., tetrahydro-2H-pyran-4-yl), morpholinyl (e.g., morpholino), oxazolinyl (e.g., 2,5-dihydrooxazol-3-yl, 3,4-dihydrooxazol-3-yl), oxazolidinyl (e.g., oxazolidin-3-yl), dihydrooxadiazolyl (e.g., 4,5-dihydro-1,2,4-oxadiazol-3-yl)) and the like];
(6) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms (e.g., methylcarbonyl, ethylcarbonyl),
  (c) a $C_{1-6}$ alkoxy-carbonyl group optionally substituted by 1 to 3 halogen atoms (e.g., methoxycarbonyl, ethoxycarbonyl),
  (d) a carbamoyl group optionally mono- or di-substituted by a $C_{1-6}$ alkyl group optionally substituted by 1 to 3 halogen atoms (e.g., methylcarbamoyl, ethylcarbamoyl), and
  (e) a formyl group;
(7) a $C_{1-6}$ alkyl-carbonyl group optionally substituted by 1 to 3 halogen atoms (e.g., methylcarbonyl, ethylcarbonyl);
(8) a $C_{1-6}$ alkyl-sulfonyl group (e.g., methylsulfonyl, ethylsulfonyl, propylsulfonyl, butylsulfonyl, pentylsulfonyl, hexylsulfonyl); and
(9) an oxo group.

The "$C_{1-6}$ alkyl group" means, unless otherwise specified, methyl, ethyl, propyl, isopropyl, n-butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 1,2,2-trimethylpropyl, 3,3-dimethylbutyl, 2-ethylbutyl and the like.

The "optionally substituted $C_{1-6}$ alkyl group" is a $C_{1-6}$ alkyl group optionally substituted by 1 to 3 substituents selected from the above-mentioned substituent group A. When the number of the substituents is two or more, the respective substituents may be the same or different.

The "$C_{2-6}$ alkenyl group" means, unless otherwise specified, vinyl, allyl, isopropenyl, butenyl, pentenyl, hexenyl and the like.

The "optionally substituted $C_{2-6}$ alkenyl group" is a $C_{2-6}$ alkenyl group optionally substituted by 1 to 3 substituents selected from the above-mentioned substituent group A. When the number of the substituents is two or more, the respective substituents may be the same or different.

The "$C_{2-6}$ alkynyl group" means, unless otherwise specified, ethynyl, propargyl, butynyl, pentynyl, hexynyl and the like.

The "optionally substituted $C_{2-6}$ alkynyl group" is a $C_{2-6}$ alkynyl group optionally substituted by 1 to 3 (e.g., 1 or 2) substituents selected from the above-mentioned substituent group A. When the number of the substituents is two or more, the respective substituents may be the same or different.

The "$C_{3-10}$ cycloalkyl group" means, unless otherwise specified, cyclopropyl, cyclobutyl, cyclopentyl, cyclohexyl, cycloheptyl, cyclooctyl, adamantyl and the like.

The "optionally substituted $C_{3-10}$ cycloalkyl group" is a $C_{3-10}$ cycloalkyl group optionally substituted by 1 to 3 substituents selected from the following substituent group (hereinafter to be abbreviated as substituent group B). When the number of the substituents is two or more, the respective substituents may be the same or different.

Substituent Group B:
(1) a halogen atom;
(2) a hydroxy group;
(3) a $C_{1-6}$ alkoxy group;
(4) a $C_{1-6}$ alkyl group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms (e.g., methylcarbonyl, ethylcarbonyl),
  (c) a $C_{1-6}$ alkoxy-carbonyl group optionally substituted by 1 to 3 halogen atoms (e.g., methoxycarbonyl, ethoxycarbonyl),
  (d) a carbamoyl group optionally mono- or di-substituted by a $C_{1-6}$ alkyl group optionally substituted by 1 to 3 halogen atoms (e.g., methylcarbamoyl, ethylcarbamoyl), and
  (e) a formyl group; and
(6) an oxo group.

Examples of the "4- to 7-membered saturated heterocyclic group" include a 4- to 7-membered (e.g., 6-membered) saturated heterocyclic group containing, besides carbon atom, 1 to 3 hetero atoms selected from an oxygen atom, a nitrogen atom and a sulfur atom and the like.

Specific examples of the "4- to 7-membered saturated heterocyclic group" include tetrahydrofuranyl (e.g., tetrahydrofuran-3-yl, tetrahydrofuran-2-yl), tetrahydropyranyl (e.g., 2-tetrahydropyranyl, 3-tetrahydropyranyl, 4-tetrahydropyranyl), pyrrolidinyl (e.g., 1-pyrrolidinyl, 2-pyrrolidinyl), piperidinyl (e.g., piperidino, 2-piperidinyl, 3-piperidinyl, 4-piperidinyl), morpholinyl (e.g., morpholino), thiomorpholinyl (e.g., thiomorpholino), tetrahydrothienyl (e.g., 2-tetrahydrothienyl, 3-tetrahydrothienyl), tetrahydrothiopyranyl (e.g., tetrahydro-2H-thiopyran-4-yl) and the like.

The "optionally substituted 4- to 7-membered saturated heterocyclic group" is a 4- to 7-membered saturated heterocyclic group optionally substituted by 1 to 3 substituents selected from the following substituent group (hereinafter to be abbreviated as substituent group C). When the number of the substituents is two or more, the respective substituents may be the same or different.

Substituent Group C:
(1) a halogen atom;
(2) a hydroxy group;
(3) a $C_{1-6}$ alkyl group;
(4) a $C_{1-6}$ alkoxy group;
(5) an amino group optionally mono- or di-substituted by substituent(s) selected from
  (a) a $C_{1-6}$ alkyl group optionally substituted by 1 to 3 halogen atoms,
  (b) a $C_{1-6}$ alkyl-carbonyl group optionally substituted by 1 to 3 halogen atoms (e.g., methylcarbonyl, ethylcarbonyl),
  (c) a $C_{1-6}$ alkoxy-carbonyl group optionally substituted by 1 to 3 halogen atoms (e.g., methoxycarbonyl, ethoxycarbonyl),
  (d) a carbamoyl group optionally mono- or di-substituted by a $C_{1-6}$ alkyl group optionally substituted by 1 to 3 halogen atoms (e.g., methylcarbamoyl, ethylcarbamoyl), and
  (e) a formyl group; and
(6) an oxo group.

Examples of the "4- to 7-membered nitrogen-containing heterocycle" include a 4- to 7-membered (e.g., 4- to 6-membered, preferably 5- or 6-membered) nitrogen-containing heterocycle containing at least one nitrogen atom as a ring-constituting atom besides carbon atom, and optionally further containing 1 to 3 hetero atoms selected from an oxygen atom, a sulfur atom and a nitrogen atom.

Specific examples of the "4- to 7-membered nitrogen-containing heterocycle" include azetidine, pyrrolidine, imidazoline, imidazolidine, pyrazolidine, pyrazoline, piperidine, piperazine, morpholine, thiomorpholine, triazoline, pyrrole, pyrazole, imidazole, triazole, azepine, dihydropyrrole, dihydrothiazole, tetrahydropyridine, azacycloheptane and the like.

The "optionally substituted 4- to 7-membered nitrogen-containing heterocycle" is a 4- to 7-membered nitrogen-containing heterocycle optionally substituted by 1 to 3 substituents selected from the above-mentioned substituent group C. When the number of the substituents is two or more, the respective substituents may be the same or different.

Examples of the "5- or 6-membered oxygen-containing heterocyclic group" include a 5- or 6-membered oxygen-containing heterocyclic group containing at least one oxygen atom as a ring-constituting atom besides carbon atom, and optionally further containing 1 to 3 hetero atoms selected from an oxygen atom, a sulfur atom and a nitrogen atom.

Specific examples of the "5- or 6-membered oxygen-containing heterocyclic group" include furyl (e.g., furan-2-yl, furan-3-yl), oxazolyl (e.g., oxazol-2-yl, oxazol-4-yl, oxazol-5-yl), isoxazolyl, oxadiazolyl (e.g., 1,2,4-oxadiazol-5-yl, 1,3,4-oxadiazol-2-yl), tetrahydrofuryl (e.g., tetrahydrofuran-2-yl, tetrahydrofuran-3-yl), pyranyl (e.g., 2H-pyranyl), tetrahydropyranyl (e.g., tetrahydro-2H-pyran-4-yl), morpholinyl (e.g., morpholino), oxazolinyl (e.g., 2,5-dihydrooxazol-3-yl, 3,4-dihydrooxazol-3-yl), oxazolidinyl (e.g., oxazolidin-3-yl), dihydrooxadiazolyl (e.g., 4,5-dihydro-1,2,4-oxadiazol-3-yl) and the like.

In the above-mentioned formula [I], preferable groups are as follows.

In the formula [I], ring AB represented by

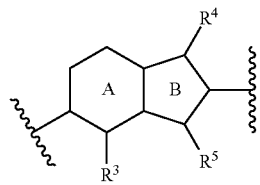

is an indole ring represented by

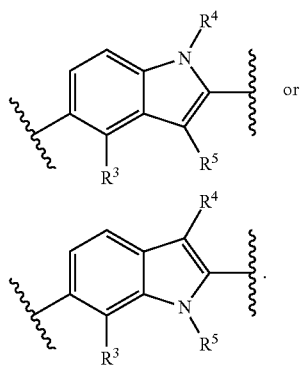

$R^1$ is
an optionally substituted $C_{1-6}$ alkoxy group,
an optionally substituted $C_{1-6}$ alkyl group,
an optionally substituted $C_{2-6}$ alkenyl group, or
an optionally substituted $C_{2-6}$ alkynyl group.

As $R^1$, for example,
(a) a $C_{1-6}$ alkoxy group optionally substituted by 1 to 3 substituents selected from
  (1) a $C_{3-10}$ cycloalkyl group optionally substituted by 1 to 3 $C_{1-6}$ alkyl groups, and
  (2) a 4- to 6-membered (e.g., 5- or 6-membered) oxygen-containing heterocyclic group (e.g., tetrahydrofuryl group) optionally substituted by 1 to 3 $C_{1-6}$ alkyl groups; or
(b) a $C_{2-6}$ alkynyl group optionally substituted by 1 to 3 substituents selected from a $C_{3-10}$ cycloalkyl group optionally substituted by 1 to 3 substituents selected from a hydroxy group and a $C_{1-6}$ alkyl group;
or the like can be mentioned.

Preferred examples of $R^1$ include
(a) a $C_{1-6}$ alkoxy group (e.g., methoxy) optionally substituted by 1 to 3 substituents selected from
  (1) a $C_{3-10}$ cycloalkyl group (e.g., cyclopropyl group), and
  (2) a 5- or 6-membered oxygen-containing heterocyclic group (e.g., tetrahydrofuryl group); or
(b) a $C_{2-6}$ alkynyl group (e.g., ethynyl group) optionally substituted by 1 to 3 substituents selected from a $C_{3-10}$ cycloalkyl group (e.g., cyclopropyl, cyclobutyl) optionally substituted by 1 to 3 hydroxy groups; or the like.

More preferred examples of $R^1$ include
(a) a methoxy group optionally substituted by one substituent selected from
  (1) a cyclopropyl group, and
  (2) a tetrahydrofuryl group (e.g., tetrahydrofuran-2-yl, tetrahydrofuran-3-yl);
(b) an ethynyl group optionally substituted by one substituent selected from
  (1) a cyclopropyl group optionally substituted by 1 to 3 (preferably, 1) hydroxy groups, and (2) a cyclobutyl group optionally substituted by 1 to 3 (preferably, 1) hydroxy groups;
and the like.

$R^2$ is a hydrogen atom or a fluorine atom.

$R^3$ is a hydrogen atom, a halogen atom or a $C_{1-6}$ alkyl group.

Preferred examples of $R^3$ include a hydrogen atom, a fluorine atom, a methyl group and the like.

$R^4$ and $R^5$ are each independently a hydrogen atom or a methyl group.

$R^6$ is a hydrogen atom or a methyl group.

$R^7$ is a hydrogen atom or a $C_{1-6}$ alkyl group.

Preferred examples of $R^7$ include a hydrogen atom, an ethyl group and the like.

More preferred examples of $R^7$ include a hydrogen atom.

$R^8$ is an optionally substituted $C_{1-6}$ alkyl group, an optionally substituted $C_{3-10}$ cycloalkyl group (e.g., $C_{5-6}$ cycloalkyl) or an optionally substituted 4- to 7-membered saturated heterocyclic group.

Preferred examples of $R^8$ include
(a) a $C_{1-6}$ alkyl group optionally substituted by 1 to 3 substituents selected from
  (1) a hydroxy group,
  (2) a $C_{1-6}$ alkoxy group,
  (3) a 4- to 6-membered (e.g., 5- or 6-membered) oxygen-containing heterocyclic group (e.g., oxetanyl group, tetrahydrofuryl group, tetrahydropyranyl group) optionally substituted by 1 to 3 $C_{1-6}$ alkyl groups,
  (4) a $C_{1-6}$ alkyl-sulfonyl group, and
  (5) a $C_{1-6}$ alkyl-carbonylamino group;
(b) a $C_{3-10}$ cycloalkyl group optionally substituted by 1 to 3 substituents selected from
  (1) a hydroxy group, and
  (2) a $C_{1-6}$ alkyl group; and
(c) a 4- to 7-membered (e.g., 6-membered) saturated heterocyclic group (e.g., tetrahydrothiopyranyl group) optionally substituted by 1 or 2 oxo groups;
and the like.

More preferred examples of $R^8$ include
(a) a methyl group, an ethyl group, a propyl group, an isobutyl group or a neopentyl group, each of which is optionally substituted by one substituent selected from
  (1) a hydroxy group.
  (2) an oxetanyl group (e.g., oxetan-3-yl), a tetrahydrofuryl group (e.g., tetrahydrofuran-2-yl, tetrahydrofuran-3-yl) or a tetrahydropyranyl group (e.g., tetrahydro-2H-pyran-4-yl), each of which is optionally substituted by 1 to 3 methyl groups,
  (3) a methylsulfonyl group, and
  (4) a $C_{1-6}$ alkyl-carbonylamino group;
(b) a cyclopentyl group or a cyclohexyl group, which is optionally substituted by 1 or 2 substituents selected from
  (1) a hydroxy group, and
  (2) a methyl group; and
(c) a tetrahydrothiopyranyl group (e.g., tetrahydro-2H-thiopyran-4-yl) optionally substituted by 1 or 2 oxo groups; and the like.

In another preferred embodiment, $R^8$ is
(a) a $C_{1-6}$ alkyl group optionally substituted by 1 to 3 substituents selected from
  (1) a hydroxy group,
  (2) a $C_{1-6}$ alkoxy group, and
  (3) a 5- or 6-membered oxygen-containing heterocyclic group (e.g., tetrahydrofuryl group, tetrahydropyranyl group), or (b) a $C_{3-10}$ cycloalkyl group optionally substituted by 1 to 3 substituents selected from
  (1) a hydroxy group, and
  (2) a $C_{1-6}$ alkyl group.

Alternatively, $R^7$ and $R^8$ may form, together with the adjacent nitrogen atom, an optionally substituted 4- to 7-membered nitrogen-containing heterocycle.

As the "4- to 7-membered nitrogen-containing heterocycle" of the optionally substituted 4- to 7-membered nitrogen-containing heterocycle formed by $R^7$ and $R^8$ together with the adjacent nitrogen atom, a 4- to 7-membered (e.g., 4- to 6-membered, preferably 5- or 6-membered) nitrogen-containing heterocycle containing at least one nitrogen atom as a ring-constituting atom besides carbon atom, and optionally further containing 1 to 3 hetero atoms selected from an oxygen atom, a sulfur atom and a nitrogen atom can be preferably mentioned. More preferred are pyrrolidine, piperidine and the like.

As the "substituent" of the optionally substituted 4- to 7-membered nitrogen-containing heterocycle formed by $R^7$ and $R^8$ together with the adjacent nitrogen, atom, a hydroxy group, a $C_{1-6}$ alkyl group and the like can be preferably mentioned. More preferred are a hydroxy group, a methyl group and the like.

As the "optionally substituted 4- to 7-membered nitrogen-containing heterocycle" formed by $R^7$ and $R^8$ together with the adjacent nitrogen atom, a 4- to 6-membered nitrogen-containing heterocycle (e.g., pyrrolidine, piperidine) optionally substituted by 1 to 3 substituents selected from a hydroxy group and a $C_{1-6}$ alkyl group, and the like can be preferably mentioned.

Preferable examples of compound (I) include the following compounds (I-A), (I-B) and (I-C).

[Compound (I-A)]

A compound, which is compound (I) wherein $R^1$ is
(a) a $C_{1-6}$ alkoxy group optionally substituted by 1 to 3 substituents selected from
  (1) a $C_{3-10}$ cycloalkyl group optionally substituted by 1 to 3 $C_{1-6}$ alkyl groups, and
  (2) a 4- to 6-membered (e.g., 5- or 6-membered) oxygen-containing heterocyclic group (e.g., tetrahydrofuryl group) optionally substituted by 1 to 3 $C_{1-6}$ alkyl groups; or
(b) a $C_{2-6}$ alkynyl group optionally substituted by 1 to 3 substituents selected from a $C_{3-10}$ cycloalkyl group optionally substituted by 1 to 3 substituents selected from a hydroxy group and a $C_{1-6}$ alkyl group;

$R^2$ is a hydrogen atom or a fluorine atom;

$R^3$ is a hydrogen atom, a halogen atom or a $C_{1-6}$ alkyl group;

$R^4$ and $R^5$ are independently a hydrogen atom or a methyl group;

$R^6$ is a hydrogen atom or a methyl group;

$R^7$ is a hydrogen atom or a $C_{1-6}$ alkyl group;

$R^8$ is
(a) a $C_{1-6}$ alkyl group optionally substituted by 1 to 3 substituents selected from
  (1) a hydroxy group,
  (2) a $C_{1-6}$ alkoxy group,
  (3) a 4- to 6-membered (e.g., 5- or 6-membered) oxygen-containing heterocyclic group (e.g., oxetanyl group, tetrahydrofuryl group, tetrahydropyranyl group) optionally substituted by 1 to 3 $C_{1-6}$ alkyl groups,
  (4) a $C_{1-6}$ alkyl-sulfonyl group, and
  (5) a $C_{1-6}$ alkyl-carbonylamino group;
(b) a $C_{3-10}$ cycloalkyl group optionally substituted by 1 to 3 substituents selected from (1) a hydroxy group, and
(2) a $C_{1-6}$ alkyl group; or
(c) a 4- to 7-membered (e.g., 6-membered) saturated heterocyclic group (e.g., tetrahydrothiopyranyl group) optionally substituted by 1 or 2 oxo groups; or
$R^7$ and $R^8$ form, together with the adjacent nitrogen atom, a 4- to 6-membered nitrogen-containing heterocycle (e.g., pyrrolidine, piperidine) optionally substituted by 1 to 3 substituents selected from a hydroxy group and a $C_{1-6}$ alkyl group,
or a salt thereof.

[Compound (I-B)]

A compound, which is compound (I) wherein
$R^1$ is
(a) a $C_{1-6}$ alkoxy group (e.g., methoxy) optionally substituted by 1 to 3 substituents selected from
   (1) a $C_{3-10}$ cycloalkyl group (e.g., cyclopropyl group), and
   (2) a 5- or 6-membered oxygen-containing heterocyclic group (e.g., tetrahydrofuryl group), or
(b) a $C_{2-6}$ alkynyl group (e.g., ethynyl group) optionally substituted by 1 to 3 substituents selected from a $C_{3-10}$ cycloalkyl group (e.g., cyclopropyl, cyclobutyl) optionally substituted by 1 to 3 hydroxy groups;
$R^2$ is a hydrogen atom or a fluorine atom;
$R^3$ is a hydrogen atom, a fluorine atom or a methyl group;
$R^4$ and $R^5$ are each independently a hydrogen atom or a methyl group;
$R^6$ is a hydrogen atom or a methyl group;
$R^7$ is a hydrogen atom; and
$R^8$ is
(a) a $C_{1-6}$ alkyl group optionally substituted by 1 to 3 substituents selected from a hydroxy group, a $C_{1-6}$ alkoxy group and a 5- or 6-membered oxygen-containing heterocyclic group (e.g., tetrahydrofuryl group, tetrahydropyranyl group), or
(b) a $C_{3-10}$ cycloalkyl group optionally substituted by 1 to 3 substituents selected from a hydroxy group and a $C_{1-6}$ alkyl group,
or a salt thereof.

[Compound (I-C)]

A compound, which is compound (I) wherein
$R^1$ is
(a) a $C_{1-6}$ alkoxy group optionally substituted by 1 to 3 substituents selected from a $C_{3-10}$ cycloalkyl group and a 5- or 6-membered oxygen-containing heterocyclic group (e.g., tetrahydrofuryl group), or
(b) a $C_{2-6}$ alkynyl group optionally substituted by 1 to 3 substituents selected from a $C_{3-10}$ cycloalkyl group optionally substituted by 1 to 3 hydroxy groups;
$R^2$ is a hydrogen atom or a fluorine atom;
$R^3$ is a hydrogen atom, a fluorine atom or a methyl group;
$R^4$ and $R^5$ are independently a hydrogen atom or a methyl group;
$R^6$ is a hydrogen atom or a methyl group;
$R^7$ and $R^8$ form, together with the adjacent nitrogen atom, a 4- to 6-membered nitrogen-containing heterocycle (e.g., pyrrolidine, piperidine) optionally substituted by 1 to 3 substituents selected from a hydroxy group and a $C_{1-6}$ alkyl group,
or a salt thereof.

More preferred examples of compound (I) include compounds described in the following Examples or salts thereof.

When compound (I) is in the form of a salt, concrete examples thereof include pharmaceutically acceptable salts, for example, salts with inorganic bases, ammonium salts, salts with organic bases, salts with inorganic acids, salts with organic acids, salts with basic or acidic amino acids and the like.

Preferable examples of the salts with inorganic bases include alkali metal salts such as sodium salt, potassium salt, and the like; alkaline earth metal salts such as calcium salts, magnesium salts, barium salts, and the like; aluminum salts, and the like.

Preferable examples of the salts with organic bases include salts with trimethylamine, triethylamine, pyridine, picoline, ethanolamine, diethanolamine, triethanolamine, dicyclohexylamine, N,N-dibenzylethylenediamine, and the like.

Preferable examples of the salts with inorganic acids include salts with hydrochloric acid, hydrobromic acid, nitric acid, sulfuric acid, phosphoric acid, and the like.

Preferable examples of the salts with organic acids include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid, and the like.

Preferable examples of the salts with basic amino acids include salts with arginine, lysine, ornithine, and the like.

Preferable examples of the salts with acidic amino acids include salts with aspartic acid, glutamic acid, and the like.

Compound (I) may be any of an anhydrate or a hydrate.

In addition, compound (I) may be any of non-solvate and solvate.

Moreover, compound (I) may be labeled with an isotope (e.g., $^3H$, $^{11}C$, $^{14}C$, $^{18}F$, $^{35}S$, $^{125}I$).

Furthermore, compound (I) may also be a deuterium exchange compound wherein $^1H$ is converted to $^2H(D)$.

Compound (I) may be a pharmaceutically acceptable cocrystal or a cocrystal salt. Here, the cocrystal or cocrystal salt means a crystalline substance, which is constituted from two or more kinds of specific solids each having different physical properties (e.g., structure, melting point, heat of fusion, hygroscopicity, solubility, stability etc.) at room temperature. The cocrystal and cocrystal salt can be produced according to a cocrystallization method known per se.

When compound (I) contains an optical isomer, a stereoisomer, a regioisomer or a rotamer, these are also encompassed in compound (I), and can be obtained as a single product according to synthesis and separation methods known per se. For example, when compound (I) has an optical isomer, an optical isomer resolved from this compound is also encompassed in compound (I).

The optical isomer can be produced by a method known per se (e.g., a fractional recrystallization method, a chiral column method, a diastereomer method).

1) Fractional Recrystallization Method

A method wherein a salt of a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine) is formed, which is separated by a fractional recrystallization method, and if desired, a free optical isomer is obtained by a neutralization step.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Chemical Industries, Ltd.) and the like, and developed with water, various buffers (e.g., phosphate buffer) and organic solvents (e.g., ethanol, methanol, isopropanol, acetonitrile, trifluoroacetic acid, diethylamine) solely or in admixture to separate the optical isomer. In the case of a gas chromatography, for example, a chiral column such as CP-Chirasil-DeX CB (manufactured by GL Sciences Inc.) and the like is used to allow separation.

3) Diastereomer Method

A method wherein a racemic mixture is prepared into a diastereomeric mixture by chemical reaction with an optically active reagent, which is made into a single substance by a typical separation means (e.g., fractional recrystallization, a chromatography method) and the like, and is subjected to a chemical treatment such as hydrolysis and the like to separate an optically active reagent moiety, whereby an optical isomer is obtained. For example, when compound (I) contains a hydroxy group, or a primary or secondary amino group in a molecule, the compound and an optically active organic acid (e.g., MTPA [α-methoxy-α-(trifluoromethyl)phenylacetic acid], (−)-menthoxyacetic acid) and the like are subjected to condensation reaction to give diastereomers in the ester form or in the amide form, respectively. When compound (I) has a carboxyl group, this compound and an optically active amine or alcohol are subjected to condensation reaction to give diastereomers in the amide form or in the ester form, respectively. The separated diastereomer is converted to an optical isomer of the original compound by acid hydrolysis or base hydrolysis.

A prodrug of compound (I) means a compound which is converted to compound (I) with a reaction due to an enzyme, a gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation);
a compound obtained by subjecting a hydroxy group in compound (I) to an acylation, alkylation, phosphorylation or boration (e.g., a compound obtained by subjecting a hydroxy group in compound (I) to an acetylation, palmitoylation, propanoylation, pivaloylation, succinylation, fumarylation, alanylation or dimethylaminomethylcarbonylation);
a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like.

Any of these compounds can be produced from compound (I) by a method known per se.

A prodrug of compound (I) may also be one which is converted into compound (I) under a physiological condition, such as those described in IYAKUHIN no KAIHATSU (Development of Pharmaceuticals), Vol. 7, Design of Molecules, p. 163-198, published by HIROKAWA SHOTEN (1990).

Compound (I) can be produced according to [production method 1-1] to [production method 3-3], which are described in detail below, or a method analogous thereto. For example, compound (I) can be produced according to the following production method; however, it is not limited thereby.

The compounds used as starting compounds and production intermediates may be used in the form of a salt. As such salt, those exemplified as the salt of the aforementioned compound (I) and the like can be used.

In each of the following reactions, the "room temperature" means 15 to 30° C.

In each of the following reactions, when a starting compound has an amino group, a carboxy group or a hydroxy group as a substituent, these groups may be protected by a protecting group generally used in the peptide chemistry and the like. In this case, the object compound can be obtained by removing the protecting group after the reaction as necessary. Protection and deprotection reactions are performed according to a method known per se, for example, the method described in Protective Groups in Organic Synthesis, 3rd Ed., John Wiley and Sons, Inc., 1999.

Examples of the amino-protecting group include a formyl group, a $C_{1-6}$ alkyl-carbonyl group, a $C_{1-6}$ alkoxy-carbonyl group, a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkoxy group and a nitro group.

Examples of the carboxy-protecting group include a $C_{1-6}$ alkyl group, a $C_{7-11}$ aralkyl group (e.g., benzyl), a phenyl group, a trityl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like.

Examples of the hydroxy-protecting group include a $C_{1-6}$ alkyl group, a phenyl group, a trityl group, a $C_{7-10}$ aralkyl group (e.g., benzyl), a formyl group, a $C_{1-6}$ alkyl-carbonyl group, a benzoyl group, a $C_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom, a $C_{1-6}$ alkyl group, a $C_{1-6}$ alkoxy group and a nitro group.

In each of the following reactions, when alkylation reaction, hydrolysis reaction, amination reaction, esterification reaction, amidation reaction, etherification reaction, oxidation reaction, reduction reaction etc. are to be conducted, these reactions are carried out according to methods known per se, for example, those described in Organic Functional Group Preparations, 2nd Ed., Academic Press Inc., 1989; Comprehensive Organic Transformations, VCH Publishers Inc., 1989; and the like.

[Production Method 1-1]

Compound (I) can be produced by, for example, a reductive amination reaction of compound (II) with compound (III) as shown in the following reaction scheme 1.

(Reaction scheme 1)

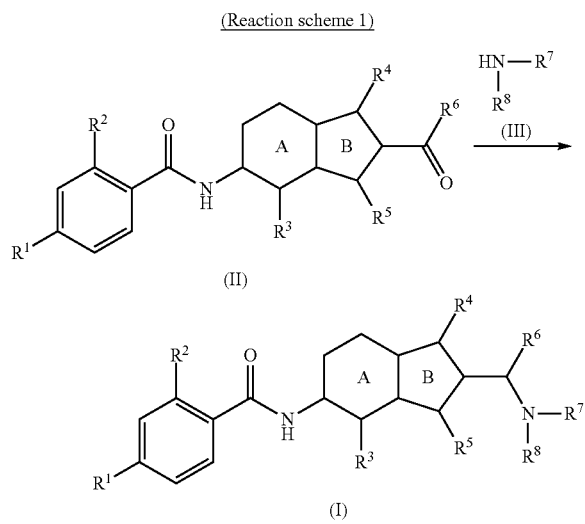

wherein the symbols are as defined above.

That is, compound (I) can be obtained by reacting compound (II) with compound (III) in an amount of 1 to 50 equivalents (preferably 1.2 to 5 equivalents) with a reducing agent in an inert solvent.

Examples of the inert solvent include methanol, ethanol, acetonitrile, tetrahydrofuran (THF), N,N-dimethylformamide (DMF), N,N-dimethylacetamide (DMA), N-methylpyrrolidone (NMP), acetic acid, water and the like can be mentioned. These solvents may be used in a mixture of two or more kinds thereof at an appropriate ratio. Of these, methanol, ethanol, DMF, DMA, NMP and the like are preferable.

As the reducing agent, sodium borohydride, sodium triacetoxyborohydride, sodium cyanoborohydride and the like are used. The amount of the reducing agent to be used is generally 1 to 20 equivalents, preferably 1 to 5 equivalents, relative to compound (II).

The reaction temperature is generally −20° C. to 150° C., preferably 0° C. to 60° C.

The reaction time is generally 5 min to 40 hr, preferably 1 hr to 24 hr.

In addition, the reaction can also be performed in the presence of an acid. Examples of the acid to be used include organic acids such as acetic acid, methanesulfonic acid and the like; inorganic acids such as hydrochloric acid, sulfuric acid and the like; and Lewis acids such as titanium tetrachloride, titanium isopropoxide and the like. Among these, acetic acid and the like are preferable. The amount of the acid to be used is generally 0.01 to 100 equivalents, relative to compound (II) for organic acid or Lewis acid, and generally 0.01 to 10 equivalents, relative to compound (II) for inorganic acid. When an organic acid is used, an excess amount of the organic acid may be used as a reaction solvent.

Compound (II) can be produced by the method described below [production method 2-2] or a method analogous thereto, or from the following compound (IVb) by an oxidation reaction known per se.

Compound (III) can be produced according to a method known per se.

[Production Method 1-2]

Compound (Ia), which is compound (I) wherein $R^7$ is a hydrogen atom, can be produced by, for example, Mitsunobu reaction of compound (IV) and compound (IIIa) and subsequent deprotection of an N-nosyl group as shown in the following reaction scheme 2.

(Reaction scheme 2)

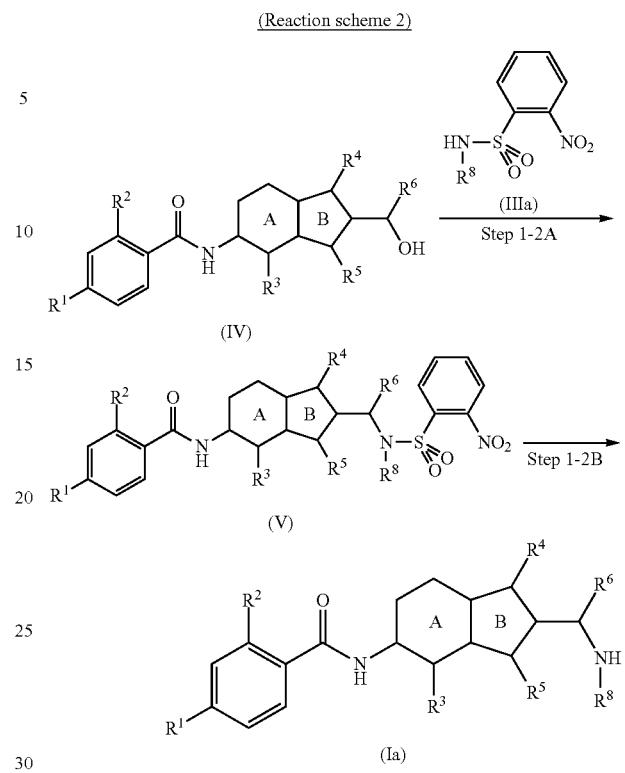

wherein the symbols are as defined above.

<Step 1-2A>

In step 1-2A, compound (IV) and compound (IIIa) are reacted using the "Mitsunobu reaction" [for example, Synthesis, 1-27, (1981)] to give compound (V).

The "Mitsunobu reaction" can be performed by reacting, for example, compound (IV) with compound (IIIa) in 0.5 to 10 equivalents (preferably 1 to 2 equivalents) relative to compound (IV) in an inert solvent in the presence of azodicarboxylic acid amide or azodicarboxylate, and trialkylphosphine or triarylphosphine.

Examples of the inert solvent include acetonitrile, DMF, NMP, DMA, acetone, THF, dioxane and the like. These solvents may be used in a mixture of two or more kinds thereof at an appropriate ratio. Preferred is THF.

As the "azodicarboxylic acid amide or azodicarboxylate", diisopropyl azodicarboxylate, diethyl azodicarboxylate, 1,1'-(azodicarbonyl)dipiperidine and the like can be used. The amount thereof to be used is generally 1 to 20 equivalents, preferably 1 to 3 equivalents, relative to compound (IV).

As the "trialkylphosphine or triarylphosphine", triphenylphosphine, tributylphosphine and the like can be used. The amount thereof to be used is generally 1 to 20 equivalents, preferably 1 to 3 equivalents, relative to compound (IV).

The reaction temperature is generally about −20° C. to 100° C., preferably 0° C. to 50° C.

The reaction time is, for example, about 0.5 hr to 1 week, preferably 3 hr to 1 day.

Compound (IV) can be produced according to the methods described in the following [production method 2-1] and [production method 2-3] or a method analogous thereto.

Compound (IIIc) can be produced by a method known per se.

<Step 1-2B>

In step 1-2B, an N-nosyl group of compound (V) is removed to give compound (Ia).

This reaction can be performed by reacting, for example, compound (V) with a base in an inert solvent. Where necessary, the reaction may be performed in the coexistence of thiols.

Examples of the inert solvent include acetonitrile, DMF, NMP, DMA, acetone, THF, water and the like. These solvents may be used in a mixture of two or more kinds thereof at an appropriate ratio. Preferred is DMF.

As the base, sodium hydroxide, potassium hydroxide, lithium hydroxide and the like are preferable. The amount of the base to be used is generally 1 to 100 equivalents, preferably 1 to 20 equivalents, relative to compound (V).

Examples of the "thiols" include mercaptoacetic acid, thiophenol, thioglycolic acid and the like, preferably thioglycolic acid. The amount of the thiols to be used is generally 1 to 100 equivalents, preferably 1 to 20 equivalents, relative to compound (V).

The reaction temperature is generally retained at −20° C. to 150° C., preferably 0° C. to 60° C.

The reaction time is generally 0.5 hr to 48 hr, preferably 1 hr to 24 hr.

[Production Method 1-3]

Compound (Ic), which is compound (I) wherein $R^1$ is an optionally substituted terminal alkynyl group, can be produced by, for example, Sonogashira coupling reaction (e.g., Tetrahedron Letters, 50, 4467-4470 (1975)) of compound (Ib) and compound (VI) as shown in the following reaction scheme 3. Particularly, the following reaction scheme 3 is explained by referring to a compound wherein $R^1$ is an optionally substituted ethynyl group.

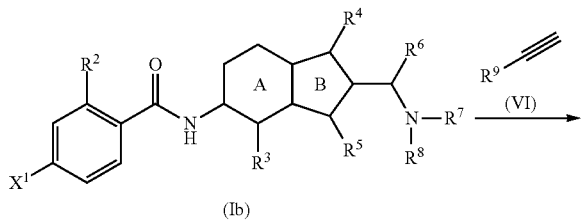

(Reaction scheme 3)

(Ib)

(Ic)

wherein $X^1$ is a halogen group such as a chloro group, a bromo group, an iodo group and the like or a trifluoromethanesulfonyloxy group, $R^9$ is a substituent, and the other symbols are as defined above.

As the "substituent" for $R^9$, those similar to the substituent that the "$C_{2-6}$ alkynyl group" of the "optionally substituted $C_{2-6}$ alkynyl group" for $R^1$ may have can be mentioned.

The "Sonogashira coupling reaction" can be performed by reacting, for example, compound (Ib) with compound (VI) in 0.5 to 50 equivalents (preferably 1 to 5 equivalents) relative to compound (Ib) in an inert solvent in the presence of a palladium catalyst, a copper catalyst and a base. In addition, trialkylphosphine or triarylphosphine can also be present.

Examples of the inert solvent include acetonitrile, DMF, NMP, DMA, dioxane, THF, pyridine and the like. These solvents may be used in a mixture of two or more kinds thereof at an appropriate ratio.

As the palladium catalyst, tetrakis(triphenylphosphine)palladium(0), dichlorobis(triphenylphosphine)palladium(II) and the like can be used. The amount thereof to be used is generally 0.001 to 1 equivalent, preferably 0.01 to 0.1 equivalent, relative to compound (Ib).

As the copper catalyst, preferred is copper iodide. The amount thereof to be used is generally 0.001 to 1 equivalent, preferably 0.01 to 0.1 equivalent, relative to compound (Ib).

Examples of the base include lithium hydride, sodium hydride, sodium carbonate, potassium carbonate, cesium carbonate, triethylamine, N,N-diisopropylethylamine, diethylamine, normal propylamine, pyridine and the like. Preferred are triethylamine, diethylamine, normal propylamine and cesium carbonate. The amount thereof to be used is generally 1 to 100 equivalents, relative to compound (Ib). In addition, when amines are used, an excess amount of a base may be used as a solvent.

As the "trialkylphosphine or triarylphosphine", triphenylphosphine, tributylphosphine and the like can be used. The amount thereof to be used is generally 1 to 20 equivalents, preferably 1 to 3 equivalents, relative to compound (Ib).

The reaction temperature is generally about 5° C. to 150° C., preferably room temperature to 100° C.

The reaction time is, for example, about 0.5 hr to 1 week, preferably 3 hr to 1 day.

Compound (Ib), the starting material, can be produced by a method similar to [production method 1-1].

Compound (VI) can be produced according to a method known per se.

[Production Method 2-1]

Compound (IIa) and compound (IVa), which are compound (II) and compound (IV) wherein $R^6$ is a hydrogen atom, can be produced by, for example, reaction scheme 4 shown below.

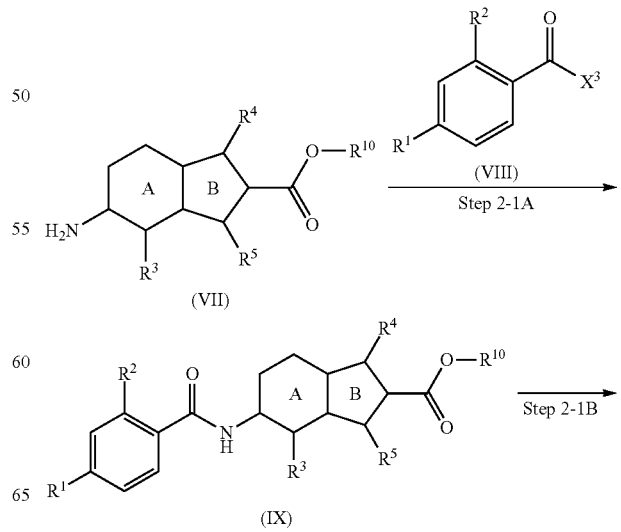

(Reaction scheme 4)

(VII)

(VIII)

Step 2-1A (IX)

Step 2-1B

-continued

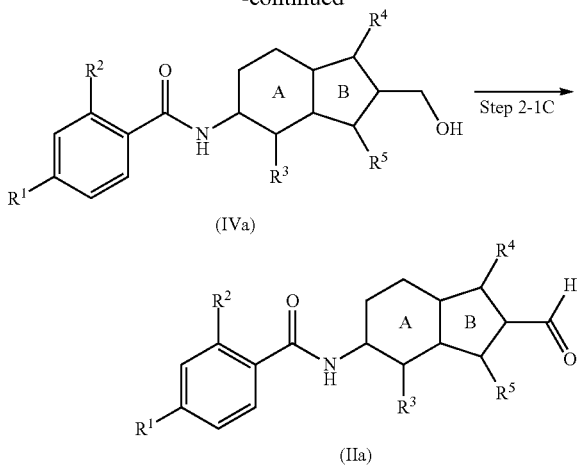

(IVa)

(IIa)

wherein $R^{10}$ is a $C_{1-6}$ alkyl group, $X^3$ is a hydroxy group, a chloro group, a bromo group or the like, and the other symbols are as defined above.

<Step 2-1A>

In step 2-1A, compound (VII) and compound (VIII) in 1 to 10 equivalents relative to compound (VII) are reacted using an amidation reaction to give compound (IX).

When $X^3$ is a chloro group, a bromo group or the like, compound (IX) can be produced by, for example, reacting compound (VII) with compound (VIII) in an inert solvent such as THF and the like in the presence of a base such as triethylamine and the like.

The amount of the base to be used is generally 1 to 30 equivalents, preferably 1 to 5 equivalents, relative to compound (VII).

The reaction temperature is generally about −20° C. to 150° C., preferably room temperature to 80° C.

The reaction time is, for example, about 0.5 hr to 1 week, preferably, 3 hr to 1 day.

When $X^3$ is a hydroxy group, compound (IX) can be produced by, for example, reacting compound (VII) with compound (VIII) by using an amidation reagent such as 1-ethyl-3-(3-dimethylaminopropyl)carbodiimide hydrochloride, 1-hydroxybenzotriazole monohydrate and the like in an inert solvent such as DMF and the like in the presence of a base such as N,N-dimethylaminopyridine and the like.

The amount of the base to be used is generally 0.01 to 10 equivalents, preferably 0.01 to 1.2 equivalents, relative to compound (VII).

The amount of the amidation reagent to be used is generally 1 to 20 equivalents, preferably 1 to 5 equivalents, relative to compound (VII).

The reaction temperature is generally about −20° C. to 100° C., preferably 0° C. to 60° C.

The reaction time is, for example, about 0.5 hr to 1 week, preferably, 3 hr to 1 day.

Compound (VIII) can be produced by a method known per se.

Compound (VII) can be produced according to the methods described in the following [production method 3-1], [production method 3-2] and [production method 3-3] or a method analogous thereto.

<Step 2-1B>

In step 2-1B, an ester group of compound (IX) is reduced to give compound (IVa).

Examples of the reducing agent to be used include lithium aluminum hydride, calcium chloride, sodium borohydride, isobutylaluminum hydride and the like. The amount of the reducing agent to be used is generally 0.5 to 10 equivalents, preferably 1 to 5 equivalents, relative to compound (IX).

Examples of the solvent to be used include THF, ethanol, dimethoxyethane, a mixed solvent thereof and the like.

The reaction temperature is generally about −20° C. to 100° C., preferably 0° C. to 80° C.

The reaction time is, for example, about 0.5 hr to 1 week, preferably, 3 hr to 1 day.

<Step 2-1C>

In step 2-1C, a hydroxy group of compound (IVa) is oxidized to give compound (IIa).

Examples of the oxidizing agent to be used include manganese dioxide and the like. The amount of the oxidizing agent to be used is generally 1 to 50 equivalents, preferably 2 to 20 equivalents, relative to compound (IVa).

Examples of the solvent to be used include THF, methylene chloride and the like.

The reaction temperature is generally about 0° C. to 150° C., preferably room temperature to 100° C.

The reaction time is, for example, about 0.5 hr to 1 week, preferably, 1 hr to 1 day.

[Production Method 2-2]

Compound (IIa), which is compound (II) wherein $R^5$ is a hydrogen atom, can also be produced by, for example, reaction scheme 5 shown below.

(Reaction scheme 5)

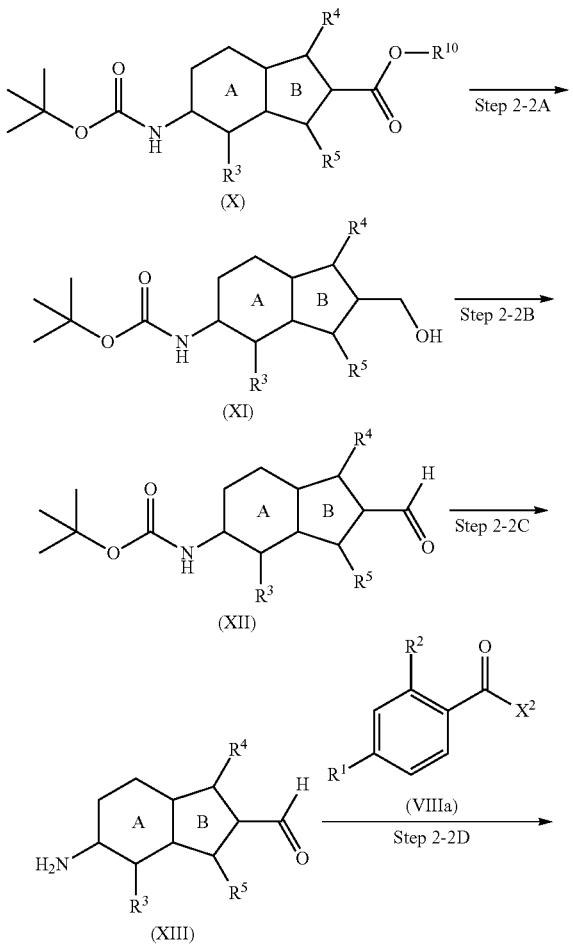

-continued

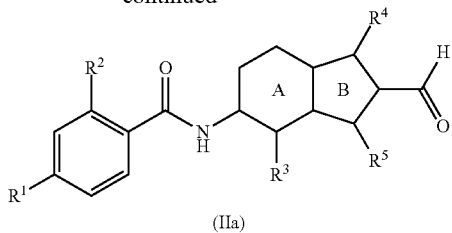

(IIa)

wherein $X^2$ is a chloro group, a bromo group or the like, and the other symbols are as defined above.

<Step 2-2A>

In step 2-2A, an ester group of compound (X) is reduced to give compound (XI).

Examples of the reducing agent to be used include lithium aluminum hydride, calcium chloride, sodium borohydride and the like. The amount of the reducing agent to be used is generally 0.5 to 10 equivalents, preferably 1 to 5 equivalents, relative to compound (X).

Examples of the solvent to be used include THF, ethanol, a mixed solvent thereof and the like.

The reaction temperature is generally about −20° C. to 100° C., preferably 0° C. to 80° C.

The reaction time is, for example, about 0.5 hr to 1 week, preferably, 3 hr to 1 day.

Compound (X) can be produced according to the production method of compound (Xa) and compound (Xb) described in [production method 3-2] shown below or a method analogous thereto.

<Step 2-2B>

In step 2-2B, a hydroxy group of compound (XI) is oxidized to give compound (XII).

Examples of the oxidizing agent to be used include manganese dioxide and the like. The amount of the oxidizing agent to be used is generally 1 to 50 equivalents, preferably 2 to 20 equivalents, relative to compound (XI).

Examples of the solvent to be used include THF, methylene chloride and the like.

The reaction temperature is generally about 0° C. to 150° C., preferably, room temperature to 100° C.

The reaction time is, for example, about 0.5 hr to 1 week, preferably, 1 hr to 1 day.

<Step 2-2C>

In step 2-2C, a tert-butoxycarbonyl group of compound (XII) is removed in the presence of an acid to give compound (XIII).

Examples of the acid to be used include hydrochloric acid, trifluoroacetic acid and the like. The amount of the acid to be used is generally 1 to 100 equivalents, preferably 5 to 50 equivalents, relative to compound (XII).

Examples of the solvent to be used include ethyl acetate, dioxane, methylene chloride and the like.

The reaction temperature is generally −20° C. to 100° C., preferably, room temperature to 80° C.

The reaction time is generally about 0.1 hr to 48 hr, preferably 1 hr to 24 hr.

<Step 2-2D>

In step 2-2D, compound (XIII) and compound (VIIIa) in 1 to 10 equivalents (preferably 1 to 3 equivalents) relative to compound (XIII) are reacted in the presence of a base to give compound (IIa).

Examples of the base to be used include triethylamine and the like. The amount of the base to be used is generally 1 to 50 equivalents, preferably 1 to 10 equivalents, relative to compound (XIII).

Examples of the solvent to be used include THF and the like.

The reaction temperature is generally about −20° C. to 150° C., preferably room temperature to 80° C.

The reaction time is, for example, about 0.5 hr to 1 week, preferably, 3 hr to 1 day.

Compound (VIIIa) can be produced by a method known per se.

[Production Method 2-3]

Compound (IVb), which is compound (IV) wherein $R^6$ is a methyl group, can be produced by, for example, a methylation reaction of compound (IIa) as shown in the following reaction scheme 6.

(Reaction scheme 6)

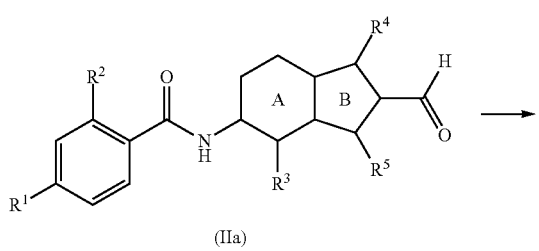

(IIa)

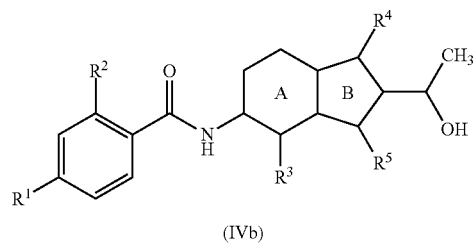

(IVb)

wherein the symbols are as defined above.

Examples of the methylating agent to be used include methylmagnesium bromide, methylmagnesium iodide, methyllithium and the like, preferably methyl magnesium bromide. The amount of the methylating, agent to be used is generally 1 to 20 equivalents, preferably 1 to 5 equivalents, relative to compound (IIa).

Examples of the solvent to be used include THF, ether, dioxane and the like, preferably THF.

The reaction temperature is generally about −70° C. to 100° C., preferably, 0° C. to 50° C.

The reaction time is, for example, about 0.5 hr to 1 week, preferably 0.5 hr to 1 day.

[Production Method 3-1]

Compound (VIIa), which is compound (VII) wherein ring AB is a 5-aminoindole ring and $R^3$ is a hydrogen atom, can be produced by, for example, the method shown in the following reaction scheme 7.

(Reaction scheme 7)

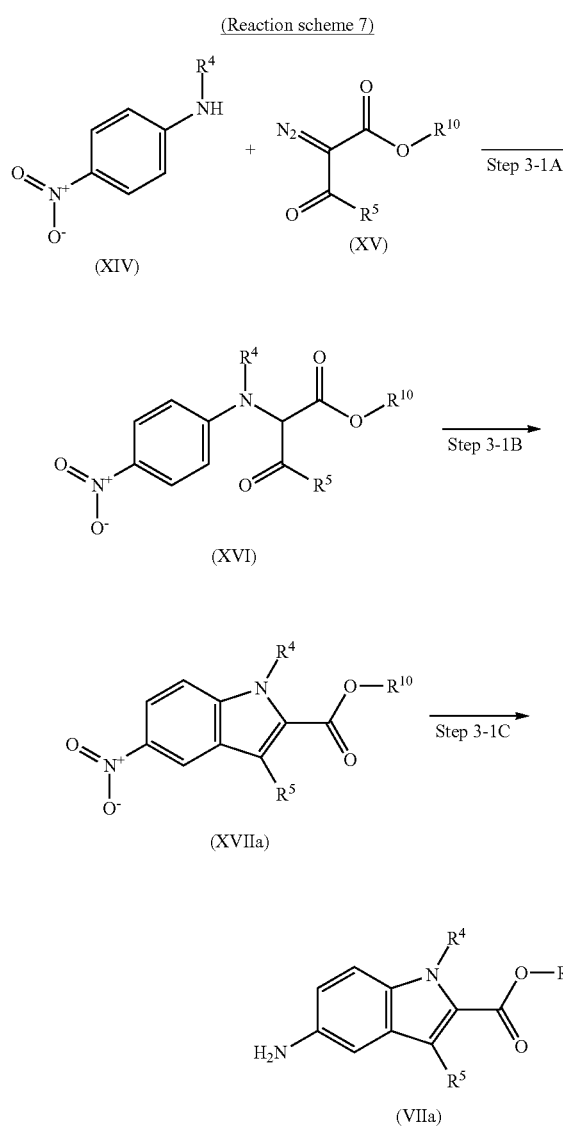

wherein the symbols are as defined above.

<Step 3-1A>

In step 3-1A, compound (XIV) and compound (XV) in 1 to 10 equivalents (preferably 1 to 3 equivalents) relative to compound (XIV) are reacted in the presence of a rhodium catalyst to give compound (XVI). This reaction is performed according to, for example, the method described in J. Chem. Soc., Perkin Trans. 1, 1672-1687 (2002).

Examples of the solvent to be used include toluene, chloroform and the like.

Preferred rhodium catalyst to be used is rhodium(II) diacetate. The amount of the rhodium catalyst to be used is generally 0.001 to 0.5 equivalents, preferably 0.01 to 0.1 equivalent, relative to compound (XIV).

The reaction temperature is generally room temperature to 120° C., preferably 50° C. to 120° C.

The reaction time is generally about 0.1 hr to 24 hr, preferably 0.5 hr to 10 hr.

Compound (XIV) and compound (XV) can be each produced by a method known per se.

<Step 3-1B>

In step 3-1B, compound (XVI) is cyclized in the presence of an acid to give compound (XVIIa). This reaction is performed according to, for example, the method described in J. Chem. Soc., Perkin Trans. 1, 1672-1687 (2002).

Examples of the acid to be used include acidic ion exchange resin Amberlyst (registered trademark) 15 and the like. The amount of the acid to be used is generally 0.01 to 100 equivalents, preferably 0.1 to 50 equivalents, relative to compound (XVI).

The reaction temperature is generally 50° C. to 120° C., preferably 80° C. to 120° C.

The reaction time is generally about 1 hr to 48 hr, preferably 5 hr to 24 hr.

<Step 3-1C>

In step 3-1C, a nitro group of compound (XVIIa) is reduced by a catalytic hydrogenation reaction to give compound (VIIa).

Examples of the solvent to be used include DMF, methanol, ethanol, THF, water and the like. These solvents may be used in a mixture of two or more kinds thereof at an appropriate ratio. Preferred are methanol and THF.

As the catalyst for a catalytic hydrogenation reaction, palladium carbon is preferable. The amount of the catalyst to be used is generally 0.001 to 1 equivalent, preferably 0.01 to 0.1 equivalent, relative to compound (XVIIa).

The hydrogen pressure is generally 1 to 10 atm, preferably 1 to 3 atm.

The reaction temperature is generally room temperature to 80° C., preferably room temperature to 50° C.

The reaction time is generally 0.5 hr to 48 hr, preferably 1 hr to 24 hr.

[Production Method 3-2]

Compound (VIIb), which is compound (VII) wherein ring AB is a 5-aminoindole ring, $R^3$ is a methyl group and $R^4$ is a hydrogen atom, and compound (VIIc), which is compound (VII) wherein ring AB is a 5-aminoindole ring, $R^3$ is a methyl group and $R^4$ is a methyl group, can be produced by, for example, the method shown in the following reaction scheme 8.

(Reaction scheme 8)

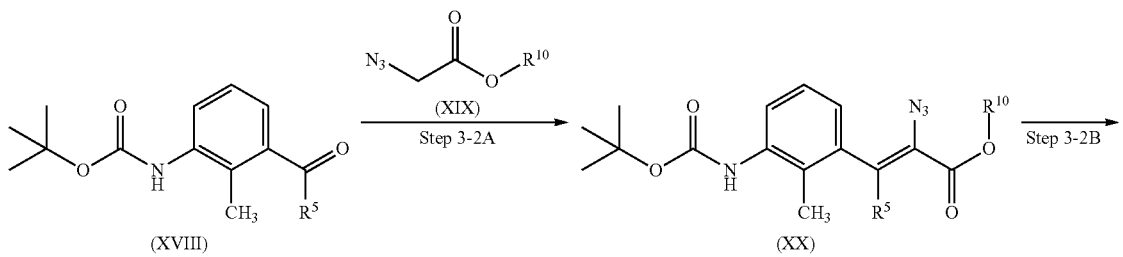

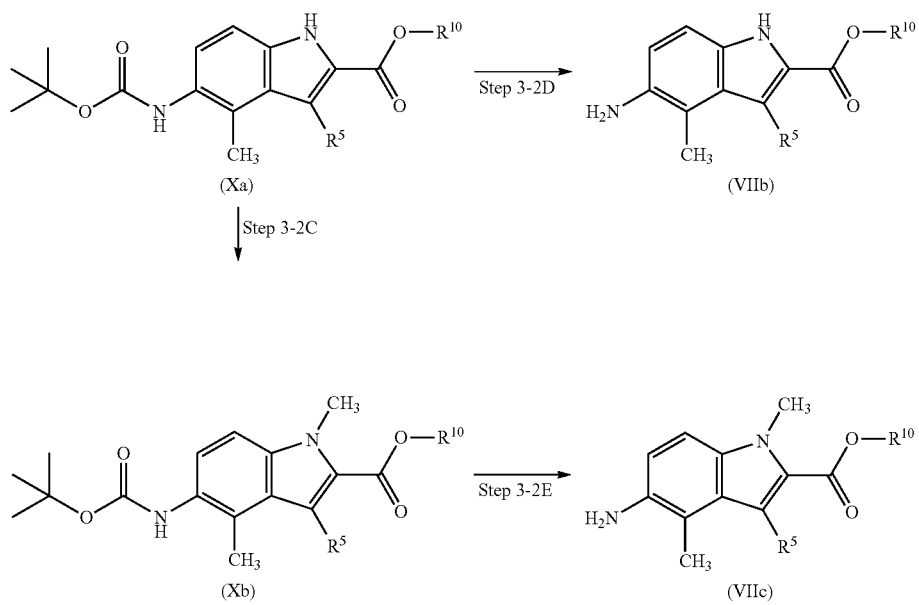

wherein the symbols are as defined above.

<Step 3-2A>

In step 3-2A, compound (XVIII) and compound (XIX) in 1 to 30 equivalents (preferably 1 to 10 equivalents) relative to compound (XVIII) are reacted in the presence of a base to give compound (XX).

Examples of the solvent to be used include methanol, ethanol, THF and the like. These solvents may be used in a mixture of two or more kinds thereof at an appropriate ratio. Preferred are methanol and ethanol.

As the base, sodium methoxide, sodium ethoxide and the like can be used, and these may be prepared by reacting sodium in an alcohol solvent. The amount of the base to be used is generally 0.1 to 100 equivalents, preferably 1 to 30 equivalents, relative to compound (XVIII).

The reaction temperature is generally −78° C. to 80° C., preferably −30° C. to room temperature.

The reaction time is generally 0.5 hr to 48 hr, preferably 1 hr to 24 hr.

Compound (XVIII) and compound (XIX) can be each produced according to a method known per se.

<Step 3-2B>

In step 3-2B, compound (XX) is cyclized by heating to give compound (Xa).

Examples of the solvent to be used include toluene, xylene, THF and the like. These solvents may be used in a mixture of two or more kinds thereof at an appropriate ratio. Preferred is toluene.

The reaction temperature is generally 50° C. to 150° C., preferably 60° C. to 120° C.

The reaction time is generally 0.5 hr to 48 hr, preferably 1 hr to 24 hr.

<Step 3-2C>

In step 3-2C, NH moiety of the indole ring of compound (Xa) is reacted with a methylating agent in the presence of a base to give compound (Xb).

Examples of the solvent to be used include DMF, NMP, THF and the like. These solvents may be used in a mixture of two or more kinds thereof at an appropriate ratio. Preferred is DMF.

As the base to be used, sodium hydride, sodium carbonate, cesium carbonate and the like can be used. The amount of the base to be used is generally 1 to 30 equivalents, preferably 1 to 5 equivalents, relative to compound (Xa).

As the methylating agent to be used, methyl iodide and the like can be used. The amount of the base to be used is generally 1 to 30 equivalents, preferably 1 to 10 equivalents, relative to compound (Xa).

The reaction temperature is generally 0° C. to 100° C., preferably room temperature to 80° C.

The reaction time is generally 0.5 hr to 100 hr, preferably 1 hr to 48 hr.

<Step 3-2D and Step 3-2E>

In step 3-2D and step 3-2E, tert-butoxycarbonyl groups of compound (Xa) and (Xb) are removed in the presence of an acid to give compound (VIIb) and (VIIc), respectively.

Examples of the acid to be used include hydrochloric acid, trifluoroacetic acid and the like. The amount of the acid to be used is generally 1 to 100 equivalents, preferably 5 to 50 equivalents, relative to compound (Xa) or (Xb).

Examples of the solvent to be used include ethyl acetate, dioxane, methylene chloride and the like.

The reaction temperature is generally −20° C. to 100° C., preferably, room temperature to 80° C.

The reaction time is generally 0.1 hr to 48 hr, preferably 1 hr to 24 hr.

[Production Method 3-3]

Compound (VIId), which is compound (VII) wherein ring AB is a 6-aminoindole ring and $R^5$ is a hydrogen atom, and compound (VIIe), which is compound (VII) wherein ring AB is a 6-aminoindole ring and $R^5$ is a methyl group, can be produced by, for example, the method shown in the following reaction scheme 9.

(Reaction scheme 9)

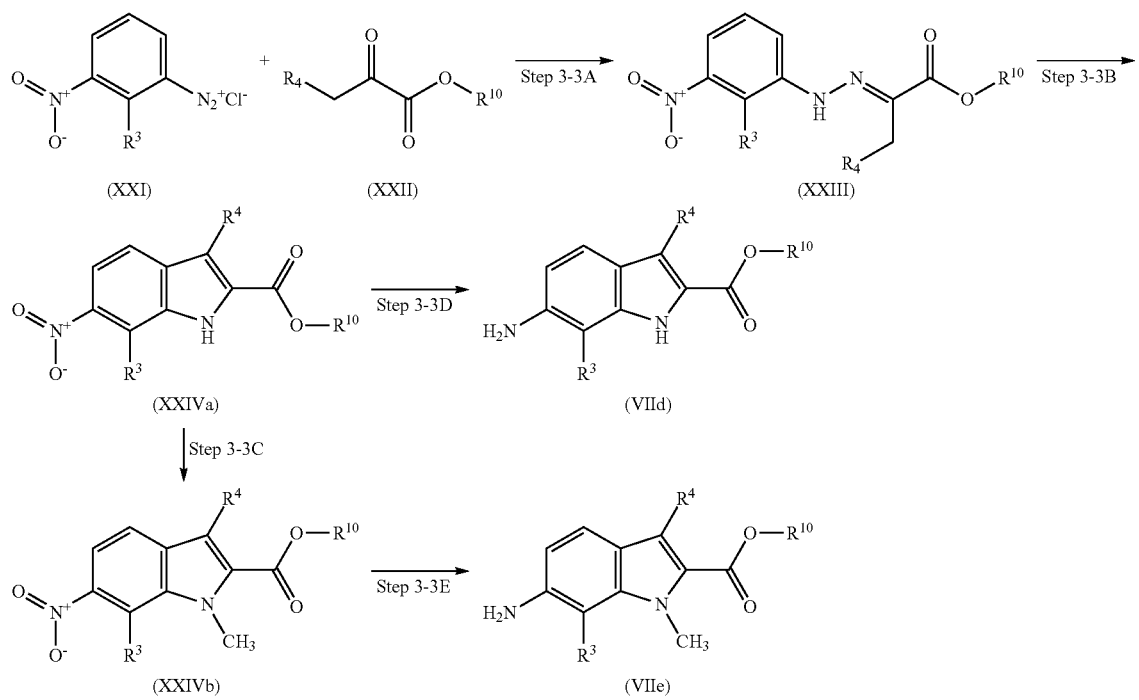

wherein the symbols are as defined above.

<Step 3-3A>

In step 3-3A, compound (XXI) induced from the corresponding aniline derivative and compound (XXII) in 1 to 10 equivalents (preferably 1 to 3 equivalents) relative to compound (XXI) are reacted in the presence of a base to give compound (XXIII).

Examples of the solvent to be used include methanol, ethanol, water and the like. These solvents may be used in a mixture of two or more kinds thereof at an appropriate ratio. Preferred are ethanol and water.

As the base, potassium hydroxide, sodium hydroxide and the like can be used. The amount of the base to be used is generally 1 to 20 equivalents, preferably 1 to 5 equivalents, relative to compound (XXI).

The reaction temperature is generally −50° C. to 80° C., preferably −30° C. to room temperature.

The reaction time is generally 0.1 hr to 48 hr, preferably, 0.1 hr to 24 hr.

Compound (XXI) and compound (XXII) can be each produced according to a method known per se.

<Step 3-3B>

In step 3-3B, compound (XXIII) is cyclized by heating in the presence of an acid to give compound (XXIVa).

Examples of the inert solvent to be used include toluene, xylene, THF and the like. These solvents may be used in a mixture of two or more kinds thereof at an appropriate ratio. Preferred is toluene.

As the acid, hydrochloric acid, sulfuric acid, Eaton's reagent (phosphorus pentoxide-methanesulfonic acid) and the like can be used. The amount of the acid to be used is generally 0.01 to 20 equivalents, preferably 0.1 to 5 equivalents, relative to compound (XXIII).

The reaction temperature is generally 50° C. to 150° C., preferably 60° C. to 120° C.

The reaction time is generally 0.5 hr to 48 hr, preferably 1 hr to 24 hr.

<Step 3-3C>

In step 3-3C, NH moiety of the indole ring of compound (XXIVa) is reacted with a methylating agent in the presence of a base to give compound (XXIVb).

Examples of the inert solvent to be used include DMF, NMP, THF and the like. These solvents may be used in a mixture of two or more kinds thereof at an appropriate ratio. Preferred is DMF.

As the base, sodium hydride, sodium carbonate, cesium carbonate and the like can be used. The amount of the base to be used is generally 1 to 30 equivalents, preferably 1 to 5 equivalents, relative to compound (XXIVa).

As the methylating agent, methyl iodide and the like can be used. The amount of the methylating agent to be used is generally 1 to 30 equivalents, preferably 1 to 10 equivalents, relative to compound (XXIVa).

The reaction temperature is generally 0° C. to 100° C., preferably room temperature to 80° C.

The reaction time is generally 0.5 hr to 100 hr, preferably 1 hr to 48 hr.

<Step 3-3D and Step 3-3E>

In step 3-3D and step 3-3E, nitro groups of compound (XXIVa) and (XXIVb) are reduced to give compound (VIId) and (VIIe), respectively. This reaction can be performed by, for example, subjecting compound (XXIVa) or (XXIVb) to a catalytic hydrogenation reaction in an inert solvent.

Examples of the inert solvent to be used include DMF, methanol, ethanol, THF, water and the like. These solvents may be used in a mixture of two or more kinds thereof at an appropriate ratio. Preferred are methanol and THF.

As the catalyst for the catalytic hydrogenation reaction, palladium carbon is preferable. The amount of the catalyst to be used is generally 0.001 to 1 equivalent, preferably 0.01 to 0.1 equivalent, relative to compound (XXIVa) or (XXIVb).

The hydrogen pressure is generally 1 to 10 atm, preferably 1 to 3 atm.

The reaction temperature is generally room temperature to 80° C., preferably room temperature to 50° C.

The reaction time is generally 0.5 hr to 48 hr, preferably 1 hr to 24 hr.

Inasmuch as compound (I) and a prodrug thereof (hereinafter abbreviated as the compound of the present invention) has a superior MCH receptor (particularly, MCH receptor 1) antagonistic action, it is useful as an agent for the prophylaxis or treatment of diseases caused by MCH.

In addition, the compound of the present invention also shows low toxicity (e.g., cardiac toxicity (e.g., hERG inhibitory activity), PLsis inducing potential, acute toxicity, chronic toxicity, genetic toxicity, reproductive toxicity, drug interaction, carcinogenicity, phototoxicity).

Moreover, the compound of the present invention is superior in oral absorbability.

Furthermore, the compound of the present invention is superior in brain transfer function.

Accordingly, the compound of the present invention is safely administered as an agent for the prophylaxis or treatment of diseases caused by MCH, and the like to mammals (e.g., rat, mouse, guinea pig, rabbit, sheep, horse, pig, cow, monkey, human).

The diseases caused by MCH include, for example, obesity [e.g., malignant mastocytosis, exogenous obesity, hyperinsulinar obesity, hyperplasmic obesity, hypophyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, central obesity and the like], hyperphagia, emotional disorder, sexual dysfunction, depression, anxiety and the like.

The compound of the present invention is also useful as a drug for the prophylaxis or treatment of a lifestyle-related diseases such as diabetes (e.g., type 1 diabetes, type 2 diabetes, gestational diabetes, obese diabetes, borderline diabetes), impaired glucose tolerance (IGT), diabetic complications (e.g., diabetic retinopathy, diabetic neuropathy, diabetic nephropathy), hyperlipidemia (e.g., hypertriglyceridemia, hypercholesterolemia, high LDL-cholesterolemia, low HDL-cholesterolemia, postprandial hyperlipemia), arteriosclerosis, arthritis in knee, metabolic syndrome and the like.

Moreover, the compound of the present invention is also useful as an anorexigenic agent.

The compound of the present invention can also be concurrently used with diet therapy (e.g., diet therapy for diabetes), or an exercise therapy.

The compound of the present invention can be used for the prophylaxis or treatment of pigmentation disorder based on abnormality of melanin or melanocyte. Here, as the pigmentation disorder, pigment proliferation, pigment decrease and the like can be mentioned. As the pigment proliferation, drug pigmentation caused by antitumor agent and the like; chromatosis and incompetence of pigment associated with diseases such as endocrine metabolism disorder (e.g., Addison's disease), genetic diseases, chronic hepatopathy, kidney failure, acanthosis nigricans, systemic scleroderma and the like; and the like can be mentioned. As the pigment decrease, phenylketonuria, systemic or localized albinism, foliaceous leukoderma or leukoderma vulgaris associated with tuberous sclerosis; depigmentation associated with systemic scleroderma and the like can be mentioned.

The compound of the present invention can be used for the prophylaxis or treatment of depigmentation due to chloasma, ephelides, sunburn and the like; and further, hyperpigmentation or hypopigmentation for cosmetic purposes.

The compound of the present invention is used as is or as a pharmaceutical composition formulated as a preparation together with a pharmacologically acceptable carrier by a method known per se, for example, the method described in the Japanese Pharmacopoeia.

Examples of the pharmacologically acceptable carrier include various organic or inorganic carrier substances conventionally used as a preparation material and, for example, excipient, lubricant, binder and disintegrant for solid preparations; solvent, solubilizing agent, suspending agent, isotonicity agent, buffer and soothing agent for liquid preparations and the like can be mentioned. Where necessary, additives such as preservatives, antioxidants, colorants, sweetening agents, adsorbent, wetting agent and the like can be used during formulation of a preparation.

Examples of the excipient include lactose, sucrose, D-mannitol, starch, cornstarch, crystalline cellulose and light anhydrous silicic acid.

Examples of the lubricant include magnesium stearate, calcium stearate, talc and colloidal silica.

Examples of the binder include crystalline cellulose, sucrose, D-mannitol, dextrin, hydroxypropylcellulose, hydroxypropylmethylcellulose, polyvinylpyrrolidone, starch, sucrose, gelatin, methylcellulose and sodium carboxymethylcellulose.

Examples of the disintegrant include starch, carboxymethylcellulose, calcium carboxymethylcellulose, croscarmellose sodium, sodium carboxymethylstarch and low-substituted hydroxypropylcellulose (L-HPC).

Examples of the solvent include water for injection, alcohol, propylene glycol, macrogol, sesame oil and corn oil.

Examples of the solubilizing agent include polyethylene glycol, propylene glycol, D-mannitol, benzyl benzoate, ethanol, trisaminomethane, cholesterol, triethanolamine, sodium carbonate and sodium citrate.

Examples of the suspending agent include surfactants such as stearyltriethanolamine, sodium lauryl sulfate, laurylaminopropionic acid, lecithin, benzalkonium chloride, benzethonium chloride, glycerol monostearate and the like; hydrophilic polymers such as polyvinyl alcohol, polyvinylpyrrolidone, sodium carboxymethylcellulose, methylcellulose, hydroxymethylcellulose, hydroxyethylcellulose, hydroxypropylcellulose and the like.

Examples of the isotonicity agent include glucose, D-sorbitol, sodium chloride, glycerol and D-mannitol.

Examples of the buffer include buffers such as phosphate, acetate, carbonate, citrate and the like.

Examples of the soothing agent include benzyl alcohol.

Examples of the preservative include p-hydroxybenzoates, chlorobutanol, benzyl alcohol, phenethyl alcohol, dehydroacetic acid and sorbic acid.

Examples of the antioxidant include sulfite and ascorbic acid.

Examples of the colorant include water-soluble food tar color (e.g., food colors such as Food Color Red No. 2 and No. 3, Food Color Yellow No. 4 and No. 5, Food Color Blue No. 1 and No. 2 and the like), water-insoluble lake dye (e.g., aluminum salt of the aforementioned water-soluble food tar color), and natural dye (e.g., β-carotene, chlorophyll, ferric oxide red).

Examples of the sweetening agent include saccharin sodium, dipotassium glycyrrhizinate, aspartame and stevia.

Examples of the adsorbent include porous starch, calcium silicate (trade name: Florite RE), magnesium aluminometasilicate (trade name: Neusilin) and light anhydrous silicic acid (trade name: Sylysia).

Examples of the wetting agent include propylene glycol monostearate, sorbitan monooleate, diethylene glycol monolaurate and polyoxyethylene lauryl ether.

Examples of the dosage form of the aforementioned pharmaceutical composition include tablet (including sugar-coated tablet, film-coated tablet, sublingual tablet, orally disintegrating tablet, buccal tablet etc.), pill, powder, granule, capsule (including soft capsule, microcapsule), troche, syrup, liquid, emulsion, suspension, controlled-release preparation (e.g., immediate-release preparation, sustained-release preparation, sustained-release microcapsule), aerosol, film (e.g., orally disintegrable film, oral mucosal patch film), injection (e.g., subcutaneous injection, intravenous injection, intramuscular injection, intraperitoneal injection, drip infusion), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, and they can be administered safely by oral or parenteral administration (e.g., intravenous, intramuscular, subcutaneous, intraorgan, intranasal, intradermal, ocular instillation, intracerebral, rectal, vaginal, intraperitoneal and intratumor administrations, administration to the vicinity of tumor etc. and direct administration to the lesion).

The content of the compound of the present invention in the pharmaceutical composition is, for example, about 0.1 to 100 wt % of the entire pharmaceutical composition.

The dose of the compound of the present invention is appropriately determined according to the subject of administration, administration route, disease and the like.

For example, the daily dose of the compound of the present invention for oral administration to an adult patient (body weight about 60 kg) with obesity is about 0.1 to about 500 mg, preferably about 1 to about 100 mg, more preferably about 5 to about 100 mg. This amount can be administered at once or in several portions (e.g., 1-3 times) for one day.

In an attempt to enhance the action (therapeutic effect for obesity, diabetes, depression, anxiety etc.) of the compound of the present invention and decrease the amount of the compound of the present invention to be used and the like, as well as prevent or treat complications and improve prognosis, for example, the compound of the present invention can be used in combination with a pharmaceutically active ingredient (hereinafter sometimes to be referred to as "concomitant drug") that does not adversely influence the compound of the present invention. Examples of such concomitant drug include "therapeutic drug for diabetes", "therapeutic drug for diabetic complications", "anti-obesity agent", "therapeutic drug for hypertension", "therapeutic drug for hyperlipidemia", "antiarteriosclerotic drug", "antithrombotic", "diuretic agent", "therapeutic drug for arthritis", "antianxiety drug", "antidepressant", "psychoneurotic agent", "sleep-inducing drug" and the like. These concomitant drugs may be low-molecular-weight compounds, or high-molecular-weight proteins, polypeptides, antibodies, vaccines or the like.

Examples of the above-mentioned "therapeutic drug for diabetes" include insulin preparations (e.g., animal insulin preparations extracted from pancreas of bovine and swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoelitazone, Alealitazar, Chigli-tazar, Lobeglitazone, PLX-204, PN-2034, GFT-505, THR-0921, compound described in WO2007/013694, WO2007/018314, WO2008/093639 or WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues (e.g., sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof), dipeptidyl peptidase IV inhibitors (e.g., Alogliptin or a salt thereof (preferably, benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compound described in WO2004/041266, WO2004/106276, WO2005/063729, WO2005/063725, WO2005/087710, WO2005/095338, WO2007/013689 or WO2008/001931), GLP-1 receptor agonists (e.g., GLP-1, GLP-1MR agent, Liraglutide, Exenatide, AVE-0010, BIM-51077, Aib(8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitors, 11β-hydroxysteroid dehydrogenase inhibitors (e.g., BVT-3498, INCB-13739), adiponectin or an agonist thereof, IKK inhibitors (e.g., AS-2868), leptin resistance-improving drugs, somatostatin receptor agonists, glucokinase activators (e.g., Piragliatin, AZD1656, AZD6370, TTP-355, compound described in WO2006/112549, WO2007/028135, WO2008/047821, WO2008/050821, WO2008/136428 or WO2008/156757), GIP (Glucose-dependent insulinotropic peptide), GPR119 agonists (e.g., PSN821), FGF21, FGF analogue and the like.

Examples of the above-mentioned "therapeutic drug for diabetic complications" include aldose reductase inhibitors (e.g., tolrestat, epalrestat, zopolrestat, fidarestat, CT-112, ranirestat (AS-3201), lidorestat), neurotrophic factor and increasing drugs thereof (e.g., NGF, NT-3, BDNF and neurotrophin production/secretion promoting agents described in WO01/14372 (e.g., 4-(4-chlorophenyl)-2-(2-methyl-1-imidazolyl)-5-[3-(2-methylphenoxy)propyl]oxazole), the compound described in WO2004/039365), PKC inhibitors (e.g., ruboxistaurin mesylate), AGE inhibitors (e.g., ALT946, N-phenacylthiazolium bromide (ALT766), EXO-226, Pyridorin, pyridoxamine), GABA receptor agonists (e.g., gabapentin, pregabalin), serotonin-noradrenaline reuptake inhibitors (e.g., duloxetine), sodium channel inhibitors (e.g., lacosamide), active oxygen scavengers (e.g., thioctic acid), cerebral vasodilators (e.g., tiapride, mexiletine), somatostatin receptor agonists (e.g., BIM23190), apoptosis signal regulating kinase-1 (ASK-1) inhibitor and the like.

Examples of the above-mentioned "anti-obesity agent" include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptors, GABA-modulating agents (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β3 agonists (e.g., N-5984), diacylglycerol acyltransferase 1 (DGAT1) inhibitors, acetyl CoA carboxylase (ACC) inhibitors, stearoyl-CoA desaturation enzyme inhibitors, microsomal triglyceride transfer protein inhibitors (e.g., R-256918), Na-glucose cotransport carrier inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparation extracted from pancreas of bovine and swine; human GLP-1 preparations genetically synthesized using Escherichia coli, yeast; fragment or derivative of GLP-1 (e.g., exenatide, liraglutide)), amylin preparations (e.g., pramlintide, AC-2307), neuropeptide Y agonists (e.g., PYY3-36, derivative of PYY3-36, obinepitide, TM-30339, TM-30335), oxyntomodulin preparations: FGF21 Preparations (e.g., animal FGF21 preparation extracted from pancreas of bovine and swine; human FGF21 preparations genetically synthesized using Escherichia coli, yeast; fragment or derivative of FGF21)), anorexigenic agents (e.g., P-57) and the like.

Examples of the above-mentioned "therapeutic drug for hypertension" include angiotensin converting enzyme inhibitors (e.g., captopril, enalapril, delapril), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil), calcium antagonists (e.g., manidipine, nifedipine, amlodipine, efonidipine, nicardipine, cilnidipine), β blockers (e.g., metoprolol, atenolol, propranolol, carvedilol, pindolol), clonidine and the like.

Examples of the above-mentioned "therapeutic drug for hyperlipidemia" include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., the compound described in WO97/10224, for example, N-[[(3R,5S)-1-(3-acetoxy-2,2-dimethylpropyl)-7-chloro-5-(2,3-dimethoxyphenyl) 2 oxo-1,2,3,5-tetrahydro-4,1-benzoxazepin-3-yl]acetyl]piperidin-4-acetic acid), fibrate compounds (e.g., bezafibrate, clofibrate, simfibrate, clinofibrate), anion exchange resins (e.g., cholestyramine), probucol, nicotinic acid drugs (e.g., nicomol, niceritrol, niaspan), ethyl icosapentate, phytosterol (e.g., soysterol, γ-oryzanol), cholesterol absorption inhibitors (e.g., zetia), CETP inhibitors (e.g., dalcetrapib, anacetrapib), ω-3 fatty acid preparations (e.g., ω-3-acid ethyl esters 90) and the like.

Examples of the above-mentioned "antiarteriosclerotic drug" include acyl coenzyme A cholesterol acyltransferase (ACAT) inhibitors (e.g., K-604), LpPLA2 inhibitors (e.g., darapladib, rilapladib), FLAP inhibitors (e.g., AM103, AM803 and the like), 5LO inhibitors (e.g., VIA-2291), sPLA2 inhibitors (e.g., A-002), apoAI mimetic peptides (e.g., D4F), HDL preparations (e.g., CSL-111) and the like.

Examples of the above-mentioned "antithrombotic" include heparin (e.g., heparin sodium, heparin calcium, enoxaparin sodium, dalteparin sodium), warfarin (e.g., warfarin potassium), anti-thrombin drugs (e.g., argatroban, dabigatran), FXa inhibitors (e.g., rivaroxaban, apixaban, edoxaban, YM150, the compound described in WO02/06234, WO2004/048363, WO2005/030740, WO2005/058823 or WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the above-mentioned "diuretic agent" include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutiazide, poly5thiazide, methylclothiazide), antialdosterone preparations (e.g., spironolactone, triamterene), carbonic anhydrase inhibitors (e.g., acetazolamide), chlorobenzenesulfonamide preparations (e.g., chlorthalidone, mefruside, indapamide), azosemide, isosorbide, ethacrynic acid, piretanide, bumetanide, furosemide and the like.

Examples of the above-mentioned "therapeutic drug for arthritis" include ibuprofen and the like.

Examples of the above-mentioned "antianxiety drug" include alprazolam, etizolam, oxazolam, tandospirone, cloxazolam, clotiazepam, clorazepate dipotassium, chlordiazepoxide, diazepam, fludiazepam, flutazolam, flutoprazepam, prazepam, bromazepam, mexazolam, medazepam, ethyl loflazepate, lorazepam and the like.

Examples of the above-mentioned "antidepressant" include tricyclic antidepressants (e.g., imipramine, trimipramine, clomipramine, amitriptyline, nortriptyline, amoxapine, lofepramine, dosulepin, desipramine), tetracyclic antidepressants (e.g., maprotiline, mianserin, seripline), selective serotonin uptake inhibitors (e.g., fluoxetine, fluvoxamine, paroxetine, sertraline, escitalopram), serotonin-noradrenaline uptake inhibitors (e.g., milnacipran, duloxetine, venlafaxine), trazodone, mirtazapine, moclobemide and the like.

Examples of the above-mentioned "psychoneurotic agent" include typical antipsychotic agents (e.g., clocapramine, chlorpromazine, phenobarbital, sultopride, tiapride, thioridazine, floropipamide, mosapramine, moperone, oxypertine, carpipramine, spiperone, sulpiride, zotepine, timiperone, nemonapride, haloperidol, pimozide, prochlorperazine, propericiazine, bromperidol, perphenazine, fluphenazine maleate, mizoribine, levomepromazine), atypical antipsychotic agents (e.g., perospirone, olanzapine, quetiapine, risperidone, clozapine, aripiprazole, ziprasidone, blonanserin, lurasidone) and the like.

Examples of the above-mentioned "sleep-inducing drug" include Ramelteon, GABAergic hypnotics (e.g., brotizolam, estazolam, flurazepam, nitrazepam, triazolam, flunitrazepam, lormetazepam, rilmazafone, quazepam, zopiclone, eszopiclone, zolpidem, zaleplon, indiplon, gabaxadol); non-GABAergic hypnotics (e.g., eplivanserin, pruvanserin, diphenhydramine, trazodone, doxepin) and the like.

The administration time of the aforementioned concomitant drug is not limited, and the compound of the present invention and the concomitant drug can be administered to an administration subject simultaneously, or may be administered at staggered times. The dosage of the concomitant drug may be determined according to the dose clinically used, and can be appropriately selected depending on an administration subject, administration route, disease, combination and the like.

The administration mode of the concomitant drug is not particularly limited, and the compound of the present invention and the concomitant drug only need to be combined on administration. Examples of such administration mode include the following:
1) administration of a single preparation obtained by simultaneously processing the compound of the present invention and the concomitant drug,
2) simultaneous administration of two kinds of preparations of the compound of the present invention and the concomitant drug, which have been separately produced, by the same administration route,
3) administration of two kinds of preparations of the compound of the present invention and the concomitant drug, which have been separately produced, by the same administration route in a staggered manner,
4) simultaneous administration of two kinds of preparations of the compound of the present invention and the concomitant drug, which have been separately produced, by different administration routes,
5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The compounding ratio of the compound of the present invention to the concomitant drug can be appropriately selected depending on the administration subject, administration route, diseases and the like.

EXAMPLES

The present invention is described in detail by way of the following Reference Examples, Examples, Formulation Examples and Experimental Examples. These are not intended to restrict the present invention, and may be modified within the range not deviating from the scope of this invention.

The "room temperature" in the following Reference Examples and Examples means a temperature of 15° C. to 30° C. For drying an organic layer, anhydrous magnesium sulfate or anhydrous sodium sulfate was employed. Unless otherwise specifically indicated, "%" means percent by weight.

Indole intermediates used in the following Reference Examples and Examples can be produced by referring to, for example, US2003/236251, Synlett, 1998, pages 135-136 and the like, and alkylamine intermediates can be produced by referring to, for example, WO2003/072554, WO2004/020434, JP-A-2008-088120 and the like.

Abbreviations used in the present specification mean the following.
Ac: acetyl
Me: methyl
Et: ethyl
s: singlet
d: doublet
t: triplet
q: quartet
dd: double doublet
dt: double triplet
m: multiplet
br: broad
J: coupling constant
Hz: Hertz
CDCl$_3$: deuterated chloroform
DMA: dimethylacetamide
THF: tetrahydrofuran
NMP: N-methylpyrrolidone
DMF: N,N-dimethylformamide
DMSO: dimethyl sulfoxide
DMSO-d$_6$: deuterated dimethyl sulfoxide
$^1$H-NMR: proton nuclear magnetic resonance
FABMS (pos): mass spectrum measured by the (+) method in the Fast Atom Bombardment Mass Spectrometry

Reference Example 1 ethyl 5-({[4-(cyclopropylmethoxy)phenyl]carbonyl}amino)-1H-indole-2-carboxylate

A solution of 4-(cyclopropylmethoxy)benzoic acid (576 mg), ethyl 5-amino-1H-indole-2-carboxylate (612 mg), 1-ethyl-3-(3-dimethylaminopropyl)carbodiimide hydrochloride (690 mg), 1-hydroxybenzotriazole (551 mg) and N,N-dimethylaminopyridine (367 mg) in DMF (20 mL) was stirred at room temperature for 2 hr. The reaction solution was extracted with ethyl acetate, washed with aqueous sodium hydrogen carbonate solution and saturated brine, and dried over anhydrous magnesium sulfate, and the solvent was evaporated under reduced pressure. The obtained residue (brown solid) was washed with a small amount of ethyl acetate to give the title compound (820 mg, yield 72%).

$^1$H NMR (300 MHz, DMSO-d$_6$) δ: 0.30-0.40 (2H, m), 0.53-0.65 (2H, m), 1.18-1.41 (4H, m), 3.91 (2H, d, J=7.2 Hz), 4.34 (2H, q, J=6.9 Hz), 7.04 (2H, d, J=8.7 Hz), 7.13 (1H, d, J=1.5 Hz), 7.41 (1H, d, J=9.1 Hz), 7.56 (1H, dd, J=8.9, 2.1 Hz), 7.96 (2H, d, J=8.7 Hz), 8.11 (1H, d, J=1.5 Hz), 10.00 (1H, s), 11.82 (1H, s).

Reference Example 2

4-(cyclopropylmethoxy)-N-(2-formyl-1H-indol-5-yl)benzamide

Ethyl 5-({[4-(cyclopropylmethoxy)phenyl]carbonyl}amino)-1H-indole-2-carboxylate (190 mg) obtained in Reference Example 1 was dissolved in tetrahydrofuran (20 mL), 1.5 M diisobutylaluminum hydride (4 mL) was added at −78° C., and the mixture was stirred for 3 hr. To the obtained mixture was added aqueous ammonium chloride solution, and the mixture was extracted with ethyl acetate, and washed with saturated brine. The obtained organic layer was dried over anhydrous magnesium sulfate, and the solvent was evaporated under reduced pressure to give a pale-yellow solid. The obtained solid and manganese dioxide (87 mg) were suspended in dimethoxyethane (20 mL) and, under a nitrogen atmosphere, the mixture was stirred overnight at 70° C. The obtained mixture was filtered through celite to remove manganese dioxide, and purified by short silica gel column chromatography to give the title compound (70 mg, yield 43%).

$^1$H NMR (300 MHz, DMSO-d$_6$) δ: 0.35 (2H, dd, J=4.5, 1.5 Hz), 0.59 (2H, dd, J=8.0, 1.9 Hz), 1.19-1.31 (1H, m), 3.91 (2H, d, J=6.8 Hz), 7.04 (2H, d, J=9.1 Hz), 7.37-7.45 (2H, m), 7.62 (1H, dd, J=8.9, 2.1 Hz), 7.96 (2H, d, J=8.7 Hz), 8.22 (1H, d, J=1.5 Hz), 9.83 (1H, s), 10.04 (1H, s), 11.92 (1H, s).

Reference Example 3 ethyl 5-({[4-(cyclopropylmethoxy)phenyl]carbonyl}amino)-1-methyl-1H-indole-2-carboxylate To a solution of ethyl 5-amino-1-methyl-1H-indole-2-carboxylate (2.293 g) and 4-(cyclopropylmethoxy)benzoic acid (1.897 g) in DMF (23 mL) were added 1-hydroxybenzotriazole monohydrate (1.965 g), 1-ethyl-3-(3-dimethylaminopropyl)carbodiimide hydrochloride (2.460 g) and N,N-dimethylaminopyridine (1.326 g), and the mixture was stirred at room temperature for 17 hr. After dilution with ethyl acetate, water was added, and the organic layer was washed successively with 1N hydrochloric acid, 1N aqueous, sodium hydroxide solution and saturated brine, and concentrated under reduced pressure. The residue was suspended in ethyl acetate, and the precipitate was collected by filtration, washed with ethyl acetate, and dried under reduced pressure to give the title compound (2.466 g, yield 64%) as a beige solid.

$^1$H NMR (300 MHz, CDCl$_3$) δ: 0.35-0.43 (2H, m), 0.64-0.73 (2H, m), 1.25-1.36 (1H, m), 1.42 (3H, t, J=7.2 Hz), 3.88 (2H, d, J=7.0 Hz), 4.08 (3H, s), 4.38 (2H, q, J=7.2 Hz), 6.98 (2H, d, J=8.9 Hz), 7.27 (1H, br. s.), 7.33-7.41 (1H, m), 7.44-7.52 (1H, m), 7.77 (1H, s), 7.86 (2H, d, J=8.7 Hz), 8.03 (1H, d, J=1.9 Hz).

Reference Example 4

4-(cyclopropylmethoxy)-N-(2-formyl-1-methyl-1H-indol-5-yl)benzamide

Lithium aluminum hydride (80%, 328 mg) was suspended in THF (33 mL), a solution of ethyl 5-({[4-(cyclopropylmethoxy)phenyl]carbonyl}amino)-1-methyl-1H-indole-2-carboxylate (2.466 g) obtained in Reference Example 3 in THF (90 mL) was added dropwise at 0° C., and the mixture was stirred at 0° C. to room temperature for 2 hr. Lithium aluminum hydride (80%, 990 mg) was added at 0° C., and the mixture was stirred at the same temperature for 1.5 hr. Sodium sulfate decahydrate (8.908 g) was added at 0° C., and the mixture was stirred at room temperature for 1 hr, and filtered. To the filtrate was added manganese dioxide (85%, 6.423 g), and the mixture was heated under reflux for 2 hr. The mixture was filtered through celite, and the filtrate was concentrated under reduced pressure. The residue was suspended in diisopropyl ether-ethyl acetate (2:1), and the precipitate was collected by filtration, washed with diisopropyl ether-ethyl acetate (2:1), and dried under reduced pressure to give the title compound (1.557 g, yield 71%) as a pale-brown solid.

$^1$H NMR (300 MHz, DMSO-d$_6$) δ: 0.31-0.40 (2H, m), 0.55-0.65 (2H, m), 1.20-1.31 (1H, m), 3.91 (2H, d, J=7.2 Hz), 4.04 (3H, s), 7.05 (2H, d, J=8.9 Hz), 7.44 (1H, s), 7.60 (1H, d, J=9.0 Hz), 7.71 (1H, dd, J=8.7, 1.8 Hz), 7.97 (2H, d, J=8.9 Hz), 8.26 (1H, d, J=1.7 Hz), 9.89 (1H, s), 10.09 (1H, s).

Reference Example 5

4-(cyclopropylmethoxy)-N-[2-(hydroxymethyl)-1-methyl-1H-indol-5-yl]benzamide

To a solution of 4-(cyclopropylmethoxy)-N-(2-formyl-1-methyl-1H-indol-5-yl)benzamide (244 mg) obtained in Reference Example 4 in THF (20 ml) were added sodium borohydride (90%, 59 mg) and methanol (2.0 mL), and the mixture was stirred at room temperature for 18 hr. The reaction solution was concentrated under reduced pressure, and the residue was suspended in water (20 mL), and the suspension was stirred at room temperature for 1 hr. The precipitate was collected by filtration, washed with water, and dried under reduced pressure to give the title compound (237 mg, yield 97%) as a pale-brown solid.

$^1$H NMR (300 MHz, CDCl$_3$) δ: 0.34-0.43 (2H, m), 0.63-0.73 (2H, m), 1.25-1.36 (1H, m), 3.82 (3H, s), 3.88 (2H, d, J=6.8 Hz), 4.81 (2H, d, J=5.7 Hz), 6.45 (1H, s), 6.98 (2H, d, J=8.7 Hz), 7.26-7.33 (1H, m), 7.33-7.40 (1H, m), 7.75 (1H, s), 7.86 (2H, d, J=8.7 Hz), 7.93 (1H, d, J=1.5 Hz).

Reference Example 6

4-(cyclopropylmethoxy)-N-[2-(1-hydroxyethyl)-1-methyl-1H-indol-5-yl]benzamide

To 4-(cyclopropylmethoxy)-N-(2-formyl-1-methyl-1H-indol-5-yl)benzamide (174 mg) obtained in Reference Example 4 was added 1 M methylmagnesium bromide (2 mL) at 0° C., and the mixture was stirred for 30 min. The mixture was poured into cold water, extracted with ethyl acetate, and washed with saturated brine. The obtained organic layer was dried over anhydrous magnesium sulfate, and the solvent was evaporated under reduced pressure. The obtained residue was washed with ethyl acetate-hexane (1:1) solution to give the title compound (120 mg, yield 66%).

$^1$H NMR (300 MHz, DMSO-d$_6$) δ: 0.31-0.39 (2H, m), 0.54-0.64 (2H, m), 1.18-1.33 (1H, m), 1.53 (3H, d, J=6.4 Hz), 3.76 (3H, s), 3.90 (2H, d, J=7.2 Hz), 4.93 (1H, quin, J=6.2 Hz), 5.23 (1H, d, J=5.7 Hz), 6.32 (1H, s), 7.03 (2 d, J=8.7 Hz), 7.31-7.45 (2H, m), 7.90-7.99 (3H, m), 9.91 (1H, s).

Reference Example 7

(2S)-tetrahydrofurfuryl alcohol (2S)-Tetrahydrofuran-2-carboxylic acid (806.2 g) was dissolved in methanol (1779.6 g), and concentrated sulfuric acid (32 mL) was added dropwise at 22° C.-35° C. The reaction solution was heated to 72° C.-75° C., and stirred for 11 hr. The reaction mixture was cooled to room temperature, and partitioned by adding water (5 L) and dichloromethane (5 L). The organic layer was washed with saturated aqueous sodium hydrogen carbonate and saturated brine, and dried over sodium sulfate. After evaporation of the solvent, the residue was purified by distillation to give methyl (2S)-tetrahydrofuran-2-carboxylate (773.2 g) as a colorless oil. THF (7.4 L) was cooled in an ice-salt-acetone bath, and lithium aluminum hydride (151.0 g) was added by portions. Thereto was added dropwise a solution of methyl (2S)-tetrahydrofuran-2-carboxylate (773.0 g) obtained earlier in THF at an inside temperature of 0° C.-10° C., and the mixture was stirred at an inside temperature of 3° C.-5° C. for 2 hr. Water (150 mL) was added dropwise to the reaction mixture at an inside temperature of 2° C.-4° C., and the reaction was quenched by dropwise addition of 15% aqueous sodium hydroxide solution (150 mL) and water (450 mL), maintained at the same temperature. The insoluble material was filtered off, and washed with THF (2 L), and the filtrate was concentrated under reduced pressure. Thereto were added dichloromethane (3 L) and saturated brine (1.5 L). The organic layer was separated and the aqueous layer was extracted 3 times with dichloromethane. The organic layers were combined, and dried over magnesium sulfate. The solvent was evaporated under reduced pressure to give the title compound (567.3 g, yield 90%) as a colorless oil.

$^1$H NMR (300 MHz, CDCl$_3$) δ: 1.62-1.70 (1H, m), 1.85-1.99 (3H, m), 2.56-2.62 (1H, m), 3.46-3.54 (1H, m), 3.63-3.70 (1H, m), 3.74-3.90 (2H, m), 3.97-4.05 (1H, m).

Reference Example 8

4-[(2S)-tetrahydrofuran-2-ylmethoxy]benzoic acid

To a solution of (2S)-tetrahydrofurfuryl alcohol (550.3 g) obtained in Reference Example 7, methyl 4-hydroxybenzoate (819.8 g) and triphenylphosphine (1625.1 g) in tetrahydrofuran (6.66 L) was slowly added dropwise a solution (3012 mL, 40% toluene solution) of diethyl azodicarboxylate in toluene such that the inside temperature was not more than 25° C., and the mixture was stirred at room temperature for 4 days. The reaction solution was concentrated, diisopropyl ether was added, and the precipitated insoluble material was filtered off. The filtrate was concentrated, and the residue was purified by NH-silica gel column chromatography [eluent; heptane:ethyl acetate=90:10 (volume ratio)], and further by silica gel column chromatography [eluent; heptane:ethyl acetate=80:20 (volume ratio)→heptane:ethyl acetate=50:50 (volume ratio)] to give a colorless oil. The obtained colorless oil was dissolved in tetrahydrofuran (2.29 L), methanol (1.76 L) and water (564 mL), 8N aqueous sodium hydroxide solution (564 mL) was added dropwise, and the mixture was stirred with heating at 90° C. for 2 hr. The reaction solution was concentrated and acidified with 8N hydrochloric acid while ice-cooling, and the precipitated crystals were collected by filtration. The crystals were dissolved in THF, partitioned by adding ethyl acetate and saturated brine, and the organic layer was dried over magnesium sulfate and concentrated under reduced pressure. During concentration, diisopropyl ether was gradually added to allow crystal precipitation, which was collected by filtration to give the title compound (547.4 g, yield 76%) as colorless crystals.

$^1$H NMR (300 MHz, DMSO-$d_6$) δ: 1.64-1.72 (1H, m), 1.82-1.92 (2H, m), 1.95-2.04 (1H, m), 3.68 (1H, g, J=7.2 Hz), 3.78 (1H, q, J=7.2 Hz), 3.95-4.06 (2H, m), 4.14-4.19 (1H, m), 7.02 (2H, d, J=8.7 Hz), 7.88 (2H, d, J=8.4 Hz), 12.62 (1H, s).

Reference Example 9 ethyl 1-methyl-5-[({4-[(2S)-tetrahydrofuran-2-ylmethoxy]phenyl}carbonyl)amino]-1H-indole-2-carboxylate 4-[(2S)-Tetrahydrofuran-2-ylmethoxy]benzoic acid (2.757 g) obtained in Reference Example 8, ethyl 5-amino-1-methyl-1H-indole-2-carboxylate (2.708 g), 1-hydroxybenzotriazole monohydrate (2.471 g), 1-ethyl-3-(3-dimethylaminopropyl)carbodiimide hydrochloride (3.093 g) and N,N-dimethylaminopyridine (1.668 g) were mixed in DMF (27 mL), and the mixture was stirred at room temperature for 24 hr. After diluting with THF, water was added, and the mixture was partitioned and extracted with ethyl acetate. The organic layer was washed with water and saturated brine, dried over sodium sulfate, and concentrated under reduced pressure. The residue was suspended in ethyl acetate, and the precipitate was collected by filtration, washed with diisopropyl ether-ethyl acetate (1:1), and dried under reduced pressure to give the title compound (3.478 g, yield 66%) as a beige solid.

$^1$H NMR (300 MHz, CDCl$_3$) δ: 1.42 (3H, t, J=7.2 Hz), 1.71-1.87 (1H, m), 1.90-2.04 (2H, m), 2.04-2.18 (1H, m), 3.80-4.01 (2H, m), 4.04 (2H, d, J=5.3 Hz), 4.08 (3H, s), 4.24-4.43 (3H, m), 7.01 (2H, d, J=8.7 Hz), 7.27 (1H, s), 7.32-7.40 (1H, m), 7.43-7.52 (1H, m), 7.78 (1H, s), 7.86 (2H, d, J=8.9 Hz), 7.99-8.08 (1H, m).

Reference Example 10

N-(2-formyl-1-methyl-1H-indol-5-yl)-4-[(2S)-tetrahydrofuran-2-ylmethoxy]benzamide Lithium aluminum hydride (80%, 1.562 g) was suspended in THF (150 mL) and a solution of ethyl 1-methyl-5-[({4-[(2S)-tetrahydrofuran-2-ylmethoxy]phenyl}carbonyl)amino]-1H-indole-2-carboxylate (3.478 g) obtained in Reference Example 9 in THF (100 mL) was added dropwise at 0° C., and the mixture was stirred at room temperature for 2 hr. Sodium sulfate decahydrate (10.61 g) was added at 0° C., and the mixture was stirred at room temperature for 1.5 hr and filtered. To the filtrate was added manganese dioxide (85%, 8.421 g), and the mixture was heated under reflux for 1 hr. The mixture was filtered through celite, and the filtrate was concentrated under reduced pressure. The residue was suspended in diisopropyl ether-ethyl acetate (3:1), and the precipitate was collected by filtration, washed with diisopropyl ether-ethyl acetate (2:1), and dried under reduced pressure to give the title compound (2.366 g, yield 76%) as a brown solid.

$^1$H NMR (300 MHz, CDCl$_3$) δ: 1.72-1.87 (1H, m), 1.89-2.04 (2H, m), 2.04-2.19 (1H, m), 3.80-3.91 (1H, m), 3.91-4.01 (1H, m), 4.04 (2H, d, J=4.9 Hz), 4.10 (3H, s), 4.25-4.38 (1H, m), 7.02 (2H, d, J=8.7 Hz), 7.24 (1H, s), 7.36-7.44 (1H, m), 7.49-7.57 (1H, m), 7.78 (1H, s), 7.86 (2H, d, J=8.7 Hz), 8.15 (1H, d, J=1.5 Hz), 9.89 (1H, s).

Reference Example 11

4-(tetrahydrofuran-3-ylmethoxy)benzoic acid

To a solution of tetrahydrofuran-3-ylmethanol (21.89 g), methyl 4-hydroxybenzoate (33.5 g) and triphenylphosphine (64.5 g) in tetrahydrofuran (400 mL) was slowly added dropwise a solution (120 mL, 40% toluene solution) of diethyl azodicarboxylate in toluene at 0° C., and the mixture was stirred at room temperature for 2 hr. The reaction solution was concentrated, and triphenylphosphine oxide was precipitated from ethyl acetate-hexane. The mixture was filtered through a glass filter to remove triphenylphosphine oxide, and the filtrate was concentrated. The residue was purified by silica gel column chromatography [eluent; hexane:ethyl acetate=90:10 (volume ratio)→hexane:ethyl acetate=40:10] to give a colorless oil. The obtained colorless oil was dissolved in tetrahydrofuran (200 mL) and methanol (100 mL), 8N aqueous sodium hydroxide solution (100 mL) was added, and the mixture was stirred with heating at 80° C. for 2 hr. The reaction solution was concentrated, cooled to 0° C., and neutralized with 6N hydrochloric acid, and the mixture was extracted with ethyl acetate. The organic layer was washed with saturated brine, and dried over anhydrous magnesium sulfate, and the solvent was evaporated under reduced pressure to give the title compound (23 g, yield 48%) as colorless crystals.

$^1$H NMR (300 MHz, DMSO-$d_6$) δ: 1.61-1.71 (1H, m), 1.97-2.08 (1H, m), 2.60-2.73 (1H, m), 3.48-3.56 (1H, m), 3.62-3.69 (1H, m), 3.73-3.82 (2H, m), 3.88-4.04 (2H, m), 7.02 (2H, d, J=9.3 Hz), 7.88 (2H, d, J=9.3 Hz), 12.59 (1H, br).

Reference Example 12 ethyl 1-methyl-5-({[4-(tetrahydrofuran-3-ylmethoxy)phenyl]carbonyl}amine)-1H-indole-2-carboxylate 4-(Tetrahydrofuran-3-ylmethoxy)benzoic acid (2.757 g) obtained in Reference Example 11, ethyl 5-amino-1-methyl-1H-indole-2-carboxylate (2.708 g), 1-hydroxybenzotriazole monohydrate (2.471 g), 1-ethyl-3-(3-dimethylaminopropyl)carbodiimide hydrochloride (3.093 g) and N,N-dimethylaminopyridine (1.668 g) were mixed in DMF (27 mL), and the mixture was stirred at room temperature for 24 hr. After diluting with THF, water was added, and the mixture was partitioned and extracted with ethyl acetate. The organic layer was washed with water and saturated brine, dried over sodium sulfate, and concentrated under reduced pressure. The residue was suspended in ethyl acetate, and the precipitate was collected by filtration, washed with diisopropyl ether-ethyl acetate (1:1), and dried under reduced pressure to give the title compound (3.140 g, yield 60%) as a beige solid.

$^1$H NMR (300 MHz, CDCl$_3$) δ: 1.42 (3H, t, J=7.1 Hz), 1.76 (1H, td, J=12.8, 7.3 Hz), 2.15 (1H, m, J=13.0, 7.9, 7.9, 5.4 Hz), 2.69-2.86 (1H, m), 3.74 (1H, dd, J=8.9, 5.2 Hz), 3.77-3.86 (1H, m), 3.88-4.05 (4H, m), 4.08 (3H, s), 4.38 (2H, q, J=7.2 Hz), 6.98 (2H, d, J=8.9 Hz), 7.27 (1H, s), 7.33-7.41 (1H, m), 7.44-7.52 (1H, m), 7.77 (1H, s), 7.86 (2H, d, J=8.7 Hz), 8.00-8.07 (1H, m).

Reference Example 13

N-(2-formyl-1-methyl-1H-indol-5-yl)-4-(tetrahydrofuran-3-ylmethoxy)benzamide

Lithium aluminum hydride (80%, 1.388 g) was suspended in THF (150 mL), a solution of ethyl 1-methyl-5-({[4-(tetrahydrofuran-3-ylmethoxy)phenyl]carbonyl}amino)-1H-indole-2-carboxylate (3.140 g) obtained in Reference Example 12 in THF (100 mL) was added dropwise at 0° C., and the mixture was stirred at room temperature for 2 hr. Sodium sulfate decahydrate (8.786 g) was added at 0° C., and the mixture was stirred at room temperature for 1.5 hr and filtered. To the filtrate was added manganese dioxide (85%, 7.602 g), and the mixture was heated under reflux for 1 hr. The mixture was filtered through celite, and the filtrate was concentrated under reduced pressure. The residue was suspended in diisopropyl ether-ethyl acetate (3:1), and the precipitate was collected by filtration, washed with diisopropyl ether-ethyl acetate (2:1), and dried under reduced pressure to give the title compound (2.155 g, yield 77%) as a brown solid.

$^1$H NMR (300 MHz, CDCl$_3$) δ: 1.70-1.84 (1H, m), 2.07-2.22 (1H, m), 2.70-2.86 (1H, m), 3.70-3.77 (1H, m), 3.82 (1H, t, J=7.2 Hz), 3.87-4.05 (4H, m), 4.10 (3H, s), 6.99 (2H, d, J=3.7 Hz), 7.24 (1H, s), 7.35-7.43 (1H, m), 7.53 (1H, dd, J=9.1, 2.3 Hz), 7.78 (1H, s), 7.87 (2H, d, J=8.7 Hz), 8.15 (1H, d, J=1.9 Hz), 9.89 (1H, s).

Reference Example 14 methyl 2-fluoro-4-hydroxybenzoate

A solution of 2-fluoro-4-hydroxybenzoic acid (50.0 g) and concentrated sulfuric acid (10 mL) in methanol (700 mL) was stirred with heating at 90° C. for 16 hr. The reaction solution was concentrated, and the resulting colorless crystals were washed with water, and dried to give the title compound (51 g, yield 94%) as colorless crystals.

$^1$H NMR (300 MHz, DMSO-d$_6$) δ: 3.79 (3H, s), 6.61-6.72 (2H, m), 7.73-7.79 (1H, m), 10.80 (1H, br).

Reference Example 15

2-fluoro-4-[(2S)-tetrahydrofuran-2-ylmethoxy]benzoic acid

To a solution of (2S)-tetrahydrofurfuryl alcohol (30.0 g) obtained in Reference Example 7, methyl 2-fluoro-4-hydroxybenzoate (50.0 g) obtained in Reference Example 14 and triphenylphosphine (88.9 g) in tetrahydrofuran (350 mL) was slowly added dropwise a solution (166 ml, 40% toluene solution) of diethyl azodicarboxylate in toluene at 0° C., and the mixture was stirred at room temperature for 2 hr. The reaction solution was concentrated, and triphenylphosphine oxide was precipitated from ethyl acetate-hexane. The mixture was filtered through a glass filter to remove triphenylphosphine oxide, and the filtrate was concentrated. The residue was purified by NH-silica gel column chromatography [eluent; hexane:ethyl acetate=95:5 (volume ratio)→hexane:ethyl acetate=90:10] to give colorless crystals. The obtained colorless crystals were dissolved in tetrahydrofuran (500 mL), 8N aqueous sodium hydroxide solution (100 mL) was added, and the mixture was stirred with heating at 60° C. for 3 hr. The reaction solution was concentrated, cooled to 0° C., neutralized with 6N hydrochloric acid, and extracted with ethyl acetate. The organic layer was washed with saturated brine, and dried over anhydrous magnesium sulfate, and the solvent was evaporated under reduced pressure to give the title compound (60.0 g, yield 85%) as colorless crystals.

$^1$H NMR (300 MHz, DMSO-d$_6$) δ: 1.60-1.71 (1H, m), 1.73-1.92 (2H, m), 1.94-2.06 (1H, m), 3.69 (1H, q, J=6.9 Hz), 3.77 (1H, q, J=6.9 Hz), 3.96-4.09 (2H, m), 4.12-4.20 (1H, m), 6.84-6.92 (2H, m), 7.78-7.84 (1H, m), 12.85 (1H, br).

Reference Example 16 ethyl 5-[({2-fluoro-4-[(2S)-tetrahydrofuran-2-ylmethoxy]phenyl}carbonyl)amino]-1-methyl-1H-indole-2-carboxylate 2-Fluoro-4-[(2S)-tetrahydrofuran-2-ylmethoxy]benzoic acid (3.3 g) obtained in Reference Example 15, oxalyl dichloride (1.75 mL) and N,N-dimethylformamide (0.50 mL) were mixed in tetrahydrofuran (100 mL), and the mixture was stirred at room temperature for 2 hr. The reaction mixture was concentrated under reduced pressure, and to the concentrated residue was added tetrahydrofuran (100 mL). To this mixture was added a solution of ethyl 5-amino-1-methyl-1H-indole-2-carboxylate (3.0 g) and triethylamine (3.07 mL) in tetrahydrofuran (150 mL) at room temperature, and the mixture was stirred at room temperature overnight. Water was added to the reaction mixture, and the mixture was extracted with ethyl acetate. The organic layer was washed with saturated brine, and dried over anhydrous magnesium sulfate, and the solvent was evaporated under reduced pressure to give the title compound (5.5 g, yield 91%) as colorless crystals.

$^1$H NMR (300 MHz, DMSO-d$_6$) δ: 1.34 (3H, t, J=7.2 Hz), 1.63-1.72 (1H, m), 1.81-1.96 (2H, m), 1.99-2.04 (1H, m), 3.32 (3H, s), 3.69 (1H, q, J=6.0 Hz), 3.79 (1H, q, J=6.0 Hz), 4.01 (2H, s), 4.03-4.19 (1H, m), 4.32 (2H, q, J=7.2 Hz), 6.88-6.99 (2H, m), 7.25 (1H, d, J=3.6 Hz), 7.56 (2H, s), 7.64 (1H, t, J=8.4 Hz), 8.14 (1H, s), 10.10 (1H, s).

Reference Example 17

2-fluoro-N-[2-(hydroxymethyl)-1-methyl-1H-indol-5-yl]-4-[(2S)-tetrahydrofuran-2-ylmethoxy]benzamide To a solution of ethyl 5-[({2-fluoro-4-[(2S)-tetrahydrofuran-2-ylmethoxy]phenyl}carbonyl)amino]-1-methyl-1H-indole-2-carboxylate (5.5 g) obtained in Reference Example 16 in tetrahydrofuran (200 mL) was added lithium aluminum hydride (15 mL, 2.0 M tetrahydrofuran solution) at 0° C., and the mixture was stirred at room temperature for 2 hr. To the reaction mixture was added sodium sulfate decahydrate, 1N aqueous hydrochloric acid solution was then added, and the mixture was extracted with ethyl acetate. The organic layer was washed with aqueous sodium hydrogen carbonate solution and saturated brine, and dried over anhydrous magnesium sulfate, and the solvent was evaporated under reduced pressure to give the title compound (4.5 g, yield 90%) as colorless crystals.

$^1$H NMR (300 MHz, DMSO-d$_6$) δ: 1.63-1.72 (1H, m), 1.80-1.92 (2H, m), 1.96-2.04 (1H, m), 3.69 (1H, q, J=6.3 Hz), 3.72 (3H, s), 3.79 (1H, q, J=6.3 Hz), 3.96-4.09 (2H, m), 4.14-4.19 (1H, m), 4.62 (2H, d, J=5.4 Hz), 5.22 (1H, t, J=5.4 Hz), 6.33 (1H, s), 6.87-6.97 (2H, m), 7.36 (1H, s), 7.27 (1H, t, J=8.4 Hz), 7.94 (1H, s), 9.94 (1H, s).

Reference Example 18

2-fluoro-N-(2-formyl-1-methyl-1H-indol-5-yl)-4-[(2S)-tetrahydrofuran-2-ylmethoxy]benzamide A solution of 2-fluoro-N-[2-(hydroxymethyl)-1-methyl-1H-indol-5-yl]-4-[(2S)-tetrahydrofuran-2-ylmethoxy]benzamide (4.5 g) obtained in Reference Example 17 and manganese dioxide (8.00 g) in tetrahydrofuran (200 mL) was refluxed for 6 hr. The reaction mixture was filtered through celite, and the solvent was evaporated under reduced pressure to give the title compound (4.1 g, yield 63%) as pale-brown crystals.

$^1$H NMR (300 MHz, DMSO-d$_6$) δ: 1.63-1.81 (1H, m), 1.83-1.93 (2H, m), 1.96-2.04 (1H, m), 3.69 (1H, q, J=6.3 Hz), 3.79 (1H, q, J=6.3 Hz), 3.97-4.10 (2H, m), 4.03 (3H, s), 6.88-6.99 (2H, m), 7.43 (1H, s), 7.57-7.67 (3H, m), 8.24 (1H, s), 9.88 (1H, s), 10.14 (1H, s).

Reference Example 19

(5-amino-1-methyl-1H-indol-2-yl)methanol

A solution of ethyl 5-amino-1-methyl-1H-indole-2-carboxylate (9.21 g) in THF (55 mL) was added dropwise to a solution of lithium aluminum hydride (2.08 g) in THF (110 mL) at 5° C., and the mixture was stirred at room temperature for 4.5 hr. To the reaction mixture was added sodium sulfate decahydrate (20.4 g), and the mixture was stirred at room temperature for 30 min. The insoluble material was filtered off and washed with THF. The filtrate was concentrated under reduced pressure to dryness to give the title compound (8.50 g, yield 100%) as a yellow solid.

$^1$H NMR (300 MHz, DMSO-d$_6$) δ: 3.62 (3H, s), 4.42 (3H, s), 4.54 (2H, d, J=5.3 Hz), 5.08 (1H, t, J=5.3 Hz), 6.05 (1H, s), 6.51 (1H, dd, J=8.5, 2.1 Hz), 6.63 (1H, d, J=1.9 Hz), 7.07 (1H, d, J=8.7 Hz).

Reference Example 20

4-bromo-N-[2-(hydroxymethyl)-1-methyl-1H-indol-5-yl]benzamide

To a solution of (5-amino-1-methyl-1H-indol-2-yl)methanol (8.50 g) obtained in Reference Example 19 and 2N aqueous sodium hydroxide solution (96 mL) in THF (290 mL) was added dropwise a solution of 4-bromobenzoyl chloride (13.76 g) in THF (5 mL) at 5° C., and the mixture was stirred at room temperature for 16 hr. The solvent was evaporated under reduced pressure, to the residue was added ethyl acetate, and the mixture was washed with water. The solvent was evaporated under reduced pressure, and the obtained crude product was washed with diisopropyl ether-ethyl acetate to give the title compound (13.6 g, yield 79%) as a pale-yellow solid.

$^1$H NMR (300 MHz, DMSO-d$_6$) δ: 3.73 (3H, s), 4.63 (2H, d, J=5.3 Hz), 5.23 (1H, t, J=5.5 Hz), 6.35 (1H, s), 7.36-7.45 (2H, m), 7.71-7.77 (2H, m), 7.90-7.97 (3H, m), 10.16 (1H, s).

Reference Example 21

4-bromo-N-(2-formyl-1-methyl-1H-indol-5-yl)benzamide

To a solution of 4-bromo-N-[2-(hydroxymethyl)-1-methyl-1H-indol-5-yl]benzamide (13.63 g) obtained in Example 20 in DMSO (136 mL) were added triethylamine (21.1 mL) and pyridine-sulfur trioxide complex (24.16 g), and the mixture was stirred at room temperature for 22 hr. The reaction mixture was poured into ice water (400 mL), and the precipitated crystals were collected by filtration, washed with water, and dried to give the title compound (12.49 g, yield 92%) as a pale-brown solid. The solid was used without purification for the next reaction.

Reference Example 22

4-bromo-N-(1-methyl-2-{[(2-methylpropyl)amino]methyl}-1H-indol-5-yl)benzamide

To a solution of 4-bromo-N-(2-formyl-1-methyl-1H-indol-5-yl)benzamide (3.09 g) obtained in Reference Example 21 in DMA (52.0 mL) were added isobutylamine (1.26 g) and acetic acid (17.3 mL), and the mixture was stirred at room temperature for 1 hr. To the reaction mixture was added sodium triacetoxyborohydride (3.67 g), and the mixture was stirred at room temperature for 15 hr. 8N Aqueous sodium hydroxide solution (43.3 mL) was added under ice-cooling, and ethyl acetate and water were further added to allow partitioning. The aqueous layer was extracted with ethyl acetate. The combined organic layer was washed with brine, and purified by silica gel column chromatography [eluent; hexane:ethyl acetate=3:7→ethyl acetate (volume ratio)]. The obtained crude product was washed with diisopropyl ether-ethyl acetate to give the title compound (709 mg, yield 20%) as a pale-brown solid.

$^1$H NMR (300 MHz, DMSO-d) δ: 0.87 (6H, d, J=6.8 Hz), 1.61-1.76 (1H, m), 2.37 (2H, d, J=6.8 Hz), 3.74 (3H, s), 3.84 (2H, s), 6.31 (1H, s), 7.33-7.43 (2H, m), 7.73 (2H, d, J=8.7 Hz), 7.90-7.97 (3H, m), 10.14 (1H, s).

Reference Example 23

4-bromo-N-(2-{[(2,2-dimethylpropyl)amino]methyl}-1-methyl-1H-indol-5-yl)benzamide To a solution of 4-bromo-N-(2-formyl-1-methyl-1H-indol-5-yl)benzamide (3.44 g) obtained in Reference Example 21 in DMA (57.9 mL) were added neopentylamine (1.67 g) and acetic acid (19.3 mL), and the mixture was stirred at room temperature for 1 hr. To the reaction mixture was added sodium triacetoxyborohydride (4.08 g), and the mixture was stirred at room temperature for 15 hr. 8N Aqueous sodium hydroxide solution (48.2 mL) was added under ice-cooling, and ethyl acetate and water were further added to allow partitioning. The aqueous layer was extracted with ethyl acetate. The combined organic layer was washed with brine, and purified by silica gel column chromatography [eluent; hexane:ethyl acetate=3:7→ethyl acetate (volume ratio)]. The obtained crude product was washed with diisopropyl ether-ethyl acetate to give the title compound (1.35 g, yield 32%) as a pale-brown solid.

$^1$H NMR (300 MHz, DMSO-d$_6$) δ: 0.86 (9H, s), 2.32 (2H, s), 3.75 (3H, s), 3.87 (2H, s), 6.31 (1H, s), 7.33-7.42 (2H, m), 7.73 (2H, d, J=8.7 Hz), 7.89-7.96 (3H, m), 10.14 (1H, s).

Reference Example 24 methyl 2-[(4-nitrophenyl)amino]-3-oxobutanoate

Under an argon atmosphere, to a solution of 4-nitroaniline (3.84 g) in toluene (278 mL) were added methyl 2-diazo-3-oxobutanoate (5.13 g) and rhodium(II) acetate dimer (250 mg), and the mixture was stirred at 120° C. for 1 hr. The solvent was evaporated under reduced pressure, and the residue was purified by silica gel column chromatography [eluent; hexane:ethyl acetate=9:1→hexane:ethyl acetate=7:3 (volume ratio)] to give the title compound (4.63 g, yield 98%) as a yellow solid.
$^1$H NMR (300 MHz, DMSO-d$_6$) δ: 2.33 (3H, s), 3.76 (3H, s), 5.46 (1H, d, J=8.3 Hz), 6.82 (2H, d, J=9.4 Hz), 7.73 (1H, d, J=8.3 Hz), 8.01-8.06 (2H, m).

Reference Example 25 methyl 3-methyl-5-nitro-1H-indole-2-carboxylate

To a solution of methyl 2-[(4-nitrophenyl)amino]-3-oxobutanoate (5.64 g) obtained in Reference Example 24 in toluene (373 mL) was added Amberlyst 15 (5.00 g), and the mixture was stirred at 135° C. for 15 hr while performing azeotropic distillation dehydration. The insoluble material was filtered off, and the filtrate was concentrated under reduced pressure. The obtained crude product was washed with diisopropyl ether-ethyl acetate to give the title compound (198 mg, yield 3.7%) as a yellow solid.
$^1$H NMR (300 MHz, DMSO-d$_6$) δ: 2.60 (3H, s), 3.91 (3H, s), 7.54 (1H, d, J=9.1 Hz), 8.12 (1H, dd, J=9.1, 2.2 Hz), 8.67 (1H, d, J=1.9 Hz), 12.26 (1H, s).

Reference Example 26 methyl 5-amino-3-methyl-1H-indole-2-carboxylate

To a solution of methyl 3-methyl-5-nitro-1H-indole-2-carboxylate (222 mg) obtained in Reference Example 25 in THF (60 mL) was added 10% palladium carbon (50% water wet, 101 mg), and the mixture was stirred at room temperature for 3 days under a hydrogen atmosphere (balloon). The insoluble material was filtered off and washed with methanol. The filtrate was concentrated under reduced pressure, and the residue was purified by silica gel column chromatography [eluent; hexane:ethyl acetate=7:3→hexane:ethyl acetate=3:2 (volume ratio)] to give the title compound (200 mg, yield 100%) as an orange solid.
$^1$H NMR (300 MHz, DMSO-d$_6$) δ: 2.41 (3H, s), 3.83 (3H, s), 4.66 (2H, s), 6.65-6.72 (2H, m), 7.11 (1H, dd, J=8.7, 0.8 Hz), 11.02 (1H, s).

Reference Example 27 methyl 3-methyl-5-({4-[(2S)-tetrahydrofuran-2-ylmethoxy]benzoyl}amino)-1H-indole-2-carboxylate Methyl 5-amino-3-methyl-1H-indole-2-carboxylate (200 mg) obtained in Reference Example 26 was dissolved in DMF (0.10 mL), 4-[(2S)-tetrahydrofuran-2-ylmethoxy]benzoic acid (239 mg) obtained in Reference Example 8, 1-ethyl-3-(3-dimethylaminopropyl)carbodiimide hydrochloride (282 mg) and 1-hydroxybenzotriazole (198 mg) were added, and the mixture was stirred at room temperature for 15 hr. The reaction mixture was diluted with ethyl acetate, and washed successively with 0.3N hydrochloric acid, aqueous sodium hydrogen carbonate solution and brine. The solvent was evaporated under reduced pressure, and the obtained crude product was washed with diisopropyl ether-ethyl acetate to give the title compound (310 mg, yield 78%) as a pale-brown solid.
$^1$H NMR (300 MHz, DMSO-d$_6$) δ: 1.62-2.09 (4H, m), 2.52 (3H, s), 3.65-3.84 (2H, m), 3.88 (3H, s), 3.97-4.09 (2H, m), 4.13-4.23 (1H, m), 7.06 (2H, d, J=8.7 Hz), 7.36 (1H, d, J=9.0 Hz), 7.57 (1H, dd, J=8.9, 2.1 Hz), 7.97 (2H, d, J=8.7 Hz), 8.09 (1H, d, J=1.9 Hz), 10.03 (1H, s), 11.48 (1H, s).

Reference Example 28

N-(2-formyl-3-methyl-1H-indol-5-yl)-4-[(2S)-tetrahydrofuran-2-ylmethoxy]benzamide To a solution of methyl 3-methyl-5-({-4-[(2S)-tetrahydrofuran-2-ylmethoxy]benzoyl}amino)-1H-indole-2-carboxylate (310 mg) obtained in Reference Example 27 in THF (60 mL) was added dropwise 2 M lithium aluminum hydride THF solution (0.57 mL) at 5° C., and the mixture was stirred at room temperature for 3 hr. To the reaction mixture was added dropwise 2 M lithium aluminum hydride THF solution (0.57 mL), and the mixture was stirred at room temperature for 1 hr. To the reaction mixture was added sodium sulfate decahydrate (980 mg). The insoluble material was filtered off and washed with THF. To the filtrate was added manganese dioxide (770 mg), and the mixture was stirred at 75° C. for 16 hr. The insoluble material was filtered off and washed with THF. The filtrate was concentrated under reduced pressure to dryness to give the title compound (260 mg, yield 92%) as a brown solid.
$^1$H NMR (300 MHz, DMSO-d$_6$) δ: 1.64-2.09 (4H, m), 2.59 (3H, s), 3.65-3.85 (2H, m), 3.97-4.10 (2H, m), 4.14-4.24 (1H, m), 7.07 (2H, d, J=8.7 Hz), 7.37 (1H, d, J=9.0 Hz), 7.63 (1H, dd, J=8.7, 1.9 Hz), 7.98 (2H, d, J=9.0 Hz), 8.18 (1H, d, J=1.5 Hz), 10.04 (1H, s), 10.06 (1H, s), 11.55 (1H, s).

Reference Example 29 methyl 5-amino-1,3-dimethyl-1H-indole-2-carboxylate

To a solution of methyl 1,3-dimethyl-5-nitro-1H-indole-2-carboxylate (5.27 g) in THF (105 mL) was added 10% palladium carbon (50% water wet, 2.25 g), and the mixture was stirred at room temperature for 3 days under a hydrogen atmosphere (balloon). The insoluble material was filtered off and washed with methanol. The filtrate was concentrated under reduced pressure, and the residue was purified by silica gel column chromatography [eluent; hexane:ethyl acetate=7:3-hexane:ethyl acetate=3:2 (volume ratio)] to give the title compound (4.63 g, yield 98%) as an orange solid.
$^1$H NMR (300 MHz, CDCl$_3$) δ: 2.49 (3H, s), 3.48 (2H, s), 3.92 (3H, s), 3.94 (3H, s), 6.83 (1H, dd, J=8.7, 2.3 Hz), 6.90 (1H, d, J=2.3 Hz), 7.15 (1H, d, J=8.3 Hz).

Reference Example 30 methyl 1,3-dimethyl-5-({4-[(2S)-tetrahydrofuran-2-ylmethoxy]benzoyl}amino)-1H-indole-2-carboxylate 4-[(2S)-Tetrahydrofuran-2-ylmethoxy]benzoic acid (2.59 g) obtained in Reference Example B was dissolved in toluene (30 mL), thionyl chloride (1.27 mL) and a catalytic amount of DMF were added, and the mixture was stirred at 45° C. for 3 hr. The reaction mixture was concentrated under reduced pressure to give acid chloride. To a solution of methyl 5-amino-1,3-dimethyl-1H-indole-2-carboxylate (2.54 g) obtained in Reference Example 29, triethylamine (4.87 mL) and N,N-dimethylaminopyridine (711 mg) in NMP (30 mL) was added dropwise a solution of acid chloride prepared earlier in NMP (5 mL), and the mixture was stirred at room temperature for 15 hr. The reaction mixture was diluted with ethyl acetate, and washed successively with dilute hydrochloric acid, aqueous sodium hydrogen carbonate solution and brine. The solvent was evaporated under reduced pressure and the obtained crude product was washed with diisopropyl ether-ethyl acetate to give the title compound (4.20 g, yield 85%) as a colorless solid.

$^1$H NMR (300 MHz, DMSO-d$_6$) δ: 1.62-2.09 (4H, m), 2.50 (3H, s), 3.65-4.24 (11H, m), 7.07 (2H, d, J=8.7 Hz), 7.52 (1H, d, J=9.1 Hz), 7.65 (1H, dd, J=8.9, 2.1 Hz), 7.98 (2H, d, J=9.1 Hz), 8.15 (1H, d, J=1.9 Hz), 10.06 (1H, s).

Reference Example 31

N-[2-(hydroxymethyl)-1,3-dimethyl-1H-indol-5-yl]-4-[(2S)-tetrahydrofuran-2-ylmethoxy]benzamide To a solution of methyl 1,3-dimethyl-5-({4-[(2S)-tetrahydrofuran-2-ylmethoxy]benzoyl}amino)-1M-indole-2-carboxylate (4.20 g) obtained in Reference Example 30 in THF (300 mL) was added dropwise 2 M lithium aluminum hydride THF solution (7.46 mL) at 5° C., and the mixture was stirred at room temperature for 1 hr. To the reaction mixture was added sodium sulfate decahydrate (4.80 g). The insoluble material was filtered off, and the filtrate was concentrated under reduced pressure to dryness to give the title compound (3.99 g, yield 100%) as a pale-yellow solid.

$^1$H NMR (300 MHz, DMSO-d$_6$) δ: 1.62-2.14 (4H, m), 2.24 (3H, s), 3.65-3.85 (5H, m), 3.93-4.10 (2H, m), 4.18 (1H, m), 4.61 (2H, d, J=5.3 Hz), 5.04 (1H, t, J=5.3 Hz), 7.06 (2H, d, J=9.0 Hz), 7.33 (1H, d, J=9.0 Hz), 7.44 (1H, dd, J=8.7, 1.9 Hz), 7.92 (1H, d, J=1.9 Hz), 7.97 (2H, d, J=9.0 Hz), 9.94 (1H, s).

Reference Example 32

N-(2-formyl-1,3-dimethyl-1H-indol-5-yl)-4-[(2S)-tetrahydrofuran-2-ylmethoxy]benzamide To a solution of N-[2-(hydroxymethyl)-1,3-dimethyl-1H-indol-5-yl]-4-[(2S)-tetrahydrofuran-2-ylmethoxy]benzamide (3.99 g) obtained in Reference Example 31 in THF (200 mL) was added manganese dioxide (8.79 g), and the mixture was stirred at 80° C. for 2 hr. The insoluble material was filtered off and washed with THF. The filtrate was concentrated under reduced pressure and the obtained crude product was washed with diisopropyl ether-ethyl acetate to give the title compound (3.97 g, yield 78%) as a pale-brown solid.

$^1$H NMR (300 MHz, DMSO-d$_6$) δ: 1.62-2.09 (4H, m), 2.59 (3H, s), 3.64-4.10 (7H, m), 4.14-4.24 (1H, m), 7.08 (2H, d, J=9.0 Hz), 7.53 (1H, d, J=9.0 Hz), 7.72 (1H, dd, J=9.0, 1.9 Hz), 7.98 (2H, d, J=8.7 Hz), 8.22 (1H, d, J=1.9 Hz), 10.10 (1H, s), 10.14 (1H, s).

Reference Example 33 methyl 5-{[4-(cyclopropylmethoxy)benzoyl]amino}-1,3-dimethyl-1H-indole-2-carboxylate 4-(Cyclopropylmethoxy)benzoic acid (1.76 g) was dissolved in toluene (20 mL), thionyl chloride (1.00 mL) and a catalytic amount of DMF were added, and the mixture was stirred at 45° C. for 3 hr. The reaction mixture was concentrated under reduced pressure to give acid chloride. The acid chloride was dissolved in NMP (20 mL), methyl 5-amino-1,3-dimethyl-1H-indole-2-carboxylate (2.00 g) obtained in Reference Example 29, triethylamine (3.83 mL) and N,N-dimethylaminopyridine (560 mg) were added, and the mixture was stirred at room temperature for 2 days. The reaction mixture was diluted with ethyl acetate, and washed successively with dilute hydrochloric acid, aqueous sodium hydrogen carbonate solution and brine. The solvent was evaporated under reduced pressure and the obtained crude product was washed with diisopropyl ether-ethyl acetate to give the title compound (3.13 g, yield 87%) as a pale-yellow solid.

$^1$H NMR (300 MHz, DMSO-d$_6$) δ: 0.32-0.38 (2H, m), 0.56-0.63 (2H, m), 1.18-1.31 (1H, m), 2.50 (3H, s), 3.89 (3H, s), 3.91 (2H, d, J=7.2 Hz), 3.94 (3H, s), 7.05 (2H, d, J=8.7 Hz), 7.52 (1H, d, J=9.0 Hz), 7.65 (1H, dd, J=9.0, 1.9 Hz), 7.97 (2H, d, J=8.7 Hz), 8.15 (1H, d, J=1.5 Hz), 10.05 (1H, s).

Reference Example 34

4-(cyclopropylmethoxy)-N-(2-formyl-1,3-dimethyl-1H-indol-5-yl)benzamide

To a solution of methyl 5-{[4-(cyclopropylmethoxy)benzoyl]amino}-1,3-dimethyl-1H-indole-2-carboxylate (3.13 g) obtained in Reference Example 33 in THF (600 mL) was added dropwise 2 M lithium aluminum hydride THF solution (5.98 mL) at 5° C., and the mixture was stirred at room temperature for 1 hr. To the reaction mixture was added sodium sulfate decahydrate (3.85 g). The insoluble material was filtered off and washed with THF. To the filtrate was added manganese dioxide (8.16 g), and the mixture was stirred at 75° C. so for 1 day. The insoluble material was filtered off and washed with THF. The filtrate was concentrated under reduced pressure and the obtained crude product was washed with diisopropyl ether-ethyl acetate to give the title compound (2.18 g, yield 75%) as a pale-brown solid.

$^1$H NMR (300 MHz, DMSO-d$_6$) δ: 0.32-0.39 (2H, m), 0.56-0.64 (2H, m), 1.19-1.33 (1H, m), 2.59 (3H, s), 3.88-3.95 (2H, m), 3.99 (3H, s), 7.05 (2H, d, J=8.7 Hz), 7.53 (1H, d, J=9.0 Hz), 7.72 (1H, dd, J=9.0, 1.9 Hz), 7.98 (2H, d, J=8.7 Hz), 8.22 (1H, d, J=1.9 Hz), 10.09 (1H, s), 10.14 (1H, s).

Reference Example 35 tert-butyl [3-(hydroxymethyl)-2-methylphenyl]carbamate

To a solution of (3-amino-2-methylphenyl)methanol (10.0 g) in THF (200 mL) were added di-tert-butyl dicarbonate (25.1 mL) and triethylamine (11.2 mL), and the mixture was stirred at room temperature for 24 hr and concentrated under reduced pressure. The residue was suspended in water-ethyl acetate, and the precipitate was filtered off. The filtrate was extracted with ethyl acetate, and the organic layer was washed with water and saturated brine, dried over sodium sulfate, and concentrated under reduced pressure. The residue was suspended in diisopropyl ether, and the precipitate was collected by filtration, washed with diisopropyl ether, and dried under reduced pressure to give the title compound (17.585 g, yield 100%) as a pale-brown solid.

$^1$H NMR (300 MHz, CDCl$_3$) δ: 1.56 (9H, s), 2.25 (3H, s), 4.70 (2H, d, J=5.7 Hz), 6.27 (1H, br. s.), 7.08-7.16 (1H, m), 7.16-7.24 (1H, m), 7.69 (1H, d, J=7.9 Hz).

Reference Example 36 tert-butyl (3-formyl-2-methylphenyl)carbamate

To a solution of tert-butyl [3-(hydroxymethyl)-2-methylphenyl]carbamate (496 g) obtained in Reference Example 35 in THF (3.5 L) was added manganese dioxide (1070 g), and the mixture was stirred at 70° C. for 15 hr. The mixture was filtered through celite, and the filtrate was concentrated under reduced pressure. The residue was suspended in petroleum ether (1 L), and the precipitate was collected by filtration, and dried under reduced pressure to give the title compound (462 g, yield 94%) as a white solid.
$^1$H NMR (300 MHz, CDCl$_3$) δ: 1.53 (9H, s), 2.57 (3H, s), 6.37 (1H, br. s.), 7.33-7.42 (1H, m), 7.57 (1H, dd, J=7.7, 1.3 Hz), 8.03 (1H, d, J=8.3 Hz), 10.24 (1H, s).

Reference Example 37 ethyl (2Z)-2-azido-3-{3-[(tert-butoxycarbonyl)amino]-2-methylphenyl}acrylate

To a solution of sodium ethoxide (163 g) in ethanol (2 L) was added dropwise at −40° C. a solution of tert-butyl (3-formyl-2-methylphenyl)carbamate (142 g) obtained in Reference Example 36 and ethyl azidoacetate (310 g) in ethanol (1 L). The reaction mixture was stirred at −10° C. for 3 hr, allowed to warm to room temperature and stirred for 15 min. After cooling to −20° C., 4N hydrochloric acid (600 mL) was added dropwise. The reaction mixture was poured into water (6 L), and the precipitated solid was collected by filtration, washed with water, and dried under reduced pressure to give the title compound (140 g, yield 67%) as a pale-yellow solid.
$^1$H NMR (300 MHz, CDCl$_3$) δ: 1.41 (3H, t, J=7.0 Hz), 1.52 (9H, s), 2.22 (3H, s), 4.39 (2H, q, J=6.9 Hz), 6.26 (1H, s), 7.13 (1H, s), 7.22 (1H, t, J=7.9 Hz), 7.53 (1H, d, J=7.9 Hz), 7.69 (1H, d, J=7.9 Hz).

Reference Example 38 ethyl 5-[(tert-butoxycarbonyl)amino]-4-methyl-1H-indole-2-carboxylate

A solution of ethyl (2Z)-2-azido-3-{3-[(tert-butoxycarbonyl)amino]-2-methylphenyl}acrylate (21.9 g) obtained in Reference Example 37 in toluene (245 mL) was stirred at 120° C. for 15 hr. After cooling to room temperature, hexane (245 mL) was added, and the mixture was stirred at room temperature for 2 hr. The precipitated solid was collected by filtration, and washed with hexane to give the title compound (21.1 g, yield 85%) as a pale-yellow solid.
$^1$H NMR (300 MHz, CDCl$_3$) δ: 1.42 (3H, t, J=7.2 Hz), 1.52 (9H, s), 2.45 (3H, s), 4.41 (2H, q, J=7.2 Hz), 6.21 (1H, s), 7.20-7.25 (2H, m), 7.44-7.55 (1H, m), 8.84 (1H, s).

Reference Example 39 ethyl 5-amino-4-methyl-1H-indole-2-carboxylate hydrochloride

Ethyl 5-[(tert-butoxycarbonyl)amino]-4-methyl-1H-indole-2-carboxylate (3.203 g) obtained in Reference Example 38 was dissolved in ethyl acetate (100 mL)-methanol (60 mL), hydrogen chloride-ethyl acetate solution (4 M, 25 mL) was added, and the mixture was stirred at room temperature for 5 hr. The precipitate was collected by filtration, washed with ethyl acetate, and dried under reduced pressure to give the title compound (2.524 g, yield 99%) as a white solid.
$^1$H NMR (300 MHz, DMSO-d$_6$) δ: 1.35 (3H, t, J=7.0 Hz), 2.51 (3H, s), 4.35 (2H, q, J=7.2 Hz), 7.23-7.28 (1H, m), 7.29 (1H, d, J=1.5 Hz), 7.33-7.41 (1H, m), 9.78 (3H, br. s.), 12.10 (1H, s).

Reference Example 40 ethyl 5-({[4-(cyclopropylmethoxy)phenyl]carbonyl}amino)-4-methyl-1H-indole-2-carboxylate Ethyl 5-amino-4-methyl-1H-indole-2-carboxylate hydrochloride (720 mg) obtained in Reference Example 39 was dissolved in DMF (10 mL), ethyldiisopropylamine (0.51 mL), 4-(cyclopropylmethoxy)benzoic acid (599 mg), 1-ethyl-3-(3-dimethylaminopropyl)carbodiimide hydrochloride (1.13 g), 1-hydroxybenzotriazole monohydrate (908 mg) and N,N-dimethylaminopyridine (398 mg) were successively added, and the mixture was stirred at room temperature for 17 hr. After dilution with ethyl acetate, water was added.

Separately, ethyl 5-amino-4-methyl-1H-indole-2-carboxylate hydrochloride (363 mg) obtained in Reference Example 39 was suspended in DMF (5.0 mL), ethyldiisopropylamine (0.24 mL), 4-(cyclopropylmethoxy)benzoic acid (288 mg), 1-ethyl-3-(3-dimethylaminopropyl)carbodiimide hydrochloride (544 mg), 1-hydroxybenzotriazole monohydrate (436 mg) and N,N-dimethylaminopyridine (192 mg) were successively added, and the mixture was stirred at room temperature for 17 hr. After dilution with ethyl acetate, water was added.

The above-mentioned two mixtures were combined, and the organic layer was washed twice with water, and concentrated under reduced pressure. The residue was suspended in diisopropyl ether, and the precipitate was collected by filtration, washed with diisopropyl ether, and dried under reduced pressure to give the title compound (1.66 g, yield 96%) as a pale-yellow solid.
$^1$H NMR (300 MHz, CDCl$_3$) δ: 0.34-0.44 (2H, m), 0.63-0.73 (2H, m), 1.25-1.37 (1H, m), 1.43 (3H, t, J=7.2 Hz), 2.50 (3H, s), 3.88 (2H, d, J=7.2 Hz), 4.42 (2H, q, J=7.1 Hz), 6.99 (2H, d, J=8.7 Hz), 7.27-7.31 (2H, m), 7.51-7.64 (2H, m), 7.88 (2H, d, J=8.7 Hz), 8.85 (1H, br. s.).

Reference Example 41

4-(cyclopropylmethoxy)-N-(2-formyl-4-methyl-1H-indol-5-yl)benzamide

Lithium aluminum hydride (80%, 800 mg) was suspended in THF (160 mL), a solution of ethyl 5-({[4-(cyclopropylmethoxy)phenyl]carbonyl}amino)-4-methyl-1H-indole-2-carboxylate (1.66 g) obtained in Reference Example 40 in THF (240 mL) was added dropwise at 0° C., and the mixture was stirred at room temperature for 1 hr. Sodium sulfate decahydrate (5.44 g) was added at 0° C., and the mixture was stirred at room temperature for 30 min and filtered. The filtrate was concentrated under reduced pressure, and the residue was suspended in diisopropyl ether. The precipitate was collected by filtration, washed with diisopropyl ether, dried under reduced pressure, and dissolved in THF (100 mL). Manganese dioxide (85%, 4.32 g) was added, and the mixture was heated under reflux for 1 hr. The mixture was filtered through celite, and the filtrate was concentrated under reduced pressure. The residue was suspended in diisopropyl ether, and the precipitate was collected by filtration, washed with diisopropyl ether, and dried under reduced pressure to give the title compound (896 mg, yield 85%) as a beige solid.

$^1$H NMR (300 MHz, CDCl$_3$) δ: 0.34-0.43 (2H, m), 0.63-0.73 (2H, m), 1.22-1.39 (1H, m), 2.53 (3H, s), 3.89 (2H, d, J=6.8 Hz), 6.99 (2H, d, J=8.7 Hz), 7.28-7.35 (2H, m), 7.54-7.66 (2H, m), 7.89 (2H, d, J=9.1 Hz), 8.93 (1H, br. s.), 9.85 (1H, s).

Reference Example 42 ethyl 4-methyl-5-[({4-[(2S)-tetrahydrofuran-2-ylmethoxy]phenyl}carbonyl)amino]-1H-indole-2-carboxylate Ethyl 5-amino-4-methyl-1H-indole-2-carboxylate hydrochloride (1.44 g) obtained in Reference Example 39 was dissolved in DMF (20 mL), 4-[(2S)-tetrahydrofuran-2-ylmethoxy]benzoic acid (1.38 g) obtained in Reference Example 8, ethyldiisopropylamine (1.02 mL), 1-ethyl-3-(3-dimethylaminopropyl)carbodiimide hydrochloride (2.26 g), 1-hydroxybenzotriazole monohydrate (1.82 g) and N,N-dimethylaminopyridine (797 mg) were successively added, and the mixture was stirred at room temperature for 17 hr. After dilution with ethyl acetate, water was added. The organic layer was washed twice with water, and concentrated under reduced pressure. The residue was suspended in diisopropyl ether, and the precipitate was collected by filtration, washed with diisopropyl ether, and dried under reduced pressure to give the title compound (2.17 g, yield 87%) as a pale-yellow solid.

$^1$H NMR (300 MHz, CDCl$_3$) δ: 1.43 (3H, t), 1.75-1.88 (1H, m), 1.89-2.21 (3H, m), 2.50 (3H, s), 3.80-3.91 (1H, m), 3.91-4.01 (1H, m), 4.04 (2H, d, J=5.3 Hz), 4.26-4.37 (1H, m), 4.42 (2H, q, J=7.2 Hz), 7.01 (2H, d, J=8.7 Hz), 7.26-7.32 (2H, m), 7.54 (1H, d, J=8.7 Hz), 7.59 (1H, s), 7.88 (2H, d, 3-8.3 Hz), 8.85 (1H, br. s)

Reference Example 43

N-(2-formyl-4-methyl-1H-indol-5-yl)-4-[(2S)-tetrahydrofuran-2-ylmethoxy]benzamide Lithium aluminum hydride (80%, 976 mg) was suspended in THF (200 mL), a solution of ethyl 4-methyl-5-[({4-[(2S)-tetrahydrofuran-2-ylmethoxy]phenyl}carbonyl)amino]-1H-indole-2-carboxylate (2.17 g) obtained in Reference Example 42 in THF (300 mL) was added dropwise at 0° C., and the mixture was stirred at room temperature for 1 hr. Sodium sulfate decahydrate (6.63 g) was added at 0° C., and the mixture was stirred at room temperature for 30 min and filtered. The filtrate was concentrated under reduced pressure, and the residue was suspended in diisopropyl ether. The precipitate was collected by filtration, washed with diisopropyl ether, dried under reduced pressure and dissolved in THF (160 mL). Manganese dioxide (85%, 5.26 g) was added, and the mixture was heated under reflux for 1 hr. The mixture was filtered through celite, and the filtrate was concentrated under reduced pressure. The residue was suspended in diisopropyl ether, and the precipitate was collected by filtration, washed with diisopropyl ether, and dried under reduced pressure to give the title compound (1.33 g, yield 84%) as a beige solid.

$^1$H NMR (300 MHz, CDCl$_3$) δ: 1.72-1.87 (1H, m), 1.90-2.05 (2H, m), 2.05-2.19 (1H, m), 2.53 (3H, s), 3.81-3.91 (1H, m), 3.96 (1H, dt, J=8.3, 6.6 Hz), 4.05 (2H, d, J=5.3 Hz), 4.25-4.37 (1H, m), 7.02 (2H, d, J=8.7 Hz), 7.27-7.34 (2H, m), 7.55-7.65 (2H, m), 7.89 (2H, d, J=8.7 Hz), 8.97 (1H, br. s.), 9.85 (1H, s).

Reference Example 44 ethyl 5-[(tert-butoxycarbonyl)amino]-1,4-dimethyl-1H-indole-2-carboxylate

To a solution of ethyl 5-[(tert-butoxycarbonyl)amino]-4-methyl-1H-indole-2-carboxylate (100 g) obtained in Reference Example 38 and methyl iodide (23.3 mL) in DMF (1 L) was added sodium hydride (60% in oil, 14 g) under ice-cooling, and the mixture was stirred at room temperature for 1 hr. Water was added to the reaction mixture, and the precipitated solid was collected by filtration. The solid was dissolved in ethyl acetate, washed twice with saturated brine, and dried over magnesium sulfate. The solvent was evaporated under reduced pressure, and a crude product was suspended in petroleum ether (300 mL) and stirred, collected by filtration again, and dried under reduced pressure to give the title compound (81 g, yield 78%) as a colorless solid.

$^1$H NMR (300 MHz, CDCl$_3$) δ: 1.42 (3H, t, J=7.0 Hz), 1.52 (9H, s), 2.44 (3H, s), 4.05 (3H, s), 4.38 (2H, q, J=7.2 Hz), 6.21 (1H, s), 7.19 (1H, d, J=9.1 Hz), 7.29 (1H, s), 7.52 (1H, d, J=6.0 Hz).

Reference Example 45 ethyl 5-amino-1,4-dimethyl-1H-indole-2-carboxylate hydrochloride

Ethyl 5-[(tert-butoxycarbonyl)amino]-1,4-dimethyl-1H-indole-2-carboxylate (3.400 g) obtained in Reference Example 44 was dissolved in ethyl acetate (100 mL), hydrogen chloride-ethyl acetate solution (4 M, 13 mL) was added, and the mixture was stirred at room temperature for 24 hr. Hydrogen chloride-ethyl acetate solution (4 M, 13 mL) was added, and the mixture was stirred at room temperature for 11 hr. The precipitate was collected by filtration, washed with ethyl acetate, and dried under reduced pressure to give the title compound (2.723 g, 50 yield 96%) as a white solid.

$^1$H NMR (300 MHz, DMSO-d$_6$) δ: 1.35 (3H, t, J=7.2 Hz), 2.51 (3H, br. s.), 4.03 (3H, s), 4.34 (2H, q, J=7.2 Hz), 7.35 (1H, d, J=8.7 Hz), 7.39 (1H, s), 7.54 (1H, J=9.1 Hz), 9.86 (3H, br. s.).

Reference Example 46 ethyl 5-({[4-(cyclopropylmethoxy)phenyl]carbonyl}amino)-1,4-dimethyl-1H-indole-2-carboxylate Ethyl 5-amino-1,4-dimethyl-1H-indole-2-carboxylate hydrochloride (400 mg) obtained in Reference Example 45 was suspended in DMF (4.0 mL), ethyldiisopropylamine (0.25 mL), 4-(cyclopropylmethoxy)benzoic acid (300 mg), 1-hydroxybenzotriazole monohydrate (456 mg), 1-ethyl-3-(3-dimethylaminopropyl)carbodiimide hydrochloride (568 mg) and N,N-dimethylaminopyridine (200 mg) were successively added, and the mixture was stirred at room temperature for 22 hr. After dilution with THF and ethyl acetate, water was added. The organic layer was washed twice with water, and concentrated under reduced pressure. The residue was suspended in diisopropyl ether, and the precipitate was collected by filtration, washed with diisopropyl ether, and dried under reduced pressure to give the title compound (547 mg, yield 90%) as a white solid.

$^1$H NMR (300 MHz, CDCl$_3$) δ: 0.34-0.44 (2H, m), 0.63-0.74 (2H, m), 1.24-1.37 (1H, m), 1.43 (3H, t, J=7.2 Hz), 2.49 (3H, s), 3.88 (2H, d, J=7.2 Hz), 4.07 (3H, s), 4.39 (2H, q,

J=7.2 Hz), 6.98 (2H, d, J=8.7 Hz), 7.22 (1H, s), 7.33 (1H, s), 7.53-7.65 (2H, m), 7.88 (2H, d, J=8.0 Hz).

Reference Example 47

4-(cyclopropylmethoxy)-N-(2-formyl-1,4-dimethyl-1H-indol-5-yl)benzamide

Lithium aluminum hydride (80%, 255 mg) was suspended in THF (50 mL), a solution of ethyl 5-({[4-(cyclopropylmethoxy)phenyl]carbonyl}amino)-1,4-dimethyl-1H-indole-2-carboxylate (547 mg) obtained in Reference Example 46 in THF (120 mL) was added dropwise at 0° C., and the mixture was stirred at room temperature for 1 hr. Sodium sulfate decahydrate (1.733 g) was added at 0° C., and the mixture was stirred at room temperature for 1 hr, and filtered. The filtrate was concentrated under reduced pressure, and the residue was suspended in diisopropyl ether. The precipitate was collected by filtration, washed with diisopropyl ether, dried under reduced pressure, and dissolved in THF (50 mL). Manganese dioxide (85%, 1.371 g) was added, and the mixture was heated under reflux for 1 hr. The mixture was filtered through celite, and the filtrate was concentrated under reduced pressure. The residue was suspended in diisopropyl ether, and the precipitate was collected by filtration, washed with diisopropyl ether, and dried under reduced pressure to give the title compound (349 mg, yield 83%) as a white solid.
$^1$H NMR (300 MHz, CDCl$_3$) δ: 0.34-0.43 (2H, m), 0.63-0.74 (2H, m), 1.24-1.38 (1H, m), 2.52 (3H, s), 3.89 (2H, d, J=6.8 Hz), 4.10 (3H, s), 6.99 (2H, d, J=8.7 Hz), 7.29 (2H, s), 7.60 (1H, s), 7.67 (1H, d, J=9.0 Hz), 7.89 (2H, d, J=8.7 Hz), 9.90 (1H, s).

Reference Example 48 tert-butyl [2-(hydroxymethyl)-1,4-dimethyl-1H-indol-5-yl]carbamate

To a solution of calcium chloride (81 g) in ethanol (147 mL) was added sodium borohydride (6.93 g) at 5° C., and the mixture was stirred at the same temperature for 30 min. To the reaction mixture was added dropwise at 5° C. a solution of ethyl 5-[(tert-butoxycarbonyl)amino]-1,4-dimethyl-1H-indole-2-carboxylate (195 g) obtained in Reference Example 44 in THF (1.2 L), and the mixture was stirred at the same temperature for 30 min and at room temperature for 15 hr. While maintaining the reaction mixture at 20° C. or below, 1N hydrochloric acid (1.4 L) was added dropwise to adjust to pH 3, and water (1 L) and saturated aqueous sodium hydrogen carbonate (190 mL) were added. The organic solvent was evaporated under reduced pressure and the residual aqueous layer was extracted with ethyl acetate. The extract was washed with saturated brine, dried over magnesium sulfate, and concentrated under reduced pressure. The precipitated solid was washed with ethyl acetate (200 mL) and petroleum ether (600 mL), and dried under reduced pressure to give the title compound (134 g, yield 79%) as colorless crystals.
$^1$H NMR (300 MHz, DMSO-d$_6$) δ: 1.44 (9H, s), 2.28 (3H, s), 3.70 (3H, s), 4.62 (2H, d, J=4.9 Hz), 5.20 (1H, t, J=5.3 Hz), 6.36 (1H, s), 6.94 (1H, d, J=8.3 Hz), 7.15 (1H, d, J=8.3 Hz), 8.39 (1H, s).

Reference Example 49 tert-butyl (2-formyl-1,4-dimethyl-1H-indol-5-yl)carbamate

To a solution of tert-butyl [2-(hydroxymethyl)-1,4-dimethyl-1H-indol-5-yl]carbamate (218 g) obtained in Reference Example 48 in THF (2.5 L) was added manganese dioxide (327 g), and the mixture was stirred at 70° C. for 15 hr. The insoluble material was filtered off through celite, and washed with THF. The filtrate was concentrated under reduced pressure and the obtained crude product was suspended in petroleum ether (1 L) and stirred. The precipitate was collected by filtration, and dried under reduced pressure to give the title compound (190 g, yield 88%) as a yellow solid.
$^1$H NMR (300 MHz, DMSO-d$_6$) δ: 1.46 (9H, s), 2.37 (3H, s), 4.01 (3H, s), 7.27 (1H, d, J=8.7 Hz), 7.37 (1H, d, J=9.1 Hz), 7.49 (1H, s), 8.61 (1H, s), 9.88 (1H, s).

Reference Example 50

5-amino-1,4-dimethyl-1H-indole-2-carbaldehyde hydrochloride

To a solution of tert-butyl (2-formyl-1,4-dimethyl-1H-indol-5-yl)carbamate (43.0 g) obtained in Reference Example 49 in ethyl acetate (860 mL) was added 4N hydrogen chloride-ethyl acetate solution (35.5 g), and the mixture was stirred at 40° C. for 3 hr. The reaction mixture was ice-cooled, and the precipitated solid was collected by filtration, and washed with ethyl acetate to give the title compound (33.5 g, yield 100%) as an orange solid.
$^1$H NMR (300 MHz, DMSO-d$_6$) δ: 2.58 (3H, s), 4.04 (3H, s), 7.48-7.65 (3H, m), 9.95 (1H, s).

Reference Example 51

N-(2-formyl-1,4-dimethyl-1H-indol-5-yl)-4-[(2S)-tetrahydrofuran-2-ylmethoxy]benzamide 4-[(2S)-Tetrahydrofuran-2-ylmethoxy]benzoic acid (4.95 g) obtained in Reference Example 8 was dissolved in THF (40 mL), oxalyl chloride (2.10 mL) and a catalytic amount of DMF were added, and the mixture was stirred at room temperature for 3 hr. The reaction mixture was concentrated under reduced pressure to give acid chloride. The acid chloride was dissolved in THF (35 mL), and the solution was added dropwise to a suspension of 5-amino-1,4-dimethyl-1H-indole-2-carbaldehyde hydrochloride (5.00 g) obtained in Reference Example 50 and triethylamine (7.75 mL) in THF (75 mL). The reaction mixture was stirred at room temperature for 18 hr. To the reaction mixture was added water (220 mL), and the precipitated solid was collected by filtration, and successively washed with water, ethyl acetate, acetonitrile and isopropyl ether to give the title compound (7.80 g, yield 89%) as a pale-yellow solid.
$^1$H NMR (300 MHz, DMSO-d$_6$) δ: 1.62-2.09 (4H, m), 2.41 (3H, s), 3.65-3.84 (2H, m), 3.97-4.10 (5H, m), 4.14-4.24 (1H, m), 7.07 (2H, d, J=8.7 Hz), 7.33 (1H, d, J=9.1 Hz), 7.45 (1H, d, J=9.1 Hz), 7.55 (1H, s), 7.99 (2H, d, J=9.1 Hz), 9.85 (1H, s), 9.91 (1H, s).

Reference Example 53 ethyl 5-[({2-fluoro-4-[(2S)-tetrahydrofuran-2-ylmethoxy]phenyl}carbonyl)amino]-1,4-dimethyl-1H-indole-2-carboxylate Ethyl 5-amino-1,4-dimethyl-1H-indole-2-carboxylate hydrochloride (1.52 g) obtained in Reference Example 45 was suspended in DMF (15 mL), ethyldiisopropylamine (0.97 mL), 2-fluoro-4-[(2S)-tetrahydrofuran-2-ylmethoxy] benzoic acid (1.43 g) obtained in Reference Example 15, 1-hydroxybenzotriazole monohydrate (1.74 g), 1-ethyl-3-(3- dimethylaminopropyl)carbodiimide hydrochloride (2.16 g) and N,N-dimethylaminopyridine (761 mg) were successively added, and the mixture was stirred at room temperature for 22 hr. After dilution with ethyl acetate, water was added. The organic layer was washed twice with water, and concentrated under reduced pressure. The residue was suspended in diisopropyl ether, and the precipitate was collected by filtration, washed with diisopropyl ether, and dried under reduced pressure to give the title compound (2.06 g, yield 80%) as a pale-brown solid.

$^1$H NMR (300 MHz, CDCl$_3$) δ: 1.43 (3H, t, J=7.2 Hz), 1.70-1.86 (1H, m), 1.90-2.22 (4H, m), 2.50 (2H, s), 3.80-4.00 (2H, m), 4.00-4.11 (5H, m), 4.25-4.34 (1H, m), 4.39 (2H, q, J=6.9 Hz), 6.74 (1H, dd, J=14.4, 2.3 Hz), 6.87 (1H, dd, J=8.9, 2.5 Hz), 7.20-7.27 (1H, m), 7.33 (1H, s), 7.72 (1H, d, J=9.1 Hz), 8.16 (1H, t, J=9.1 Hz), 8.26 (1H, d, J=15.9 Hz).

Reference Example 54

2-fluoro-N-(2-formyl-1,4-dimethyl-1H-indol-5-yl)-4-[(2S)-tetrahydrofuran-2-ylmethoxy]benzamide Lithium aluminum hydride (80%, 860 mg) was suspended in THF (180 mL), a solution of ethyl 5-[({2-fluoro-4-[(2S)-tetrahydrofuran-2-ylmethoxy]phenyl}carbonyl)amino]-1,4-dimethyl-1H-indole-2-carboxylate (2.06 g) obtained in Reference Example 53 in THF (270 mL) was added dropwise at 0° C., and the mixture was stirred at room temperature for 1 hr. Sodium sulfate decahydrate (5.84 g) was added at 0° C., and the mixture was stirred at room temperature for 1 hr, and filtered. The filtrate was concentrated under reduced pressure, and the residue was suspended in diisopropyl ether. The precipitate was collected by filtration, washed with diisopropyl ether, dried under reduced pressure and dissolved in THF (150 mL) at 50° C. Manganese dioxide (85%, 4.64 g) was added, and the mixture was heated under reflux for 1 hr. The mixture was filtered through celite, and the filtrate was concentrated under reduced pressure. The residue was suspended in diisopropyl ether, and the precipitate was collected by filtration, washed with diisopropyl ether, and dried under reduced pressure to give the title compound (1.29 g, yield 83%) as a pale-yellow solid.

$^1$H NMR (300 MHz, CDCl$_3$) δ: 1.71-1.86 (1H, m), 1.90-2.05 (2H, m), 2.05-2.19 (1H, m), 2.53 (3H, s), 3.86 (1H, q, J=7.3 Hz), 3.91-4.01 (1H, m), 4.01-4.07 (2H, m), 4.10 (3H, s), 4.25-4.36 (1H, m), 6.75 (1H, dd, J=13.9, 1.9 Hz), 6.88 (1H, dd, J=9.0, 1.9 Hz), 7.29 (2H, s), 7.82 (1H, d, J=8.7 Hz), 8.16 (1H, t, J=9.2 Hz), 8.27 (1H, d, J=17.0 Hz), 9.89 (1H, s).

Reference Example 55 ethyl 2-[(2-methyl-3-nitrophenyl)hydrazono]propanoate

2-Methyl-3-nitroaniline (50.0 g) was suspended in a mixed solvent of acetonitrile (75 mL) and 2N aqueous hydrochloric acid solution (411 mL), and the mixture was cooled to −10° C. A solution of sodium nitrite (27.3 g) in water (50 mL) was added dropwise at an inside temperature of −5° C. or below. After stirring at the same temperature for 30 min, the reaction mixture was filtered through celite. Ethyl 2-methylacetoacetate (46.6 mL) and potassium hydroxide (64.6 g) were dissolved in a mixed solvent of water (350 mL) and ethanol (350 mL), and the mixture was cooled to −6° C. and the above-mentioned filtrate was added dropwise at an inside temperature of 2° C. or below. After stirring at the same temperature for 10 min, 6N aqueous hydrochloric acid solution (100 mL) was added, and the mixture was stirred at 0° C. for 1 hr. The resulting solid was collected by filtration, dissolved in ethyl acetate, washed with saturated brine, dried over anhydrous sodium sulfate, and concentrated under reduced pressure to give the title compound (76.7 g, yield 88%) as a red solid.

$^1$H NMR (300 MHz, DMSO-d$_6$) δ: 1.27 (3H, t, J=7.0 Hz), 2.15 (3H, s), 2.33 (3H, s), 4.22 (2H, q, J=7.0 Hz), 7.38-7.48 (2H, m), 7.68 (1H, dd, J=7.3, 2.1 Hz), 8.94 (1H, s).

Reference Example 56 ethyl 7-methyl-6-nitro-1H-indole-2-carboxylate

Methanesulfonic acid (37.5 mL) and Eaton's reagent (37.0 mL) were added to toluene (250 mL), and the mixture was stirred at 80° C. for 20 min. Ethyl 2-[(2-methyl-3-nitrophenyl)hydrazono]propanoate (27.8 g) obtained in Reference Example 55 was added over 5 min, and rinsed with toluene (20 mL). After stirring at the same temperature for 15 min, the organic layer was separated by a gradient method. Furthermore, a resultant product was separated from a tar residue by a gradient method using toluene. The separated organic layers were combined, diluted with ethyl acetate, washed with saturated aqueous sodium hydrogen carbonate solution and saturated brine, dried over anhydrous sodium sulfate, and concentrated under reduced pressure. The residue was washed with a mixed solvent of ethyl acetate and hexane and dried to give the title compound (8.55 g, yield 33%) as a pale-yellow solid.

$^1$H NMR (300 MHz, DMSO-d$_6$) δ: 1.32-1.43 (3H, m), 2.77 (3H, s), 4.38 (2H, q, J=7.1 Hz), 7.29 (1H, s), 7.68 (2H, s), 12.41 (1H, brs).

Reference Example 57 ethyl 6-amino-7-methyl-1H-indole-2-carboxylate

Ethyl 7-methyl-6-nitro-1H-indole-2-carboxylate (1.50 g) obtained in Reference Example 56 and palladium on activated carbon (Pd: 10%, 50% water wet, 150 mg) were mixed in a mixed solvent of ethanol (10 mL) and tetrahydrofuran (20 mL), and the mixture was stirred under a hydrogen atmosphere (1 atm) at room temperature for 20 hr. The mixture was filtered through celite, and the filtrate was concentrated under reduced pressure. The residue was purified by NH silica gel column chromatography [eluent; hexane:ethyl acetate=80:20 (volume ratio)→hexane:ethyl acetate=60:40 (volume ratio)] and concentrated under reduced pressure to give the title compound (1.21 g, yield 92%) as a yellow solid.

$^1$H NMR (300 MHz, DMSO-d$_6$) δ: 1.31 (3H, t, J=7.1 Hz), 2.21 (3H, s), 4.27 (2H, q, J=7.0 Hz), 4.87 (2H, s), 6.54 (1H, d, J=8.2 Hz), 6.95 (1H, d, J=2.2 Hz), 7.15 (1H, d, J=8.8 Hz), 10.90 (1H, s).

Reference Example 58

4-(cyclopropylmethoxy)-N-(2-formyl-7-methyl-1H-indol-6-yl)benzamide

Ethyl 6-amino-7-methyl-1H-indole-2-carboxylate (883 mg) obtained in Reference Example 57 and 4-(cyclopropylmethoxy)benzoic acid (778 mg) were dissolved in N,N-dimethylformamide (27 mL), 1-hydroxybenzotriazole (657 mg), 1-ethyl-3-(3-dimethylaminopropyl)carbodiimide hydrochloride (932 mg) and N,N-dimethylaminopyridine (495 mg) were added at room temperature, and the mixture was stirred for 18 hr. Water was added to the reaction mixture, and the mixture was extracted with ethyl acetate. The organic layer was washed with 1N aqueous hydrochloric acid solution, saturated aqueous sodium hydrogen carbonate solution and saturated brine, and concentrated under reduced pressure. The residue was suspended in tetrahydrofuran (81 mL), and lithium aluminum hydride (6.08 mL, 2.0 M tetrahydrofuran solution) was added dropwise at 0° C. After completion of the dropwise addition, the mixture was stirred at room temperature for 2.5 hr. To the reaction mixture was gradually added sodium sulfate decahydrate at 0° C. until completion of bubbling, and the mixture was stirred at room temperature for 1 hr. The reaction mixture was filtered through celite, and the filtrate was concentrated under reduced pressure. The residue and manganese dioxide (4.14 g) were suspended in tetrahydrofuran (177 mL), and the mixture was heated under reflux for 1 hr. The reaction mixture was filtered through celite, and the filtrate was concentrated under reduced pressure. The residue was washed with a mixed solvent of ethyl acetate and hexane to give the title compound (755 mg, yield 54%) as a pale-brown solid.

$^1$H NMR (300 MHz, DMSO-$d_6$) δ: 0.32-0.40 (2H, m), 0.55-0.65 (2H, m), 1.19-1.31 (1H, m), 2.38 (3H, s), 3.91 (2H, d, J=7.1 Hz), 7.00-7.09 (3H, m), 7.39 (1H, s), 7.55 (1H, d, J=8.8 Hz), 7.96 (2H, d, J=9.1 Hz), 9.82 (1H, s), 9.86 (1H, s), 11.85 (1H, s).

Reference Example 59

N-(2-formyl-7-methyl-1H-indol-6-yl)-4-[(2S)-tetrahydrofuran-2-ylmethoxy]benzamide Ethyl 6-amino-7-methyl-1H-indole-2-carboxylate (1.77 g) obtained in Reference Example 57 and 4-[(2S)-tetrahydrofuran-2-ylmethoxy]benzoic acid (1.80 g) obtained in Reference Example 8 were dissolved in N,N-dimethylformamide (54 mL), 1-hydroxybenzotriazole (1.31 g), 1-ethyl-3-(3-dimethylaminopropyl)carbodiimide hydrochloride (1.86 g) and N,N-dimethylaminopyridine (990 mg) were added at room temperature, and the mixture was stirred for 22 hr. Water was added to the reaction mixture, and the mixture was extracted with ethyl acetate. The organic layer was washed with 1N aqueous hydrochloric acid solution, saturated aqueous sodium hydrogen carbonate solution and saturated brine, and concentrated under reduced pressure. The residue was suspended in tetrahydrofuran (160 mL), and lithium aluminum hydride (12.1 mL, 2.0 M tetrahydrofuran solution) was added dropwise at 0° C. After completion of the dropwise addition, the mixture was stirred at room temperature for 3.5 hr. To the reaction mixture was gradually added sodium sulfate decahydrate at 0° C. until completion of bubbling, and the mixture was stirred at room temperature for 1 hr. The reaction mixture was filtered through celite, and the filtrate was concentrated under reduced pressure. The residue and manganese dioxide (8.27 g) were suspended in tetrahydrofuran (160 mL), and the mixture was heated under reflux for 2 hr. The reaction mixture was filtered through celite, and the filtrate was concentrated under reduced pressure. The residue was washed with a mixed solvent of ethyl acetate and hexane to give the title compound (1.73 g, yield 56%) as a pale-brown solid.

$^1$H NMR (300 MHz, DMSO-$d_6$) δ: 1.63-2.11 (5H, m), 2.39 (3H, s), 3.65-3.74 (1H, m), 3.75-3.86 (1H, m), 3.96-4.11 (2H, m), 4.13-4.24 (1H, m), 7.04-7.10 (2H, m), 7.41 (1H, s), 7.56 (1H, d, J=8.7 Hz), 7.98 (2H, d, J=8.7 Hz), 9.84 (1H, s), 9.89 (1H, s), 11.87 (1H, s).

Reference Example 60 ethyl 6-[({2-fluoro-4-[(2S)-tetrahydrofuran-2-ylmethoxy]phenyl}carbonyl)amino]-7-methyl-1H-indole-2-carboxylate 2-Fluoro-4-[(2S)-tetrahydrofuran-2-ylmethoxy]benzoic acid (0.997 g) obtained in Reference Example 15, oxalyl dichloride (0.508 mL) and N,N-dimethylformamide (0.10 mL) were mixed with tetrahydrofuran (50 mL), and the mixture was stirred at room temperature for 2 hr. The reaction mixture was concentrated under reduced pressure, and tetrahydrofuran (100 mL) was added to the concentrated residue. To this mixture was added a solution of ethyl 6-amino-7-methyl-1H-indole-2-carboxylate (0.88 g) obtained in Reference Example 57 and triethylamine (0.976 mL) in tetrahydrofuran (100 mL) at room temperature, and the mixture was stirred at room temperature overnight. Water was added to the reaction mixture, and the mixture was extracted with ethyl acetate. The organic layer was washed with saturated brine, and dried over anhydrous magnesium sulfate, and the solvent was evaporated under reduced pressure to give the title compound (1.52 g, yield 86%) as colorless crystals.

$^1$H NMR (300 MHz, DMSO-$d_6$) δ: 1.35 (3H, t, J=7.2 Hz), 1.63-1.72 (1H, m), 1.81-1.93 (2H, m), 1.96-2.04 (1H, m), 2.44 (3H, s), 3.69 (1H, q, J=6.9 Hz), 3.79 (1H, q, J=6.9 Hz), 3.97-4.10 (2H, m), 4.13-4.19 (1H, m), 4.35 (2H, q, J=7.2 Hz), 6.89-6.99 (2H, m), 7.12-7.16 (2H, m), 7.46 (1H, d, J=8.4 Hz), 7.70 (1H, t, J=8.7 Hz), 9.68 (1H, d, J=2.1 Hz), 11.67 (1H, s).

Reference Example 61

2-fluoro-N-[2-(hydroxymethyl)-7-methyl-1H-indol-6-yl]-4-[(2S)-tetrahydrofuran-2-ylmethoxy]benzamide To a solution of ethyl 6-[({2-fluoro-4-[(2S)-tetrahydrofuran-2-ylmethoxy]phenyl}carbonyl)amino]-7-methyl-1H-indole-2-carboxylate (1.52 g) obtained in Reference Example 60 in tetrahydrofuran (150 mL) was added lithium aluminum hydride (3.5 mL, 2.0 M tetrahydrofuran solution) at 0° C., and the mixture was stirred at room temperature for 3 hr. To the reaction mixture was added sodium sulfate decahydrate, 1N aqueous hydrochloric acid solution was added, and the mixture was extracted with ethyl acetate. The organic layer was washed with aqueous sodium hydrogen carbonate solution and saturated brine, and dried over anhydrous magnesium sulfate, and the solvent was evaporated under reduced pressure to give the title compound (1.25 g, yield 91%) as pale-yellow crystals.

$^1$H NMR (300 MHz, DMSO-$d_6$) δ: 1.63-1.78 (1H, m), 1.83-1.90 (2H, m), 1.94-2.06 (1H, m), 2.36 (3H, s), 3.69 (1H, q, J=6.3 Hz), 3.79 (1H, q, J=6.3 Hz), 3.97-4.08 (2H, m), 4.09-4.18 (1H, m), 4.60 (1H, d, J=5.4 Hz), 5.15 (1H, t, J=5.7 Hz), 6.27 (1H, s), 6.84-6.97 (3H, m), 7.25 (1H, d, J=8.4 Hz), 7.68 (1H, t, J=8.7 Hz), 9.55 (1H, d, J=2.4 Hz), 10.89 (1H, s).

Reference Example 62

2-fluoro-N-(2-formyl-7-methyl-1H-indol-6-yl)-4-[(2S)-tetrahydrofuran-2-ylmethoxy]benzamide A solution of 2-fluoro-N-[2-(hydroxymethyl)-7-methyl-1H-indol-6-yl]-4-[(2S)-tetrahydrofuran-2-ylmethoxy]benzamide (1.2 g) obtained in Reference Example 61 and manganese dioxide (4.00 g) in tetrahydrofuran (220 mL) was stirred overnight at 40° C. The reaction mixture was filtered through celite, and the solvent was evaporated under reduced pressure to give the title compound (0.8 g, yield 67%) as brown crystals.

$^1$H NMR (300 MHz, DMSO-d$_6$) δ: 1.64-1.72 (1H, m), 1.85-1.92 (2H, m), 1.96-2.01 (1H, m), 2.42 (3H, s), 3.69 (1H, q, J=6.6 Hz), 3.79 (1H, q, J=6.6 Hz), 4.01-4.10 (2H, m), 4.15-4.19 (1H, m), 6.89-7.08 (3H, m), 7.39 (1H, s), 7.55 (1H, d, J=8.1 Hz), 7.70 (1H, t, J=8.1 Hz), 9.73 (1H, s), 9.82 (1H, s), 11.86 (1H, s).

Reference Example 63 ethyl 1,7-dimethyl-6-nitro-1H-indole-2-carboxylate

Ethyl 7-methyl-6-nitro-1H-indole-2-carboxylate (8.55 g) obtained in Reference Example 56 was dissolved in N,N-dimethylformamide (103 mL), and sodium hydride (in oil, 60%, 1.65 g) and methyl iodide (6.43 mL) were added at 0° C. The mixture was stirred at room temperature for 1.5 hr, diluted with ethyl acetate, washed with brine, dried over anhydrous magnesium sulfate, and concentrated under reduced pressure. The residue was purified by silica gel column chromatography [eluent; hexane:ethyl acetate=95:5 (volume ratio)→hexane:ethyl acetate=70:30 (volume ratio)], and concentrated under reduced pressure to give the title compound (8.85 g, yield 98%) as a yellow solid.

$^1$H NMR (300 MHz, DMSO-d$_6$) δ: 1.34 (3H, t, J=7.2 Hz), 2.80 (3H, s), 4.30-4.40 (5H, m), 7.35 (1H, s), 7.52 (1H, d, J=8.7 Hz), 7.69 (1H, d, J=8.7 Hz).

Reference Example 64 ethyl 6-amino-1,7-dimethyl-1H-indole-2-carboxylate

Ethyl 1,7-dimethyl-6-nitro-1H-indole-2-carboxylate (8.85 g) obtained in Reference Example 63 and palladium on activated carbon (Pd: 10%, 50% water wet, 885 mg) were mixed with ethyl acetate (120 mL), and the mixture was stirred under a hydrogen atmosphere (1 atm) at room temperature for 18 hr. The mixture was filtered through celite and the filtrate was concentrated under reduced pressure. The residue was purified by NH silica gel column chromatography [eluent; hexane:ethyl acetate=90:10 (volume ratio)→hexane:ethyl acetate=60:40 (volume ratio)], and concentrated under reduced pressure to give the title compound (7.11 g, yield 91%) as a yellow solid.

$^1$H NMR (300 MHz, DMSO-d$_6$) δ: 1.29 (3H, t, J=7.2 Hz), 2.40 (3H, s), 4.12 (3H, s), 4.24 (2H, q, J=6.9 Hz), 5.00 (2H, s), 6.59 (1H, d, J=8.7 Hz), 7.06 (1H, s), 7.17 (1H, d, J=8.7 Hz).

Reference Example 65

4-(cyclopropylmethoxy)-N-(2-formyl-1,7-dimethyl-1H-indol-6-yl)benzamide 4-(Cyclopropylmethoxy)benzoic acid (3.64 g) was dissolved in toluene (42 mL), thionyl chloride (2.07 mL) and N,N-dimethylformamide (141 µL) were added, and the mixture was stirred at 40° C. for 5 hr. After concentration under reduced pressure, the residue was diluted with NMP (28 mL), and a solution of ethyl 6-amino-1,3-dimethyl-1H-indole-2-carboxylate (4.00 g) obtained in Reference Example 64 and triethylamine (3.60 mL) in NMP (24 mL) was added at 0° C. The mixture was stirred at room temperature for 20 hr, and water was added at 0° C. The resulting solid was collected by filtration, washed with water and dried. The obtained solid was suspended in tetrahydrofuran (258 mL), and lithium aluminum hydride (43.0 mL, 2.0 M tetrahydrofuran solution) was added dropwise at 0° C. After completion of the dropwise addition, the mixture was stirred at room temperature for 2.5 hr. To the reaction mixture was gradually added sodium sulfate decahydrate at 0° C. until completion of bubbling, and the mixture was stirred at room temperature for 1 hr. The reaction mixture was filtered through celite, and the filtrate was concentrated under reduced pressure to the liquid volume of about 600 mL. Manganese dioxide (26.4 g) was added, and the mixture was heated under reflux for 20 hr. The reaction mixture was filtered through celite, and the filtrate was concentrated under reduced pressure. The residue was washed with a mixed solvent of ethyl acetate and hexane to give the title compound (4.93 g, yield 79%) as a pale-brown solid.

$^1$H NMR (300 MHz, DMSO-d$_6$) δ: 0.32-0.41 (2H, m), 0.55-0.65 (2H, m), 1.20-1.33 (1H, m), 2.57 (3H, s), 3.91 (2H, d, J=7.2 Hz), 4.33 (3H, s), 7.05 (3H, d, J=8.7 Hz), 7.43 (1H, s), 7.57 (1H, d, J=8.7 Hz), 7.98 (2H, d, J=8.7 Hz), 9.84 (1H, s), 9.97 (1H, s).

Reference Example 66

N-(2-formyl-1,7-dimethyl-1H-indol-6-yl)-4-[(2S)-tetrahydrofuran-2-ylmethoxy]benzamide 4-[(2S)-Tetrahydrofuran-2-ylmethoxy]benzoic acid (3.27 g) obtained in Reference Example 8 was dissolved in toluene (33 mL), thionyl chloride (1.60 mL) and N,N-dimethylformamide (100 µL) were added, and the mixture was stirred at 40° C. for 4 hr. After concentration under reduced pressure, the residue was diluted with NMP (22 mL), and a solution of ethyl 6-amino-1,7-dimethyl-1H-indole-2-carboxylate (3.08 g) obtained in Reference Example 64 and triethylamine (2.80 mL) in NMP (22 mL) was added at 0° C. The mixture was stirred at room temperature for 17 hr, and water was added. The resulting solid was collected by filtration, washed with water and dried. The obtained solid was suspended in tetrahydrofuran (265 mL), and lithium aluminum hydride (9.95 mL, 2.0 M tetrahydrofuran solution) was added dropwise at 0° C. After completion of the dropwise addition, the mixture was stirred at room temperature for 2 hr. To the reaction mixture was gradually added sodium sulfate decahydrate at 0° C. until completion of bubbling, and the mixture was stirred at room temperature for 1 hr. The reaction mixture was filtered through celite, and the filtrate was concentrated under reduced pressure. The residue and manganese dioxide (13.6 g) were suspended in tetrahydrofuran (398 mL), and the mixture was heated under reflux for 3 hr. The reaction mixture was filtered through celite, and the filtrate was concentrated under reduced pressure. The residue was washed with a mixed solvent of ethyl acetate and hexane to give the title compound (3.75 g, yield 72%) as a yellow solid.

$^1$H NMR (300 MHz, DMSO-d$_6$) δ: 1.63-2.11 (4H, m), 2.57 (3H, s), 3.65-3.74 (1H, m), 3.76-3.85 (1H, m), 3.96-4.10 (2H, m), 4.19 (1H, qd, J=6.6, 4.4 Hz), 4.33 (3H, s), 7.01-7.13 (3H, m), 7.43 (1H, s), 7.57 (1H, d, J=8.7 Hz), 7.99 (2H, d, J=8.7 Hz), 9.84 (1H, s), 9.98 (1H, s).

Reference Example 67 ethyl 6-[({2-fluoro-4-[(2S)-tetrahydrofuran-2-ylmethoxy]phenyl}carbonyl)amino]-1,7-dimethyl-1H-indole-2-carboxylate 2-Fluoro-4-[(2S)-tetrahydrofuran-2-ylmethoxy]benzoic acid (4.44 g) obtained in Reference Example 15, oxalyl dichloride (2.37 mL) and N,N-dimethylformamide (0.50 mL)

were mixed with tetrahydrofuran (200 mL), and the mixture was stirred at room temperature for 2 hr. The reaction mixture was concentrated under reduced pressure, and tetrahydrofuran (100 mL) was added to the concentrated residue. To the mixture was added a solution of ethyl 6-amino-1,7-dimethyl-1H-indole-2-carboxylate (4.19 g) obtained in Reference Example 64 and triethylamine (3.76 mL) in tetrahydrofuran (250 mL) at room temperature, and the mixture was stirred at room temperature overnight. Water was added to the reaction mixture, and the mixture was extracted with ethyl acetate. The organic layer was washed with saturated brine, and dried over anhydrous magnesium sulfate, and the solvent was evaporated under reduced pressure to give the title compound (7.95 g, yield 97%) as colorless crystals.

$^1$H NMR (300 MHz, DMSO-$d_6$) δ: 1.34 (3H, t, J=6.9 Hz), 1.63-1.72 (1H, m), 1.80-1.93 (2H, m), 1.96-2.04 (1H, m), 2.61 (3H, s), 3.69 (1H, q, J=7.2 Hz), 3.79 (1H, q, J=7.2 Hz), 3.97-4.10 (2H, m), 4.13-4.21 (1H, m), 4.27 (3H, s), 4.31 (2H, q, J=6.9 Hz), 6.89-7.07 (3H, m), 7.24 (1H, s), 7.47 (1H, d, J=8.4 Hz), 7.69 (1H, t, J=8.7 Hz), 9.81 (1H, s).

Reference Example 68

2-fluoro-N-[2-(hydroxymethyl)-1,7-dimethyl-1H-indol-6-yl]-4-[(2S)-tetrahydrofuran-2-ylmethoxy]benzamide To a solution of ethyl 6-[({2-fluoro-4-[(2S)-tetrahydrofuran-2-ylmethoxy]phenyl}carbonyl)amino]-1,7-dimethyl-1H-indole-2-carboxylate (7.95 g) obtained in Reference Example 67 in tetrahydrofuran (500 mL) was added lithium aluminum hydride (20 mL, 2.0 M tetrahydrofuran solution) at 0° C., and the mixture was stirred at room temperature for 3 hr. To the reaction mixture was added sodium sulfate decahydrate, 1N aqueous hydrochloric acid solution was added, and the mixture was extracted with ethyl acetate. The organic layer was washed with aqueous sodium hydrogen carbonate solution and saturated brine, and dried over anhydrous magnesium sulfate, and the solvent was evaporated under reduced pressure to give the title compound (6.5 g, yield 90%) as pale-yellow crystals.

$^1$H NMR (300 MHz, DMSO-$d_6$) δ: 1.64-1.72 (1H, m), 1.83-1.93 (2H, m), 1.96-2.05 (1H, m), 2.59 (3H, s), 3.69 (1H, q, J=6.9 Hz), 3.79 (1H, q, J=6.9 Hz), 3.99 (3H, s), 4.03-4.10 (2H, m), 4.13-4.19 (1H, m), 4.59 (1H, d, J=5.1 Hz), 5.21 (1H, t, J=5.7 Hz), 6.31 (1H, s), 6.87-6.98 (3H, m), 7.27 (1H, d, J=8.7 Hz), 7.68 (1H, t, J=8.7 Hz), 9.64 (1H, s).

Reference Example 69

2-fluoro-N-(2-formyl-1,7-dimethyl-1H-indol-6-yl)-4-[(2S)-tetrahydrofuran-2-ylmethoxy]benzamide A solution of 2-fluoro-N-[2-(hydroxymethyl)-1,7-dimethyl-1H-indol-6-yl]-4-[(2S)-tetrahydrofuran-2-ylmethoxy]benzamide (6.5 g) obtained in Reference Example 68 and manganese dioxide (16.0 g) in tetrahydrofuran (300 mL) was stirred at 30° C. overnight. The reaction mixture was filtered through celite, and the solvent was evaporated under reduced pressure to give the title compound (5.07 g, yield 78%) as brown crystals.

$^1$H NMR (300 MHz, DMSO-$d_6$) δ: 1.63-1.72 (1H, m), 1.82-1.93 (2H, m), 1.97-2.05 (1H, m), 2.61 (3H, s), 3.69 (1H, q, J=6.6 Hz), 3.79 (1H, q, J=6.6 Hz), 3.98-4.10 (2H, m), 4.13-4.21 (1H, m), 4.33 (3H, s), 6.90-7.00 (2H, m), 7.11 (1H, d, J=8.7 Hz), 7.42 (1H, s), 7.56 (1H, t, J=8.7 Hz), 7.69 (1H, t, J=8.4 Hz), 9.83 (1H, s), 9.86 (1H, s).

Reference Example 70 ethyl 6-{[(4-bromophenyl)carbonyl]amino}-1,7-dimethyl-1H-indole-2-carboxylate Ethyl 6-amino-1,7-dimethyl-1H-indole-2-carboxylate (4.43 g) obtained in Reference Example 64 and triethylamine (3.18 mL) were dissolved in NMP (57 mL), and 4-bromobenzoyl chloride (4.60 g) was added at 0° C. The mixture was stirred at room temperature for 3 days, and water was added. The resulting solid was collected by filtration, washed with water, and dried to give a crude product (8.09 g) of the title compound as a pale-brown solid.

$^1$H NMR (300 MHz, DMSO-$d_6$) δ: 1.34 (3H, t, J=7.2 Hz), 2.58 (3H, s), 4.24-4.38 (5H, m), 7.01 (1H, d, J=8.3 Hz), 7.25 (1H, s), 7.50 (1H, d, J=8.3 Hz), 7.75 (2H, d, J=8.7 Hz), 7.96 (2H, d, J=8.3 Hz), 10.19 (1H, s).

Reference Example 71

4-bromo-N-[2-(hydroxymethyl)-1,7-dimethyl-1H-indol-6-yl]benzamide

The crude product (7.69 g) of ethyl 6-{[(4-bromophenyl)carbonyl]amino}-1,7-dimethyl-1H-indole-2-carboxylate obtained in Reference Example 70 and lithium borohydride (3.76 g) were suspended in tetrahydrofuran (1.4 L), and the mixture was stirred at 40° C. for 14 hr. A saturated aqueous ammonium chloride solution was added at 0° C., and the organic layer was washed with brine, dried over anhydrous magnesium sulfate, and concentrated under reduced pressure to give a crude product (7.60 g) of the title compound as a pale-yellow solid.

$^1$H NMR (300 MHz, DMSO-$d_6$) δ: 2.55 (3H, s), 3.99 (3H, s), 4.60 (2H, d, J=5.5 Hz), 5.21 (1H, t, J=5.5 Hz), 6.31 (1H, s), 6.84 (1H, d, J=8.2 Hz), 7.28 (1H, d, J=8.2 Hz), 7.73 (2H, d, J=8.2 Hz), 7.95 (2H, d, J=8.5 Hz), 10.03 (1H, s).

Reference Example 72

4-bromo-N-(2-formyl-1,7-dimethyl-1H-indol-6-yl)benzamide

The crude product (7.69 g) of 4-bromo-N-[2-(hydroxymethyl)-1,7-dimethyl-1H-indol-6-yl]benzamide obtained in Reference Example 71 and manganese dioxide (18.9 g) were suspended in tetrahydrofuran (800 mL), and the mixture was stirred at room temperature for 18 hr and heated under reflux for 6 hr. The reaction mixture was filtered through celite, and the filtrate was concentrated under reduced pressure. The residue was washed with a mixed solvent of ethyl acetate and hexane to give the title compound (6.23 g, yield 91%, 3 steps) as a brown solid.

$^1$H NMR (300 MHz, DMSO-$d_6$) δ: 2.58 (3H, s), 4.34 (3H, s), 7.06 (1H, d, J=8.7 Hz), 7.44 (1H, s), 7.59 (1H, d, J=8.7 Hz), 7.76 (2H, d, J=8.3 Hz), 7.96 (2H, d, J=8.7 Hz), 9.85 (1H, s), 10.22 (1H, s).

Reference Example 73

4-bromo-N-(1,7-dimethyl-2-{[(2-methylpropyl)amino]methyl}-1H-indol-6-yl)benzamide 4-Bromo-N-(2-formyl-1,7-dimethyl-1H-indol-6-yl)benzamide (2.00 g) obtained in Reference Example 72, 2-methylpropan-1-amine (803 μL) and acetic acid (10.8 mL) were added to N,N-dimethylacetamide (30 mL), and the mixture was stirred at room temperature for 1 hr. Sodium triacetoxyborohydride (2.28 g) was added, and the mixture was stirred at room temperature for 13 hr. The reaction mixture was cooled to 0° C., and 8N aqueous sodium hydroxide solution (27.0 mL) was added dropwise. Water was added and the resulting solid was collected by filtration, washed with water, and dried to give the title compound (2.17 g, yield 94%) as a yellow solid.

$^1$H NMR (300 MHz, DMSO-$d_6$) δ: 0.94 (6H, d, J=6.3 Hz), 1.82-1.99 (1H, m), 2.56 (3H, s), 2.72 (2H, brs), 4.00 (3H, s), 4.22 (2H, brs), 6.55 (1H, brs), 6.84-6.93 (1H, m), 7.34 (1H, d, J=8.0 Hz), 7.74 (2H, d, J=8.2 Hz), 7.94 (2H, d, J=8.5 Hz), 10.08 (1H, s).

Reference Example 74

4-bromo-N-(2-{[(2,2-dimethylpropyl)amino]methyl}-1,7-dimethyl-1H-indol-6-yl)benzamide 4-Bromo-N-(2-formyl-1,7-dimethyl-1H-indol-6-yl)benzamide (2.00 g) obtained in Reference Example 72, 2,2-dimethylpropan-1-amine (952 μL) and acetic acid (10.8 mL) were added to N,N-dimethylacetamide (60 mL), and the mixture was stirred at room temperature for 1 hr. Sodium triacetoxyborohydride (2.28 g) was added, and the mixture was stirred at room temperature for 13 hr. The reaction mixture was cooled to 0° C., and 8N aqueous sodium hydroxide solution (27.0 mL) was added dropwise. Water so was added and the resulting solid was collected by filtration, washed with water, and dried to give the title compound (2.12 g, yield 89%) as a yellow solid.

$^1$H NMR (300 MHz, DMSO-$d_6$) δ: 0.87 (9H, s), 2.32 (2H, brs), 2.54 (3H, s), 3.84 (2H, s), 4.01 (3H, s), 6.28 (1H, s), 6.82 (1H, d, J=8.2 Hz), 7.25 (1H, d, J=8.2 Hz), 7.72 (2H, d, J=8.5 Hz), 7.94 (2H, d, J=8.5 Hz), 10.01 (1H, s).

Reference Example 75

4-bromo-N-(1,7-dimethyl-2-{[(tetrahydro-2H-pyran-4-ylmethyl)amino]methyl}-1H-indol-6-yl)benzamide 4-Bromo-N-(2-formyl-1,7-dimethyl-1H-indol-6-yl)benzamide (2.00 g) obtained in Reference Example 72, 1-(tetrahydro-2H-pyran-4-yl)methanamine (931 mg) and acetic acid (10.8 mL) were added to N,N-dimethylacetamide (30 mL), and the mixture was stirred at room temperature for 1 hr. Sodium triacetoxyborohydride (2.28 g) was added, and the mixture was stirred at room temperature for 13 hr. The reaction mixture was cooled to 0° C. and 8N aqueous sodium hydroxide solution (27.0 mL) was added dropwise. Water was added, and the resulting solid was collected by filtration, washed with water and dried to give the title compound (2.25 g, yield 89%) as a yellow solid.

$^1$H NMR (300 MHz, DMSO-$d_6$) δ: 1.04-1.24 (2H, m), 1.52-1.71 (3H, m), 2.44 (2H, d, J=6.9 Hz), 2.54 (3H, s), 3.21-3.30 (2H, m), 3.78-3.87 (4H, m), 3.99 (3H, s), 6.28 (1H, s), 6.82 (1H, d, J=8.0 Hz), 7.25 (1H, d, J=8.0 Hz), 7.73 (2H, d, J=8.2 Hz), 7.94 (2H, d, J=8.2 Hz), 10.02 (1H, s).

Reference Example 76 ethyl 2-[(2-methyl-3-nitrophenyl)hydrazono]butanoate

2-Methyl-3-nitroaniline (24.0 g) was suspended in a mixed solvent of acetonitrile (36 mL) and 2N aqueous hydrochloric acid solution (139 mL), and the mixture was cooled to −20° C. Sodium nitrite (13.1 g) was dissolved in water (24 mL), and added dropwise thereto at the same temperature. After stirring for 30 min, the mixture was filtered through celite. Ethyl 2-ethylacetoacetate (25.0 g) and potassium hydroxide (25.0 g) were dissolved in a mixed solvent of water (168 mL) and ethanol (168 mL), and the above-mentioned filtrate was added dropwise at −20° C. The mixture was stirred at the same temperature for 10 min, 6N aqueous hydrochloric acid solution (50 mL) was added, and the mixture was stirred at 0° C. for 1 hr. The resulting solid was collected by filtration, dissolved in ethyl acetate, washed with water, dried over anhydrous sodium sulfate, and concentrated under reduced pressure to give the title compound (20.8 g, yield 47%) as a red solid.

$^1$H NMR (300 MHz, DMSO-$d_6$) δ: 1.02-1.35 (6H, m), 2.24 (1.5H, s), 2.33 (1.5H, s), 2.48-2.75 (2H, m), 4.08-4.35 (3H, m), 7.36-7.80 (3H, m), 9.15 (0.5H, s), 12.12 (0.5H, s).

Reference Example 77 ethyl 3,7-dimethyl-6-nitro-1H-indole-2-carboxylate p-Toluenesulfonic acid monohydrate (15.6 g) was suspended in toluene (300 mL), and the suspension was subjected to azeotropic distillation dehydration for 2 hr. A solution of ethyl 2-[(2-methyl-3-nitrophenyl)hydrazono]butanoate (20.8 g) obtained in Reference Example 76 in toluene (50 mL) was added at 85° C., and the mixture was stirred at the same temperature for 18 hr. Saturated aqueous sodium hydrogen carbonate solution was added, and the mixture was extracted with ethyl acetate. The organic layer was washed with saturated brine, dried over anhydrous sodium sulfate, and concentrated under reduced pressure. The residue was washed with a mixed solvent of ethyl acetate and hexane to give the title compound (12.8 g, yield 66%) as a brown solid.

$^1$H NMR (300 MHz, DMSO-$d_6$) δ: 1.38 (3H, t, J=7.0 Hz), 2.55 (3H, s), 2.75 (3H, s), 4.39 (2H, q, J=7.0 Hz), 7.65 (1H, d, J=8.8 Hz), 7.70 (1H, d, J=8.8 Hz), 11.95 (1H, s).

Reference Example 78 ethyl 6-amino-3,7-dimethyl-1H-indole-2-carboxylate

Ethyl 3,7-dimethyl-6-nitro-1H-indole-2-carboxylate (2.75 g) obtained in Reference Example 77 and palladium on activated carbon (Pd: 10%, 50% water wet, 275 mg) were suspended in tetrahydrofuran (250 mL), and under a hydrogen atmosphere (1 atm), the suspension was stirred at room temperature for 1 week. The mixture was filtered through celite, and the filtrate was concentrated under reduced pressure. The residue was purified by NH silica gel column chromatography [eluent; hexane:ethyl acetate=90:10 (volume ratio)→hexane:ethyl acetate=0:100 (volume ratio)], and concentrated under reduced pressure to give the title compound (1.93 g, yield 79%) as a brown solid.

$^1$H NMR (300 MHz, DMSO-$d_6$) δ: 1.33 (3H, t, J=7.2 Hz), 2.19 (3H, s), 2.41-2.47 (3H, m), 4.29 (2H, q, J=7.1 Hz), 4.86 (2H, s), 6.54 (1H, d, J=8.7 Hz), 7.16 (1H, d, J=8.7 Hz), 10.42 (1H, s).

Reference Example 79

N-(2-formyl-3,7-dimethyl-1H-indol-6-yl)-4-[(2S)-tetrahydrofuran-2-ylmethoxy]benzamide Ethyl 6-amino-3,7-dimethyl-1H-indole-2-carboxylate (645 mg) obtained in Reference Example 78 and 4-[(2S)- tetrahydrofuran-2-ylmethoxy]benzoic acid (618 mg) obtained in Reference Example 8 were dissolved in N,N-dimethylformamide (19 mL), 1-hydroxybenzotriazole (450 mg), 1-ethyl-3-(3-dimethylaminopropyl)carbodiimide hydrochloride (638 mg) and N,N-dimethylaminopyridine (340 mg) were added at room temperature, and the mixture was stirred for 6 days. Water was added at 0° C., and the mixture was extracted with ethyl acetate. The organic layer was washed with 1N aqueous hydrochloric acid solution, saturated aqueous sodium hydrogen carbonate solution and saturated brine, dried over anhydrous sodium sulfate, and concentrated under reduced pressure. The residue was suspended in tetrahydrofuran (50 mL), and lithium aluminum hydride (6.26 mL, 2.0 M tetrahydrofuran solution) was added dropwise at 0° C. After completion of the dropwise addition, the mixture was stirred at room temperature for 4.3 hr. To the reaction mixture was gradually added sodium sulfate decahydrate at 0° C. until completion of bubbling, and the mixture was stirred at room temperature for 17 hr. The reaction mixture was filtered through celite, and the filtrate was concentrated under reduced pressure. The residue and manganese dioxide (2.84 g) were suspended in tetrahydrofuran (167 mL), and the mixture was heated under reflux for 7 hr. The reaction mixture was filtered through celite, and the filtrate was concentrated under reduced pressure. The residue was washed with a mixed solvent of ethyl acetate and hexane to give the title compound (521 mg, yield 48%) as a pale-brown solid.

$^1$H NMR (300 MHz, DMSO-$d_6$) δ: 1.60-2.07 (4H, m), 2.35 (3H, s), 2.59 (3H, s), 3.63-3.85 (2H, m), 3.94-4.10 (2H, m), 4.12-4.22 (1H, m), 7.02-7.07 (3H, m), 7.52 (1H, d, J=8.2 Hz), 7.96 (2H, d, J=8.8 Hz), 9.85 (1H, s), 10.01 (1H, s), 11.45 (1H, s).

Reference Example 80 ethyl 6-[({2-fluoro-4-[(2S)-tetrahydrofuran-2-ylmethoxy]phenyl}carbonyl)amino]-3,7-dimethyl-1H-indole-2-carboxylate 2-Fluoro-4-[(2S)-tetrahydrofuran-2-ylmethoxy]benzoic acid (1.35 g) obtained in Reference Example 15, oxalyl dichloride (0.711 mL) and N,N-dimethylformamide (0.10 mL) were mixed with tetrahydrofuran (100 mL), and the mixture was stirred at room temperature for 2 hr. The reaction mixture was concentrated under reduced pressure, and to the concentrated residue was added tetrahydrofuran (100 mL). To the mixture was added a solution of ethyl 6-amino-3,7-dimethyl-1H-indole-2-carboxylate (1.29 g) obtained in Reference Example 78 and triethylamine (1.39 mL) in tetrahydrofuran (100 mL) at room temperature, and the mixture was stirred at room temperature overnight. Water was added to the reaction mixture, and the mixture was extracted with ethyl acetate. The organic layer was washed with saturated brine, and dried over anhydrous magnesium sulfate, and the solvent was evaporated under reduced pressure to give the title compound (2.15 g, yield 85%) as colorless crystals.

$^1$H NMR (300 MHz, DMSO-$d_6$) δ: 1.37 (3H, t, J=7.2 Hz), 1.66-1.70 (1H, m), 1.86-1.90 (2H, m), 1.96-2.00 (1H, m), 2.42 (3H, s), 2.53 (3H, s), 3.69 (1H, q, J=6.6 Hz), 3.79 (1H, q, J=6.6 Hz), 4.01-4.07 (2H, m), 4.14-4.18 (1H, m), 4.36 (2H, q, J=7.2 Hz), 6.89-6.99 (2H, m), 7.13 (1H, d, J=8.7 Hz), 7.46 (1H, d, J=8.4 Hz), 7.68 (1H, t, J=8.4 Hz), 9.66 (1H, s), 11.19 (1H, s).

Reference Example 81

2-fluoro-N-[2-(hydroxymethyl)-3,7-dimethyl-1H-indol-6-yl]-4-[(2S)-tetrahydrofuran-2-ylmethoxy]benzamide To a solution of ethyl 6-[({2-fluoro-4-[(2S)-tetrahydrofuran-2-ylmethoxy]phenyl}carbonyl)amino]-3,7-dimethyl-1H-indole-2-carboxylate (2.15 g) obtained in Reference Example 80 in tetrahydrofuran (150 mL) was added lithium aluminum hydride (15.0 mL, 2.0 M tetrahydrofuran solution) at 0° C., and the mixture was stirred at room temperature for 3 hr. To the reaction mixture were added sodium sulfate decahydrate, then 1N aqueous hydrochloric acid solution, and the mixture was extracted with ethyl acetate. The organic layer was washed with aqueous sodium hydrogen carbonate solution and saturated brine, and dried over anhydrous magnesium sulfate, and the solvent was evaporated under reduced pressure to give the title compound (1.7 g, yield 87%) as colorless crystals.

$^1$H NMR (300 MHz, DMSO-$d_6$) δ: 1.66-1.78 (1H, m), 1.83-1.90 (2H, m), 1.93-2.00 (1H, m), 2.22 (3H, s), 2.35 (3H, s), 3.69 (1H, q, J=6.6 Hz), 3.79 (1H, q, J=6.6 Hz), 3.99-4.09 (2H, m), 4.15-4.17 (1H, m), 4.58 (1H, d, J=5.4 Hz), 4.97 (1H, t, J=5.4 Hz), 6.88-7.05 (3H, m), 7.23 (1H, d, J=8.7 Hz), 7.68 (1H, t, J=8.7 Hz), 9.54 (1H, s), 10.65 (1H, s).

Reference Example 82

2-fluoro-N-(2-formyl-3,7-dimethyl-1H-indol-6-yl)-4-[(2S)-tetrahydrofuran-2-ylmethoxy]benzamide A solution of 2-fluoro-N-[2-(hydroxymethyl)-3,7-dimethyl-1H-indol-6-yl]-4-[(2S)-tetrahydrofuran-2-ylmethoxy]benzamide (1.7 g) obtained in Reference Example 81 and manganese dioxide (7.00 g) in tetrahydrofuran (220 mL) was stirred at room temperature overnight. The reaction mixture was filtered through celite, and the solvent was evaporated under reduced pressure to give the title compound (1.15 g, yield 68%) as pale-brown crystals.

$^1$H NMR (300 MHz, DMSO-$d_6$) δ: 1.63-1.72 (1H, m), 1.83-1.90 (2H, m), 1.96-2.02 (1H, m), 2.40 (3H, s), 2.59 (3H, s), 3.69 (1H, q, J=6.6 Hz), 3.79 (1H, q, J=6.6 Hz), 3.97-4.10 (2H, m), 4.15-4.19 (1H, m), 6.89-7.07 (3H, m), 7.53 (1H, d, J=6.1 Hz), 7.70 (1H, d, J=8.1 Hz), 9.71 (1H, s), 10.02 (1H, s), 11.47 (1H, s).

Reference Example 83

N-(2-fluoro-3-nitrophenyl)-4-[(2S)-tetrahydrofuran-2-ylmethoxy]benzamide

4-[(2S)-Tetrahydrofuran-2-ylmethoxy]benzoic acid (7.83 g) obtained in Reference Example 8 was dissolved in toluene (50 mL), thionyl chloride (3.51 mL) and a catalytic amount of DMF were added, and the mixture was stirred at 50° C. for 3 hr. The reaction mixture was concentrated under reduced pressure to give acid chloride. To a solution of 2-fluoro-3-nitroaniline (5.00 g) and triethylamine (6.70 mL) in NMP (50 mL) was added dropwise at 5° C. a solution of acid chloride prepared earlier in NMP (50 mL), and the mixture was stirred at room temperature for 3 days. The reaction mixture was diluted with ethyl acetate and successively washed with aqueous sodium hydrogen carbonate solution, 0.3N hydrochloric acid and aqueous sodium hydrogen carbonate solution. The solvent was evaporated under reduced pressure and the obtained crude product was washed with diisopropyl ether-ethyl acetate to give the title compound (6.74 g, yield 58%) as a brown solid.

$^1$H NMR (300 MHz, DMSO-d$_6$) δ: 1.62-2.08 (4H, m), 3.64-3.85 (2H, m), 3.97-4.11 (2H, m), 4.13-4.24 (1H, m), 7.07-7.13 (2H, m), 7.46 (1H, td, J=8.3, 1.5 Hz), 7.94-8.03 (4H, m), 10.31 (1H, s).

Reference Example 84 ethyl (2E)-2-{[2-fluoro-3-({4-[(2S)-tetrahydrofuran-2-ylmethoxy]benzoyl}amino)phenyl]hydrazono}butanoate To a solution of N-(2-fluoro-3-nitrophenyl)-4-[(2S)-tetrahydrofuran-2-ylmethoxy]benzamide (6.74 g) obtained in Reference Example 83 in THF (250 mL) was added 10% palladium carbon (50% water wet, 796 mg), and the mixture was stirred under a hydrogen atmosphere (balloon) at room temperature for 15 hr. The insoluble material was filtered off and washed with THF. The filtrate was concentrated under reduced pressure. The residue was dissolved in acetonitrile (20 mL) and 2N hydrochloric acid (23.3 mL), and an aqueous solution (3 mL) of sodium nitrite (1.55 g) were added dropwise at −20° C. over 30 min. The insoluble material was filtered off, and washed with water. To an aqueous solution (20 mL) of ethyl 2-ethylacetoacetate (2.96 g) and potassium hydroxide (3.67 g) was added dropwise the above filtrate at −20° C. After stirring for 10 min, 6N hydrochloric acid (5.92 mL) was added dropwise, and the mixture was stirred at 0° C. for 1 hr. The precipitate was collected by filtration, and washed with water. This was dissolved in acetonitrile, and dried over sodium sulfate. The solvent was evaporated under reduced pressure to give the title compound (7.34 g, yield 86%) as a red solid.

$^1$H NMR (300 MHz, DMSO-d$_6$) δ: 1.02 (3H, t, J=7.4 Hz), 1.28 (3H, so t, J=7.0 Hz), 1.61-2.09 (4H, m), 2.70 (2H, q, J=7.6 Hz), 3.65-3.84 (2H, m), 3.97-4.33 (5H, m), 7.04-7.18 (4H, m), 7.35 (1H, td, J=7.6, 1.9 Hz), 7.96 (2H, d, J=9.1 Hz), 9.55 (1H, s), 9.95 (1H, s).

Reference Example 85 ethyl 7-fluoro-3-methyl-6-({4-[(2S)-tetrahydrofuran-2-ylmethoxy]benzoyl}amino)-1H-indole-2-carboxylate p-Toluenesulfonic acid (3.36 g) was dissolved in toluene (100 mL), and subjected to azeotropic distillation dehydration for 2 hr. After cooling to 100° C., a solution of ethyl (2E)-2-{[2-fluoro-3-({4-[(2S)-tetrahydrofuran-2-ylmethoxy]benzoyl}amino)phenyl]hydrazono}butanoate (7.34 g) obtained in Reference Example 84 in toluene (50 mL) was added dropwise, and the mixture was refluxed for 2 hr. After cooling to room temperature, aqueous sodium hydrogen carbonate solution and ethyl acetate were added. The precipitate was collected by filtration, washed with ethyl acetate-toluene, and dried. The filtrate was purified by silica gel column chromatography [eluent; hexane:ethyl acetate=4:1→hexane:ethyl acetate=3:2 (volume ratio)], and the object fraction and the precipitate were combined to give the title compound (2.61 g, yield 36%) as a pink solid.

$^1$H NMR (300 MHz, DMSO-d$_6$) δ: 1.36 (3H, t, J=7.1 Hz), 1.62-2.09 (4H, m), 2.54 (3H, s), 3.64-3.84 (2H, m), 3.96-4.10 (2H, m), 4.14-4.23 (1H, m), 4.34 (2H, q, J=7.1 Hz), 7.06 (2H, d, J=8.8 Hz), 7.14 (1H, dd, J=8.5, 6.6 Hz), 7.45 (1H, d, J=8.8 Hz), 7.97 (2H, d, J=8.8 Hz), 10.00 (1H, s), 11.95 (1H, s).

Reference Example 86

N-(7-fluoro-2-formyl-3-methyl-1H-indol-6-yl)-4-[(2S)-tetrahydrofuran-2-ylmethoxy]benzamide To a solution of ethyl 7-fluoro-3-methyl-6-({4-[(2S)-tetrahydrofuran-2-ylmethoxy]benzoyl}amino)-1H-indole-2-carboxylate (1.20 g) obtained in Reference Example 85 in THF (50 mL) was added dropwise under ice-cooling 1 M lithium aluminum hydride THF solution (8.17 mL), and the mixture was stirred at room temperature for 2 hr. To the reaction mixture was added sodium sulfate decahydrate (2.63 g), and the mixture was stirred at room temperature for 30 min. The insoluble material was filtered off, and washed with THF (50 mL). To the filtrate was added manganese dioxide (2.79 g), and the mixture was stirred at 70° C. for 5 hr. The insoluble material was filtered off and washed with THF. The filtrate was concentrated under reduced pressure to dryness to give the title compound (860 mg, yield 72%) as a pale-brown solid.

$^1$H NMR (300 MHz, DMSO-d$_6$) δ: 1.62-2.09 (4H, m), 2.61 (3H, s), 3.65-3.85 (2H, m), 3.97-4.11 (2H, m), 4.13-4.24 (1H, m), 7.08 (2H, d, J=8.7 Hz), 7.20 (1H, dd, J=8.5, 6.2 Hz), 7.53 (1H, d, J=8.3 Hz), 7.99 (2H, d, J=8.7 Hz), 10.06 (2H, s), 12.11 (1H, s).

Reference Example 87 ethyl 1,3,7-trimethyl-6-nitro-1H-indole-2-carboxylate

Ethyl 3,7-dimethyl-6-nitro-1H-indole-2-carboxylate (7.00 g) obtained in Reference Example 77 was dissolved in N,N-dimethylformamide (80 mL), and sodium hydride (in oil, 60%, 1.26 g) and methyl iodide (4.98 mL) were added at 0° C. After stirring at room temperature for 1.5 hr, water was added at 0° C. The mixture was extracted with ethyl acetate, washed with brine, dried over anhydrous magnesium sulfate, and concentrated under reduced pressure. The residue was purified by silica gel column chromatography [eluent; hexane:ethyl acetate=95:5 (volume ratio)→hexane:ethyl acetate=70:30 (volume ratio)] and concentrated under reduced pressure to give the title compound (6.21 g, yield 84%) as a yellow solid.

$^1$H NMR (300 MHz, DMSO-d$_6$) δ: 1.37 (3H, t, J=7.0 Hz), 2.47 (3H, s), 2.78 (3H, s), 4.14 (3H, s), 4.38 (2H, q, J=7.1 Hz), 7.52 (1H, d, J=8.5 Hz), 7.69 (1H, d, J=8.8 Hz).

Reference Example 88 ethyl 6-amino-1,3,7-trimethyl-1H-indole-2-carboxylate

Ethyl 1,3,7-trimethyl-6-nitro-1H-indole-2-carboxylate (6.21 g) obtained in Reference Example 87 and palladium on activated carbon (Pd: 10%, 50% water wet, 620 mg) were mixed in a mixed solvent of ethanol (150 mL) and tetrahydrofuran (100 mL) and, under a hydrogen atmosphere (1 atm), the mixture was stirred at room temperature for 12 hr. The mixture was filtered through celite, and the filtrate was concentrated under reduced pressure to give the title compound (5.07 g, yield 92%) as a yellow solid.

¹H NMR (300 MHz, DMSO-d₆) δ: 1.32 (3H, t, J=7.1 Hz), 2.36 (3H, s), 2.38 (3H, s), 3.94 (3H, s), 4.27 (2H, q, J=7.0 Hz), 4.98 (2H, s), 6.58 (1H, d, J=8.5 Hz), 7.17 (1H, d, J=8.5 Hz).

Reference Example 89

N-[2-(hydroxymethyl)-1,3,7-trimethyl-1H-indol-6-yl]-4-[(2S)-tetrahydrofuran-2-ylmethoxy]benzamide 4-[(2S)-Tetrahydrofuran-2-ylmethoxy]benzoic acid (2.98 g) obtained in Reference Example 8 was dissolved in toluene (27 mL), thionyl chloride (1.47 mL) and N,N-dimethylformamide (100 μL) were added, and the mixture was stirred at 40° C. for 3 hr. After concentration under reduced pressure, the residue was diluted with NMP (9 mL), and a solution of ethyl 6-amino-1,3,7-trimethyl-1H-indole-2-carboxylate (3.00 g) obtained in Reference Example 88 and triethylamine (2.54 mL) in NMP (18 mL) was added at 0° C. After stirring at room temperature for 16 hr, water was added. The resulting solid was collected by filtration, washed with water, and dried. The obtained solid was suspended in tetrahydrofuran (444 mL), and lithium aluminum hydride (54.8 mL, 2.0 M tetrahydrofuran solution) was added dropwise at 0° C. After completion of the dropwise addition, the mixture was stirred at room temperature for 6 hr. To the reaction mixture was gradually added sodium sulfate decahydrate at 0° C. until completion of bubbling, and the mixture was stirred at room temperature for 1 hr. The reaction mixture was filtered through celite, and concentrated under reduced pressure to give the title compound (3.37 g, yield 68%) as a yellow solid.

¹H NMR (300 MHz, DMSO-d₆) δ: 1.63-2.09 (2H, m), 2.21 (3H, s), 2.54 (3H, s), 3.61-3.84 (2H, m), 3.94-4.07 (5H, m), 4.10-4.22 (1H, m), 4.28-4.41 (1H, m), 4.58 (2H, brs), 4.98-5.09 (1H, m), 6.82-6.87 (2H, m), 7.00-7.08 (2H, m), 7.25 (1H, d, J=9.1 Hz), 7.97 (2H, d, J=8.5 Hz), 9.81 (1H, s).

Reference Example 90

N-(2-formyl-1,3,7-trimethyl-1H-indol-6-yl)-4-[(2S)-tetrahydrofuran-2-ylmethoxy]benzamide To a solution of N-[2-(hydroxymethyl)-1,3,7-trimethyl-1H-indol-6-yl]-4-[(2S)-tetrahydrofuran-2-ylmethoxy]benzamide (3.37 g) obtained in Reference Example 89 in THF (400 mL) was added manganese dioxide (7.17 g), and the mixture was stirred at 80° C. for 24 hr. The insoluble material was filtered off and washed with THF. The filtrate was concentrated under reduced pressure and the obtained crude product was washed with diisopropyl ether-ethyl acetate to give the title compound (1.73 g, yield 51%) as a pale-brown solid.

¹H NMR (300 MHz, DMSO-d₆) δ: 1.62-2.09 (4H, m), 2.54 (3H, s), 2.57 (3H, s), 3.65-3.84 (2H, m), 3.96-4.11 (2H, m), 4.12-4.23 (1H, m), 4.25 (3H, s), 7.00-7.10 (3H, m), 7.55 (1H, d, J=8.2 Hz), 7.98 (2H, d, J=8.8 Hz), 9.98 (1H, s), 10.09 (1H, s).

Reference Example 91 ethyl 6-[({2-fluoro-4-[(2S)-tetrahydrofuran-2-ylmethoxy]phenyl}carbonyl)amino]-1,3,7-trimethyl-1H-indole-2-carboxylate 2-Fluoro-4-[(2S)-tetrahydrofuran-2-ylmethoxy]benzoic acid (1.97 g) obtained in Reference Example 15, oxalyl dichloride (1.02 mL) and N,N-dimethylformamide (0.20 mL) were mixed with tetrahydrofuran (100 mL), and the mixture was stirred at room temperature for 2 hr. The reaction mixture was concentrated under reduced pressure, and to the concentrated residue was added tetrahydrofuran (100 mL). To the mixture was added a solution of ethyl 6-amino-1,3,7-trimethyl-1H-indole-2-carboxylate (2.00 g) obtained in Reference Example 88 and triethylamine (1.67 mL) in tetrahydrofuran (120 mL) at room temperature, and the mixture was stirred at room temperature overnight. Water was added to the reaction mixture, and the mixture was extracted with ethyl acetate. The organic layer was washed with saturated brine, and dried over anhydrous magnesium sulfate, and the solvent was evaporated under reduced pressure to give the title compound (3.40 g, yield 89%) as colorless crystals.

¹H NMR (300 MHz, DMSO-d₆) δ: 1.37 (3H, t, J=7.2 Hz), 1.64-1.72 (1H, m), 1.82-1.93 (2H, m), 1.97-2.05 (1H, m), 2.47 (3H, s), 2.58 (3H, s), 3.69 (1H, q, J=6.9 Hz), 3.79 (1H, q, J=6.9 Hz), 3.88-4.07 (2H, m), 4.10 (3H, s), 4.16-4.19 (1H, m), 4.34 (2H, q, J=7.2 Hz), 6.89-7.09 (2H, m), 7.07 (1H, d, J=8.7 Hz), 7.48 (1H, d, J=8.4 Hz), 7.69 (1H, t, J=8.4 Hz), 9.80 (1H, s).

Reference Example 92

2-fluoro-N-[2-(hydroxymethyl)-1,3,7-trimethyl-1H-indol-6-yl]-4-[(2S)-tetrahydrofuran-2-ylmethoxy]benzamide To a solution of ethyl 6-[({2-fluoro-4-[(2S)-tetrahydrofuran-2-ylmethoxy]phenyl}carbonyl)amino]-1,3,7-trimethyl-1H-indole-2-carboxylate (3.37 g) obtained in Reference Example 91 in tetrahydrofuran (250 mL) was added lithium aluminum hydride (6 mL, 2.0 M tetrahydrofuran solution) at 0° C., and the mixture was stirred at room temperature for 3 hr. To the reaction mixture were added sodium sulfate decahydrate, and then 1N aqueous hydrochloric acid solution, and the mixture was extracted with ethyl acetate. The organic layer was washed with aqueous sodium hydrogen carbonate solution and saturated brine, and dried over anhydrous magnesium sulfate, and the solvent was evaporated under reduced pressure to give the title compound (2.90 g, yield 95%) as colorless crystals.

¹H NMR (300 MHz, DMSO-d₆) δ: 1.63-1.79 (1H, m), 1.83-1.90 (2H, m), 1.96-2.04 (1H, m), 2.21 (3H, s), 2.58 (3H, s), 3.69 (1H, q, J=6.9 Hz), 3.75-3.81 (2H, m), 3.98 (3H, s), 4.03-4.10 (2H, m), 4.13-4.19 (1H, m), 4.59 (2H, s), 6.88-6.98 (3H, m), 7.25 (1H, d, J=8.1 Hz), 7.68 (1H, t, J=8.4 Hz), 9.65 (1H, s).

Reference Example 93

2-fluoro-N-(2-formyl-1,3,7-trimethyl-1H-indol-6-yl)-4-[(2S)-tetrahydrofuran-2-ylmethoxy]benzamide A solution of 2-fluoro-N-[2-(hydroxymethyl)-1,3,7-trimethyl-1H-indol-6-yl]-4-[(2S)-tetrahydrofuran-2-ylmethoxy]benzamide (2.90 g) obtained in Reference Example 92 and manganese dioxide (8.00 g) in tetrahydrofuran (200 mL) was refluxed for 3 hr. The reaction mixture was filtered through celite, and the solvent was evaporated under reduced pressure to give the title compound (1.82 g, yield 63%) as colorless crystals.

¹H NMR (300 MHz, DMSO-d₆) δ: 1.63-1.72 (1H, m), 1.79-1.90 (2H, m), 1.93-2.07 (1H, m), 2.57 (3H, s), 2.58 (3H, s), 3.69 (1H, q, J=6.3 Hz), 3.79 (1H, q, J=6.9 Hz), 3.97-4.10 (2H, m), 4.13-4.21 (1H, m), 4.24 (3H, s), 6.88-6.99 (2H, m), 7.10 (1H, d, J=8.7 Hz), 7.55 (1H, d, J=8.7 Hz), 7.64-7.72 (1H, m), 9.85 (1H, s), 10.08 (1H, s).

Reference Example 94 ethyl 7-fluoro-1,3-dimethyl-6-({4-[(2S)-tetrahydro-furan-2-ylmethoxy]benzoyl}amino)-1H-indole-2-carboxylate To a solution of ethyl 7-fluoro-3-methyl-6-({4-[(2S)-tetrahydrofuran-2-ylmethoxy]benzoyl}amino)-1H-indole-2-carboxylate (1.00 g) obtained in Reference Example 85 in DMF (20 mL) was added sodium hydride (60% in oil, 95 mg) at 5° C., and the mixture was stirred at 5° C. for 1 hr. To the reaction mixture was added methyl iodide (354 mg), and the mixture was stirred at room temperature for 15 hr. To the reaction mixture was added ethyl acetate, and the mixture was washed twice with brine. The solvent was evaporated under reduced pressure, and the residue was purified by silica gel column chromatography [eluent; hexane:ethyl acetate=4:1→hexane:ethyl acetate=7:3 (volume ratio)] to give the title compound (359 mg, yield 34%) as a colorless solid.

$^1$H NMR (300 MHz, DMSO-$d_6$) δ: 1.37 (3H, t, J=7.1 Hz), 1.62-2.08 (4H, m), 2.51 (3H, s), 3.65-3.85 (2H, m), 3.96-4.23 (6H, m), 4.36 (2H, q, J=7.1 Hz), 7.06 (2H, d, J=8.5 Hz), 7.17 (1H, dd, J=8.5, 6.3 Hz), 7.48 (d, J=8.5 Hz, 1H), 7.97 (2H, d, J=8.5 Hz), 10.02 (1H, s).

Reference Example 95

N-(7-fluoro-2-formyl-1,3-dimethyl-1H-indol-6-yl)-4-[(2S)-tetrahydrofuran-2-ylmethoxy]benzamide To a solution of ethyl 7-fluoro-1,3-dimethyl-6-({4-[(2S)-tetrahydrofuran-2-ylmethoxy]benzoyl}amino)-1H-indole-2-carboxylate (359 mg) obtained in Reference Example 94 in THF (40 mL) was added dropwise 1 M lithium aluminum hydride THF solution (1.18 mL), and the mixture was stirred at room temperature for 3 days. To the reaction mixture was added sodium sulfate decahydrate (382 mg). The insoluble material was filtered off, to the filtrate was added manganese dioxide (808 mg), and the mixture was stirred at 80° C. for 2 hr. The insoluble material was filtered off, and the filtrate was concentrated under reduced pressure and the obtained crude product was washed with diisopropyl ether-ethyl acetate to give the title compound (198 mg, yield 61%) as a pale-yellow solid.

$^1$H NMR (300 MHz, DMSO-$d_6$) δ: 1.63-2.08 (4H, m), 2.60 (3H, s), 3.65-3.85 (2H, m), 3.95-4.11 (2H, m), 4.14-4.23 (4H, m), 7.08 (2H, d, J=9.0 Hz), 7.22 (1H, dd, J=8.7, 6.4 Hz), 7.56 (1H, d, J=8.3 Hz), 7.99 (2H, d, J=8.7 Hz), 10.08 (1H, s), 10.14 (1H, s).

Reference Example 96

2-methyl-2-(methylsulfonyl)propanenitrile

To a solution of methylsulfonylacetonitrile (25 g) and methyl iodide (27.4 mL) in N,N-dimethylformamide (300 mL) was added sodium hydride (20 g) at 0° C., and the mixture was stirred at room temperature overnight. Water was added to the reaction mixture, and the mixture was extracted with ethyl acetate. The organic layer was washed with saturated brine, and dried over anhydrous magnesium sulfate, and the solvent was evaporated under reduced pressure to give the title compound (18 g, yield 58%) as colorless crystals.

$^1$H NMR (300 MHz, CDCl$_3$) δ: 1.78 (6H, s), 3.14 (3H, s).

Reference Example 97

2-methyl-2-(methylsulfonyl)propan-1-amine hydrochloride

To a solution of 2-methyl-2-(methylsulfonyl)propanenitrile (18 g) obtained in Reference Example 96 in tetrahydrofuran (400 mL) was added lithium aluminum hydride (80 mL, 2.0 M tetrahydrofuran solution) at 0° C., and the mixture was stirred at 0° C. for 4 hr. To the reaction mixture was added sodium sulfate decahydrate at 0° C., and the mixture was filtered through celite. The solvent was evaporated under reduced pressure and the obtained residue was dissolved in ethyl acetate (200 mL). 4N Hydrochloric acid-ethyl acetate (40 mL) was added and the resulting crystals were filtered, and dried under reduced pressure to give the title compound (11.3 g, yield 49%) as colorless crystals.

$^1$H NMR (300 MHz, DMSO-$d_6$) δ: 1.40 (6H, s), 3.05 (3H, s), 3.15-3.23 (2H, m), 3.43 (3H, br).

Reference Example 98 trans-4-(dibenzylamino)cyclohexanol

To methanol (1 kg) were added trans-4-aminocyclohexanol (200 g), benzaldehyde (553 g) and 10% palladium carbon (20 g), and the mixture was stirred under a hydrogen atmosphere at 60° C. for 24 hr. After cooling to room temperature, the catalyst was filtered off and washed with methanol (400 g). The filtrate and washings were added dropwise to water (2 kg) at 50° C. After cooling to room temperature, the precipitate was collected by filtration, washed with water:methanol=2:1 (volume ratio, 400 g) and dried under reduced pressure to give the title compound (472 g, yield 92%) as a white solid.

Reference Example 99

4-(dibenzylamino)cyclohexanone trans-4-(Dibenzylamino)cyclohexanol (200 g) obtained in Reference Example 98 and diphosphorus pentoxide (173 g) were added to dichloromethane (1400 g). Dimethyl sulfoxide (106 g) was added at 0° C. and the mixture was stirred at the same temperature for 1 hr. Triethylamine (240 g) was added dropwise at 0° C., the mixture was stirred at the same temperature for 2 hr and water (600 g) was added dropwise. The mixture was partitioned, to the organic layer was added aqueous sodium hypochlorite solution (1000 g), and the mixture was stirred at room temperature for 40 min. 20% Sodium sulfite (800 g) was added, and the mixture was stirred for 20 min and partitioned. The organic layer was washed with 10% brine (1000 g). The organic layer was concentrated under reduced pressure to 1000 g. Methanol (1100 g) was added, and the mixture was concentrated under reduced pressure to 500 g, and water (1200 g) was added dropwise. After stirring at 0° C. for 30 min, the precipitate was collected by filtration, washed with water:methanol=2:1 (volume ratio, 800 g) and dried under reduced pressure to give the title compound (165 g, yield 83%) as pale-yellow crystals.

Reference Example 100 trans-4-(dibenzylamino)-1-methylcyclohexanol

Under a nitrogen stream, 0.31 M ethylaluminum bis(2,6-di-tert-butyl-4-methylphenoxide) toluene solution (6600 mL) was cooled to −78° C. 4-(Dibenzylamino)cyclohexanone (200 g) obtained in Reference Example 99 was dissolved in toluene (600 g) and added dropwise. Then, 1 M methyllithium diethyl ether solution (1363 mL) was added dropwise at −78° C., and the mixture was stirred at the same temperature for 2 hr. The temperature was raised to 0° C., and 30% aqueous Rochelle salt solution (6000 g) was added dropwise. After partitioning, the organic layer was washed with 30% aqueous Rochelle salt solution (4000 g). The organic layer was extracted with 6N hydrochloric acid (1000 g), and then with 6N hydrochloric acid (600 g). The aqueous layers were combined, and washed with toluene (1000 g). The aqueous layer was added dropwise to a mixture of toluene (2000 g) and 10N aqueous sodium hydroxide solution (1250 g). After partitioning, the organic layer was concentrated under reduced pressure to 1400 g. Heptane (2000 g) was added dropwise at 50° C. After cooling to 0° C., the mixture was stirred for 1 hr, the precipitate was collected by filtration, washed with heptane (400 g) and dried under reduced pressure to give the title compound (160 g, yield 76%) as a white solid.

Reference Example 101 trans-4-amino-1-methylcyclohexanol trans-4-(Dibenzylamino)-1-methylcyclohexanol (200 g) obtained in Reference Example 100 was added to methanol (2000 g). 4.5% Pd-0.5% Pt carbon powder (20 g) was added, and the mixture was stirred under a hydrogen atmosphere at room temperature for 18 hr. The catalyst was filtered off, and washed with methanol (400 g). The filtrate was concentrated under reduced pressure to 1920 g, ethyl acetate (1900 g) was added, and the mixture was concentrated under reduced pressure to 1700 g. Heptane (800 g) was added dropwise at 60° C., the mixture was cooled to 2° C., and stirred for 1 hr. The precipitated solid was collected by filtration, washed with heptane (400 g) and dried under reduced pressure to give the title compound (75 g, yield 90%) as a white solid.

$^1$H NMR (300 MHz, CDCl$_3$) δ: 1.18-1.87 (14H, m), 2.76-2.87 (1H, m).

Reference Example 102

2-nitro-N-(tetrahydro-2H-thiopyran-4-yl)benzenesulfonamide

To a suspension of tetrahydro-2H-thiopyran-4-amine hydrochloride (80.0 g) in THF (800 mL) were added triethylamine (239 mL) and 2-nitrobenzenesulfonyl chloride (126.9 g) under ice-cooling at an inside temperature of 2-24° C., and the mixture was stirred at room temperature for 23 hr. The reaction solution was partitioned and extracted with ethyl acetate and water, and the organic layer was washed with water and saturated brine, dried over magnesium sulfate, and concentrated under reduced pressure to the extent crystals do not precipitate and purified by silica gel column chromatography [eluent; hexane:ethyl acetate=50:50 (volume ratio)]. The obtained solid was washed with ethanol-diisopropyl ether (1:4), and dried under reduced pressure to give the title compound (145.6 g, yield 92%) as a pale-green solid.

$^1$H NMR (300 MHz, CDCl$_3$) δ: 1.60-1.77 (2H, m), 2.05-2.18 (2H, m), 2.54-2.70 (4H, m), 3.32-3.47 (1H, m), 5.29 (1H, d, J=7.6 Hz), 7.70-7.80 (2H, m), 7.84-7.92 (1H, m), 8.12-8.20 (1H, m).

Reference Example 103

N-(1,1-dioxidotetrahydro-2H-thiopyran-4-yl)-2-nitrobenzenesulfonamide

To a solution of 2-nitro-N-(tetrahydro-2H-thiopyran-4-yl)benzenesulfonamide (65.8 g) obtained in Reference Example 102 in acetone (2180 mL) was added dropwise an aqueous solution (871 mL) of oxone (174 g) at room temperature over 20 min. The reaction mixture was stirred at room temperature for 16 hr. To the reaction mixture was added an aqueous solution (729 mL) of sodium hydrogen carbonate (73.1 g). The solvent was evaporated under reduced pressure. To the residue were added water (1.60 L) and ethyl acetate (329 mL), and the mixture was vigorously stirred at room temperature for 1 hr. The precipitated solid was collected by filtration, washed with water, and dried under reduced pressure to give the title compound (64.4 g, yield 89%) as a colorless solid.

$^1$H NMR (300 MHz, DMSO-d$_6$) δ: 1.86-2.03 (4H, m), 2.98-3.25 (4H, m), 3.51-3.65 (1H, m), 7.83-8.08 (4H, m), 8.42 (1H, s).

Example 1

4-(cyclopropylmethoxy)-N-[2-({[(3-methyloxetan-3-yl)methyl]amino}methyl)-1H-indol-5-yl]benzamide

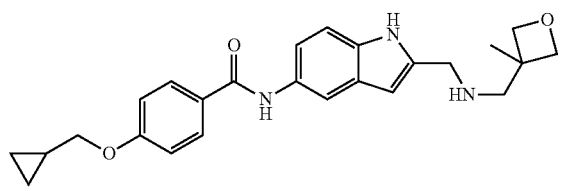 [SMILES: CC1(CNCc2cc3cc(NC(=O)c4ccc(OCC5CC5)cc4)ccc3[nH]2)COC1]

4-(Cyclopropylmethoxy)-N-(2-formyl-1H-indol-5-yl)benzamide (50 mg) obtained in Reference Example 2,1-(3-methyloxetan-3-yl)methanamine (30 mg) and acetic acid (200 μL) were dissolved in tetrahydrofuran (4 mL)-DMF (1 mL), and the mixture was stirred for 30 min. Sodium triacetoxyborohydride (165 mg) was added and the mixture was stirred at room temperature overnight. To the reaction mixture was added aqueous sodium hydrogen carbonate solution, and the mixture was extracted with ethyl acetate, and washed with saturated brine. The obtained organic layer was dried over anhydrous magnesium sulfate, and the solvent was evaporated under reduced pressure. The residue was purified by silica gel column chromatography [eluent; ethyl acetate:methanol=100:0 (volume ratio)→ethyl acetate:methanol=80:20 (volume ratio)] to give the title compound (40 mg, yield 64%) as a pale-yellow solid.

$^1$H NMR (300 MHz, DMSO-d$_6$) δ: 0.31-0.38 (2H, m), 0.55-0.63 (2H, m), 1.19-1.30 (5H, m), 2.66 (2H, s), 3.84 (2H, s), 3.90 (2H, d, J=7.2 Hz), 4.17 (2H, d, J=5.7 Hz), 4.35 (2H, d, J=5.7 Hz), 6.25 (1H, s), 7.03 (2H, d, J=9.1 Hz), 7.29 (2H, q, J=8.7 Hz), 7.85 (1H, s), 7.95 (2H, d, J=8.7 Hz), 9.86 (1H, s), 10.83 (1H, s).

melting point: 166-167° C.

elemental analysis ($C_{25}H_{29}N_3O_3$)

Calculated: C, 71.57; H, 6.97; N, 10.02.

Found: C, 71.26; H, 7.00; N, 9.99.

Example 2

4-(cyclopropylmethoxy)-N-(2-{[(2,2-dimethylpropyl)amino]methyl}-1H-indol-5-yl)benzamide

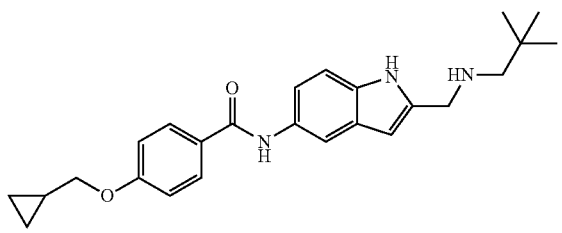 [SMILES: CC(C)(C)CNCc1cc2cc(NC(=O)c3ccc(OCC4CC4)cc3)ccc2[nH]1]

4-(Cyclopropylmethoxy)-N-(2-formyl-1H-indol-5-yl)benzamide (300 mg) obtained in Reference Example 2, 2,2-dimethylpropan-1-amine (211 µL) and acetic acid (1.79 mL) were added to N,N-dimethylacetamide (5.5 mL), and the mixture was stirred at room temperature for 1 hr. Sodium triacetoxyborohydride (379 mg) was added, and the mixture was stirred at room temperature for 17 hr. 8N Aqueous sodium hydroxide solution (4.49 mL) was added dropwise at 0° C. The mixture was extracted with ethyl acetate, washed with aqueous sodium hydrogen carbonate solution and brine, dried over anhydrous sodium sulfate, and concentrated under reduced pressure. The residue was purified by silica gel-NH silica gel serial column chromatography [eluent; hexane:ethyl acetate=30:70 (volume ratio)→hexane:ethyl acetate=0:100 (volume ratio)→ethyl acetate:methanol=100:0 (volume ratio)→ethyl acetate:methanol=90:10 (volume ratio)], and crystallized from ethyl acetate, diisopropyl ether and heptane to give the title compound (285 mg, yield 78%) as a yellow solid.

$^1$H NMR (300 MHz, DMSO-$d_6$) δ: 0.32-0.39 (2H, m), 0.54-0.63 (2H, m), 0.87 (9H, s), 1.20-1.31 (1H, m), 2.26 (2H, s), 3.80 (2H, s), 3.90 (2H, d, J=6.9 Hz), 6.21 (1H, d, J=1.1 Hz), 7.02 (2H, d, J=8.8 Hz), 7.21-7.32 (2H, m), 7.83 (1H, s), 7.93 (2H, d, J=8.8 Hz), 9.84 (1H, s), 10.79 (1H, s).

elemental analysis ($C_{25}H_{31}N_3O_2 \cdot 0.8H_2O$)
Calculated: C, 71.50; H, 7.82; N, 10.01.
Found: C, 71.60; H, 7.85; N, 9.77.

Example 3

4-(cyclopropylmethoxy)-N-(2-{[(tetrahydro-2H-pyran-4-ylmethyl)amino]methyl}-1H-indol-5-yl)benzamide

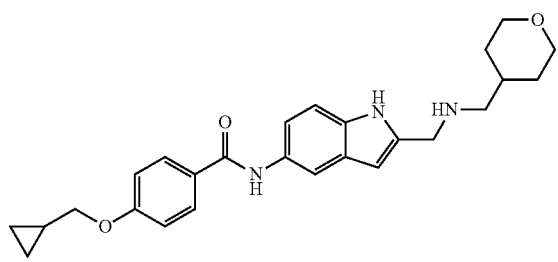 [SMILES: O=C(Nc1ccc2[nH]c(CNCC3CCOCC3)cc2c1)c1ccc(OCC2CC2)cc1]

4-(Cyclopropylmethoxy)-N-(2-formyl-1H-indol-5-yl)benzamide (300 mg) obtained in Reference Example 2, 1-(tetrahydro-2H-pyran-4-yl)methanamine (206 mg) and acetic acid (1.79 mL) were added to N,N-dimethylacetamide (5.5 mL), and the mixture was stirred at room temperature for 1 hr. Sodium triacetoxyborohydride (379 mg) was added, and the mixture was stirred at room temperature for 17 hr. 8N Aqueous sodium hydroxide solution (4.49 mL) was added dropwise at 0° C. The mixture was extracted with ethyl acetate, washed with aqueous sodium hydrogen carbonate solution and brine, dried over anhydrous sodium sulfate, and concentrated under reduced pressure. The residue was purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (316 mg, yield 81%) as a yellow solid.

$^1$H NMR (300 MHz, DMSO-$d_6$) δ: 0.31-0.39 (2H, m), 0.59 (2H, dd, J=7.8, 1.8 Hz), 1.04-1.30 (4H, m), 1.54-1.69 (3H, m), 2.40 (2H, d, J=6.0 Hz), 3.21-3.30 (2H, m), 3.77-3.86 (4H, m), 3.90 (2H, d, J=7.1 Hz), 6.22 (1H, s), 7.02 (2H, d, J=8.8 Hz), 7.24 (1H, d, J=8.8 Hz), 7.29 (1H, dd, J=9.1, 1.9 Hz), 7.83 (1H, s), 7.94 (2H, d, J=8.8 Hz), 9.84 (1H, s), 10.81 (1H, s).

melting point: 160° C.
elemental analysis ($C_{26}H_{31}N_3O_3 \cdot 0.35H_2O$)
Calculated: C, 71.00; H, 7.26; N, 9.55.
Found: C, 71.28; H, 7.21; N, 9.30.

Example 4

4-(cyclopropylmethoxy)-N-[1-methyl-2-({[(3-methyloxetan-3-yl)methyl]amino}methyl)-1H-indol-5-yl]benzamide 4-(Cyclopropylmethoxy)-N-(2-formyl-1-methyl-1H-indol-5-yl)benzamide (300 mg) obtained in Reference Example 4 and 1-(3-methyloxetan-3-yl)methanamine (130 mg) were suspended in NMP (3.0 mL), acetic acid (1.0 mL) was added at room temperature, and the mixture was stirred at the same temperature for 1.5 hr. Sodium triacetoxyborohydride (629 mg) was added, the mixture was stirred at room temperature for 3.5 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=100:0 (volume ratio)→ethyl acetate:methanol=90:10 (volume ratio)] and the obtained solid was recrystallized from ethyl acetate to give the title compound (323 mg, yield 87%) as a white solid.

$^1$H NMR (300 MHz, CDCl$_3$) δ: 0.34-0.42 (2H, m), 0.62-0.72 (2H, m), 1.23-1.38 (4H, m), 2.87 (2H, s), 3.79 (3H, s), 3.87 (2H, d, J=6.8 Hz), 3.97 (2H, s), 4.36 (2H, d, J=5.7 Hz), 4.47 (2H, d, J=5.7 Hz), 6.37 (1H, s), 6.97 (2H, d, J=9.1 Hz), 7.23-7.29 (1H, m), 7.29-7.36 (1H, m), 7.75 (1H, s), 7.81-7.92 (3H, m).

melting point: 154-155° C.
elemental analysis ($C_{26}H_{31}N_3O_3$)

Calculated: C, 72.03; H, 7.21; N, 9.69.
Found: C, 71.76; H, 7.23; N, 9.47.

Example 5

4-(cyclopropylmethoxy)-N-(2-{[(2-hydroxy-2-methylpropyl)amino]methyl}-1-methyl-1H-indol-5-yl)benzamide

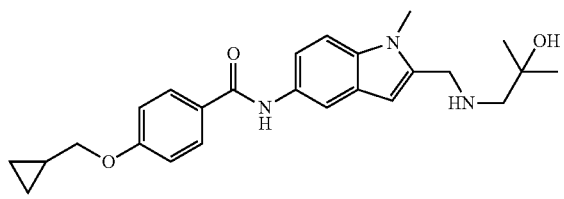 [SMILES: Cn1c(CNCC(C)(C)O)cc2cc(NC(=O)c3ccc(OCC4CC4)cc3)ccc21]

4-(Cyclopropylmethoxy)-N-(2-formyl-1-methyl-1H-indol-5-yl)benzamide (174 mg) obtained in Reference Example 4, 1-amino-2-methyl-propan-2-ol (89 mg) and acetic acid (200 μL) were dissolved in tetrahydrofuran (3 mL)-DMF (1 mL), and the mixture was stirred for 30 min. Sodium triacetoxyborohydride (424 mg) was added and the mixture was stirred at room temperature overnight. To the reaction mixture was added aqueous sodium hydrogen carbonate solution, and the mixture was extracted with ethyl acetate and washed with saturated brine. The obtained organic layer was dried over anhydrous magnesium sulfate, and the solvent was evaporated under reduced pressure. The residue was purified by silica gel column chromatography and the obtained solid was further washed with ethyl acetate to give the title compound (140 mg, yield 66%) as a white solid.

$^1$H NMR (300 MHz, DMSO-d$_6$) δ: 0.31-0.39 (2H, m), 0.55-0.63 (2H, m), 1.09 (6H, s), 1.20-1.32 (1H, m), 2.46 (2H, s), 3.74 (3H, s), 3.86-3.93 (4H, m), 4.20 (1H, s), 6.30 (1H, s), 7.03 (2H, d, J=8.7 Hz), 7.31-7.42 (2H, m), 7.89 (1H, d, J=1.5 Hz), 7.95 (2H, d, J=9.1 Hz), 9.89 (1H, s).

melting point: 188-189° C.
elemental analysis (C$_{25}$H$_{31}$N$_3$O$_3$·0.3H$_2$O)
Calculated: C, 70.33; H, 7.46; N, 9.84.
Found: C, 70.49; H, 7.28; N, 9.86.

Example 6

4-(cyclopropylmethoxy)-N-(2-{[(1,1-dioxidotetrahydro-2H-thiopyran-4-yl)amino]methyl}-1-methyl-1H-indol-5-yl)benzamide

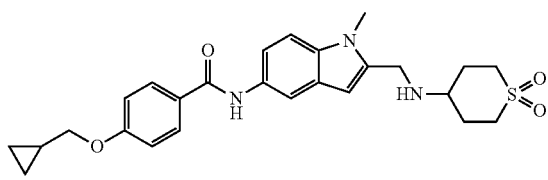 [SMILES: Cn1c(CNC2CCS(=O)(=O)CC2)cc2cc(NC(=O)c3ccc(OCC4CC4)cc3)ccc21]

4-(Cyclopropylmethoxy)-N-(2-formyl-1-methyl-1H-indol-5-yl)benzamide (279 mg) obtained in Reference Example 4, tetrahydro-2H-thiopyran-4-amine 1,1-dioxide hydrochloride (297 mg), triethylamine (162 mg) and acetic acid (400 μL) were dissolved in tetrahydrofuran (4 mL)-DMF (1 mL), and the mixture was stirred for 30 min. Sodium triacetoxyborohydride (678 mg) was added and the mixture was stirred at room temperature overnight. To the reaction mixture was added aqueous sodium hydrogen carbonate solution, and the mixture was extracted with ethyl acetate and washed with saturated brine. The obtained organic layer was dried over anhydrous magnesium sulfate, and the solvent was evaporated under reduced pressure. The residue was purified by silica gel column chromatography and the obtained solid was further washed with ethyl acetate to give the title compound (235 mg, yield 61%) as a white solid.

$^1$H NMR (300 MHz, DMSO-d$_6$) δ: 0.31-0.41 (2H, m), 0.54-0.63 (2H, m), 1.18-1.32 (1H, m), 1.87-2.15 (4H, m), 2.77-3.19 (5H, m), 3.26-3.29 (1H, m), 3.74 (3H, s), 3.85-3.94 (4H, m), 6.34 (1H, s), 7.03 (2H, d, J=9.1 Hz), 7.31-7.43 (2H, m), 7.88-7.98 (3H, m), 9.89 (1H, s).

melting point: 200-201° C.
elemental analysis (C$_{26}$H$_{31}$N$_3$O$_4$S)
Calculated: C, 64.84; H, 6.49; N, 8.72.
Found: C, 64.56; H, 6.46; N, 8.57.

Example 7

4-(cyclopropylmethoxy)-N-[1-methyl-2-({[2-methyl-2-(methylsulfonyl)propyl]amino}methyl)-1H-indol-5-yl]benzamide

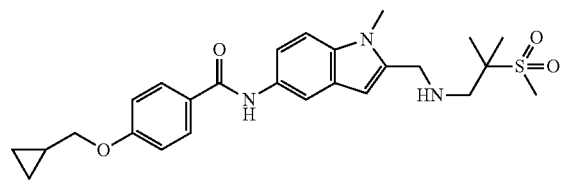 [SMILES: Cn1c(CNCC(C)(C)S(C)(=O)=O)cc2cc(NC(=O)c3ccc(OCC4CC4)cc3)ccc21]

4-(Cyclopropylmethoxy)-N-(2-formyl-1-methyl-1H-indol-5-yl)benzamide (348 mg) obtained in Reference Example 4,2-methyl-2-(methylsulfonyl)propan-1-amine hydrochloride (282 mg) obtained in Reference Example 97, triethylamine (101 mg) and acetic acid (200 μL) were dissolved in tetrahydrofuran (3 mL)-DMF (2 mL), and the mixture was stirred for 30 min. Sodium triacetoxyborohydride (636 mg) was added and the mixture was stirred at room temperature overnight. To the reaction mixture was added aqueous sodium hydrogen carbonate solution, and the mixture was extracted with ethyl acetate and washed with saturated brine. The obtained organic layer was dried over anhydrous magnesium sulfate, and the solvent was evaporated under reduced pressure. The residue was purified by silica gel column chromatography and the obtained solid was further recrystallized from ethyl acetate and hexane to give the title compound (360 mg, yield 74%) as a white solid.

$^1$H NMR (300 MHz, DMSO-d$_6$) δ: 0.31-0.39 (2H, m), 0.54-0.63% (2H, m), 1.13-1.32 (7H, m), 2.24-2.39 (1H, m), 2.85 (2H, s), 2.94 (3H, s), 3.73 (3H, s), 3.86-3.93 (4H, m), 6.33 (1H, s), 7.03 (2H, d, J=8.7 Hz), 7.31-7.44 (2H, m), 7.88-7.98 (3H, m), 9.90 (1H, s).

melting point: 168-169° C.
elemental analysis (C$_{26}$H$_{33}$N$_3$O$_4$S)
Calculated: C, 64.57; H, 6.88; N, 8.69.
Found: C, 64.52; H, 6.96; N, 8.59.

Example 8

4-(cyclopropylmethoxy)-N-(2-{[(trans-4-hydroxycyclohexyl)amino]methyl}-1-methyl-1H-indol-5-yl)benzamide

4-(Cyclopropylmethoxy)-N-(2-formyl-1-methyl-1H-indol-5-yl)benzamide (348 mg) obtained in Reference Example 4, trans-4-aminocyclohexanol (173 mg) and acetic acid (200 μL) were dissolved in tetrahydrofuran (3 mL)-DMF (2 mL), and the mixture was stirred for 30 min. Sodium triacetoxyborohydride (636 mg) was added and the mixture was stirred at room temperature overnight. To the reaction mixture was added aqueous sodium hydrogen carbonate solution, and the mixture was extracted with ethyl acetate and washed with saturated brine. The obtained organic layer was dried over anhydrous magnesium sulfate, and the solvent was evaporated under reduced pressure. The residue was purified by silica gel column chromatography and the obtained solid was further recrystallized from methanol and diisopropyl ether to give the title compound (170 mg, yield 38%) as a white solid.

$^1$H NMR (300 MHz, DMSO-$d_6$) δ: 0.31-0.39 (2H, m), 0.54-0.63 (2H, m), 1.01-1.34 (5H, m), 1.73-1.97 (4H, m), 2.25-2.45 (1H, m), 3.28-3.31 (1H, m), 3.34-3.44 (1H, m), 3.72 (3H, s), 3.85-3.94 (4H, m), 4.47 (1H, d, J=4.2 Hz), 6.31 (1H, s), 7.03 (2H, d, J=9.1 Hz), 7.31-7.42 (2H, m), 7.88-7.98 (3H, m), 9.90 (1H, s).

melting point: 196-197° C.

elemental analysis ($C_{27}H_{33}N_3O_3$)

Calculated: C, 72.46; H, 7.43; N, 9.39.

Found: C, 72.30; H, 7.34; N, 9.36.

Example 9

N-[2-({[2-(acetylamino)ethyl]amino}methyl)-1-methyl-1H-indol-5-yl]-4-(cyclopropylmethoxy)benzamide

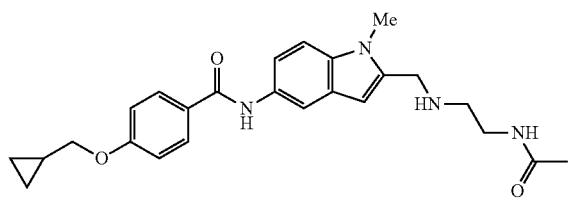 [SMILES: CC(=O)NCCNCc1cc2cc(NC(=O)c3ccc(OCC4CC4)cc3)ccc2n1C]

4-(Cyclopropylmethoxy)-N-(2-formyl-1-methyl-1H-indol-5-yl)benzamide (300 mg) obtained in Reference Example 4 and N-(2-aminoethyl)acetamide (132 mg) were suspended in NMP (3.0 mL), acetic acid (1.0 mL) was added at room temperature and so the mixture was stirred at the same temperature for 2 hr. Sodium triacetoxyborohydride (629 mg) was added, the mixture was stirred at room temperature for 14 hr, and diluted with ethyl acetate, and 2N aqueous sodium hydroxide solution (15 mL) was added at room temperature. The mixture was poured into water, and the organic layer was washed with water and then with saturated brine, dried over sodium sulfate, and concentrated under reduced pressure. The obtained solid was suspended in ethyl acetate and the precipitate was collected by filtration, washed with ethyl acetate, and dried under reduced pressure to give the title compound (293 mg, yield 78%) as a beige solid.

$^1$H NMR (300 MHz, CDCl$_3$) δ: 0.34-0.42 (2H, m), 0.63-0.73 (2H, m), 1.22-1.37 (1H, m), 1.96 (3H, s), 2.84 (2H, t, J=5.9 Hz), 3.36 (2H, q, J=5.7 Hz), 3.76 (3H, s), 3.87 (2H, d, J=7.2 Hz), 3.93 (2H, s), 5.85 (1H, br. s.), 6.36 (1H, s), 6.97 (2H, d, J=8.7 Hz), 7.22-7.29 (1H, m), 7.30-7.37 (1H, m), 7.76 (1H, s), 7.85 (3H, d, J=8.7 Hz).

Example 10

4-(cyclopropylmethoxy)-N-[1-methyl-2-({[(2R)-tetrahydrofuran-2-ylmethyl]amino}methyl)-1H-indol-5-yl]benzamide

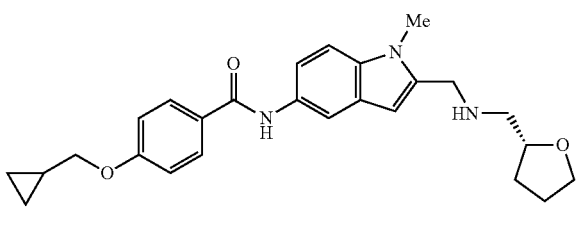 [SMILES: Cn1c(CNC[C@H]2CCCO2)cc2cc(NC(=O)c3ccc(OCC4CC4)cc3)ccc21]

4-(Cyclopropylmethoxy)-N-(2-formyl-1-methyl-1H-indol-5-yl)benzamide (235 mg) obtained in Reference Example 4 and 1-[(2R)-tetrahydrofuran-2-yl]methanamine (102 mg) were suspended in NMP (3.0 mL), acetic acid (1.0 mL) was added at room temperature, and the mixture was stirred at the same temperature for 0.5 hr. Sodium triacetoxyborohydride (286 mg) was added, the mixture was stirred at room temperature for 13 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=99:1 (volume ratio)→ethyl acetate:methanol=80:20 (volume ratio)] and the obtained solid was recrystallized from ethyl acetate to give the title compound (193 mg, yield 66%) as a white solid.

$^1$H NMR (300 MHz, CDCl$_3$) δ: 0.34-0.43 (2H, m), 0.63-0.73 (2H, m), 1.24-1.37 (1H, m), 1.49-1.66 (1H, m), 1.81-2.02 (3H, m), 2.63-2.82 (2H, m), 3.68-3.80 (4H, m), 3.80-3.92 (3H, m), 3.92-4.09 (3H, m), 6.36 (1H, s), 6.97 (2H, d, J=8.9 Hz), 7.22-7.29 (1H, m), 7.30-7.37 (1H, m), 7.74 (1H, s), 7.80-7.91 (3H, m).

melting point: 138-139° C.

elemental analysis ($C_{26}H_{31}N_3O_3$)

Calculated: C, 72.03; H, 7.21; N, 9.69.

Found: C, 71.84; H, 7.15; N, 9.61.

Example 11

4-(cyclopropylmethoxy)-N-[1-methyl-2-({[(2S)-tetrahydrofuran-2-ylmethyl]amino}methyl)-1H-indol-5-yl]benzamide

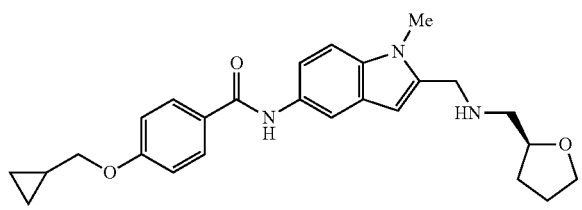 [SMILES: Cn1c(CNC[C@@H]2CCCO2)cc2cc(NC(=O)c3ccc(OCC4CC4)cc3)ccc21]

4-(Cyclopropylmethoxy)-N-(2-formyl-1-methyl-1H-indol-5-yl)benzamide (235 mg) obtained in Reference Example 4 and 1-[(2S)-tetrahydrofuran-2-yl]methanamine (102 mg) were suspended in NMP (3.0 mL), acetic acid (1.0 mL) was added at room temperature and the mixture was stirred at the same temperature for 0.5 hr. Sodium triacetoxyborohydride (286 mg) was added, the mixture was stirred at room temperature for 13 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=99:1 (volume ratio)→ethyl acetate:methanol=80:20 (volume ratio)] and the obtained solid was recrystallized from ethyl acetate to give the title compound (204 mg, yield 70%) as a white solid.

$^1$H NMR (300 MHz, CDCl$_3$) δ: 0.34-0.42 (2H, m), 0.63-0.73 (2H, m), 1.23-1.38 (1H, m), 1.50-1.65 (1H, m), 1.81-2.01 (3H, m), 2.64-2.81 (2H, m), 3.69-3.80 (4H, m), 3.80-3.91 (3H, m), 3.96 (2H, s), 3.97-4.07 (1H, m), 6.36 (1H, s), 6.97 (2H, d, J=8.9 Hz), 7.25 (1H, d, J=8.7 Hz), 7.29-7.37 (1H, m), 7.74 (1H, s), 7.81-7.90 (3H, m).

melting point: 139-139° C.
elemental analysis (C$_{26}$H$_{31}$N$_3$O$_3$)
Calculated: C, 72.03; H, 7.21; N, 9.69.
Found: C, 71.75; H, 7.13; N, 9.64.

Example 12

4-(cyclopropylmethoxy)-N-(2-{[(trans-4-hydroxy-4-methylcyclohexyl)amino]methyl}-1-methyl-1H-indol-5-yl)benzamide

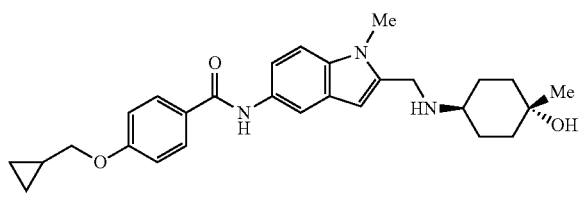 [SMILES: Cn1c(CN[C@H]2CC[C@](C)(O)CC2)cc2cc(NC(=O)c3ccc(OCC4CC4)cc3)ccc21]

4-(Cyclopropylmethoxy)-N-(2-formyl-1-methyl-1H-indol-5-yl)benzamide (240 mg) obtained in Reference Example 4 and trans-4-amino-1-methylcyclohexanol (178 mg) obtained in Reference Example 101 were suspended in NMP (3.0 mL), acetic acid (1.0 mL) was added at room temperature, and the mixture was stirred at the same temperature for 7 hr. Sodium triacetoxyborohydride (292 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=90:10 (volume ratio)→ethyl acetate:methanol=70:30 (volume ratio)] and NH-silica gel column chromatography [eluent; ethyl acetate:methanol=90:10 (volume ratio)] and the obtained solid was recrystallized from ethyl acetate to give the title compound (231 mg, yield 73%) as a white solid.

$^1$H NMR (300 MHz, CDCl$_3$) δ: 0.34-0.42 (2H, m), 0.64-0.72 (2H, m), 1.22-1.52 (8H, m), 1.69-1.81 (2H, m), 1.85-1.97 (2H, m), 2.71 (1H, tt, J=8.1, 3.9 Hz), 3.77 (3H, s), 3.87 (2H, d, J=7.2 Hz), 3.92 (2H, s), 6.36 (1H, s), 6.97 (2H, d, J=8.7 Hz), 7.22-7.29 (1H, m), 7.30-7.37 (1H, m), 7.74 (1H, s), 7.81-7.91 (3H, m).

melting point: 179-180° C.
elemental analysis (C$_{25}$H$_{35}$N$_3$O$_3$·0.3H$_2$O)
Calculated: C, 72.01; H, 7.68; N, 9.00.
Found: C, 72.06; H, 7.73; N, 8.87.

Example 13

4-(cyclopropylmethoxy)-N-{2-[(4-hydroxy-4-methylpiperidin-1-yl)methyl]-1-methyl-1H-indol-5-yl}benzamide

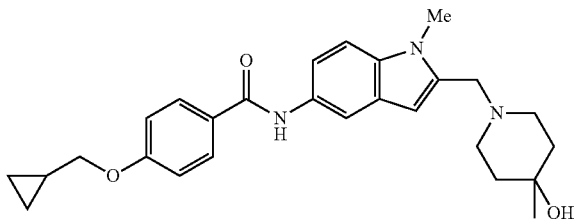 [SMILES: Cn1c(CN2CCC(C)(O)CC2)cc2cc(NC(=O)c3ccc(OCC4CC4)cc3)ccc21]

4-(Cyclopropylmethoxy)-N-[2-(hydroxymethyl)-1-methyl-1H-indol-5-yl]benzamide (237 mg) obtained in Reference Example 5 was dissolved in NMP (3.0 mL), thionyl chloride (0.10 mL) was added, and the mixture was stirred at room temperature for 14 hr. 4-Methylpiperidin-4-ol hydrochloride (307 mg) and ethyldiisopropylamine (0.58 mL) were added, the mixture was stirred at 40° C. for 70 hr, and diluted with ethyl acetate, and water was added. The mixture was poured into water, and the organic layer was washed with water and then with saturated brine, dried over sodium sulfate, and concentrated under reduced pressure. The residue was purified by silica gel column chromatography [eluent; ethyl acetate:methanol=95:5 (volume ratio)→ethyl acetate:methanol=70:30 (volume ratio)] and NH-silica gel column chromatography [eluent; hexane:ethyl acetate=50:50 (volume ratio)→hexane:ethyl acetate=0:100 (volume ratio)], and the obtained solid was recrystallized from ethyl acetate-diisopropyl ether to give the title compound (23 mg, yield 8%) as a white solid.

$^1$H NMR (300 MHz, CDCl$_3$) δ: 0.38 (2H, q, J=4.9 Hz), 0.63-0.73 (2H, m), 1.24 (3H, s), 1.25-1.36 (1H, m), 1.60-1.70 (4H, m), 2.33-2.49 (2H, m), 2.50-2.65 (2H, m), 3.63 (2H, s), 3.79 (3H, s), 3.87 (2H, d, J=6.8 Hz), 6.34 (1H, s), 6.97 (2H, d, J=9.0 Hz), 7.23-7.30 (1H, m), 7.30-7.38 (1H, m), 7.74 (1H, s), 7.80-7.91 (3H, m).
elemental analysis (C$_{27}$H$_{33}$N$_3$O$_3$)
Calculated: C, 72.46; H, 7.43; N, 9.39.
Found: C, 72.16; H, 7.44; N, 9.34.

Example 14

4-(cyclopropylmethoxy)-N-(2-{1-[(1,1-dioxidotet-rahydro-2H-thiopyran-4-yl)amino]ethyl}-1-methyl-1H-indol-5-yl)benzamide hydrochloride

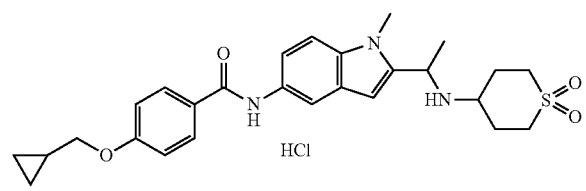 [SMILES: CC(NC1CCS(=O)(=O)CC1)c1cc2cc(NC(=O)c3ccc(OCC4CC4)cc3)ccc2n1C ; Cl]

To a solution of 4-(cyclopropylmethoxy)-N-[2-(1-hydroxyethyl)-1-methyl-1H-indol-5-yl]benzamide (292 mg) obtained in Reference Example 6, N-(1,1-dioxidotetrahydro-2H-thiopyran-4-yl)-2-nitrobenzenesulfonamide (321 mg) obtained in Reference Example 103 and triphenylphosphine (393 mg) in tetrahydrofuran (10 mL) was added 2.2 M diethyl azodicarboxylate toluene solution (0.68 mL), and the mixture was stirred overnight. The reaction mixture was extracted with ethyl acetate, and washed with saturated brine. The organic layer was dried over anhydrous magnesium sulfate, and the solvent was evaporated under reduced pressure. The residue was purified by silica gel column chromatography and the obtained solid was dissolved in DMF (5 mL). 2N Aqueous lithium hydroxide solution (1.6 mL) and thioglycolic acid (147 mg) were added, and the mixture was stirred at room temperature overnight. The reaction mixture was extracted with ethyl acetate, and washed with saturated brine. The organic layer was dried over anhydrous magnesium sulfate, and the solvent was evaporated under reduced pressure. The obtained residue was purified by silica gel column chromatography and 2N hydrochloric acid-containing ethyl acetate was further added to the obtained compound to give the title compound (40 mg, yield 9%) as a white solid.
$^1$H NMR (300 MHz, DMSO-d$_6$) δ: 0.30-0.40 (2H, m), 0.53-0.66 (2H, m), 1.17-1.32 (1H, m), 1.71 (3H, d, J=6.4 Hz), 2.03-2.24 (2H, m), 2.42-2.58 (2H, m), 3.14-3.29 (3H, m), 3.50 (1H, br. s.), 3.78 (3H, s), 3.91 (2H, d, J=7.2 Hz), 4.90 (1H, br. s.), 6.82 (1H, s), 7.04 (2H, d, J=9.1 Hz), 7.44-7.54 (2H, m), 7.92-8.09 (3H, m), 9.40 (1H, br. s.), 9.82 (1H, br. s.), 9.98 (1H, s).
melting point: 177-178° C.
elemental analysis (C$_{27}$H$_{33}$N$_4$O$_4$S.HCl.1.5H$_2$O)
Calculated: C, 58.00; H, 6.67; N, 7.52.
Found: C, 57.60; H, 6.64; N, 7.32.

Example 15

N-(2-{[(2,2-dimethylpropyl)amino]methyl}-1-methyl-1H-indol-5-yl)-4-[(2S)-tetrahydrofuran-2-yl-methoxy]benzamide acetate

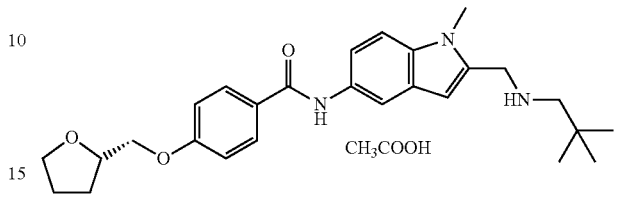

N-(2-Formyl-1-methyl-1H-indol-5-yl)-4-[(2S)-tetrahydrofuran-2-ylmethoxy]benzamide (308 mg) obtained in Reference Example 10 and neopentylamine (365 mg) were suspended in NMP (12 mL), acetic acid (2.0 mL) was added at room temperature, and the mixture was stirred at the same temperature for 10 min. The reaction solution was ice-cooled, sodium triacetoxyborohydride (360 mg) was added, and the mixture was allowed to warm to room temperature and stirred for 16 hr. 1N Aqueous sodium hydroxide solution (35 mL) was added at room temperature to dilute the mixture, and the obtained precipitate was collected by filtration, washed with water, and dried under reduced pressure. The obtained crude product was purified by silica gel column chromatography [eluent; ethyl acetate→ethyl acetate:methanol=80:20 (volume ratio)] and the obtained solid was recrystallized from ethyl acetate to give the title compound (128 mg, yield 31%) as a white solid.
$^1$H NMR (300 MHz, DMSO-d$_6$) δ: 0.86 (9H, s) 1.61-2.13 (4H, m) 1.91 (3H, s) 2.32 (2H, s) 3.63-3.84 (2H, m) 3.75 (3H, s) 3.87 (2H, s) 3.95-4.10 (2H, m) 4.18 (1H, qd, J=6.69, 3.79 Hz) 6.30 (1H, s) 7.03 (2H, d, J=8.71 Hz) 7.34 (1H, d, J=8.71 Hz) 7.39 (1H, tt, J=8.71, 1.89 Hz) 7.89 (1H, d, J=1.51 Hz) 7.96 (2H, d, J=9.09 Hz) 9.90 (1H, s).
melting point: 150-151° C.
elemental analysis (C$_{27}$H$_{35}$N$_3$O$_3$.0.9C$_2$H$_4$O$_2$)
Calculated: C, 68.68; H, 7.73; N, 8.34.
Found: C, 68.65; H, 7.64; N, 8.27.

Example 16

N-(1-methyl-2-{[(2-methylpropyl)amino]methyl}-1H-indol-5-yl)-4-[(2S)-tetrahydrofuran-2-yl-methoxy]benzamide

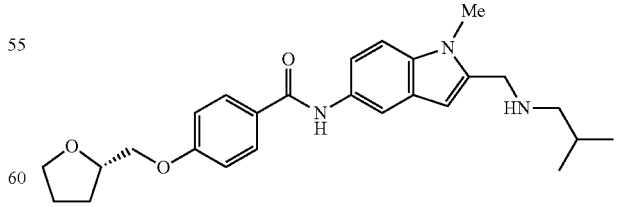

N-(2-Formyl-1-methyl-1H-indol-5-yl)-4-[(2S)-tetrahydrofuran-2-ylmethoxy]benzamide (300 mg) obtained in Reference Example 10 and isobutylamine (87 mg) were suspended in NMP (3.0 mL), acetic acid (1.0 mL) was added at room temperature, and the mixture was stirred at the same temperature for 3 hr. Sodium triacetoxyborohydride (336 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=100:0 (volume ratio) →ethyl acetate:methanol=90:10 (volume ratio)], and the obtained solid was recrystallized from ethyl acetate-diisopropyl ether to give the title compound (260 mg, yield 75%) as a pale-yellow solid.

$^1$H NMR (300 MHz, CDCl$_3$) δ: 0.93 (6H, d), 1.68-1.87 (2H, m), 1.90-2.19 (3H, m), 2.50 (2H, d, J=6.8 Hz), 3.78 (3H, s), 3.81-4.00 (4H, m), 4.04 (2H, d, J=5.3 Hz), 4.25-4.37 (1H, m), 6.35 (1H, s), 7.00 (2H, d, J=8.7 Hz), 7.22-7.29 (1H, m), 7.29-7.37 (1H, m), 7.75 (1H, s), 7.85 (3H, d, J=8.3 Hz).

melting point: 132-133° C.
elemental analysis (C$_{26}$H$_{33}$N$_3$O$_3$)
Calculated: C, 71.70; H, 7.64; N, 9.65.
Found: C, 71.55; H, 7.64; N, 9.57.

Example 17

N-(1-methyl-2-{[(tetrahydro-2H-pyran-4-ylmethyl)amino]methyl}-1H-indol-5-yl)-4-[(2S)-tetrahydrofuran-2-ylmethoxy]benzamide

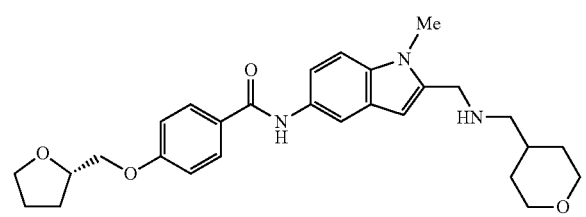 [SMILES: Cn1c(CNCC2CCOCC2)cc2cc(NC(=O)c3ccc(OC[C@@H]4CCCO4)cc3)ccc21]

N-(2-formyl-1-methyl-1H-indol-5-yl)-4-[(2S)-tetrahydrofuran-2-ylmethoxy]benzamide (300 mg) obtained in Reference Example 10 and 1-(tetrahydro-2H-pyran-4-yl)methanamine (137 mg) were suspended in NMP (3.0 mL), acetic acid (1.0 mL) was added at room temperature, and the mixture was stirred at the same temperature for 3.5 hr. Sodium triacetoxyborohydride (336 mg) was added, the mixture was stirred at room temperature for 14 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=95:5 (volume ratio)→ethyl acetate:methanol=65:35], and the obtained solid was recrystallized from ethyl acetate-diisopropyl ether to give the title compound (287 mg, yield 76%) as a pale-brown solid.

$^1$H NMR (300 MHz, CDCl$_3$) δ: 1.22-1.41 (2H, m), 1.61-1.87 (4H, m), 1.90-2.18 (3H, m), 2.59 (2H, d, J=6.4 Hz), 3.39 (2H, td, J=11.6, 1.7 Hz), 3.71-4.02 (10H, m), 4.04 (2H, J=4.9 Hz), 4.25-4.37 (1H, m), 6.35 (1H, s), 7.00 (2H, J=9.0 Hz), 7.26 (1H, d, J=8.1 Hz), 7.32 (1H, dd, J=8.4, 2.1 Hz), 7.74 (1H, s), 7.86 (3H, d, J=8.7 Hz).

melting point: 157-158° C.
elemental analysis (C$_{28}$H$_{35}$N$_3$O$_4$.0.1H$_2$O)
Calculated: C, 70.15; H, 7.40; N, 8.77.
Found: C, 70.08; H, 7.48; N, 8.65.

Example 18

N-(2-{[(trans-4-hydroxy-4-methylcyclohexyl)amino]methyl}-1-methyl-1H-indol-5-yl)-4-[(2S)-tetrahydrofuran-2-ylmethoxy]benzamide

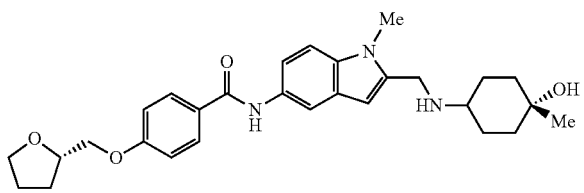

N-(2-Formyl-1-methyl-1H-indol-5-yl)-4-[(2S)-tetrahydrofuran-2-ylmethoxy]benzamide (300 mg) obtained in Reference Example 10 and trans-4-amino-1-methylcyclohexanol (205 mg) obtained in Reference Example 101 were suspended in NMP (3.3 mL), acetic acid (1.0 mL) was added at room temperature, and the mixture was stirred at the same temperature for 4.5 hr. Sodium triacetoxyborohydride (336 mg) was added, the mixture was stirred at room temperature for 17 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=95:5 (volume ratio)→ethyl acetate:methanol=65:35 (volume ratio)] and NH-silica gel column chromatography [eluent; ethyl acetate:methanol=90:10 (volume ratio)], and the obtained solid was recrystallized from ethyl acetate-diisopropyl ether to give the title compound (306 mg, yield 79%) as a pale-brown solid.

$^1$H NMR (300 MHz, CDCl$_3$) δ: 1.22-1.41 (2H, m), 1.61-1.87 (4H, m), 1.90-2.18 (3H, m), 2.59 (2H, d, J=6.4 Hz), 3.39 (2H, td, J=11.6, 1.7 Hz), 3.71-4.02 (10H, m), 4.04 (2H, d, J=4.9 Hz), 4.25-4.37 (1H, m), 6.35 (1H, s), 7.00 (2H, d, J=9.0 Hz), 7.26 (1H, d, J=8.1 Hz), 7.32 (1H, dd, J=8.4, 2.1 Hz), 7.74 (1H, s), 7.86 (3H, d, J=8.7 Hz).

melting point: 154° C.
elemental analysis (C$_{29}$H$_{37}$N$_3$O$_4$.0.3H$_2$O)
Calculated: C, 70.08; H, 7.63; N, 8.45.
Found: C, 70.05; H, 7.54; N, 8.46.

Example 19

N-(2-{[(2-hydroxy-2-methylpropyl)amino]methyl}-1-methyl-1H-indol-5-yl)-4-[(2S)-tetrahydrofuran-2-ylmethoxy]benzamide

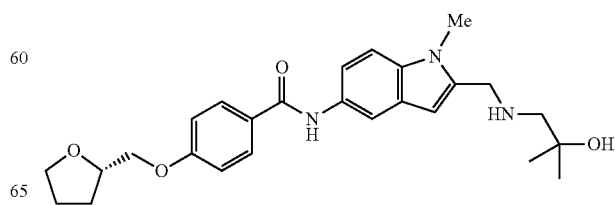

N-(2-Formyl-1-methyl-1H-indol-5-yl)-4-[(2S)-tetrahydrofuran-2-ylmethoxy]benzamide (300 mg) obtained in Reference Example 10 and 1-amino-2-methylpropan-2-ol (143 mg) were suspended in NMP (3.0 mL), acetic acid (1.0 mL) was added at room temperature, and the mixture was stirred at the same temperature for 3 hr. Sodium triacetoxyborohydride (336 mg) was added, the mixture was stirred at room temperature for 90 hr, and diluted with ethyl acetate, and 2N aqueous sodium hydroxide solution (20 mL) was added at room temperature. The mixture was poured into THF-water, and the organic layer was washed twice with saturated brine, dried over sodium sulfate, and concentrated under reduced pressure. The obtained solid was suspended in ethyl acetate, and the precipitate was collected by filtration, washed with ethyl acetate, and dried under reduced pressure to give the title compound (323 mg, yield 90%) as a pale-brown solid.

$^1$H NMR (300 MHz, CDCl$_3$) δ: 1.19 (6H, s), 1.71-1.88 (1H, m), 1.90-2.20 (3H, m), 2.65 (2H, s), 2.77 (1H, br. s.), 3.78 (3H, s), 3.80-3.90 (1H, m), 3.90-4.01 (3H, m), 4.04 (2H, d, J=4.9 Hz), 4.31 (1H, tt, J=7.0, 5.3 Hz), 6.38 (1H, s), 7.01 (2H, d, J=8.7 Hz), 7.24-7.29 (1H, m), 7.30-7.36 (1H, m), 7.75 (1H, s), 7.86 (2H, d, J=9.1 Hz), 7.88 (1H, s).

melting point: 188-190° C.
elemental analysis (C$_{26}$H$_{33}$N$_3$O$_4$)
Calculated: C, 69.16; H, 7.37; N, 9.31.
Found: C, 69.02; H, 7.47; N, 9.30.

Example 20

N-(1-methyl-2-{[(tetrahydrofuran-3-ylmethyl)amino]methyl}-1H-indol-5-yl)-4-[(2S)-tetrahydrofuran-2-ylmethoxy]benzamide

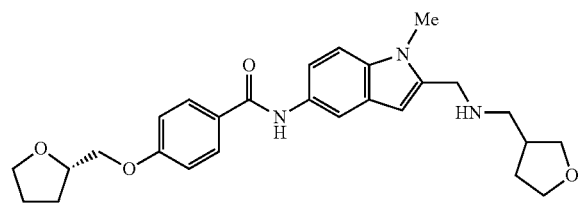 [SMILES: Cn1c(CNCC2CCOC2)cc2cc(NC(=O)c3ccc(OC[C@@H]4CCCO4)cc3)ccc21]

N-(2-Formyl-1-methyl-1H-indol-5-yl)-4-[(2S)-tetrahydrofuran-2-ylmethoxy]benzamide (300 mg) obtained in Reference Example 10 and 1-(tetrahydrofuran-3-yl)methanamine (96 mg) were suspended in NMP (3.0 mL), acetic acid (1.0 mL) was added at room temperature, and the mixture was stirred at the same temperature for 7 hr. Sodium triacetoxyborohydride (336 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=90:10 (volume ratio)→ethyl acetate:methanol=70:30 (volume ratio)] and NH-silica gel column chromatography [eluent; ethyl acetate:methanol=90:10 (volume ratio)] and the obtained solid was recrystallized from ethyl acetate to give the title compound (238 mg, yield 65%) as a pale-yellow solid.

$^1$H NMR (300 MHz, CDCl$_3$) δ: 1.58-1.66 (1H, m), 1.71-1.87 (1H, m), 1.90-2.18 (4H, m), 2.38 (1H, dt, J=14.1, 6.9 Hz), 2.61-2.77 (2H, m), 3.52 (1H, dd, J=8.3, 6.0 Hz), 3.68-4.00 (10H, m), 4.03 (2H, d, J=5.3 Hz), 4.25-4.36 (1H, m), 6.35 (1H, s), 7.00 (2H, d, J=8.7 Hz), 7.22-7.29 (1H, m), 7.29-7.36 (1H, m), 7.75 (1H, s), 7.85 (3H, d, J=8.7 Hz).

melting point: 128-129° C.
elemental analysis (C$_{27}$H$_{33}$N$_3$O$_4$.0.2H$_2$O)
Calculated: C, 69.42; H, 7.21; N, 8.99.
Found: C, 69.32; H, 7.19; N, 8.91.

Example 21

N-(1-methyl-2-{[(2-methylpropyl)amino]methyl}-1H-indol-5-yl)-4-(tetrahydrofuran-3-ylmethoxy)benzamide

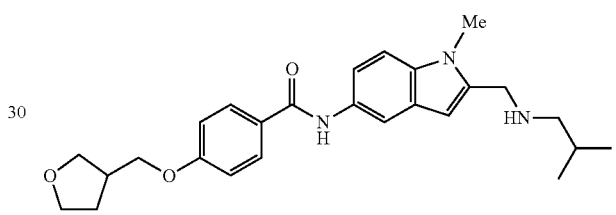

N-(2-Formyl-1-methyl-1H-indol-5-yl)-4-(tetrahydrofuran-3-ylmethoxy)benzamide (300 mg) obtained in Reference Example 13 and isobutylamine (87 mg) were suspended in NMP (3.0 mL), acetic acid (1.0 mL) was added at room temperature, and the mixture was stirred at the same temperature for 3 hr. Sodium triacetoxyborohydride (336 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=100:0 (volume ratio)→ethyl acetate:methanol=90:10 (volume ratio)], and the obtained solid was recrystallized from ethyl acetate-diisopropyl ether to give the title compound (299 mg, yield 87%) as a pale-yellow solid.

$^1$H NMR (300 MHz, CDCl$_3$) δ: 0.92 (6H, d, J=6.4 Hz), 1.68-1.84 (2H, m), 2.07-2.22 (1H, m), 2.50 (2H, d, J=6.4 Hz), 2.77 (1H, m, J=13.4, 6.7, 6.7, 6.7, 6.7 Hz), 3.67-3.85 (5H, m), 3.87-4.04 (6H, m), 6.35 (1H, s), 6.97 (2H, d, J=8.7 Hz), 7.26 (1H, d, J=8.7 Hz), 7.30-7.37 (1H, m), 7.75 (1H, s), 7.81-7.91 (3H, m).

melting point: 125-126° C.
elemental analysis (C$_{26}$H$_{33}$N$_3$O$_3$)
Calculated: C, 71.70; H, 7.64; N, 9.65.
Found: C, 71.54; H, 7.67; N, 9.47.

Example 22

N-(2-{[(2,2-dimethylpropyl)amino]methyl}-1-methyl-1H-indol-5-yl)-4-(tetrahydrofuran-3-ylmethoxy)benzamide

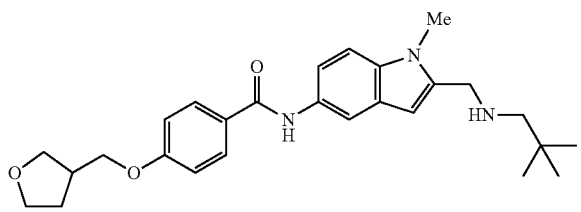 [SMILES: Cn1c(CNCC(C)(C)C)cc2cc(NC(=O)c3ccc(OCC4CCOC4)cc3)ccc21]

N-(2-Formyl-1-methyl-1H-indol-5-yl)-4-(tetrahydrofuran-3-ylmethoxy)benzamide (300 mg) obtained in Reference Example 13 and 2,2-dimethylpropan-1-amine (104 mg) were suspended in NMP (3.0 mL), acetic acid (1.0 mL) was added at room temperature, and the mixture was stirred at the same temperature for 3.5 hr. Sodium triacetoxyborohydride (336 mg) was added, the mixture was stirred at room temperature for 14 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=100:0 (volume ratio)→ethyl acetate:methanol=94:6 (volume ratio)], and the obtained solid was recrystallized from ethyl acetate-diisopropyl ether to give the title compound (308 mg, yield 66%) as a pale-brown solid.

$^1$H NMR (300 MHz, CDCl$_3$) δ: 0.91 (9H, s), 1.76 (1H, td, J=13.2, 7.2 Hz), 2.07-2.22 (1H, m), 2.42 (2H, s), 2.77 (1H, quin, J=6.9 Hz), 3.69-3.86 (5H, m), 3.87-4.05 (6H, m), 6.35 (1H, s), 6.97 (2H, d, J=8.7 Hz), 7.26 (1H, d, J=8.7 Hz), 7.30-7.37 (1H, m), 7.74 (1H, s), 7.81-7.92 (3H, m).

melting point: 162-163° C.
elemental analysis (C$_{27}$H$_{35}$N$_3$O$_3$·0.1H$_2$O)
Calculated: C, 71.84; H, 7.86; N, 9.31.
Found: C, 71.88; H, 7.88; N, 9.03.

Example 23

N-(1-methyl-2-{[(tetrahydro-2H-pyran-4-ylmethyl)amino]methyl}-1H-indol-5-yl)-4-(tetrahydrofuran-3-ylmethoxy)benzamide

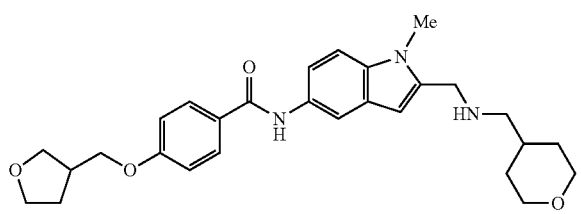 [SMILES: Cn1c(CNCC2CCOCC2)cc2cc(NC(=O)c3ccc(OCC4CCOC4)cc3)ccc21]

N-(2-Formyl-1-methyl-1H-indol-5-yl)-4-(tetrahydrofuran-3-ylmethoxy)benzamide (300 mg) obtained in Reference Example 13 and 1-(tetrahydro-2H-pyran-4-yl)methanamine (137 mg) were suspended in NMP (3.0 mL), acetic acid (1.0 mL) was added at room temperature, and the mixture was stirred at the same temperature for 3.5 hr. Sodium triacetoxyborohydride (336 mg) was added, the mixture was stirred at room temperature for 14 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=95:5 (volume ratio)→ethyl acetate:methanol=65:35 (volume ratio)] and NH-silica gel column chromatography [eluent; ethyl acetate], and the obtained solid was recrystallized from ethyl acetate-diisopropyl ether to give the title compound (302 mg, yield 80%) as a pale-yellow solid.

$^1$H NMR (300 MHz, CDCl$_3$) δ: 1.24-1.41 (2H, m), 1.61-1.84 (4H, m), 2.07-2.22 (1H, m), 2.59 (2H, d, J=6.1 Hz), 2.77 (1H, dt, J=13.3, 6.8 Hz), 3.39 (2H, td, J=11.7, 1.9 Hz), 3.69-3.86 (5H, m), 3.87-4.05 (8H, m), 6.36 (1H, s), 6.97 (2H, d, J=8.7 Hz), 7.23-7.30 (1H, m), 7.30-7.36 (1H, m), 7.74 (1H, s), 7.81-7.92 (3H, m).

melting point: 153-154° C.
elemental analysis (C$_{28}$H$_{35}$N$_3$O$_4$)
Calculated: C, 70.42; H, 7.39; N, 8.80.
Found: C, 70.18; H, 7.26; N, 8.64.

Example 24

N-(2-{[(trans-4-hydroxy-4-methylcyclohexyl)amino]methyl}-1-methyl-1H-indol-5-yl)-4-(tetrahydrofuran-3-ylmethoxy)benzamide

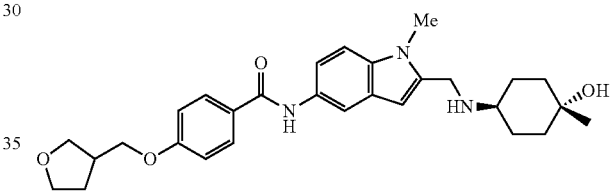

N-(2-Formyl-1-methyl-1H-indol-5-yl)-4-(tetrahydrofuran-3-ylmethoxy)benzamide (300 mg) obtained in Reference Example 13 and trans-4-amino-1-methylcyclohexanol (205 mg) obtained in Reference Example 101 were suspended in NMP (3.0 mL), acetic acid (1.0 mL) was added at room temperature, and the mixture was stirred at the same temperature for 4.5 hr. Sodium triacetoxyborohydride (336 mg) was added, the mixture was stirred at room temperature for 17 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=95:5 (volume ratio)→ethyl acetate:methanol=60:40 (volume ratio)] and NH-silica gel column chromatography [eluent; ethyl acetate:methanol=90:10], and the obtained solid was so recrystallized from ethyl acetate-diisopropyl ether to give the title compound (305 mg, yield 78%) as a pale-brown solid.

$^1$H NMR (300 MHz, CDCl$_3$) δ: 1.24 (1H, br. s.), 1.27 (3H, s), 1.30-1.50 (4H, m), 1.68-1.83 (3H, m), 1.84-1.99 (2H, m), 2.14 (1H, m, J=13.0, 7.9, 7.9, 5.7 Hz), 2.64-2.85 (2H, m), 3.68-3.86 (5H, m), 3.87-4.05 (6H, m), 6.36 (1H, s), 6.97 (2H, d, J=8.7 Hz), 7.25 (1H, d, J=8.4 Hz), 7.33 (1H, dd, J=8.7, 1.8 Hz), 7.74 (1H, s), 7.82-7.91 (3H, m).

melting point: 181-182° C.
elemental analysis (C$_{29}$H$_{37}$N$_3$O$_4$)
Calculated: C, 70.59; H, 7.60; N, 8.52.
Found: C, 70.54; H, 7.59; N, 8.45.

Example 25

N-(2-{[(2-hydroxy-2-methylpropyl)amino]methyl}-1-methyl-1H-indol-5-yl)-4-(tetrahydrofuran-3-ylmethoxy)benzamide

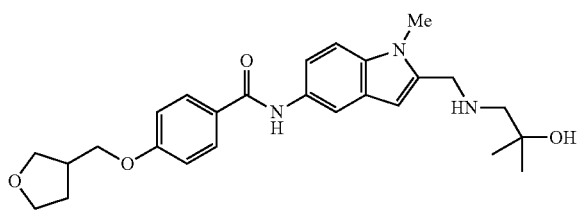 [SMILES: Cn1c(CNCC(C)(C)O)cc2cc(NC(=O)c3ccc(OCC4CCOC4)cc3)ccc21]

N-(2-Formyl-1-methyl-1H-indol-5-yl)-4-(tetrahydrofuran-3-ylmethoxy)benzamide (300 mg) obtained in Reference Example 13 and 1-amino-2-methylpropan-2-ol (143 mg) were suspended in NMP (3.0 mL), acetic acid (1.0 mL) was added at room temperature, and the mixture was stirred at the same temperature for 3 hr. Sodium triacetoxyborohydride (336 mg) was added, the mixture was stirred at room temperature for 90 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (330 mg, yield 92%) as a pale-brown solid.

$^1$H NMR (300 MHz, CDCl$_3$) δ: 1.19 (6H, s), 1.69-1.84 (1H, m), 2.07-2.22 (1H, m), 2.65 (2H, s), 2.69-2.86 (2H, m), 3.70-3.85 (5H, m), 3.87-4.05 (6H, m), 6.38 (1H, s), 6.97 (2H, d, J=8.7 Hz), 7.24-7.30 (1H, m), 7.30-7.36 (1H, m), 7.74 (1H, s), 7.86 (2H, d, J=8.7 Hz), 7.89 (1H, br. s.).

melting point: 169° C.
elemental analysis (C$_{26}$H$_{33}$N$_3$O$_4$)
Calculated: C, 69.16; H, 7.37; N, 9.31.
Found: C, 68.95; H, 7.39; N, 9.21.

Example 26

N-(1-methyl-2-{[(tetrahydrofuran-3-ylmethyl)amino]methyl}-1H-indol-5-yl)-4-(tetrahydrofuran-3-ylmethoxy)benzamide

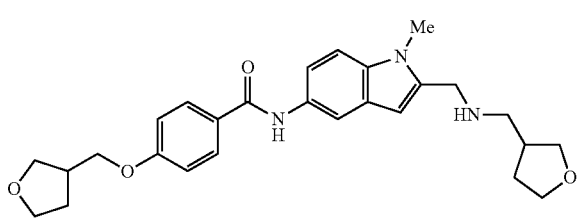 [SMILES: Cn1c(CNCC2CCOC2)cc2cc(NC(=O)c3ccc(OCC4CCOC4)cc3)ccc21]

N-(2-Formyl-1-methyl-1H-indol-5-yl)-4-(tetrahydrofuran-3-ylmethoxy)benzamide (300 mg) obtained in Reference Example 13 and 1-(tetrahydrofuran-3-yl)methanamine (96 mg) were suspended in NMP (3.0 mL), acetic acid (1.0 mL) was added at room temperature, and the mixture was stirred at the same temperature for 7 hr. Sodium triacetoxyborohydride (336 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=90:10 (volume ratio)→ethyl acetate:methanol=70:30 (volume ratio)] and NH-silica gel column chromatography [eluent; ethyl acetate:methanol=90:10] and the obtained solid was recrystallized from ethyl acetate to give the title compound (179 mg, yield 49%) as a pale-brown solid.

$^1$H NMR (300 MHz, CDCl$_3$) δ: 1.53-1.67 (1H, m), 1.76 (1H, td, J=12.9, 7.3 Hz), 1.97-2.22 (2H, m), 2.30-2.47 (1H, m), 2.61-2.86 (3H, m), 3.52 (1H, dd, J=8.3, 6.0 Hz), 3.68-4.04 (14H, m), 6.35 (1H, s), 6.97 (2H, d, J=8.7 Hz), 7.22-7.29 (1H, m), 7.29-7.36 (1H, m), 7.75 (1H, s), 7.82-7.92 (3H, m).

melting point: 131-133° C.
elemental analysis (C$_{27}$H$_{33}$N$_3$O$_4$)
Calculated: C, 69.95; H, 7.18; N, 9.06.
Found: C, 69.77; H, 7.17; N, 9.09.

Example 27

2-fluoro-N-(2-{[(2-hydroxy-2-methylpropyl)amino]methyl}-1-methyl-1H-indol-5-yl)-4-[(2S)-tetrahydrofuran-2-ylmethoxy]benzamide

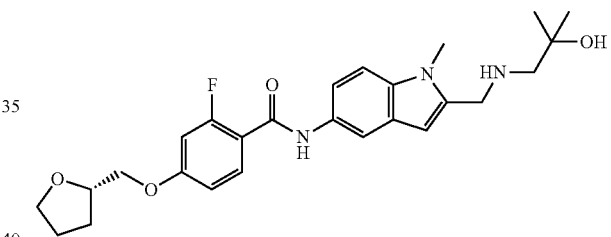

2-Fluoro-N-(2-formyl-1-methyl-1H-indol-5-yl)-4-[(2S)-tetrahydrofuran-2-ylmethoxy]benzamide (1.5 g) obtained in Reference Example 18 and 1-amino-2-methylpropan-2-ol (800 mg) were suspended in NMP (20 mL) and acetic acid (7.0 mL), and the mixture was stirred at room temperature for 3 hr. Sodium triacetoxyborohydride (3.0 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (1.1 g, yield 62%) as a colorless solid.

$^1$H NMR (300 MHz, DMSO-d$_6$) δ: 1.09 (6H, s), 1.64-1.93 (3H, m), 1.96-2.04 (1H, m), 2.46 (2H, s), 3.69 (1H, q, J=6.6 Hz), 3.74 (3H, s), 3.79 (1H, q, J=6.6 Hz), 3.88 (2H, s), 3.97-4.09 (2H, m), 4.14-4.20 (2H, m), 6.30 (1H, s), 6.87-6.97 (2H, m), 7.34 (2H, s), 7.62 (1H, t, J=8.4 Hz), 7.89 (1H, s), 9.92 (1H, s).

melting point: 159-160° C.
elemental analysis (C$_{26}$H$_{32}$N$_3$O$_4$F)
Calculated: C, 66.51; H, 6.87; N, 8.95.
Found: C, 66.60; H, 6.73; N, 9.01.

Example 28

2-fluoro-N-(2-{[(trans-4-hydroxy-4-methylcyclohexyl)amino]methyl}-1-methyl-1H-indol-5-yl)-4-[(2S)-tetrahydrofuran-2-ylmethoxy]benzamide

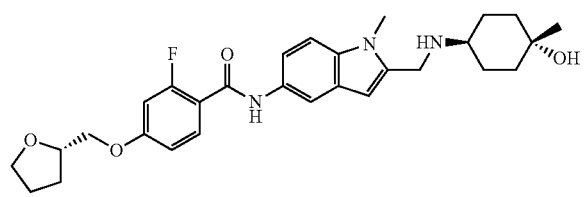 [SMILES: Cn1c(CN[C@H]2CC[C@](C)(O)CC2)cc2cc(NC(=O)c3ccc(OC[C@@H]4CCCO4)cc3F)ccc21]

2-Fluoro-N-(2-formyl-1-methyl-1H-indol-5-yl)-4-[(2S)-tetrahydrofuran-2-ylmethoxy]benzamide (1.5 g) obtained in Reference Example 18 and trans-4-amino-1-methylcyclohexanol (600 mg) obtained in Reference Example 101 were suspended in NMP (20 mL) and acetic acid (7.0 mL), and the mixture was stirred at room temperature for 3 hr. Sodium triacetoxyborohydride (3.0 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (520 mg, yield 27%) as a colorless solid.

$^1$H NMR (300 MHz, DMSO-$d_6$) δ: 1.10 (3H, s), 1.20-1.36 (4H, m), 1.53-1.61 (2H, m), 1.63-1.72 (1H, m), 1.78-1.92 (5H, m), 1.96-2.05 (1H, m), 2.50-2.51 (1H, m), 3.69 (1H, q, J=6.3 Hz), 3.72 (3H, s), 3.79 (1H, q, J=6.3 Hz), 3.84 (2H, s), 3.96-4.10 (3H, m), 4.13-4.19 (1H, m), 6.29 (1H, s), 6.86-6.97 (2H, m), 7.33 (2H, s), 7.62 (1H, t, J=8.4 Hz), 7.89 (1H, s), 9.92 (1H, s).

melting point: 138-139° C.
elemental analysis ($C_{29}H_{36}N_3O_4F$·$0.2H_2O$)
Calculated: C, 67.87; H, 7.15; N, 8.19.
Found: C, 68.00; H, 7.07; N, 8.24.

Example 29

4-[(1-hydroxycyclobutyl)ethynyl]-N-(2-{[(2-methylpropyl)amino]methyl}-1-methyl-1H-indol-5-yl)benzamide

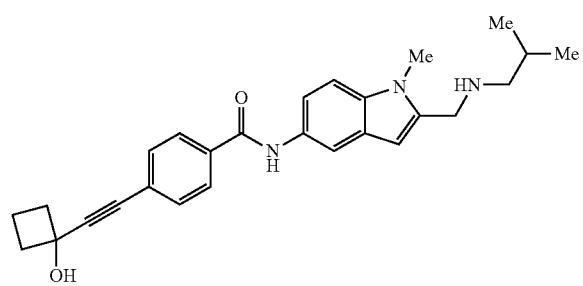 [SMILES: CC(C)CNCc1cc2cc(NC(=O)c3ccc(C#CC4(O)CCC4)cc3)ccc2n1C]

Under an argon atmosphere, to a solution of 4-bromo-N-(1-methyl-2-{[(2-methylpropyl)amino]methyl}-1H-indol-5-yl)benzamide (350 mg) obtained in Reference Example 22 in pyridine (2.3 mL) were added triphenylphosphine (25 mg), copper(I) iodide (6.6 mg), triethylamine (2.3 mL), 1-ethynylcyclobutanol (97 mg) and dichlorobis(triphenylphosphine)palladium(II) (7.1 mg), and the mixture was stirred at 65° C. for 15 hr. The mixture was allowed to cool to room temperature, and the insoluble material was filtered off and washed with toluene. The filtrate was purified by silica gel column chromatography [eluent; hexane:ethyl acetate=3:7→ethyl acetate (volume ratio)] and the obtained crude product was washed with isopropyl ether-ethyl acetate to give the title compound (326 mg, yield 90%) as pale-yellow crystals.

$^1$H NMR (300 MHz, DMSO-$d_6$) δ: 0.87 (6H, d, J=6.4 Hz), 1.61-1.88 (3H, m), 2.17-2.31 (2H, m), 2.34-2.46 (4H, m), 3.74 (3H, s), 3.84 (2H, s), 5.94 (1H, s), 6.31 (1H, s), 7.33-7.44 (2H, m), 7.56 (2H, d, J=8.3 Hz), 7.92 (1H, s), 7.99 (2H, d, J=8.3 Hz), 10.13 (1H, s).

melting point: 168-169° C.
elemental analysis ($C_{27}H_{31}N_3O_2$)
Calculated: C, 75.49; H, 7.27; N, 9.78.
Found: C, 74.96; H, 7.38; N, 9.19.

Example 30

N-(2-{[(2,2-dimethylpropyl)amino]methyl}-1-methyl-1H-indol-5-yl)-4-[(1-hydroxycyclobutyl)ethynyl]benzamide

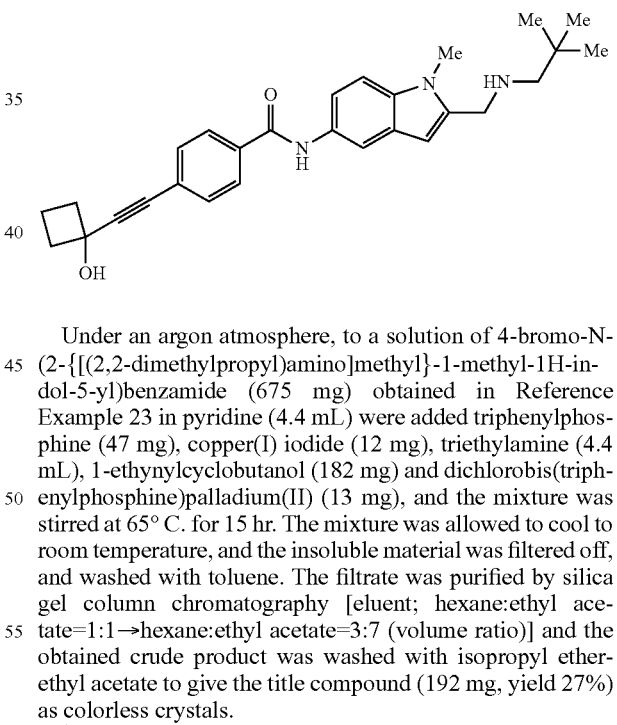

Under an argon atmosphere, to a solution of 4-bromo-N-(2-{[(2,2-dimethylpropyl)amino]methyl}-1-methyl-1H-indol-5-yl)benzamide (675 mg) obtained in Reference Example 23 in pyridine (4.4 mL) were added triphenylphosphine (47 mg), copper(I) iodide (12 mg), triethylamine (4.4 mL), 1-ethynylcyclobutanol (182 mg) and dichlorobis(triphenylphosphine)palladium(II) (13 mg), and the mixture was stirred at 65° C. for 15 hr. The mixture was allowed to cool to room temperature, and the insoluble material was filtered off, and washed with toluene. The filtrate was purified by silica gel column chromatography [eluent; hexane:ethyl acetate=1:1→hexane:ethyl acetate=3:7 (volume ratio)] and the obtained crude product was washed with isopropyl ether-ethyl acetate to give the title compound (192 mg, yield 27%) as colorless crystals.

$^1$H NMR (300 MHz, DMSO-$d_6$) δ: 0.86 (9H, s), 1.73-1.88 (2H, m), 2.18-2.30 (2H, m), 2.33 (2H, s), 2.36-2.46 (2H, m), 3.76 (3H, s), 3.87 (2H, s), 5.94 (1H, s), 6.31 (1H, s), 7.34-7.43 (2H, m), 7.56 (2H, d, J=8.3 Hz), 7.92 (1H, d, J=1.1 Hz), 7.98 (2H, d, J=8.3 Hz), 10.13 (1H, s).

melting point: 160-161° C.
elemental analysis ($C_{28}H_{33}N_3O_2$)
Calculated: C, 75.81; H, 7.50; N, 9.47.
Found: C, 75.11; H, 7.37; N, 9.29.

Example 31

N-(2-{[(2,2-dimethylpropyl)amino]methyl}-1-methyl-1H-indol-5-yl)-4-[(1-hydroxycyclopropyl)ethynyl]benzamide

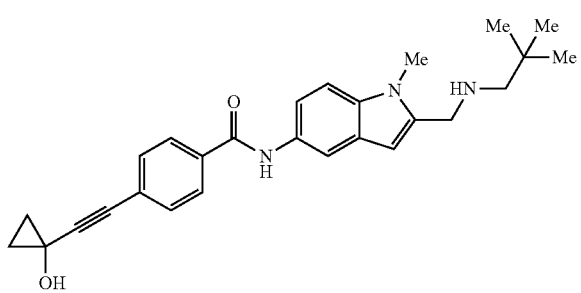 [SMILES: Cn1c(CNCC(C)(C)C)cc2cc(NC(=O)c3ccc(C#CC4(O)CC4)cc3)ccc21]

Under an argon atmosphere, to a solution of 4-bromo-N-(2-{[(2,2-dimethylpropyl)amino]methyl}-1-methyl-1H-indol-5-yl)benzamide (675 mg) obtained in Reference Example 23 in pyridine (4.4 mL) were added triphenylphosphine (47 mg), copper(I) iodide (12 mg), triethylamine (4.4 mL), 1-ethynylcyclopropanol (155 mg) and dichlorobis(triphenylphosphine)palladium(II) (13 mg), and the mixture was stirred at 65° C. for 15 hr. The mixture was allowed to cool to room temperature, and the insoluble material was filtered off, and washed with toluene. The filtrate was purified by silica gel column chromatography [eluent; hexane:ethyl acetate=1:1→hexane:ethyl acetate=1:4 (volume ratio)] and the obtained crude product was washed with isopropyl ether-ethyl acetate to give the title compound (192 mg, yield 27%) as colorless crystals.

$^1$H NMR (300 MHz, DMSO-d$_6$) δ: 0.86 (9H, s), 1.01 (4H, q, J=3.0 Hz), 2.32 (2H, s), 3.75 (3H, s), 3.87 (2H, s), 6.31 (1H, s), 6.35 (1H, s), 7.33-7.42 (2H, m), 7.52 (2H, d, J=8.3 Hz), 7.92 (1H, d, J=1.1 Hz), 7.96 (2H, d, J=8.3 Hz), 10.12 (1H, s).

melting point: 173° C.

elemental analysis (C$_{27}$H$_{31}$N$_3$O$_2$)

Calculated: C, 75.49; H, 7.27; N, 9.78.

Found: C, 75.70; H, 7.55; N, 9.05.

Example 32

4-[(1-hydroxycyclopropyl)ethynyl]-N-(1-methyl-2-{[(2-methylpropyl)amino]methyl}-1H-indol-5-yl)benzamide

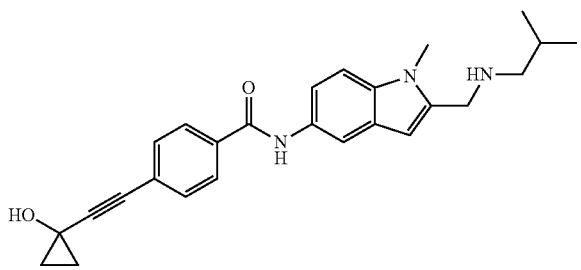 [SMILES: CC(C)CNCc1cc2cc(NC(=O)c3ccc(C#CC4(O)CC4)cc3)ccc2n1C]

4-Bromo-N-(1-methyl-2-{[(2-methylpropyl)amino]methyl}-1H-indol-5-yl)benzamide (350 mg) obtained in Reference Example 22, 1-ethynylcyclopropanol (104 mg), triphenylphosphine (25.1 mg), copper(I) iodide (6.6 mg) and bis(triphenylphosphine)palladium(II) dichloride (7.1 mg) were suspended in a mixed solvent of triethylamine (2.4 mL) and pyridine (2.4 mL), and the mixture was stirred under an argon atmosphere at 65° C. for 15 hr. The mixture was cooled to room temperature, and the precipitate was filtered off. The filtrate was purified by silica gel-NH silica gel serial column chromatography [eluent; hexane:ethyl acetate=40:60 (volume ratio)→hexane:ethyl acetate=0:100 (volume ratio)→ethyl acetate:methanol=100:0 (volume ratio)→ethyl acetate:methanol=90:10] and crystallized from ethyl acetate and heptane to give the title compound (225 mg, yield 64%) as a pale-yellow solid.

$^1$H NMR (300 MHz, DMSO-d$_6$) δ: 0.87 (6H, d, J=6.6 Hz), 0.98-1.04 (4H, m), 1.63-1.74 (1H, m), 2.36 (2H, d, J=6.6 Hz), 3.73 (3H, s), 3.83 (2H, s), 6.29 (1H, s), 6.35 (1H, s), 7.32-7.41 (2H, m), 7.51 (2H, d, J=8.2 Hz), 7.90 (1H, d, J=1.1 Hz), 7.95 (2H, d, J=8.0 Hz), 10.11 (1H, s).

melting point: 172-174° C.

Example 33

N-(3-methyl-2-{[(tetrahydro-2H-pyran-4-ylmethyl)amino]methyl}-1H-indol-5-yl)-4-[(2S)-tetrahydrofuran-2-ylmethoxy]benzamide

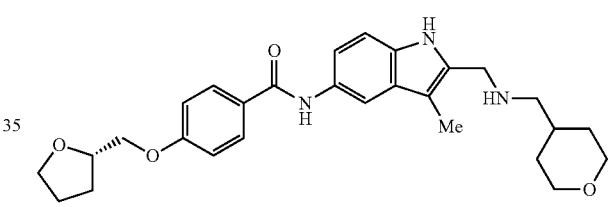

To a solution of N-(2-formyl-3-methyl-1H-indol-5-yl)-4-[(2S)-tetrahydrofuran-2-ylmethoxy]benzamide (263 mg) in N,N-dimethylacetamide (4 mL) obtained in Reference Example 28 were added 4-aminomethyltetrahydropyran (160 mg), sodium triacetoxyborohydride (295 mg) and acetic acid (1.39 mL), and the mixture was stirred at room temperature for 15 hr. Under ice-cooling, 8N aqueous sodium hydroxide solution (4.18 mL) and ethyl acetate were added, and the mixture was successively washed with water and brine. The organic layer was purified by silica gel column chromatography [eluent; ethyl acetate→ethyl acetate:methanol=1:1 (volume ratio)] and the obtained crude product was washed with diisopropyl ether-ethyl acetate to give the title compound (141 mg, yield 42%) as colorless crystals.

$^1$H NMR (300 MHz, DMSO-d$_6$) δ: 1.04-1.21 (2H, m), 1.56-2.08 (8H, m), 2.18 (3H, s), 2.38 (2H, d, J=6.0 Hz), 3.21-3.31 (2H, m), 3.65-3.86 (6H, m), 3.96-4.09 (2H, m), 4.14-4.23 (1H, m), 7.05 (2H, d, J=8.7 Hz), 7.22 (1H, d, J=8.7 Hz), 7.32 (1H, dd, J=8.7, 1.9 Hz), 7.81 (1H, d, J=1.9 Hz), 7.97 (2H, d, J=8.7 Hz), 9.88 (1H, s), 10.55 (1H, s).

melting point: 146-147° C.

elemental analysis (C$_{28}$H$_{35}$N$_3$O$_4$)

Calculated: C, 70.42; H, 7.39; N, 8.80.

Found: C, 70.29; H, 7.45; N, 8.66.

Example 34

N-(2-{[(2-methylpropyl)amino]methyl}-1,3-dimethyl-1H-indol-5-yl)-4-[(2S)-tetrahydrofuran-2-ylmethoxy]benzamide

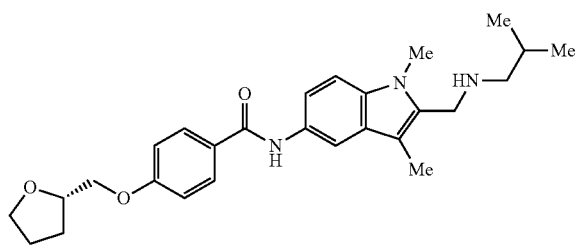 [SMILES: Cc1c(CNCC(C)C)n(C)c2ccc(NC(=O)c3ccc(OC[C@@H]4CCCO4)cc3)cc12]

To a solution of N-(2-formyl-1,3-dimethyl-1H-indol-5-yl)-4-[(2S)-tetrahydrofuran-2-ylmethoxy]benzamide (350 mg) obtained in Reference Example 32 in N,N-dimethylacetamide (5.36 mL) were added isobutylamine (130 mg), sodium triacetoxyborohydride (378 mg) and acetic acid (1.79 mL), and the mixture was stirred at room temperature for 15 hr. Under ice-cooling, 8N aqueous sodium hydroxide solution (4.46 mL) was added, and ethyl acetate and water were added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=9:1 (volume ratio)] and the obtained crude product was washed with diisopropyl ether-ethyl acetate to give the title compound (279 mg, yield 70%) as colorless crystals.

$^1$H NMR (300 MHz, DMSO-$d_6$) δ: 0.86 (6H, d, J=6.4 Hz), 1.58-2.09 (6H, m), 2.22 (s, 3H), 2.34 (2H, d, J=6.8 Hz), 3.65-3.85 (7H, m), 3.96-4.10 (2H, m), 4.14-4.23 (1H, m), 7.05 (2H, d, J=9.0 Hz), 7.30 (1H, d, J=8.7 Hz), 7.40 (dd, J=8.7, 1.9 Hz, 1H), 7.88 (1H, d, J=1.9 Hz), 7.97 (2H, d, J=8.7 Hz), 9.92 (s, 1H).

melting point: 145-146° C.
elemental analysis ($C_{27}H_{35}N_3O_3$)
Calculated: C, 72.13; H, 7.85; N, 9.35.
Found: C, 72.24; H, 7.71; N, 9.31.

Example 35

N-(1,3-dimethyl-2-{[(tetrahydro-2H-pyran-4-ylmethyl)amino]methyl}-1H-indol-5-yl)-4-[(2S)-tetrahydrofuran-2-ylmethoxy]benzamide

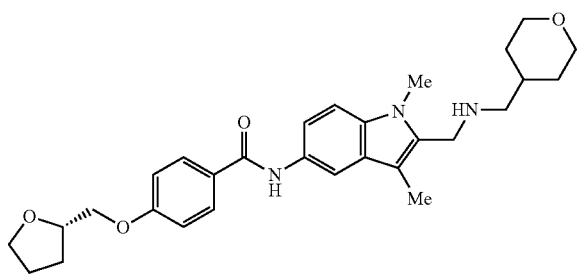 [SMILES: Cc1c(CNCC2CCOCC2)n(C)c2ccc(NC(=O)c3ccc(OC[C@@H]4CCCO4)cc3)cc12]

To a solution of N-(2-formyl-1,3-dimethyl-1H-indol-5-yl)-4-[(2S)-tetrahydrofuran-2-ylmethoxy]benzamide (350 mg) obtained in Reference Example 32 in N,N-dimethylacetamide (5.36 mL) were added 4-aminomethyltetrahydropyran (205 mg), sodium triacetoxyborohydride (378 mg) and acetic acid (1.79 mL), and the mixture was stirred at room temperature for 15 hr. Under ice-cooling, 8N aqueous sodium hydroxide solution (4.46 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=1:1 (volume ratio)] and the obtained crude product was washed with diisopropyl ether-ethyl acetate to give the title compound (375 mg, yield 86%) as colorless crystals.

$^1$H NMR (300 MHz, DMSO-$d_6$) δ: 1.04-1.24 (2H, m), 1.56-2.09 (8H, m), 2.22 (3H, s), 2.41 (2H, d, J=6.0 Hz), 3.19-3.30 (2H, m), 3.65-3.86 (9H, m), 3.96-4.09 (2H, m), 4.13-4.23 (1H, m), 7.05 (2H, d, J=8.7 Hz), 7.30 (1H, d, J=8.7 Hz), 7.41 (1H, dd, J=8.7, 1.9 Hz), 7.88 (1H, d, J=1.9 Hz), 7.97 (2H, d, J=9.0 Hz), 9.92 (1H, s).

melting point: 185-186° C.
elemental analysis ($C_{29}H_{37}N_3O_4$)
Calculated: C, 70.85; H, 7.59; N, 8.55.
Found: C, 70.55; H, 7.41; N, 3.35.

Example 36

N-(2-{[(2-hydroxy-2-methylpropyl)amino]methyl}-1,3-dimethyl-1H-indol-5-yl)-4-[(2S)-tetrahydrofuran-2-ylmethoxy]benzamide

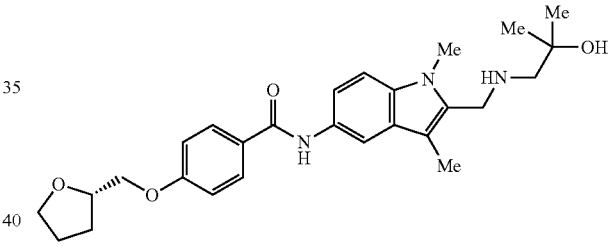

To a solution of N-(2-formyl-1,3-dimethyl-1H-indol-5-yl)-4-[(2S)-tetrahydrofuran-2-ylmethoxy]benzamide (350 mg) obtained in Reference Example 32 in N,N-dimethylacetamide (5.36 mL) were added 1-amino-2-methylpropan-2-ol (159 mg), sodium triacetoxyborohydride (378 mg) and acetic acid (1.79 mL), and the mixture was stirred at room temperature for 15 hr. Under ice-cooling, 8N aqueous sodium hydroxide solution (4.46 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=1:1 (volume ratio)] and the obtained crude product was washed with diisopropyl ether-ethyl acetate to give the title compound (305 mg, yield 73%) as colorless crystals.

$^1$H NMR (300 MHz, DMSO-$d_6$) δ: 1.07 (6H, s), 1.62-2.09 (5H, m), 2.23 (3H, s), 2.43 (2H, s), 3.65-3.84 (5H, m), 3.88 (2H, s), 3.96-4.09 (2H, m), 4.14-4.23 (2H, m), 7.05 (2H, d, J=9.0 Hz), 7.31 (1H, d, J=8.7 Hz), 7.41 (1H, dd, J=8.7, 1.9 Hz), 7.88 (1H, d, J=1.9 Hz), 7.97 (2H, d, J=8.7 Hz), 9.93 (1H, s).

melting point: 145-146° C.
elemental analysis ($C_{27}H_{35}N_3O_4$)
Calculated: C, 69.65; H, 7.58; N, 9.03.
Found: C, 69.35; H, 7.38; N, 8.84.

Example 37

N-(2-{[(2,2-dimethylpropyl)amino]methyl}-1,3-dimethyl-1H-indol-5-yl)-4-[(2S)-tetrahydrofuran-2-ylmethoxy]benzamide

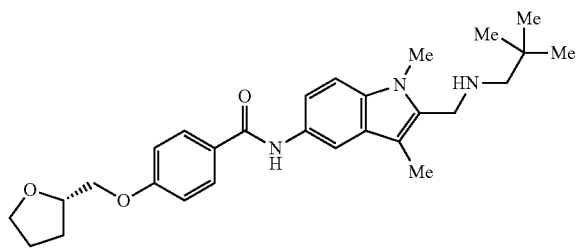 [SMILES: Cc1c(CNCC(C)(C)C)n(C)c2ccc(NC(=O)c3ccc(OC[C@@H]4CCCO4)cc3)cc12]

To a solution of N-(2-formyl-1,3-dimethyl-1H-indol-5-yl)-4-[(2S)-tetrahydrofuran-2-ylmethoxy]benzamide (350 mg) obtained in Reference Example 32 in N,N-dimethylacetamide (5.36 mL) were added neopentylamine (155 mg), sodium triacetoxyborohydride (378 mg) and acetic acid (1.79 mL), and the mixture was stirred at room temperature for 15 hr. Under ice-cooling, 8N aqueous sodium hydroxide solution (4.46 mL) was added, and ethyl acetate and water were further added. The mixture was partitioned, and the aqueous layer was extracted with tetrahydrofuran. The combined organic layer was purified by silica gel column chromatography [eluent; ethyl acetate:methanol=9:1→ethyl acetate:methanol=1:1 (volume ratio)] and the obtained crude product was washed with diisopropyl ether-ethyl acetate to give the title compound (319 mg, yield 77%) as colorless crystals.

$^1$H NMR (300 MHz, DMSO-$d_6$) δ: 0.84 (9H, s), 1.62-2.08 (5H, m), 2.22 (3H, s), 2.30 (2H, s), 3.65-3.89 (7H, m), 3.96-4.09 (2H, m), 4.13-4.23 (1H, m), 7.05 (2H, d, J=9.0 Hz), 7.31 (1H, d, J=8.7 Hz), 7.40 (1H, dd, J=9.0 1.9 Hz), 7.88 (1H, d, J=1.5 Hz), 7.97 (2H, d, J=8.7 Hz), 9.92 (1H, s).

melting point: 165-166° C.
elemental analysis ($C_{28}H_{37}N_3O_3$)
Calculated: C, 72.54; H, 8.04; N, 9.06.
Found: C, 72.55; H, 7.89; N, 8.92.

Example 38

N-(2-{[(trans-4-hydroxy-4-methylcyclohexyl)amino]methyl}-1,3-dimethyl-1H-indol-5-yl)-4-[(2S)-tetrahydrofuran-2-ylmethoxy]benzamide

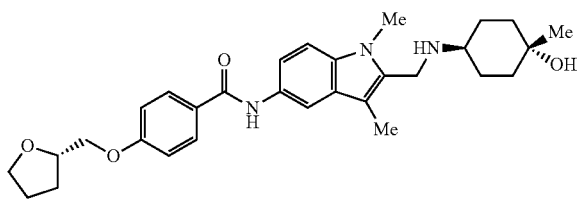 [SMILES: Cc1c(CN[C@H]2CC[C@](C)(O)CC2)n(C)c2ccc(NC(=O)c3ccc(OC[C@@H]4CCCO4)cc3)cc12]

To a solution of N-(2-formyl-1,3-dimethyl-1H-indol-5-yl)-4-[(2S)-tetrahydrofuran-2-ylmethoxy]benzamide (350 mg) obtained in Reference Example 32 in N,N-dimethylacetamide (5.36 mL) were added trans-4-amino-1-methylcyclohexanol (230 mg) obtained in Reference Example 101, sodium triacetoxyborohydride (378 mg) and acetic acid (1.79 mL), and the mixture was stirred at room temperature for 15 hr. Under ice-cooling, 8N aqueous sodium hydroxide solution (4.46 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate:methanol=9:1→ethyl acetate:methanol=1:1 (volume ratio)] and the obtained crude product was washed with diisopropyl ether-ethyl acetate to give the title compound (318 mg, yield 70%) as colorless crystals.

$^1$H NMR (300 MHz, DMSO-$d_6$) δ: 1.09 (3H, s), 1.15-1.39 (4H, m), 1.50-2.09 (9H, m), 2.21 (3H, s), 3.65-3.85 (7H, m), 3.96-4.12 (3H, m), 4.14-4.23 (1H, m), 7.05 (2H, d, J=9.0 Hz), 7.30 (1H, d, J=8.7 Hz), 7.41 (1H, dd, J=9.0 1.9 Hz), 7.88 (1H, d, J=1.9 Hz), 7.97 (2H, d, J=9.0 Hz), 9.92 (1H, s).

melting point: 172-173° C.
elemental analysis ($C_{30}H_{39}N_3O_4$)
Calculated: C, 71.26; H, 7.77; N, 8.31.
Found: C, 70.17; H, 7.68; N, 8.06.

Example 39

4-(cyclopropylmethoxy)-N-(2-{[(2-methylpropyl)amino]methyl}-1,3-dimethyl-1H-indol-5-yl)benzamide

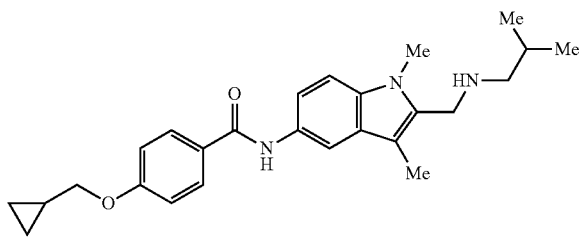 [SMILES: Cc1c(CNCC(C)C)n(C)c2ccc(NC(=O)c3ccc(OCC4CC4)cc3)cc12]

To a solution of 4-(cyclopropylmethoxy)-N-(2-formyl-1,3-dimethyl-1H-indol-5-yl)benzamide (350 mg) obtained in Reference Example 34 in N,N-dimethylacetamide (5.36 mL) were added isobutylamine (141 mg), sodium triacetoxyborohydride (409 mg) and acetic acid (1.94 mL), and the mixture was stirred at room temperature for 15 hr. Under ice-cooling, 8N aqueous sodium hydroxide solution (4.83 mL) was added, and ethyl acetate and water were further added. The mixture was partitioned, and the aqueous layer was extracted with ethyl acetate. The combined organic layer was washed with brine. The organic layer was purified by silica gel column chromatography [hexane:ethyl acetate=1:3→ethyl acetate (volume ratio)] and the obtained crude product was washed with diisopropyl ether to give the title compound (236 mg, yield 58%) as pale-brown crystals.

$^1$H NMR (300 MHz, DMSO-$d_6$) δ: 0.32-0.38 (2H, m), 0.56-0.63 (2H, m), 0.86 (6H, d, J=6.4 Hz), 1.18-1.33 (1H, m), 1.60-1.75 (1H, m), 2.22 (3H, s), 2.35 (2H, d, J=6.8 Hz), 3.73 (3H, s), 3.83 (2H, s), 3.90 (2H, d, J=7.2 Hz), 7.03 (2H, d, J=8.7 Hz), 7.31 (1H, d, J=8.7 Hz), 7.40 (1H, dd, J=8.7, 1.9 Hz), 7.88 (1H, d, J=1.9 Hz), 7.96 (2H, a, J=9.0 Hz), 9.91 (1H, s).

melting point: 142-143° C.
elemental analysis ($C_{26}H_{33}N_3O_2$)
Calculated: C, 74.43; H, 7.93; N, 10.02.
Found: C, 74.29; H, 7.87; N, 9.94.

Example 40

4-(cyclopropylmethoxy)-N-(1,3-dimethyl-2-{[(tetrahydro-2H-pyran-4-ylmethyl)amino]methyl}-1H-indol-5-yl)benzamide

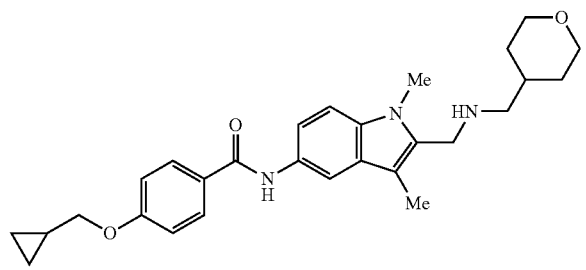 [SMILES: Cc1c(CNCC2CCOCC2)n(C)c2ccc(NC(=O)c3ccc(OCC4CC4)cc3)cc12]

To a solution of 4-(cyclopropylmethoxy)-N-(2-formyl-1,3-dimethyl-1H-indol-5-yl)benzamide (350 mg) obtained in Reference Example 34 in N,N-dimethylacetamide (5.36 mL) were added 4-aminomethyltetrahydropyran (222 mg), sodium triacetoxyborohydride (409 mg) and acetic acid (1.94 mL), and the mixture was stirred at room temperature for 15 hr. Under ice-cooling, 8N aqueous sodium hydroxide solution (4.83 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=7:3 (volume ratio)] and the obtained crude product was washed with diisopropyl ether to give the title compound (342 mg, yield 77%) as pale-brown crystals.

$^1$H NMR (300 MHz, DMSO-$d_6$) δ: 0.32-0.39 (2H, m), 0.56-0.63 (2H, m), 1.04-1.33 (3H, m), 1.56-1.72 (3H, m), 2.22 (3H, s), 2.42 (2H, d, J=6.0 Hz), 3.20-3.30 (2H, m), 3.72 (3H, s), 3.77-3.85 (4H, m), 3.90 (2H, d, J=7.2 Hz), 7.03 (2H, d, J=9.0 Hz), 7.30 (1H, d, J=8.7 Hz), 7.41 (1H, dd, J=9.0 1.9 Hz), 7.88 (1H, d, J=1.9 Hz), 7.96 (2H, d, J=8.7 Hz), 9.91 (1H, s).

melting point: 176-177° C.
elemental analysis ($C_{28}H_{35}N_3O_3$)
Calculated: C, 72.86; H, 7.64; N, 9.10.
Found: C, 72.65; H, 7.61; N, 9.04.

Example 41

4-(cyclopropylmethoxy)-N-(2-{[(2,2-dimethylpropyl)amino]methyl}-1,3-dimethyl-1H-indol-5-yl)benzamide

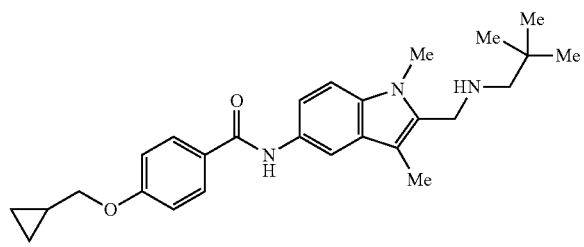 [SMILES: Cc1c(CNCC(C)(C)C)n(C)c2ccc(NC(=O)c3ccc(OCC4CC4)cc3)cc12]

To a solution of 4-(cyclopropylmethoxy)-N-(2-formyl-1,3-dimethyl-1H-indol-5-yl)benzamide (350 mg) obtained in Reference Example 34 in N,N-dimethylacetamide (5.36 mL) were added neopentylamine (168 mg), sodium triacetoxyborohydride (409 mg) and acetic acid (1.94 mL), and the mixture was stirred at room temperature for 15 hr. Under ice-cooling, 8N aqueous sodium hydroxide solution (4.83 mL) was added, and ethyl acetate and water were further added. The mixture was partitioned, and the aqueous layer was extracted with tetrahydrofuran. The combined organic layer was purified by silica gel column chromatography [hexane:ethyl acetate=1:1→hexane:ethyl acetate=1:4 (volume ratio)] and the obtained crude product was washed with diisopropyl ether to give the title compound (330 mg, yield 79%) as pale-brown crystals.

$^1$H NMR (300 MHz, DMSO-$d_6$) δ: 0.32-0.39 (2H, m), 0.55-0.65 (2H, m), 0.84 (9H, s), 1.18-1.33 (1H, m), 2.22 (3H, s), 2.30 (2H, s), 3.75 (3H, s), 3.85 (2H, s), 3.90 (2H, d, J=7.2 Hz), 7.03 (2H, d, J=8.7 Hz), 7.31 (1H, d, J=8.7 Hz), 7.40 (1H, dd, J=9.0 1.9 Hz), 7.88 (1H, d, J=1.9 Hz), 7.96 (2H, d, J=8.7 Hz), 9.91 (1H, s).

melting point: 169-170° C.
elemental analysis ($C_{27}H_{35}N_3O_2$)
Calculated: C, 74.79; H, 8.14; N, 9.69.
Found: C, 74.69; H, 8.12; N, 9.58.

Example 42

4-(cyclopropylmethoxy)-N-(2-{[(trans-4-hydroxy-4-methylcyclohexyl)amino]methyl}-1,3-dimethyl-1H-indol-5-yl)benzamide

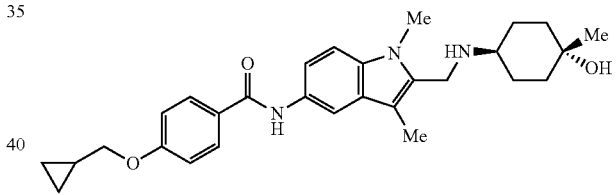

To a solution of 4-(cyclopropylmethoxy)-N-(2-formyl-1,3-dimethyl-1H-indol-5-yl)benzamide (350 mg) obtained in Reference Example 34 in N,N-dimethylacetamide (5.36 mL) were added trans-4-amino-1-methylcyclohexanol (250 mg) obtained in Reference Example 101, sodium triacetoxyborohydride (409 mg) and acetic acid (1.94 mL), and the mixture was stirred at room temperature for 15 hr. Under ice-cooling, 8N aqueous sodium hydroxide solution (4.83 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=7:3 (volume ratio)] and the obtained crude product was washed with diisopropyl ether to give the title compound (238 mg, yield 51%) as pale-brown crystals.

$^1$H NMR (300 MHz, DMSO-$d_6$) δ: 0.32-0.39 (2H, m), 0.56-0.63 (2H, m), 1.09 (3H, s), 1.17-1.38 (5H, m), 1.50-1.85 (4H, m), 2.21 (3H, s), 3.72 (3H, s), 3.82 (2H, s), 3.90 (2H, d, J=6.8 Hz), 4.11 (1H, s), 7.03 (2H, d, J=8.7 Hz), 7.30 (1H, d, J=8.7 Hz), 7.40 (1H, dd, J=9.0 1.9 Hz), 7.88 (1H, d, J=1.5 Hz), 7.96 (2H, d, J=8.7 Hz), 9.91 (1H, s).

melting point: 191° C.
elemental analysis ($C_{29}H_{37}N_3O_3$)

Example 43

4-(cyclopropylmethoxy)-N-(4-methyl-2-{[(tetrahydro-2H-pyran-4-ylmethyl)amino]methyl}-1H-indol-5-yl)benzamide

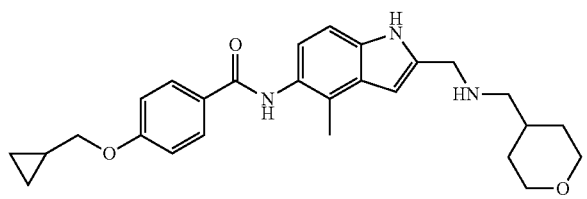 [SMILES: Cc1c(NC(=O)c2ccc(OCC3CC3)cc2)ccc2[nH]c(CNCC3CCOCC3)cc12]

4-(Cyclopropylmethoxy)-N-(2-formyl-4-methyl-1H-indol-5-yl)benzamide (298 mg) obtained in Reference Example 41 and 1-(tetrahydro-2H-pyran-4-yl)methanamine (197 mg) were suspended in NMP (3.0 mL), acetic acid (1.0 mL) was added at room temperature, and the mixture was stirred at the same temperature for 2 hr. Sodium triacetoxyborohydride (363 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=90:10 (volume ratio)→ethyl acetate:methanol=50:50 (volume ratio)] and the obtained solid was recrystallized from ethyl acetate to give the title compound (220 mg, yield 57%) as a brown solid.

$^1$H NMR (300 MHz, CDCl$_3$) δ: 0.34-0.43 (2H, m), 0.63-0.73 (2H, m), 1.23-1.41 (3H, m), 1.60-1.81 (3H, m), 2.45 (3H, s), 2.55 (2H, d, J=6.4 Hz), 3.39 (2H, td, J=11.8, 2.1 Hz), 3.88 (2H, d, J=6.8 Hz), 3.93-3.98 (3H, m), 4.00 (1H, d, J=3.8 Hz), 6.37 (1H, d, J=1.1 Hz), 6.98 (2H, d, J=8.7 Hz), 7.19 (1H, d, J=8.7 Hz), 7.35 (1H, d, J=7.9 Hz), 7.58 (1H, s), 7.88 (2H, d, J=8.3 Hz), 8.47 (1H, s).

melting point: 181-182° C.
elemental analysis (C$_{27}$H$_{33}$N$_3$O$_3$)
Calculated: C, 72.46; H, 7.43; N, 9.39.
Found: C, 72.16; H, 7.40; N, 9.27.

Example 44

4-(cyclopropylmethoxy)-N-(2-{[(2-hydroxy-2-methylpropyl)amino]methyl}-4-methyl-1H-indol-5-yl)benzamide

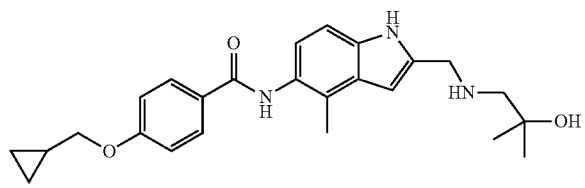 [SMILES: Cc1c(NC(=O)c2ccc(OCC3CC3)cc2)ccc2[nH]c(CNCC(C)(C)O)cc12]

4-(Cyclopropylmethoxy)-N-(2-formyl-4-methyl-1H-indol-5-yl)benzamide (298 mg) obtained in Reference Example 41 and 1-amino-2-methylpropan-2-ol (153 mg) were suspended in NMP (3.0 mL), acetic acid (1.0 mL) was added at room temperature, and the mixture was stirred at the same temperature for 2 hr. Sodium triacetoxyborohydride (363 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (307 mg, yield 85%) as a brown solid.

$^1$H NMR (300 MHz, CDCl$_3$) δ: 0.34-0.43 (2H, m), 0.63-0.72 (2H, m), 1.22 (6H, s), 1.25-1.36 (1H, m), 2.45 (3H, s), 2.61 (2H, s), 3.88 (2H, d, J=7.2 Hz), 4.02 (2H, s), 6.38 (1H, d, J=1.1 Hz), 6.98 (2H, d, J=8.3 Hz), 7.19 (1H, d, J=8.3 Hz), 7.34 (1H, d, J=7.6 Hz), 7.58 (1H, br. s.), 7.88 (2H, d, J=8.0 Hz), 8.48 (1H, br. s.).

melting point: 186° C.
elemental analysis (C$_{25}$H$_{31}$N$_3$O$_3$.0.2H$_2$O)
Calculated: C, 70.63; H, 7.44; N, 9.88.
Found: C, 70.57; H, 7.38; N, 9.68.

Example 45

N-{2-[(cyclopentylamino)methyl]-4-methyl-1H-indol-5-yl}-4-(cyclopropylmethoxy)benzamide

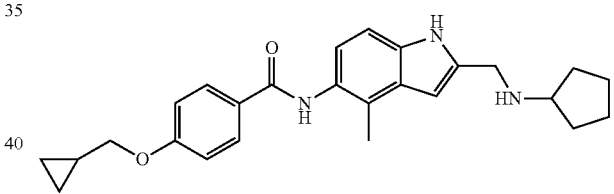

4-(Cyclopropylmethoxy)-N-(2-formyl-4-methyl-1H-indol-5-yl)benzamide (298 mg) obtained in Reference Example 41 and cyclopentylamine (146 mg) were suspended in NMP (3.0 mL), acetic acid (1.0 mL) was added at room temperature, and the mixture was stirred at the same temperature for 2 hr. Sodium triacetoxyborohydride (363 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (279 mg, yield 78%) as a brown solid.

$^1$H NMR (300 MHz, CDCl$_3$) δ: 0.34-0.43 (2H, m), 0.63-0.73 (2H, m), 1.25-1.45 (3H, m), 1.47-1.78 (4H, m), 1.80-1.95 (2H, m), 2.45 (3H, s), 3.13 (1H, quin, J=6.7 Hz), 3.87 (2H, d, J=6.8 Hz), 3.95 (2H, s), 6.35 (1H, d, J=1.1 Hz), 6.97 (2H, d), 7.17 (1H, d, J=8.3 Hz), 7.33 (1H, d, J=8.3 Hz), 7.52-7.65 (1H, m), 7.88 (2H, d, J=8.7 Hz), 8.61 (1H, br. s.).

melting point: 207-208° C.
elemental analysis (C$_{26}$H$_{31}$N$_3$O$_2$)

Calculated: C, 74.79; H, 7.48; N, 10.06.
Found: C, 74.66; H, 7.38; N, 9.83.

Example 46

N-(4-methyl-2-{[(2-methylpropyl)amino]methyl}-1H-indol-5-yl)-4-[(2S)-tetrahydrofuran-2-yl-methoxy]benzamide

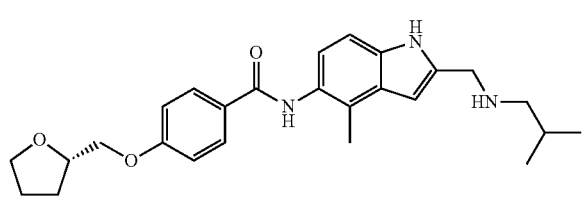 [SMILES: Cc1c(NC(=O)c2ccc(OC[C@@H]3CCCO3)cc2)ccc2[nH]c(CNCC(C)C)cc12]

N-(2-Formyl-4-methyl-1H-indol-5-yl)-4-[(2S)-tetrahydrofuran-2-ylmethoxy]benzamide (333 mg) obtained in Reference Example 43 and isobutylamine (130 mg) were suspended in NMP (3.0 mL), acetic acid (1.0 mL) was added at room temperature, and the mixture was stirred at the same temperature for 2 hr. Sodium triacetoxyborohydride (378 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (168 mg, yield 43%) as a beige solid.

$^1$H NMR (300 MHz, CDCl$_3$) δ: 0.93 (6H, d), 1.69-1.87 (2H, m), 1.90-2.19 (3H, m), 2.42-2.49 (5H, m), 3.80-3.90 (1H, m), 3.91-4.00 (3H, m), 4.04 (2H, d, J=5.3 Hz), 4.25-4.37 (1H, m), 6.36 (1H, d, J=1.1 Hz), 7.01 (2H, d, J=8.3 Hz), 7.19 (1H, d, J=8.7 Hz), 7.34 (1H, d, J=9.1 Hz), 7.58 (1H, br. s.), 7.88 (2H, d, J=8.3 Hz), 8.54 (1H, br. s.).

Example 47

N-(4-methyl-2-{[(tetrahydro-2H-pyran-4-ylmethyl)amino]methyl}-1H-indol-5-yl)-4-[(2S)-tetrahydrofuran-2-ylmethoxy]benzamide

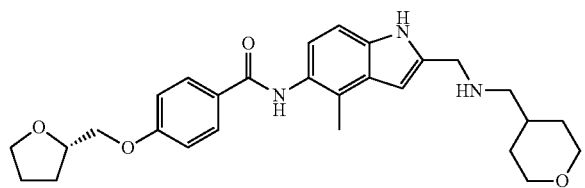 [SMILES: Cc1c(NC(=O)c2ccc(OC[C@@H]3CCCO3)cc2)ccc2[nH]c(CNCC3CCOCC3)cc12]

N-(2-Formyl-4-methyl-1H-indol-5-yl)-4-[(2S)-tetrahydrofuran-2-ylmethoxy]benzamide (333 mg) obtained in Reference Example 43 and 1-(tetrahydro-2H-pyran-4-yl)methanamine (205 mg) were suspended in NMP (3.0 mL), acetic acid (1.0 mL) was added at room temperature, and the mixture was stirred at the same temperature for 2 hr. Sodium triacetoxyborohydride (378 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=90:10 (volume ratio)→ethyl acetate:methanol=50:50 (volume ratio)] and the obtained solid was recrystallized from ethyl acetate to give the title compound (272 mg, yield 64%) as a beige solid.

$^1$H NMR (300 MHz, CDCl$_3$) δ: 1.23-1.40 (2H, m), 1.65-1.86 (4H, m), 1.90-2.19 (3H, m), 2.45 (3H, s), 2.55 (2H, J=6.4 Hz), 3.39 (2H, td, J=11.7, 1.9 Hz), 3.80-3.90 (1H, m), 3.91-4.01 (5H, m), 4.04 (2H, d, J=5.3 Hz), 4.24-4.37 (1H, m), 6.37 (1H, d, J=0.8 Hz), 7.01 (2H, d, J=8.3 Hz), 7.20 (1H, d, J=8.3 Hz), 7.34 (1H, d, J=6.0 Hz), 7.59 (1H, s), 7.88 (2H, d, J=7.9 Hz), 8.59 (1H, br. s.).

melting point: 166-167° C.

elemental analysis (C$_{28}$H$_{35}$N$_3$O$_4$.0.3H$_2$O)
Calculated: C, 69.63; H, 7.43; N, 8.70.
Found: C, 69.65; H, 7.35; N, 8.62.

Example 48

N-(2-{[(2-hydroxy-2-methylpropyl)amino]methyl}-4-methyl-1H-indol-5-yl)-4-[(2S)-tetrahydrofuran-2-ylmethoxy]benzamide

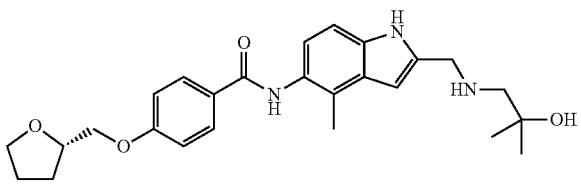 [SMILES: Cc1c(NC(=O)c2ccc(OC[C@@H]3CCCO3)cc2)ccc2[nH]c(CNCC(C)(C)O)cc12]

N-(2-Formyl-4-methyl-1H-indol-5-yl)-4-[(2S)-tetrahydrofuran-2-ylmethoxy]benzamide (333 mg) obtained in Reference Example 43 and 1-amino-2-methylpropan-2-ol (160 mg) were suspended in NMP (3.0 mL), acetic acid (1.0 mL) was added at room temperature, and the mixture was stirred at the same temperature for 2 hr. Sodium triacetoxyborohydride (378 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (308 mg, yield 77%) as a brown solid.

$^1$H NMR (300 MHz, CDCl$_3$) δ: 1.21 (6H, s), 1.72-1.89 (1H, m), 1.90-2.04 (2H, m), 2.04-2.18 (1H, m), 2.45 (3H, s), 2.61 (2H, s), 3.80-3.91 (1H, m), 3.96 (1H, dt, J=8.3, 6.6 Hz), 4.00-4.08 (4H, m), 4.24-4.37 (1H, m), 6.38 (1H, d, J=1.5 Hz), 7.00 (2H, d, J=8.7 Hz), 7.18 (1H, d, J=8.7 Hz), 7.33 (1H, d, J=8.7 Hz), 7.59 (1H, br. s.), 7.88 (2H, d, J=8.0 Hz), 8.50 (1H, s).

melting point: 169-170° C.

elemental analysis (C$_{26}$H$_{33}$N$_3$O$_4$.0.09H$_2$O)
Calculated: C, 68.91; H, 7.38; N, 9.27.
Found: C, 69.20; H, 7.32; N, 8.97.

Example 49

N-{2-[(cyclopentylamino)methyl]-4-methyl-1H-indol-5-yl}-4-[(2S)-tetrahydrofuran-2-ylmethoxy]benzamide

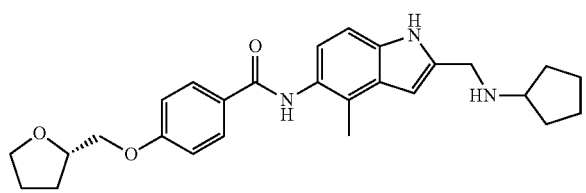 [SMILES: Cc1c(NC(=O)c2ccc(OC[C@@H]3CCCO3)cc2)ccc2[nH]c(CNC3CCCC3)cc12]

N-(2-Formyl-4-methyl-1H-indol-5-yl)-4-[(2S)-tetrahydrofuran-2-ylmethoxy]benzamide (333 mg) obtained in Reference Example 43 and cyclopentylamine (152 mg) were suspended in NMP (3.0 mL), acetic acid (1.0 mL) was added at room temperature, and the mixture was stirred at the same temperature for 2 hr. Sodium triacetoxyborohydride (378 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed with water and then with saturated brine, dried over sodium sulfate, and concentrated under reduced pressure. The residue was purified by silica gel column chromatography [eluent; ethyl acetate:methanol=90:10 (volume ratio) →ethyl acetate:methanol=50:50 (volume ratio)] and the obtained solid was recrystallized from ethyl acetate to give the title compound (243 mg, yield 61%) as a beige solid.

$^1$H NMR (300 MHz, CDCl$_3$) δ: 1.29-1.44 (2H, m), 1.63-2.19 (10H, m), 2.45 (3H, s), 3.14 (1H, quin, J=6.7 Hz), 3.80-3.90 (1H, m), 3.91-4.01 (3H, m), 4.04 (2H, d, J=4.9 Hz), 4.24-4.36 (1H, m), 6.36 (1H, d, J=1.1 Hz), 7.01 (2H, d, J=8.3 Hz), 7.19 (1H, d, J=8.7 Hz), 7.34 (1H, d, J=7.2 Hz), 7.57 (1H, s), 7.88 (2H, d, J=7.9 Hz), 8.53 (1H, s).

melting point: 191-192° C.
elemental analysis (C$_{27}$H$_{33}$N$_3$O$_3$)
Calculated: C, 72.46; H, 7.43; N, 9.39.
Found: C, 72.30; H, 7.39; N, 9.28.

Example 50

4-(cyclopropylmethoxy)-N-(2-{[(2-hydroxy-2-methylpropyl)amino]methyl}-1,4-dimethyl-1H-indol-5-yl)benzamide

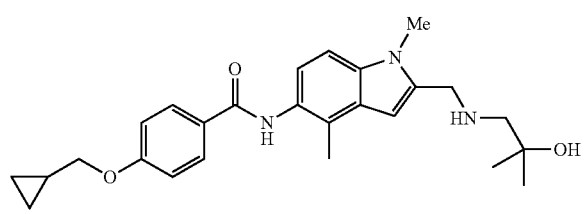 [SMILES: Cc1c(NC(=O)c2ccc(OCC3CC3)cc2)ccc2c1cc(CNCC(C)(C)O)n2C]

4-(Cyclopropylmethoxy)-N-(2-formyl-1,4-dimethyl-1H-indol-5-yl)benzamide (349 mg) obtained in Reference Example 47 and 1-amino-2-methylpropan-2-ol (173 mg) were suspended in NMP (3.0 mL), acetic acid (1.0 mL) was added at room temperature, and the mixture was stirred at the same temperature for 3 hr. Sodium triacetoxyborohydride (408 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (395 mg, yield 94%) as a pale-yellow solid.

$^1$H NMR (300 MHz, CDCl$_3$) δ: 0.34-0.43 (2H, m), 0.68 (2H, q, J=6.1 Hz), 1.23-1.37 (1H, m), 2.46 (3H, s), 2.65 (2H, s), 2.75 (1H, br. s.), 3.77 (3H, s), 3.88 (2H, d, J=6.8 Hz), 4.00 (2H, s), 6.41 (1H, s), 6.98 (2H, d, J=8.7 Hz), 7.17 (1H, d, J=8.7 Hz), 7.42 (1H, d, J=8.0 Hz), 7.59 (1H, br. s.), 7.88 (2H, d, J=8.0 Hz).

melting point: 175-176° C.
elemental analysis (C$_{26}$H$_{33}$N$_3$O$_3$)
Calculated: C, 71.70; H, 7.64; N, 9.65.
Found: C, 71.40; H, 7.65; N, 9.38.

Example 51

N-(2-{[(2,2-dimethylpropyl)amino]methyl}-1,4-dimethyl-1H-indol-5-yl)-4-[(2S)-tetrahydrofuran-2-ylmethoxy]benzamide

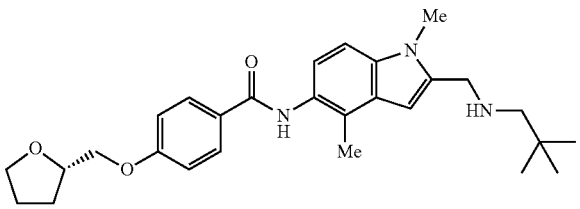 [SMILES: Cc1c(NC(=O)c2ccc(OC[C@@H]3CCCO3)cc2)ccc2c1cc(CNCC(C)(C)C)n2C]

N-(2-Formyl-1,4-dimethyl-1H-indol-5-yl)-4-[(2S)-tetrahydrofuran-2-ylmethoxy]benzamide (283 mg) obtained in Reference Example 51 and neopentylamine (358 mg) were suspended in DMA (10 mL), acetic acid (1.0 mL) was added at room temperature, and the mixture was stirred at the same temperature for 10 min. The reaction solution was ice-cooled, sodium triacetoxyborohydride (360 mg) was added, and the mixture was allowed to warm to room temperature and stirred for 17 hr. The mixture was diluted with ethyl acetate, and the organic layer was washed with 1N sodium hydroxide and water, and then with saturated brine, dried over sodium sulfate, and concentrated under reduced pressure. The residue was purified by silica gel column chromatography [eluent, hexane:ethyl acetate=30:70 (volume ratio)→ethyl acetate], and the obtained solid was recrystallized from a mixed solvent of ethyl acetate and hexane to give the title compound (249 mg, yield 74%) as a pale-yellow solid.

$^1$H NMR (300 MHz, DMSO-d$_6$) δ: 0.87 (9H, s), 1.62-1.78 (1H, m), 1.78-1.96 (2H, m), 1.96-2.10 (1H, m), 2.30 (3H, s), 2.34 (2H, s), 3.64-3.75 (1H, m), 3.76 (3H, s), 3.78-3.86 (1H, m), 3.91 (2H, br. s.), 3.96-4.13 (2H, m), 4.18 (1H, qd, J=6.69, 3.79 Hz), 6.39 (1H, s), 6.98 (1H, d, J=8.71 Hz), 7.04 (2H, d, J=9.09 Hz), 7.22 (1H, d, J=8.71 Hz), 7.98 (2H, d, J=8.71 Hz), 9.71 (1H, s).

melting point: 179° C.
elemental analysis (C$_{28}$H$_{37}$N$_3$O$_3$)
Calculated: C, 72.54; H, 8.04; N, 9.06.
Found: C, 72.30; H, 7.99; N, 8.95.

Example 52

N-(2-{[(2-hydroxy-2-methylpropyl)amino]methyl}-1,4-dimethyl-1H-indol-5-yl)-4-[(2S)-tetrahydrofuran-2-ylmethoxy]benzamide

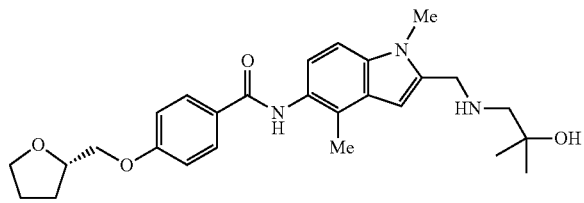 [SMILES: Cc1c(NC(=O)c2ccc(OC[C@@H]3CCCO3)cc2)ccc2c1cc(CNCC(C)(C)O)n2C]

N-(2-Formyl-1,4-dimethyl-1H-indol-5-yl)-4-[(2S)-tetrahydrofuran-2-ylmethoxy]benzamide (286 mg) obtained in Reference Example 51 and 1-amino-2-methylpropan-2-ol (365 mg) were suspended in DMA (10 mL), acetic acid (1.0 mL) was added at room temperature, and the mixture was stirred at the same temperature for 10 min. The reaction solution was ice-cooled, sodium triacetoxyborohydride (360 mg) was added, and the mixture was allowed to warm to room temperature. The mixture was stirred for 17 hr, and diluted with ethyl acetate, and the organic layer was washed with 1N sodium hydroxide and water, and then with saturated brine, dried over sodium sulfate, and concentrated under reduced pressure. The residue was purified by silica gel column chromatography [eluent; ethyl acetate→ethyl acetate:methanol=80:20 (volume ratio)], and the obtained solid was recrystallized from a mixed solvent of ethyl acetate and hexane to give the title compound (261 mg, yield 77%) as a pale-yellow solid.

$^1$H NMR (300 MHz, DMSO-$d_6$) δ: 1.09 (6H, s), 1.62-1.76 (1H, m), 1.78-1.95 (2H, m), 1.95-2.10 (1H, m), 2.30 (3H, s), 2.46 (2H, s), 3.64-3.74 (1H, m), 3.76 (3H, s), 3.78-3.85 (1H, m), 3.91 (2H, s), 3.95-4.12 (2H, m), 4.12-4.26 (2H, m), 6.38 (1H, s), 6.98 (1H, d, J=8.33 Hz), 7.04 (2H, d, J=8.71 Hz), 7.22 (1H, d, J=8.71 Hz), 7.98 (2H, d, J=8.71 Hz), 9.71 (1H, s).
melting point: 160-162° C.
elemental analysis ($C_{27}H_{35}N_3O_4$)
Calculated: C, 69.65; H, 7.58; N, 9.03.
Found: C, 69.47; H, 7.53; N, 8.99.

Example 53-1

N-(2-{[(trans-4-hydroxy-4-methylcyclohexyl)amino]methyl}-1,4-dimethyl-1H-indol-5-yl)-4-[(2S)-tetrahydrofuran-2-ylmethoxy]benzamide hydrochloride

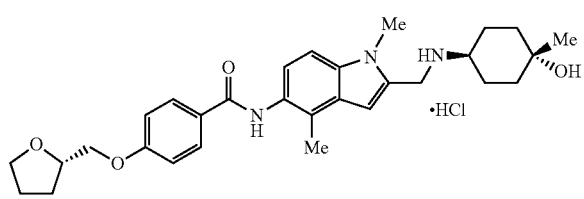 [SMILES: Cc1c(NC(=O)c2ccc(OC[C@@H]3CCCO3)cc2)ccc2c1cc(CN[C@H]1CC[C@](C)(O)CC1)n2C ; Cl]

To a solution of N-(2-formyl-1,4-dimethyl-1H-indol-5-yl)-4-[(2S)-tetrahydrofuran-2-ylmethoxy]benzamide (80.0 g) obtained in Reference Example 51 in DMA (800 mL) was added trans-4-amino-1-methylcyclohexanol (31.6 g) obtained in Reference Example 101, and the mixture was stirred at 60° C. for 4 hr. The reaction mixture was ice-cooled, acetic acid (35.0 mL) and sodium triacetoxyborohydride (108 g) were added, and the mixture was stirred at room temperature for 16 hr. 1N Hydrochloric acid (815 mL) was added at 20° C. or below, and the mixture was stirred at 5° C. for 4 hr. The precipitated solid was collected by filtration, and successively washed with water, acetonitrile and diethyl ether to give a crude product (104 g). The obtained crude product (100 g) was suspended in THF (3 L), 1N aqueous sodium hydroxide solution (739 mL) was added, and the mixture was stirred at 55° C. for 15 min. The insoluble material was removed by filtration, and 2N hydrochloric acid (399 mL) was added dropwise to the filtrate at 55° C. The mixture was stirred at room temperature for 3 hr, and the precipitated solid was collected by filtration, and successively washed with water, acetonitrile and diethyl ether, and dried under reduced pressure to give the title compound (96.8 g, yield 92%) as pale-brown crystals.

$^1$H NMR (300 MHz, DMSO-$d_6$) δ: 1.15 (3H, s), 1.33-1.49 (2H, m), 1.56-2.13 (10H, m), 2.34 (3H, s), 3.17 (1H, br. s.), 3.65-3.74 (1H, m), 3.76-3.84 (4H, m), 3.96-4.10 (2H, m), 4.14-4.24 (1H, m), 4.41 (2H, br. s.), 4.44 (1H, s), 6.75 (1H, s), 7.05 (2H, d, J=8.69 Hz), 7.10 (1H, d, J=8.69 Hz), 7.33 (1H, d, J=8.69 Hz), 7.98 (2H, d, J=8.69 Hz), 9.14 (1H, br. s.), 9.79 (1H, s).
melting point: 278° C.
elemental analysis ($C_{30}H_{40}N_3O_4Cl$)
Calculated: C, 66.47; H, 7.44; N, 7.75.
Found: C, 66.23; H, 7.43; N, 7.76.

Example 53-2

N-(2-{[(trans-4-hydroxy-4-methylcyclohexyl)amino]methyl}-1,4-dimethyl-1H-indol-5-yl)-4-[(2S)-tetrahydrofuran-2-ylmethoxy]benzamide N-(2-{[(trans-4-hydroxy-4-methylcyclohexyl)amino]methyl}-1,4-dimethyl-1H-indol-5-yl)-4-[(2S)-tetrahydrofuran-2-ylmethoxy]benzamide hydrochloride (521 g) obtained in Example 53-1 was suspended in THF (18.3 L), 1N aqueous sodium hydroxide solution (2.89 L) was added, and the mixture was stirred at 60° C. After complete dissolution, the mixture was partitioned, and the organic layer was washed with saturated brine, and dried over anhydrous sodium sulfate. The solvent was evaporated under reduced pressure. The obtained solid was finely ground, suspended in ethyl acetate (14.1 L), and the mixture was stirred at 70° C. for 30 hr. The reaction mixture was cooled to 10° C. or below, and the precipitated crystals were collected by filtration, washed with ethyl acetate, and dried so to give the title compound (444 g, yield 91%) as pale-brown crystals.

$^1$H NMR (300. MHz, DMSO-$d_6$) δ: 1.10 (3H, s), 1.17-1.38 (4H, m), 1.49-2.09 (9H, m), 2.29 (3H, s), 2.47-2.59 (1H, m), 3.65-3.84 (5H, m), 3.87 (2H, s), 3.95-4.09 (2H, m), 4.11 (1H, s), 4.14-4.23 (1H, m), 6.37 (1H, s), 6.98 (1H, d, J=8.7 Hz), 7.04 (2H, d, J=9.1 Hz), 7.21 (1H, d, J=8.7 Hz), 7.98 (2H, d, J=9.1 Hz), 9.72 (1H, s).
melting point: 200° C.
elemental analysis ($C_{30}H_{39}N_3O_4$)
Calculated: C, 71.26; H, 7.77; N, 8.31.
Found: C, 71.28; H, 7.50; N, 8.37.

Example 54

N-(1,4-dimethyl-2-{[(2-methylpropyl)amino]methyl}-1H-indol-5-yl)-4-[(2S)-tetrahydrofuran-2-ylmethoxy]benzamide

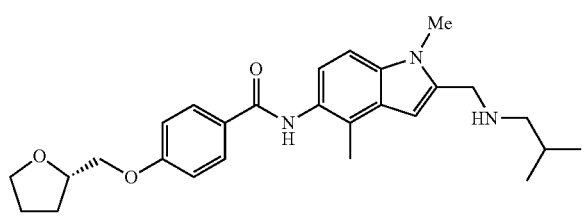 [SMILES: Cc1c(NC(=O)c2ccc(OC[C@@H]3CCCO3)cc2)ccc2c1cc(CNCC(C)C)n2C]

N-(2-Formyl-1,4-dimethyl-1H-indol-5-yl)-4-[(2S)-tetrahydrofuran-2-ylmethoxy]benzamide (251 mg) obtained in Reference Example 51 and isobutylamine (94 mg) were suspended in NMP (3.0 mL), acetic acid (1.0 mL) was added at room temperature, and the mixture was stirred at the same temperature for 3 hr. Sodium triacetoxyborohydride (271 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in ethyl acetate, and the precipitate was collected by filtration, washed with ethyl acetate, and dried under reduced pressure to give the title compound (183 mg, yield 63%) as a pale-yellow solid.

$^1$H NMR (300 MHz, CDCl$_3$) δ: 0.93 (6H, d, J=6.3 Hz), 1.69-1.87 (2H, m), 1.90-2.03 (2H, m), 2.03-2.18 (1H, m), 2.46 (3H, s), 2.50 (2H, d, J=6.8 Hz), 3.77 (3H, s), 3.79-4.00 (4H, m), 4.04 (2H, d, J=5.3 Hz), 4.24-4.37 (1H, m), 6.39 (1H, s), 7.00 (2H, d, J=8.7 Hz), 7.16 (1H, d, J=8.3 Hz), 7.41 (1H, d, J=8.7 Hz), 7.58 (1H, br. s.), 7.88 (2H, d, J=7.6 Hz).

melting point: 162° C.
elemental analysis (C$_{27}$H$_{35}$N$_3$O$_3$)
Calculated: C, 72.13; H, 7.85; N, 9.35.
Found: C, 71.98; H, 7.86; N, 9.35.

Example 55

N-(1,4-dimethyl-2-{[(tetrahydro-2H-pyran-4-ylmethyl)amino]methyl}-1H-indol-5-yl)-4-[(2S)-tetrahydrofuran-2-ylmethoxy]benzamide

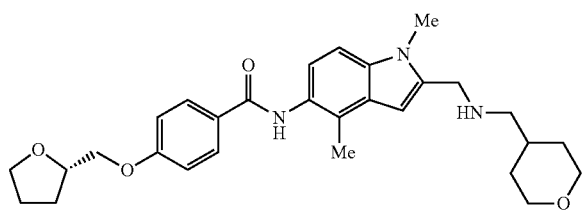 [SMILES: Cc1c(NC(=O)c2ccc(OC[C@@H]3CCCO3)cc2)ccc2c1cc(CNCC1CCOCC1)n2C]

N-(2-Formyl-1,4-dimethyl-1H-indol-5-yl)-4-[(2S)-tetrahydrofuran-2-ylmethoxy]benzamide (251 mg) obtained in Reference Example 51 and 1-(tetrahydro-2H-pyran-4-yl)methanamine (148 mg) were suspended in NMP (3.0 mL), acetic acid (1.0 mL) was added at room temperature, and the mixture was stirred at the same temperature for 3 hr. Sodium triacetoxyborohydride (271 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in ethyl acetate-diisopropyl ether, and the precipitate was collected by filtration, washed with ethyl acetate-diisopropyl ether, and dried under reduced pressure to give the title compound (290 mg, yield 92%) as a pale-yellow solid.

$^1$H NMR (300 MHz, CDCl$_3$) δ: 1.32 (2H, ad, J=12.3, 4.0 Hz), 1.61-1.86 (4H, m), 1.90-2.19 (3H, m), 2.46 (3H, s), 2.59 (2H, d, J=6.1 Hz), 3.39 (2H, td, J=11.7, 1.9 Hz), 3.76 (3H, s), 3.80-3.90 (1H, m), 3.90-4.01 (5H, m), 4.04 (2H, d, J=5.3 Hz), 4.24-4.38 (1H, m), 6.39 (1H, s), 7.01 (2H, d, J=8.7 Hz), 7.16 (1H, d, J=8.7 Hz), 7.41 (1H, d, J=9.1 Hz), 7.58 (1H, br. s.), 7.88 (2H, d, J=8.7 Hz).

melting point: 166-167° C.
elemental analysis (C$_{29}$H$_{37}$N$_3$O$_4$)
Calculated: C, 70.85; H, 7.59; N, 8.55.
Found: C, 70.65; H, 7.55; N, 8.33.

Example 56

N-{2-[(cyclopentylamino)methyl]-1,4-dimethyl-1H-indol-5-yl}-4-[(2S)-tetrahydrofuran-2-ylmethoxy]benzamide

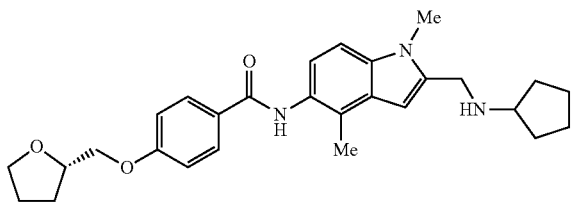 [SMILES: Cc1c(NC(=O)c2ccc(OC[C@@H]3CCCO3)cc2)ccc2c1cc(CNC1CCCC1)n2C]

N-(2-Formyl-1,4-dimethyl-1H-indol-5-yl)-4-[(2S)-tetrahydrofuran-2-ylmethoxy]benzamide (251 mg) obtained in Reference Example 51 and cyclopentylamine (109 mg) were suspended in NMP (3.0 mL), acetic acid (1.0 mL) was added at room temperature, and the mixture was stirred at the same temperature for 3 hr. Sodium triacetoxyborohydride (271 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in ethyl acetate-diisopropyl ether, and the precipitate was collected by filtration, washed with ethyl acetate-diisopropyl ether, and dried under reduced pressure to give the title compound (277 mg, yield 94%) as a pale-yellow solid.

$^1$H NMR (300 MHz, CDCl$_3$) δ: 1.33-1.47 (2H, m), 1.56-1.62 (2H, m), 1.64-1.93 (5H, m), 1.93-2.19 (3H, m), 2.45 (3H, s), 3.18 (1H, quin, J=6.4 Hz), 3.76 (3H, s), 3.80-4.01 (4H, m), 4.04 (2H, d, J=5.3 Hz), 4.24-4.37 (1H, m), 6.40 (1H, s), 7.00 (2H, d, J=8.3 Hz), 7.15 (1H, d, J=8.7 Hz), 7.41 (1H, d, J=8.7 Hz), 7.58 (1H, br. s.), 7.88 (2H, d, J=8.3 Hz).

melting point: 189° C.
elemental analysis (C$_{28}$H$_{35}$N$_3$O$_3$)
Calculated: C, 72.86; H, 7.64; N, 9.10.
Found: C, 72.62; H, 7.69; N, 8.86.

Example 57

N-{1,4-dimethyl-2-[(propylamino)methyl]-1H-indol-5-yl}-4-[(2S)-tetrahydrofuran-2-ylmethoxy]benzamide

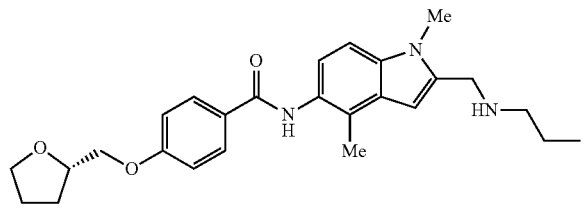 [SMILES: CCCNCc1cc2c(C)c(NC(=O)c3ccc(OC[C@@H]4CCCO4)cc3)ccc2n1C]

N-(2-Formyl-1,4-dimethyl-1H-indol-5-yl)-4-[(2S)-tetrahydrofuran-2-ylmethoxy]benzamide (300 mg) obtained in Reference Example 51 and propylamine (0.126 mL) were added to N,N-dimethylacetamide (3.0 mL), and the mixture was stirred at room temperature for 4 hr. Acetic acid (0.131 mL) and sodium triacetoxyborohydride (405 mg) were added at 0° C., and the mixture was stirred at room temperature for 19 hr. 8N Aqueous sodium hydroxide solution (1.72 mL) was added dropwise at 0° C. The mixture was extracted with ethyl acetate, washed with aqueous sodium hydrogen carbonate solution and brine, dried over anhydrous sodium sulfate, and concentrated under reduced pressure. The residue was purified by silica gel column chromatography [eluent; ethyl acetate:methanol=100:0 (volume ratio)→ethyl acetate:methanol=60:40 (volume ratio)] and crystallized from ethyl acetate and heptane to give the title compound (302 mg, yield 91%) as a white solid.

$^1$H NMR (300 MHz, DMSO-d$_6$) δ: 0.83-0.93 (3H, m), 1.23 (1H, s), 1.38-1.52 (2H, m), 1.63-2.11 (4H, m), 2.29 (3H, s), 2.51-2.57 (2H, m), 3.64-3.84 (5H, m), 3.86 (2H, s), 3.96-4.11 (2H, m), 4.13-4.25 (1H, m), 6.37 (1H, s), 6.98 (1H, d, J=8.5 Hz), 7.04 (2H, d, J=8.8 Hz), 7.21 (1H, d, J=8.8 Hz), 7.97 (2H, d, J=8.8 Hz), 9.71 (1H, s).

melting point: 225° C.
elemental analysis (C$_{26}$H$_{33}$N$_3$O$_3$·0.2H$_2$O)
Calculated: C, 71.11; H, 7.67; N, 9.57.
Found: C, 71.16; H, 7.61; N, 9.27.

Example 58

N-{2-[(4-hydroxy-4-methylpiperidin-1-yl)methyl]-1,4-dimethyl-1H-indol-5-yl}-4-[(2S)-tetrahydrofuran-2-ylmethoxy]benzamide

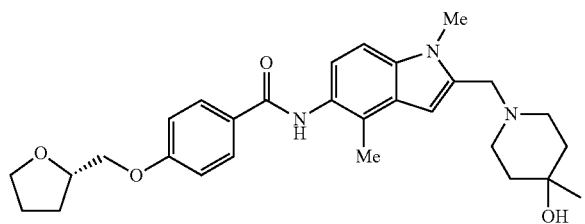 [SMILES: Cc1c(NC(=O)c2ccc(OC[C@@H]3CCCO3)cc2)ccc2c1cc(CN1CCC(C)(O)CC1)n2C]

N-(2-Formyl-1,4-dimethyl-1H-indol-5-yl)-4-[(2S)-tetrahydrofuran-2-ylmethoxy]benzamide (313 mg) obtained in Reference Example 51 and 4-methylpiperidin-4-ol (152 mg) were added to N,N-dimethylacetamide (6.1 mL), and the mixture was stirred at room temperature for 2 hr. Acetic acid (137 μL) and sodium triacetoxyborohydride (339 mg) were added at 0° C., and the mixture was stirred at room temperature for 17 hr. 8N Aqueous sodium hydroxide solution (1.8 mL) was added dropwise at 0° C. The mixture was extracted with ethyl acetate, washed with brine, purified by silica gel-NH silica gel serial column chromatography [eluent; ethyl acetate:methanol=100:0 (volume ratio)→ethyl acetate:methanol=70:30 (volume ratio)] and NH silica gel column chromatography [eluent; hexane:ethyl acetate=50:50 (volume ratio)→hexane:ethyl acetate=0:100 (volume ratio)] and crystallized from ethyl acetate and heptane to give the title compound (230 mg, yield 58%) as a white solid.

$^1$H NMR (300 MHz, DMSO-d$_6$) δ: 1.10 (3H, s), 1.38-1.53 (4H, m), 1.61-2.08 (4H, m), 2.29 (3H, s), 2.36-2.47 (4H, m), 3.61 (2H, s), 3.64-3.84 (5H, m), 3.95-4.22 (4H, m), 6.36 (1H, s), 6.98 (1H, d, J=8.5 Hz), 7.04 (2H, d, J=8.8 Hz), 7.21 (1H, d, J=8.8 Hz), 7.97 (2H, d, J=8.8 Hz), 9.71 (1H, s).

melting point: 210° C.
elemental analysis (C$_{29}$H$_{37}$N$_3$O$_4$)
Calculated: C, 70.85; H, 7.59; N, 8.55.
Found: C, 70.70; H, 7.69; N, 8.31.

Example 59

2-fluoro-N-(2-{[(trans-4-hydroxy-4-methylcyclohexyl)amino]methyl}-1,4-dimethyl-1H-indol-5-yl)-4-[(2S)-tetrahydrofuran-2-ylmethoxy]benzamide 2-Fluoro-N-(2-formyl-1,4-dimethyl-1H-indol-5-yl)-4-[(2S)-tetrahydrofuran-2-ylmethoxy]benzamide (321 mg) obtained in Reference Example 54 and trans-4-amino-1-methylcyclohexanol (203 mg) obtained in Reference Example 101 were suspended in NMP (3.0 mL), acetic acid (1.0 mL) was added at room temperature, and the mixture was stirred at the same temperature for 3 hr. Sodium triacetoxyborohydride (332 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in diisopropyl ether, and the precipitate was collected by filtration, washed with diisopropyl ether, and dried under reduced pressure to give the title compound (296 mg, yield 72%) as a pale-brown solid.

$^1$H NMR (300 MHz, CDCl$_3$) δ: 1.21-1.50 (7H, m), 1.68-1.85 (3H, m), 1.85-2.04 (4H, m), 2.04-2.18 (1H, m), 2.46 (3H, s), 2.64-2.77 (1H, m), 3.76 (3H, s), 3.80-3.90 (1H, m), 3.90-4.00 (3H, m), 4.02 (1H, d, J=1.1 Hz), 4.04 (1H, s), 4.24-4.36 (1H, m), 6.40 (1H, s), 6.73 (1H, dd, J=14.2, 2.5 Hz), 6.86 (1H, dd, J=8.7, 2.3 Hz), 7.16 (1H, d, J=8.7 Hz), 7.56 (1H, d, J=8.7 Hz), 8.16 (1H, t, J=9.3 Hz), 8.24 (1H, d, J=15.9 Hz).

melting point: 124° C.
elemental analysis (C$_{30}$H$_{38}$N$_3$O$_4$F·0.2H$_2$O)
Calculated: C, 68.34; H, 7.34; N, 7.97.
Found: C, 68.38; H, 7.20; N, 7.82.

Example 60

2-fluoro-N-(2-{[(2-hydroxy-2-methylpropyl)amino]methyl}-1,4-dimethyl-1H-indol-5-yl)-4-[(2S)-tetrahydrofuran-2-ylmethoxy]benzamide

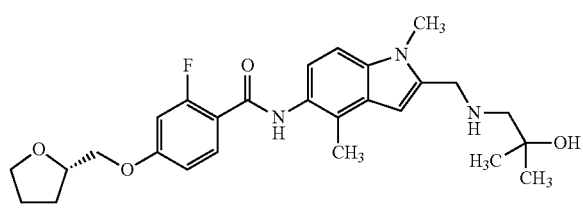 [SMILES: Cc1c(NC(=O)c2ccc(OC[C@@H]3CCCO3)cc2F)ccc2c1cc(CNCC(C)(C)O)n2C]

2-Fluoro-N-(2-formyl-1,4-dimethyl-1H-indol-5-yl)-4-[(2S)-tetrahydrofuran-2-ylmethoxy]benzamide (321 mg) obtained in Reference Example 54 and 1-amino-2-methyl-propan-2-ol (141 mg) were suspended in NMP (3.0 mL), acetic acid (1.0 mL) was added at room temperature, and the mixture was stirred at the same temperature for 3 hr. Sodium triacetoxyborohydride (332 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in diisopropyl ether, and the precipitate was collected by filtration, washed with diisopropyl ether, and dried under reduced pressure to give the title compound (316 mg, yield 83%) as a pale-brown solid.

$^1$H NMR (300 MHz, CDCl$_3$) δ: 1.20 (6H, s), 1.71-1.86 (1H, m), 1.90-2.04 (2H, m), 2.04-2.19 (1H, m), 2.47 (3H, s), 2.65 (2H, s), 2.75 (1H, br. s.), 3.77 (3H, s), 3.80-3.90 (1H, m), 3.91-3.98 (1H, m), 3.99 (2H, s), 4.02 (1H, d, J=1.5 Hz), 4.04 (1H, s), 4.24-4.36 (1H, m), 6.41 (1H, s), 6.74 (1H, dd, J=14.2, 2.5 Hz), 6.86 (1H, dd, J=8.9, 2.5 Hz), 7.17 (1H, d, J=8.7 Hz), 7.57 (1H, d, J=8.7 Hz), 8.16 (1H, t, J=9.1 Hz), 8.24 (1H, d, J=15.5 Hz).

melting point: 118-118° C.
elemental analysis (C$_{27}$H$_{34}$N$_3$O$_4$F)
Calculated: C, 67.06; H, 7.09; N, 8.69.
Found: C, 66.92; H, 7.07; N, 8.47.

Example 61

N-(1,4-dimethyl-2-{[(2-methylpropyl)amino]methyl}-1H-indol-5-yl)-2-fluoro-4-[(2S)-tetrahydrofuran-2-ylmethoxy]benzamide

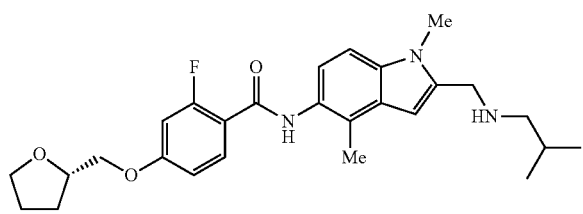

2-Fluoro-N-(2-formyl-1,4-dimethyl-1H-indol-5-yl)-4-[(2S)-tetrahydrofuran-2-ylmethoxy]benzamide (321 mg) obtained in Reference Example 54 and isobutylamine (115 mg) were suspended in NMP (3.0 mL), acetic acid (1.0 mL) was added at room temperature, and the mixture was stirred at the same temperature for 3 hr. Sodium triacetoxyborohydride (332 mg) was added, the mixture was stirred at room temperature for 15 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in ethyl acetate-diisopropyl ether, and the precipitate was collected by filtration, washed with ethyl acetate-diisopropyl ether, and dried under reduced pressure to give the title compound (238 mg, yield 65%) as a pale-yellow solid.

$^1$H NMR (300 MHz, CDCl$_3$) δ: 0.93 (6H, d, J=6.8 Hz), 1.69-1.85 (2H, m), 1.90-2.04 (2H, m), 2.04-2.18 (1H, m), 2.47 (3H, s), 2.50 (2H, d, J=6.8 Hz), 3.77 (3H, s), 3.80-3.90 (1H, m), 3.91-4.00 (3H, m), 4.02 (1H, d, J=1.1 Hz), 4.04 (1H, s), 4.25-4.35 (1H, m), 6.39 (1H, s), 6.73 (1H, dd, J=14.0, 2.3 Hz), 6.86 (1H, dd, J=8.9, 2.5 Hz), 7.16 (1H, d, J=8.7 Hz), 7.55 (1H, d, J=8.7 Hz), 8.16 (1H, J=9.1 Hz), 8.24 (1H, d, J=15.9 Hz).

melting point: 104-105° C.
elemental analysis (C$_{27}$H$_{34}$N$_3$O$_3$F)
Calculated: C, 69.30; H, 7.33; N, 8.99.
Found: C, 69.29; H, 7.35; N, 8.82.

Example 62

N-(1,4-dimethyl-2-{[(tetrahydro-2H-pyran-4-ylmethyl)amino]methyl}-1H-indol-5-yl)-2-fluoro-4-[(2S)-tetrahydrofuran-2-ylmethoxy]benzamide

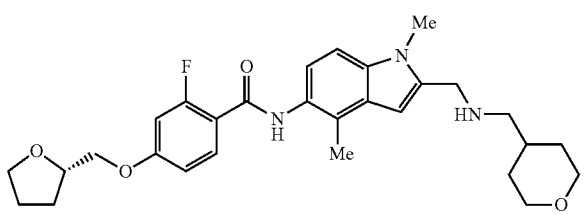

2-Fluoro-N-(2-formyl-1,4-dimethyl-1H-indol-5-yl)-4-[(2S)-tetrahydrofuran-2-ylmethoxy]benzamide (321 mg) obtained in Reference Example 54 and 1-(tetrahydro-2H-pyran-4-yl)methanamine (181 mg) were suspended in NMP (3.0 mL), acetic acid (1.0 mL) was added at room temperature, and the mixture was stirred at the same temperature for 3 hr. Sodium triacetoxyborohydride (332 mg) was added, the mixture was stirred at room temperature for 16 hr, and diluted with ethyl acetate, and 2N aqueous sodium hydroxide solution (20 mL) was added at room temperature. The mixture was poured into water, and the organic layer was washed twice with water and then with saturated brine, dried over sodium sulfate, and concentrated under reduced pressure. The residue was suspended in ethyl acetate-diisopropyl ether, and the precipitate was collected by filtration, washed with ethyl acetate-diisopropyl ether, and dried under reduced pressure to give the title compound (378 mg, yield 95%) as a pale-brown solid.

$^1$H NMR (300 MHz, CDCl$_3$) δ: 1.22-1.41 (2H, m), 1.62-1.85 (4H, m), 1.90-2.03 (2H, m), 2.03-2.19 (1H, m), 2.46 (3H, s), 2.59 (2H, d, J=6.1 Hz), 3.39 (2H, td, J=11.8, 1.7 Hz), 3.77 (3H, s), 3.80-3.90 (1H, m), 3.90-4.08 (7H, m), 4.25-4.36 (1H, m), 6.39 (1H, s), 6.74 (1H, dd, J=14.0, 2.3 Hz), 6.86 (1H, dd, J=8.7, 2.3 Hz), 7.16 (1H, d, J=8.7 Hz), 7.56 (1H, d, J=8.3 Hz), 8.16 (1H, t, J=9.1 Hz), 8.24 (1H, d, J=16.3 Hz).

melting point: 149° C.
elemental analysis (C$_{29}$H$_{36}$N$_3$O$_4$F)
Calculated: C, 68.35; H, 7.12; N, 8.25.
Found: C, 68.26; H, 7.03; N, 8.06.

Example 63

4-(cyclopropylmethoxy)-N-(2-{[(2-hydroxy-2-methylpropyl)amino]methyl}-7-methyl-1H-indol-6-yl)benzamide

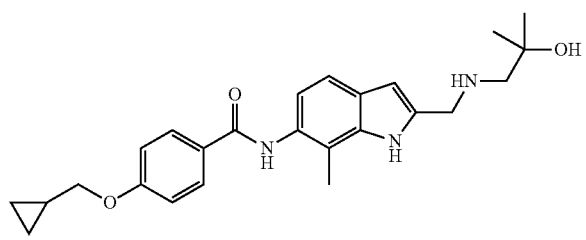 [SMILES: Cc1c(NC(=O)c2ccc(OCC3CC3)cc2)ccc2cc(CNCC(C)(C)O)[nH]c12]

4-(Cyclopropylmethoxy)-N-(2-formyl-7-methyl-1H-indol-6-yl)benzamide (357 mg) obtained in Reference Example 58, 1-amino-2-methylpropan-2-ol (136 mg) and acetic acid (2.04 mL) were added to N,N-dimethylacetamide (6.7 mL), and the mixture was stirred at room temperature for 30 min. Sodium triacetoxyborohydride (432 mg) was added, and the mixture was stirred at room temperature for 12 hr. 8N Aqueous sodium hydroxide solution (5.10 mL) was added dropwise at 0° C. The mixture was extracted with ethyl acetate, washed with aqueous sodium hydrogen carbonate solution and brine, dried over anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (360 mg, yield 84%) as a pale-brown solid.

$^1$H NMR (300 MHz, DMSO-$d_6$) δ: 0.31-0.39 (2H, m), 0.56-0.63 (2H, m), 1.09 (6H, s), 1.16-1.32 (1H, m), 2.30 (3H, s), 2.41 (2H, s), 3.84 (2H, s), 3.90 (2H, d, J=7.1 Hz), 4.20 (1H, s), 6.24 (1H, s), 6.83 (1H, d, J=8.5 Hz), 7.01 (2H, d, J=9.1 Hz), 7.23 (1H, d, J=8.2 Hz), 7.95 (2H, d, J=9.1 Hz), 9.72 (1H, s), 10.79 (1H, s).

melting point: 170° C.
elemental analysis ($C_{25}H_{31}N_3O_3 \cdot 0.4H_2O$)
Calculated: C, 70.04; H, 7.48; N, 9.80.
Found: C, 70.05; H, 7.52; N, 9.67.

Example 64

4-(cyclopropylmethoxy)-N-(7-methyl-2-{[(2-methylpropyl)amino]methyl}-1H-indol-6-yl)benzamide

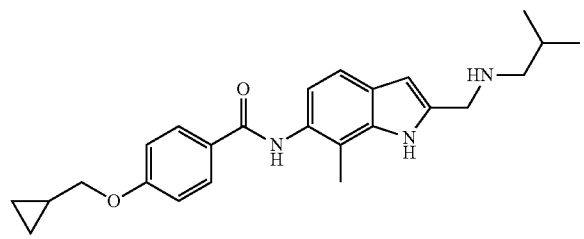 [SMILES: Cc1c(NC(=O)c2ccc(OCC3CC3)cc2)ccc2cc(CNCC(C)C)[nH]c12]

4-(Cyclopropylmethoxy)-N-(2-formyl-7-methyl-1H-indol-6-yl)benzamide (244 mg) obtained in Reference Example 58, 2-methylpropan-1-amine (139 μL) and acetic acid (1.39 mL) were added to N,N-dimethylacetamide (4.0 mL), and the mixture was stirred at room temperature for 30 min. Sodium triacetoxyborohydride (296 mg) was added, and the mixture was stirred at room temperature for 14 hr. 8N Aqueous sodium hydroxide solution (3.50 mL) was added dropwise at 0° C. The mixture was extracted with ethyl acetate, washed with aqueous sodium hydrogen carbonate solution and brine, dried over anhydrous sodium sulfate, and concentrated under reduced pressure. The residue was purified by silica gel-NH silica gel serial column chromatography [eluent; hexane:ethyl acetate=50:50 (volume ratio)→hexane:ethyl acetate=0:100 (volume ratio)→ethyl acetate:methanol=100:0 (volume ratio)→ethyl acetate:methanol=80:20 (volume ratio)], and crystallized from ethyl acetate and diisopropyl ether to give the title compound (172 mg, yield 61%) as a pale-gray solid.

$^1$H NMR (300 MHz, DMSO-$d_6$) δ: 0.31-0.39 (2H, m), 0.55-0.64 (2H, m), 0.87 (6H, d, J=6.6 Hz), 1.19-1.32 (1H, m), 1.60-1.75 (1H, m), 2.30 (3H, s), 2.32 (2H, d, J=6.6 Hz), 3.80 (2H, s), 3.90 (2H, d, J=7.1 Hz), 6.24 (1H, d, J=1.9 Hz), 6.83 (1H, d, J=8.0 Hz), 7.02 (2H, d, J=9.1 Hz), 7.23 (1H, d, J=8.2 Hz), 7.96 (2H, d, J=8.5 Hz), 9.72 (1H, s), 10.75 (1H, s).

melting point: 176-177° C.
elemental analysis ($C_{25}H_{31}N_3O_2$)
Calculated: C, 74.04; H, 7.70; N, 10.36.
Found: C, 73.70; H, 7.70; N, 10.19.

Example 65

4-(cyclopropylmethoxy)-N-(2-{[(2,2-dimethylpropyl)amino]methyl}-7-methyl-1H-indol-6-yl)benzamide

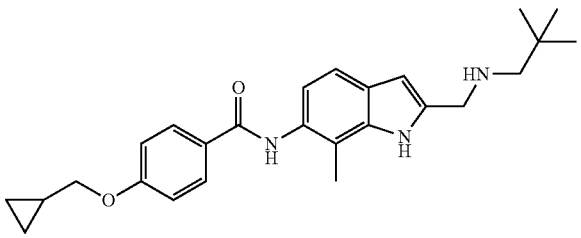 [SMILES: Cc1c(NC(=O)c2ccc(OCC3CC3)cc2)ccc2cc(CNCC(C)(C)C)[nH]c12]

4-(Cyclopropylmethoxy)-N-(2-formyl-7-methyl-1H-indol-6-yl)benzamide (244 mg) obtained in Reference Example 58, 2,2-dimethylpropan-1-amine (165 μL) and acetic acid (1.39 mL) were added to N,N-dimethylacetamide (4.0 mL), and the mixture was stirred at room temperature for 30 min. Sodium triacetoxyborohydride (296 mg) was added, and the mixture was stirred at room temperature for 14 hr. 8N Aqueous sodium hydroxide solution (3.50 mL) was added dropwise at 0° C. The mixture was extracted with ethyl acetate, washed with aqueous sodium hydrogen carbonate solution and brine, dried over anhydrous sodium sulfate, and concentrated under reduced pressure. The residue was purified by silica gel-NH silica gel serial column chromatography [eluent; hexane:ethyl acetate=50:50 (volume ratio)→hexane:ethyl acetate=0:100 (volume ratio)→ethyl acetate:methanol=100:0 (volume ratio)→ethyl aceate:methanol=80:20 (volume ratio)] and crystallized from ethyl acetate and heptane to give the title compound (231 mg, yield 79%) as a pale-gray solid.

$^1$H NMR (300 MHz, DMSO-$d_6$) δ: 0.31-0.39 (2H, m), 0.55-0.64 (2H, m), 0.87 (9H, s), 1.20-1.34 (1H, m), 2.25 (2H, s), 2.30 (3H, s), 3.82 (2H, s), 3.90 (2H, d, J=6.9 Hz), 6.23 (1H, s), 6.83 (1H, d, J=8.5 Hz), 7.02 (2H, d, J=8.8 Hz), 7.23 (1H, d, J=8.5 Hz), 7.96 (2H, d, J=8.5 Hz), 9.73 (1H, s), 10.74 (1H, s).

melting point: 199° C.
elemental analysis ($C_{26}H_{33}N_3O_2$)
Calculated: C, 74.43; H, 7.93; N, 10.02.
Found: C, 74.10; H, 7.88; N, 9.85.

Example 66

4-(cyclopropylmethoxy)-N-(7-methyl-2-{[(tetrahydro-2H-pyran-4-ylmethyl)amino]methyl}-1H-indol-6-yl)benzamide

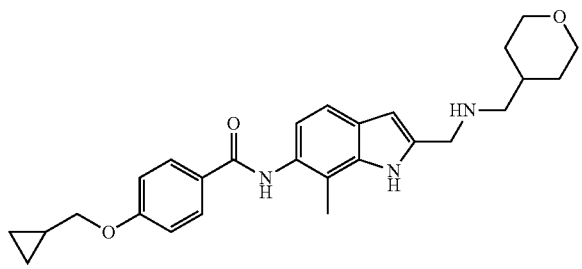 [SMILES: Cc1c(NC(=O)c2ccc(OCC3CC3)cc2)ccc2cc(CNCC3CCOCC3)[nH]c12]

4-(Cyclopropylmethoxy)-N-(2-formyl-7-methyl-1H-indol-6-yl)benzamide (250 mg) obtained in Reference Example 58, 1-(tetrahydro-2H-pyran-4-yl)methanamine (165 mg) and acetic acid (1.44 mL) were added to N,N-dimethylacetamide (4.0 mL), and the mixture was stirred at room temperature for 30 min. Sodium triacetoxyborohydride (304 mg) was added, and the mixture was stirred at room temperature for 18 hr. 8N Aqueous sodium hydroxide solution (3.59 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (292 mg, yield 91%) as a pale-pink solid.

$^1$H NMR (300 MHz, DMSO-d$_6$) δ: 0.32-0.39 (2H, m), 0.54-0.64 (2H, m), 1.06-1.34 (4H, m), 1.57-1.68 (2H, m), 2.30 (3H, s), 2.39 (2H, d, J=5.8 Hz), 3.20-3.29 (2H, m), 3.78-3.85 (4H, m), 3.90 (2H, d, J=6.9 Hz), 6.24 (1H, d, J=1.4 Hz), 6.83 (1H, d, J=8.2 Hz), 7.01 (2H, d, J=9.1 Hz), 7.23 (1H, d, J=8.5 Hz), 7.95 (2H, d, J=8.5 Hz), 9.72 (1H, s), 10.74 (1H, s).

melting point: 167-168° C.
elemental analysis (C$_{27}$H$_{33}$N$_3$O$_3$.0.2H$_2$O)
Calculated: C, 71.88; H, 7.46; N, 9.31.
Found: C, 71.78; H, 7.42; N, 9.10.

Example 67

4-(cyclopropylmethoxy)-N-(2-{[(trans-4-hydroxy-4-methylcyclohexyl)amino]methyl}-7-methyl-1H-indol-6-yl)benzamide

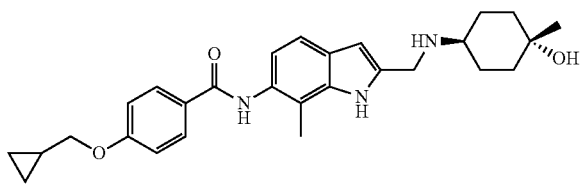 [SMILES: Cc1c(NC(=O)c2ccc(OCC3CC3)cc2)ccc2cc(CN[C@H]3CC[C@](C)(O)CC3)[nH]c12]

4-(Cyclopropylmethoxy)-N-(2-formyl-7-methyl-1H-indol-6-yl)benzamide (250 mg) obtained in Reference Example 58, trans-4-amino-1-methylcyclohexanol (185 mg) obtained in Reference Example 101 and acetic acid (1.44 mL) were added to N,N-dimethylacetamide (4.0 mL), and the mixture was stirred at room temperature for 30 min. Sodium triacetoxyborohydride (304 mg) was added, and the mixture was stirred at room temperature for 18 hr. 8N Aqueous sodium hydroxide solution (3.59 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (273 mg, yield 69%) as a pale-pink solid.

$^1$H NMR (300 MHz, DMSO-d$_6$) δ: 0.34 (2H, s), 0.59 (2H, d, J=7.7 Hz), 0.83-0.89 (1H, m), 1.09 (3H, s), 1.14-1.35 (8H, m), 1.50-1.60 (2H, m), 1.71-1.81 (2H, m), 1.98 (3H, s), 2.30 (3H, s), 3.82 (2H, s), 3.90 (2H, d, J=7.4 Hz), 3.97-4.09 (3H, m), 6.23 (1H, d, J=1.9 Hz), 6.83 (1H, d, J=8.2 Hz), 7.01 (2H, d, J=9.1 Hz), 7.22 (1H, d, J=8.2 Hz), 7.95 (2H, d, J=8.2 Hz), 9.72 (1H, s), 10.73 (1H, s).

melting point: 91-103° C.
elemental analysis (C$_{28}$H$_{35}$N$_3$O$_3$.CH$_3$CO$_2$C$_2$H$_5$)
Calculated: C, 69.92; H, 7.88; N, 7.64.
Found: C, 69.69; H, 7.81; N, 7.88.

Example 68

4-(cyclopropylmethoxy)-N-{2-[(4-hydroxy-4-methylpiperidin-1-yl)methyl]-7-methyl-1H-indol-6-yl}benzamide

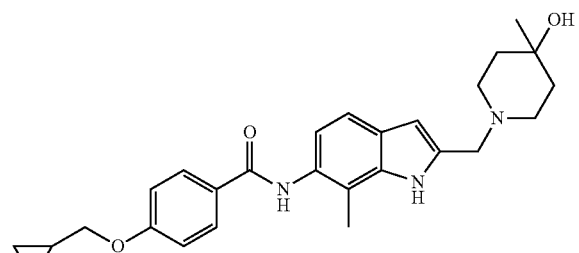

4-(Cyclopropylmethoxy)-N-(2-formyl-7-methyl-1H-indol-6-yl)benzamide (250 mg) obtained in Reference Example 58, 4-methylpiperidin-4-ol hydrochloride (217 mg), triethylamine (200 µL) and acetic acid (1.43 mL) were added to N,N-dimethylacetamide (10.4 mL), and the mixture was stirred at room temperature for 2 hr. Sodium triacetoxyborohydride (304 mg) was added, and the mixture was stirred at room temperature for 20 hr. 8N Aqueous sodium hydroxide solution (3.59 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (266 mg, yield 83%) as a white solid.

$^1$H NMR (300 MHz, DMSO-d$_6$) δ: 0.32-0.39 (2H, m), 0.54-0.65 (2H, m), 1.09 (3H, s), 1.22-1.30 (2H, m), 1.42-1.52 (4H, m), 2.31 (3H, s), 2.38-2.47 (3H, m), 3.58 (2H, s), 3.91 (2H, d, J=6.8 Hz), 4.08 (1H, s), 6.25 (1H, d, J=1.5 Hz), 6.85 (1H, d, J=8.3 Hz), 7.02 (2H, d, J=8.7 Hz), 7.24 (1H, d, J=8.3 Hz), 7.96 (2H, d, J=8.7 Hz), 9.73 (1H, s), 10.84 (1H, s).

melting point: 195° C.
elemental analysis (C$_{27}$H$_{33}$N$_3$O$_3$.0.2H$_2$O)
Calculated: C, 71.88; H, 7.46; N, 9.31.
Found: C, 71.86; H, 7.56; N, 9.07.

Example 69

N-(2-{[(2,2-dimethylpropyl)amino]methyl}-7-methyl-1H-indol-6-yl)-4-[(2S)-tetrahydrofuran-2-ylmethoxy]benzamide

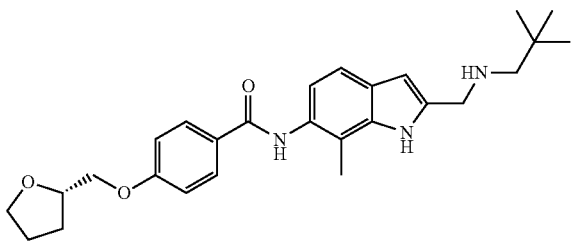 [SMILES: Cc1c(NC(=O)c2ccc(OC[C@@H]3CCCO3)cc2)ccc2cc(CNCC(C)(C)C)[nH]c12]

N-(2-Formyl-7-methyl-1H-indol-6-yl)-4-[(2S)-tetrahydrofuran-2-ylmethoxy]benzamide (247 mg) obtained in Reference Example 59, 2,2-dimethylpropan-1-amine (153 μl) and acetic acid (1.30 mL) were added to N,N-dimethylacetamide (4.0 mL), and the mixture was stirred at room temperature for 1 hr. Sodium triacetoxyborohydride (276 mg) was added, and the mixture was stirred at room temperature for 17 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)], and crystallized from a mixed solvent of ethyl acetate, diisopropyl ether and heptane to give the title compound (231 mg, yield 79%) as a pale-brown solid.

$^1$H NMR (300 MHz, DMSO-$d_6$) δ: 0.86 (9H, s), 1.62-2.09 (4H, m), 2.25 (2H, s), 2.29 (3H, s), 3.62-3.90 (4H, m), 3.93-4.10 (2H, m), 4.11-4.24 (1H, m), 6.24 (1H, s), 6.83 (1H, d, J=8.3 Hz), 7.04 (2H, d, J=8.7 Hz), 7.23 (1H, d, J=8.0 Hz), 7.96 (2H, d, J=8.7 Hz), 9.74 (1H, s), 10.74 (1H, s).

melting point: 168° C.
elemental analysis ($C_{27}H_{35}N_3O_3 \cdot 0.2H_2O$)
Calculated: C, 71.56; H, 7.87; N, 9.27.
Found: C, 71.56; H, 7.72; N, 9.17.

Example 70

N-(7-methyl-2-{[(tetrahydro-2H-pyran-4-ylmethyl)amino]methyl}-1H-indol-6-yl)-4-[(2S)-tetrahydrofuran-2-ylmethoxy]benzamide

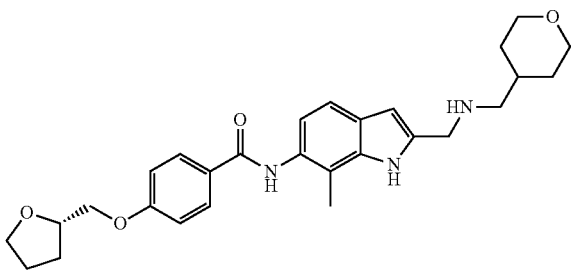 [SMILES: Cc1c(NC(=O)c2ccc(OC[C@@H]3CCCO3)cc2)ccc2cc(CNCC3CCOCC3)[nH]c12]

N-(2-Formyl-7-methyl-1H-indol-6-yl)-4-[(2S)-tetrahydrofuran-2-ylmethoxy]benzamide (247 mg) obtained in Reference Example 59, 1-(tetrahydro-2H-pyran-4-yl)methanamine (150 mg) and acetic acid (1.30 mL) were added to N,N-dimethylacetamide (4.0 mL), and the mixture was stirred at room temperature for 1 hr. Sodium triacetoxyborohydride (276 mg) was added, and the mixture was stirred at room temperature for 17 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (229 mg, yield 74%) as a pale-brown solid.

$^1$H NMR (300 MHz, DMSO-$d_6$) δ: 1.05-1.29 (2H, m), 1.58-2.09 (7H, m), 2.30 (3H, s), 2.40 (2H, d, J=6.1 Hz), 3.21-3.30 (2H, m), 3.64-3.88 (6H, m), 3.95-4.10 (2H, m), 4.13-4.25 (1H, m), 6.25 (1H, s), 6.84 (1H, d, J=8.3 Hz), 7.05 (2H, d, J=9.1 Hz), 7.24 (1H, d, J=8.0 Hz), 7.97 (2H, d, J=8.7 Hz), 9.75 (1H, s), 10.76 (1H, s).

melting point: 161-162° C.
elemental analysis ($C_{28}H_{35}N_3O_4 \cdot 0.7H_2O$)
Calculated: C, 68.60; H, 7.48; N, 8.57.
Found: C, 68.87; H, 7.47; N, 8.38.

Example 71

N-{7-methyl-2-[(propylamino)methyl]-1H-indol-6-yl}-4-[(2S)-tetrahydrofuran-2-ylmethoxy]benzamide

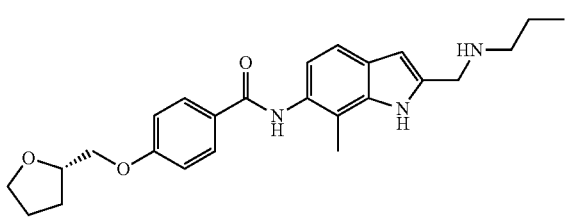 [SMILES: CCCNCc1cc2ccc(NC(=O)c3ccc(OC[C@@H]4CCCO4)cc3)c(C)c2[nH]1]

N-(2-Formyl-7-methyl-1H-indol-6-yl)-4-[(2S)-tetrahydrofuran-2-ylmethoxy]benzamide (247 mg) obtained in Reference Example 59, propylamine (107 μL) and acetic acid (1.30 mL) were added to N,N-dimethylacetamide (4.0 mL), and the mixture was stirred at room temperature for 1 hr. Sodium triacetoxyborohydride (276 mg) was added, and the mixture was stirred at room temperature for 17 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (203 mg, yield 74%) as a pale-pink solid.

$^1$H NMR (300 MHz, DMSO-$d_6$) δ: 0.87 (3H, t, J=7.6 Hz), 1.37-1.52 (2H, m), 1.62-2.09 (6H, m), 2.30 (3H, s), 3.64-3.88 (4H, m), 3.96-4.10 (2H, m), 4.13-4.25 (1H, m), 6.25 (1H, s), 6.84 (1H, d, J=8.3 Hz), 7.05 (2H, d, J=8.7 Hz), 7.24 (1H, d, J=8.3 Hz), 7.97 (2H, d, J=8.3 Hz), 9.75 (1H, s), 10.78 (1H, s).

melting point: 117-119° C.

Example 72

N-(7-methyl-2-{[(2-methylpropyl)amino]methyl}-1H-indol-6-yl)-4-[(2S)-tetrahydrofuran-2-ylmethoxy]benzamide

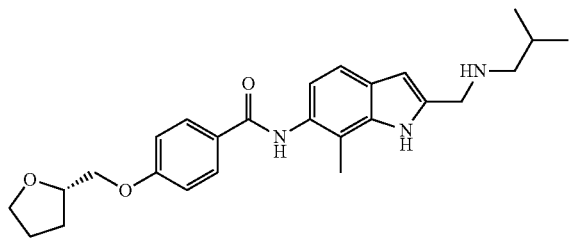

N-(2-Formyl-7-methyl-1H-indol-6-yl)-4-[(2S)-tetrahydrofuran-2-ylmethoxy]benzamide (247 mg) obtained in Reference Example 59, 2-methylpropan-1-amine (129 μL) and acetic acid (1.30 mL) were added to N,N-dimethylacetamide (4.0 mL), and the mixture was stirred at room temperature for 1 hr. Sodium triacetoxyborohydride (276 mg) was added, and the mixture was stirred at room temperature for 17 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (185 mg, yield 65%) as a pale-brown solid.

$^1$H NMR (300 MHz, DMSO-$d_6$) δ: 0.87 (6H, d, J=6.4 Hz), 1.60-2.08 (5H, m), 2.29-2.35 (5H, m), 3.64-3.87 (4H, m), 3.95-4.10 (2H, m), 4.13-4.23 (1H, m), 6.25 (1H, d, J=1.9 Hz), 6.84 (1H, d, J=8.3 Hz), 7.05 (2H, d, J=8.7 Hz), 7.24 (1H, d, J=8.3 Hz), 7.97 (2H, d, J=8.7 Hz), 9.75 (1H, s), 10.77 (1H, s).

melting point: 159° C.
elemental analysis ($C_{26}H_{33}N_3O_3$)
Calculated: C, 71.70; H, 7.64; N, 9.65.
Found: C, 71.34; H, 7.56; N, 9.59.

Example 73

N-{2-[(cyclopentylamino)methyl]-7-methyl-1H-indol-6-yl}-4-[(2S)-tetrahydrofuran-2-ylmethoxy]benzamide

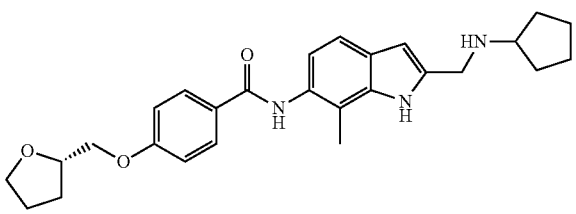 [SMILES: Cc1c(NC(=O)c2ccc(OC[C@@H]3CCCO3)cc2)ccc2cc(CNC3CCCC3)[nH]c12]

N-(2-Formyl-7-methyl-1H-indol-6-yl)-4-[(2S)-tetrahydrofuran-2-ylmethoxy]benzamide (247 mg) obtained in Reference Example 59, cyclopentylamine (128 μL) and acetic acid (1.30 mL) were added to N,N-dimethylacetamide (4.0 mL), and the mixture was stirred at room temperature for 1 hr. Sodium triacetoxyborohydride (276 mg) was added, and the mixture was stirred at room temperature for 17 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (229 mg, yield 78%) as a pale-brown solid.

$^1$H NMR (300 MHz, DMSO-d) δ: 1.22-2.09 (12H, m), 2.31 (3H, s), 2.95-3.07 (1H, m), 3.65-3.90 (4H, m), 3.96-4.10 (2H, m), 4.13-4.25 (1H, m), 6.25 (1H, d, J=1.5 Hz), 6.84 (1H, d, J=8.7 Hz), 7.05 (2H, d, J=8.7 Hz), 7.23 (1H, d, J=8.0 Hz), 7.97 (2H, d, J=8.3 Hz), 9.75 (1H, s), 10.76 (1H, s).

melting point: 159-163° C.
elemental analysis ($C_{27}H_{33}N_3O_3$·0.7$H_2O$)
Calculated: C, 70.47; H, 7.53; N, 9.13.
Found: C, 70.72; H, 7.60; N, 8.87.

Example 74

N-[7-methyl-2-(pyrrolidin-1-ylmethyl)-1H-indol-6-yl]-4-[(2S)-tetrahydrofuran-2-ylmethoxy]benzamide

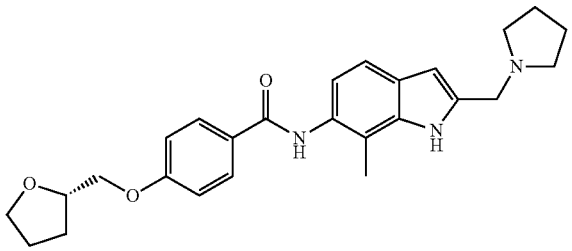 [SMILES: Cc1c(NC(=O)c2ccc(OC[C@@H]3CCCO3)cc2)ccc2cc(CN3CCCC3)[nH]c12]

N-(2-Formyl-7-methyl-1H-indol-6-yl)-4-[(2S)-tetrahydrofuran-2-ylmethoxy]benzamide (247 mg) obtained in Reference Example 59, pyrrolidine (544 μL) and acetic acid (1.30 mL) were added to N,N-dimethylacetamide (4 mL), and the mixture was stirred at room temperature for 1 hr. Sodium triacetoxyborohydride (276 mg) was added, and the mixture was stirred at room temperature for 20 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (215 mg, yield 76%) as a pale-yellow solid.

$^1$H NMR (300 MHz, DMSO-$d_6$) δ: 1.63-2.10 (12H, m), 2.31 (3H, s), 3.63-3.85 (4H, m), 3.93-4.11 (2H, m), 4.12-4.25 (1H, m), 6.25 (1H, d, J=1.9 Hz), 6.84 (1H, d, J=8.0 Hz), 7.04 (2H, d, J=8.8 Hz), 7.23 (1H, d, J=8.2 Hz), 7.96 (2H, d, J=8.8 Hz), 9.73 (1H, s), 10.90 (1H, s).

melting point: 172-173° C.
elemental analysis ($C_{26}H_{31}N_3O_3$·0.3$H_2O$)
Calculated: C, 71.14; H, 7.26; N, 9.57.
Found: C, 71.29; H, 7.31; N, 9.32.

Example 75

N-{2-[(4-hydroxy-4-methylpiperidin-1-yl)methyl]-7-methyl-1H-indol-6-yl}-4-[(2S)-tetrahydrofuran-2-ylmethoxy]benzamide

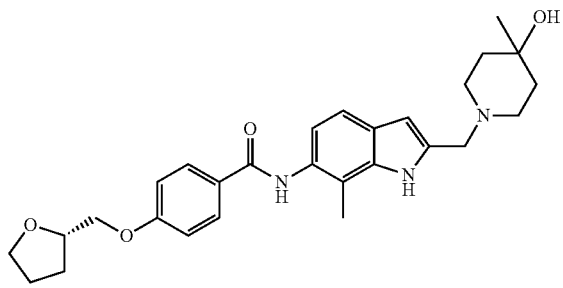 [SMILES: Cc1c(NC(=O)c2ccc(OC[C@@H]3CCCO3)cc2)ccc2cc(CN3CCC(C)(O)CC3)[nH]c12]

N-(2-Formyl-7-methyl-1H-indol-6-yl)-4-[(2S)-tetrahydrofuran-2-ylmethoxy]benzamide (247 mg) obtained in Reference Example 59, 4-methylpiperidin-4-ol hydrochloride (157 mg), triethylamine (144 µL) and acetic acid (1.30 mL) were added to N,N-dimethylacetamide (4 mL), and the mixture was stirred at room temperature for 1 hr. Sodium triacetoxyborohydride (276 mg) was added, and the mixture was stirred at room temperature for 20 hr. 8N Aqueous sodium hydroxide solution (3.26 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (206 mg, yield 71%) as a white solid.

$^1$H NMR (300 MHz, DMSO-$d_6$) δ: 1.10 (3H, s), 1.17-1.33 (1H, m), 1.43-2.11 (8H, m), 2.32 (3H, s), 2.39-2.50 (3H, m), 3.59 (2H, s), 3.66-3.88 (2H, m), 3.97-4.27 (4H, m), 6.25 (1H, s), 6.85 (1H, d, J=8.3 Hz), 7.05 (2H, d, J=8.7 Hz), 7.25 (1H, d, J=8.0 Hz), 7.97 (2H, d, J=8.7 Hz), 9.74 (1H, s), 10.85 (1H, s).

melting point: 169° C.
elemental analysis ($C_{28}H_{35}N_3O_4 \cdot 0.6H_2O$)
Calculated: C, 68.86; H, 7.47; N, 8.60.
Found: C, 68.77; H, 7.66; N, 8.32.

Example 76

2-fluoro-N-(2-{[(2-hydroxy-2-methylpropyl)amino]methyl}-7-methyl-1H-indol-6-yl)-4-[(2S)-tetrahydrofuran-2-ylmethoxy]benzamide

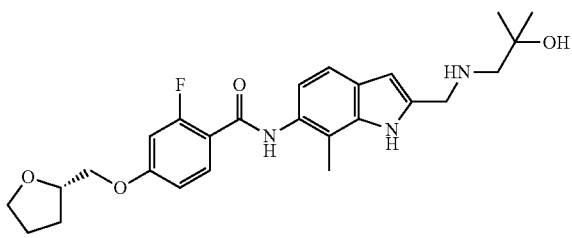 [SMILES: Cc1c(NC(=O)c2ccc(OC[C@@H]3CCCO3)cc2F)ccc2cc(CNCC(C)(C)O)[nH]c12]

2-Fluoro-N-(2-formyl-7-methyl-1H-indol-6-yl)-4-[(2S)-tetrahydrofuran-2-ylmethoxy]benzamide (0.40 g) obtained in Reference Example 62 and 1-amino-2-methylpropan-2-ol (446 mg) were suspended in NMP (20 mL) and acetic acid (7.0 mL), and the mixture was stirred at room temperature for 3 hr. Sodium triacetoxyborohydride (2.5 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (120 mg, yield 25%) as a colorless solid.

$^1$H NMR (300 MHz, DMSO-$d_6$) δ: 1.09 (6H, s), 1.63-1.72 (1H, m), 1.78-1.90 (2H, m), 1.96-2.07 (1H, m), 2.18 (1H, br), 2.35 (3H, s), 2.41 (2H, s), 3.68 (1H, q, J=6.3 Hz), 3.78 (1H, q, J=6.3 Hz), 3.85 (2H, s), 3.97-4.09 (2H, m), 4.13-4.18 (1H, m), 4.21 (1H, s), 6.24 (1H, s), 6.87-6.98 (3H, m), 7.23 (1H, d, J=8.4 Hz), 7.68 (1H, t, J=8.7 Hz), 9.56 (1H, d, J=2.1 Hz), 10.82 (1H, s).

melting point: 148-149° C.
elemental analysis ($C_{26}H_{32}N_3O_4F$)
Calculated: C, 66.51; H, 6.87; N, 8.95.
Found: C, 66.39; H, 6.96; N, 8.72.

Example 77

2-fluoro-N-(2-{[(trans-4-hydroxy-4-methylcyclohexyl)amino]methyl}-7-methyl-1H-indol-6-yl)-4-[(2S)-tetrahydrofuran-2-ylmethoxy]benzamide

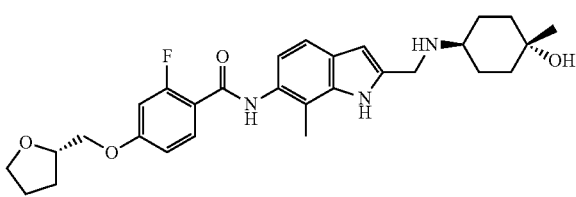 [SMILES: Cc1c(NC(=O)c2ccc(OC[C@@H]3CCCO3)cc2F)ccc2cc(CN[C@H]3CC[C@](C)(O)CC3)[nH]c12]

2-Fluoro-N-(2-formyl-7-methyl-1H-indol-6-yl)-4-[(2S)-tetrahydrofuran-2-ylmethoxy]benzamide (0.4 g) obtained in Reference Example 62 and trans-4-amino-1-methylcyclohexanol (340 mg) obtained in Reference Example 101 were suspended in NMP (20 mL) and acetic acid (7.0 mL), and the mixture was stirred at room temperature for 3 hr. Sodium triacetoxyborohydride (2.5 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (180 mg, yield 35%) as a colorless solid.

$^1$H NMR (300 MHz, DMSO-$d_6$) δ: 1.09 (3H, s), 1.17-1.35 (4H, m), 1.54-1.58 (2H, m), 1.63-1.70 (1H, m), 1.76-1.90 (5H, m), 1.96-2.04 (1H, m), 2.35 (3H, s), 3.34 (1H, br), 3.68 (1H, q, J=6.6 Hz), 3.79 (1H, q, J=6.6 Hz), 3.85 (2H, s), 3.97-4.10 (3H, m), 4.13-4.19 (1H, m), 6.25 (1H, s), 6.88-6.97 (3H, m), 7.23 (1H, d, J=8.4 Hz), 7.68 (1H, t, J=8.7 Hz), 9.56 (1H, s), 10.78 (1H, s).
melting point: 152-153° C.
elemental analysis ($C_{29}H_{36}N_3O_4F.0.5H_2O$)
Calculated: C, 67.16; H, 7.19; N, 8.10.
Found: C, 67.24; H, 7.12; N, 7.86.

Example 78

4-(cyclopropylmethoxy)-N-(2-{[(2-hydroxy-2-methylpropyl)amino]methyl}-1,7-dimethyl-1H-indol-6-yl)benzamide

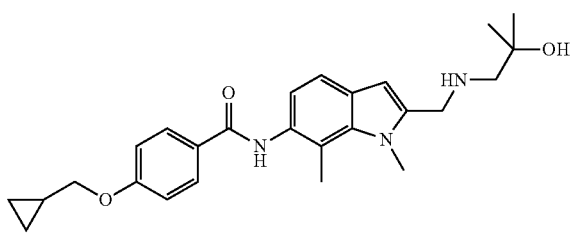 [SMILES: Cc1c(NC(=O)c2ccc(OCC3CC3)cc2)ccc2cc(CNCC(C)(C)O)n(C)c12]

4-(Cyclopropylmethoxy)-N-(2-formyl-1,7-dimethyl-1H-indol-6-yl)benzamide (500 mg) obtained in Reference Example 65, 1-amino-2-methylpropan-2-ol (183 mg) and acetic acid (2.75 mL) were added to N,N-dimethylacetamide (18.4 mL), and the mixture was stirred at room temperature for 1 hr. Sodium triacetoxyborohydride (582 mg) was added, and the mixture was stirred at room temperature for 24 hr. 8N Aqueous sodium hydroxide solution (6.85 mL) was added dropwise at 0° C. The mixture was extracted with ethyl acetate, washed with brine, dried over anhydrous sodium sulfate, purified by silica gel column chromatography [eluent; ethyl acetate:methanol=100:0 (volume ratio)→ethyl acetate:methanol=70:30 (volume ratio)], and crystallized from ethyl acetate and diisopropyl ether to give the title compound (425 mg, yield 71%) as a beige solid.
$^1$H NMR (300 MHz, DMSO-$d_6$) δ: 0.29-0.40 (2H, m), 0.55-0.65 (2H, m), 1.00-1.36 (7H, m), 2.46 (2H, s), 2.54 (3H, s), 3.84-3.95 (4H, m), 4.01 (3H, s), 4.20 (1H, s), 6.29 (1H, s), 6.82 (1H, d, J=8.3 Hz), 7.03 (2H, d, J=8.7 Hz), 7.25 (1H, d, J=8.0 Hz), 7.97 (2H, d, J=8.7 Hz), 9.78 (1H, s).
melting point: 180° C.
elemental analysis ($C_{26}H_{33}N_3O_3.0.2H_2O$)
Calculated: C, 71.11; H, 7.67; N, 9.57.
Found: C, 71.17; H, 7.47; N, 9.45.

Example 79

4-(cyclopropylmethoxy)-N-(2-{[(trans-4-hydroxy-4-methylcyclohexyl)amino]methyl}-1,7-dimethyl-1H-indol-6-yl)benzamide

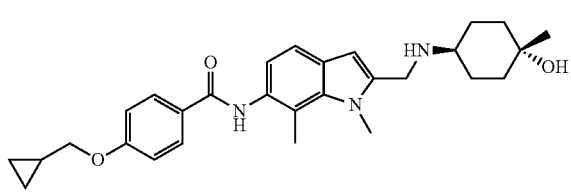 [SMILES: Cc1c(NC(=O)c2ccc(OCC3CC3)cc2)ccc2cc(CN[C@H]3CC[C@](C)(O)CC3)n(C)c12]

4-(Cyclopropylmethoxy)-N-(2-formyl-1,7-dimethyl-1H-indol-6-yl)benzamide (250 mg) obtained in Reference Example 65, trans-4-amino-1-methylcyclohexanol (178 mg) obtained in Reference Example 101 and acetic acid (1.37 mL) were added to N,N-dimethylacetamide (9.2 mL), and the mixture was stirred at room temperature for 1 hr. Sodium triacetoxyborohydride (292 mg) was added, and the mixture was stirred at room temperature for 18 hr. 8N Aqueous sodium hydroxide solution (3.44 mL) was added dropwise at 0° C. The mixture was extracted with ethyl acetate, washed with brine, dried over anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate and diisopropyl ether to give the title compound (280 mg, yield 85%) as a solid.
$^1$H NMR (300 MHz, DMSO-$d_6$) δ: 0.30-0.41 (2H, m), 0.55-0.67 (2H, m), 1.10 (3H, s), 1.18-1.41 (5H, m), 1.51-1.62 (2H, m), 1.75-1.88 (2H, m), 2.54 (3H, brs), 3.83 (2H, s), 3.91 (2H, d, J=7.2 Hz), 3.97-4.17 (1H, m), 3.99 (3H, s), 4.10 (1H, s), 6.28 (1H, s), 6.82 (1H, d, J=8.0 Hz), 7.03 (2H, d, J=8.7 Hz), 7.25 (1H, d, J=8.3 Hz), 7.97 (2H, d, J=8.7 Hz), 9.78 (1H, s).
melting point: 167° C.
elemental analysis ($C_{29}H_{37}N_3O_3.H_2O$)
Calculated: C, 70.56; H, 7.96; N, 8.51.
Found: C, 70.55; H, 7.79; N, 8.28.

Example 80

4-(cyclopropylmethoxy)-N-{2-[(4-hydroxy-4-methylpiperidin-1-yl)methyl]-1,7-dimethyl-1H-indol-6-yl}benzamide

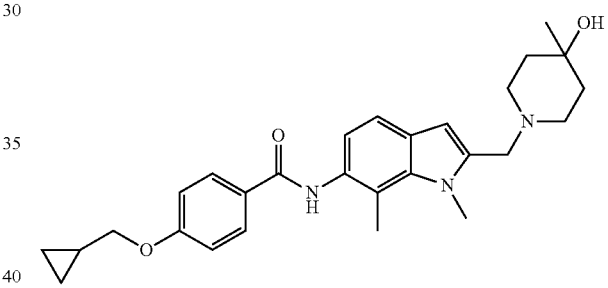

4-(Cyclopropylmethoxy)-N-(2-formyl-1,7-dimethyl-1H-indol-6-yl)benzamide (241 mg) obtained in Reference Example 65, 4-methylpiperidin-4-ol hydrochloride (201 mg), triethylamine (185 μL) and acetic acid (1.33 mL) were added to N,N-dimethylacetamide (29 mL), and the mixture was stirred at room temperature for 1 hr. Sodium triacetoxyborohydride (281 mg) was added, and the mixture was stirred at room temperature for 3 days. 8N Aqueous sodium hydroxide solution (3.33 mL) was added dropwise at 0° C. The mixture was extracted with ethyl acetate, washed with brine, dried over anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (164 mg, yield 54%) as a white solid.
$^1$H NMR (300 MHz, DMSO-$d_6$) δ: 0.30-0.38 (2H, m), 0.54-0.63 (2H, m), 1.09 (3H, s), 1.18-1.30 (1H, m), 1.39-1.49 (3H, m), 2.35-2.46 (5H, m), 2.53 (3H, s), 3.55 (2H, s), 3.89 (2H, d, J=7.1 Hz), 4.00 (3H, s), 4.09 (1H, s), 6.26 (1H, s), 6.80 (1H, d, J=8.2 Hz), 7.01 (2H, d, J=9.1 Hz), 7.23 (1H, d, J=8.0 Hz), 7.95 (2H, d, J=8.8 Hz), 9.78 (1H, s).
melting point: 152-155° C.
elemental analysis ($C_{28}H_{35}N_3O_3.0.4H_2O$)
Calculated: C, 71.74; H, 7.70; N, 8.96.
Found: C, 71.95; H, 7.82; N, 8.67.

Example 81

N-(2-{[(2,2-dimethylpropyl)amino]methyl}-1,7-dimethyl-1H-indol-6-yl)-4-[(2S)-tetrahydrofuran-2-ylmethoxy]benzamide

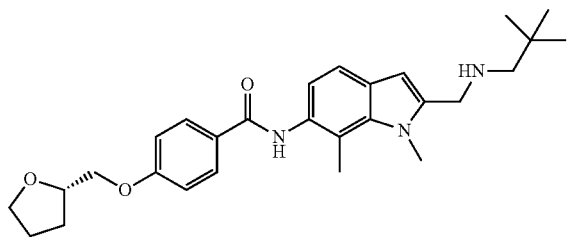 [SMILES: Cc1c(NC(=O)c2ccc(OC[C@@H]3CCCO3)cc2)ccc2cc(CNCC(C)(C)C)n(C)c12]

N-(2-Formyl-1,7-dimethyl-1H-indol-6-yl)-4-[(2S)-tetrahydrofuran-2-ylmethoxy]benzamide (500 mg) obtained in Reference Example 66, 2,2-dimethylpropan-1-amine (225 µL) and acetic acid (2.54 mL) were added to N,N-dimethylacetamide (8.4 mL), and the mixture was stirred at room temperature for 1 hr. Sodium triacetoxyborohydride (538 mg) was added, and the mixture was stirred at room temperature for 24 hr. 8N Aqueous sodium hydroxide solution (6.35 mL) was added dropwise at 0° C. The mixture was extracted with ethyl acetate, washed with brine, dried over anhydrous sodium sulfate, and concentrated under reduced pressure. The residue was purified by silica gel column chromatography [eluent; hexane:ethyl acetate=80:20 (volume ratio)→hexane:ethyl acetate=0:100 (volume ratio)→ethyl acetate:methanol=100:0 (volume ratio)→ethyl acetate:methanol=90:10 (volume ratio)], and crystallized from ethyl acetate and diisopropyl ether to give the title compound (459 mg, yield 78%) as a beige solid.

$^1$H NMR (300 MHz, DMSO-$d_6$) δ: 0.87 (9H, s), 1.62-1.76 (1H, m), 1.78-2.09 (3H, m), 2.33 (2H, s), 2.54 (3H, s), 3.28 (1H, s), 3.65-3.90 (4H, m), 3.96-4.09 (5H, m), 4.13-4.25 (1H, m), 6.29 (1H, s), 6.82 (1H, d, J=8.0 Hz), 7.05 (2H, d, J=8.7 Hz), 7.25 (1H, d, J=8.0 Hz), 7.98 (2H, d, J=8.7 Hz), 9.79 (1H, s).

melting point: 201° C.
elemental analysis ($C_{28}H_{37}N_3O_3$)
Calculated: C, 72.54; H, 8.04; N, 9.06.
Found: C, 72.24; H, 7.89; N, 9.01.

Example 82

N-(2-{[(2-hydroxy-2-methylpropyl)amino]methyl}-1,7-dimethyl-1H-indol-6-yl)-4-[(2S)-tetrahydrofuran-2-ylmethoxy]benzamide

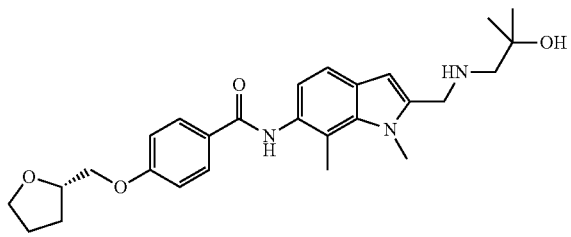 [SMILES: Cc1c(NC(=O)c2ccc(OC[C@@H]3CCCO3)cc2)ccc2cc(CNCC(C)(C)O)n(C)c12]

N-(2-Formyl-1,7-dimethyl-1H-indol-6-yl)-4-[(2S)-tetrahydrofuran-2-ylmethoxy]benzamide (300 mg) obtained in Reference Example 66, 1-amino-2-methylpropan-2-ol (102 mg) and acetic acid (1.53 mL) were added to N,N-dimethylacetamide (5 mL), and the mixture was stirred at room temperature for 1 hr. Sodium triacetoxyborohydride (324 mg) was added, and the mixture was stirred at room temperature for 21 hr. 8N Aqueous sodium hydroxide solution (3.82 mL) was added dropwise at 0° C. The mixture was extracted with ethyl acetate, washed with brine, dried over anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate and diisopropyl ether to give the title compound (289 mg, yield 81%) as a beige solid.

$^1$H NMR (300 MHz, DMSO-$d_6$) δ: 1.10 (6H, s), 1.59-2.10 (4H, m), 2.46 (2H, s), 2.55 (3H, s), 3.65-3.74 (1H, m), 3.76-3.85 (1H, m), 3.87 (2H, s), 3.96-4.12 (5H, m), 4.13-4.25 (2H, m), 6.29 (1H, s), 6.82 (1H, d, J=8.3 Hz), 7.05 (2% H, d, J=8.7 Hz), 7.26 (1H, d, J=8.3 Hz), 7.98 (2H, d, J=8.7 Hz), 9.80 (1H, s).

melting point: 197-200° C.
elemental analysis ($C_{27}H_{35}N_3O_4 \cdot 0.2H_2O$)
Calculated: C, 69.12; H, 7.60; N, 8.96.
Found: C, 69.06; H, 7.41; N, 8.83.

Example 83

N-(1,7-dimethyl-2-{[(tetrahydro-2H-pyran-4-ylmethyl)amino]methyl}-1H-indol-6-yl)-4-[(2S)-tetrahydrofuran-2-ylmethoxy]benzamide

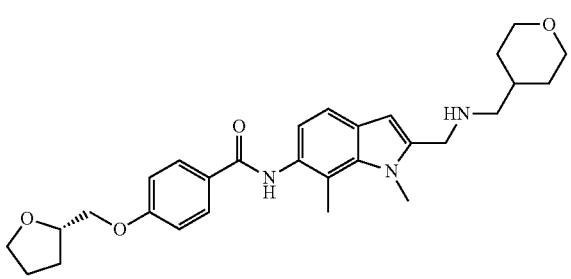 [SMILES: Cc1c(NC(=O)c2ccc(OC[C@@H]3CCCO3)cc2)ccc2cc(CNCC3CCOCC3)n(C)c12]

N-(2-Formyl-1,7-dimethyl-1H-indol-6-yl)-4-[(2S)-tetrahydrofuran-2-ylmethoxy]benzamide (300 mg) obtained in Reference Example 66, 1-(tetrahydro-2H-pyran-4-yl)methanamine (132 mg) and acetic acid (1.53 mL) were added to N,N-dimethylacetamide (5 mL), and the mixture was stirred at room temperature for 1 hr. Sodium triacetoxyborohydride (324 mg) was added, and the mixture was stirred at room temperature for 21 hr. 8N Aqueous sodium hydroxide solution (3.82 mL) was added dropwise at 0° C. The mixture was extracted with ethyl acetate, washed with brine, dried over anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate and diisopropyl ether to give the title compound (306 mg, yield 81%) as a white solid.

$^1$H NMR (300 MHz, DMSO-$d_6$) δ: 1.04-1.29 (2H, m), 1.52-2.14 (7H, m), 2.45 (2H, d, J=6.0 Hz), 2.54 (3H, brs), 3.21-3.30 (2H, m), 3.65-3.91 (6H, m), 3.95-4.12 (5H, m), 4.13-4.25 (1H, m), 6.29 (1H, s), 6.82 (1H, d, J=8.1 Hz), 7.05 (2H, d, J=8.9 Hz), 7.25 (1H, d, J=8.3 Hz), 7.98 (2H, d, J=8.9 Hz), 9.80 (1H, s).

melting point: 197-198° C.
elemental analysis ($C_{29}H_{37}N_3O_4 \cdot 0.2H_2O$)
Calculated: C, 70.33; H, 7.61; N, 8.48.
Found: C, 70.26; H, 7.42; N, 8.45.

Example 84

N-(2-{[(trans-4-hydroxy-4-methylcyclohexyl)amino]methyl}-1,7-dimethyl-1H-indol-6-yl)-4-[(2S)-tetrahydrofuran-2-ylmethoxy]benzamide

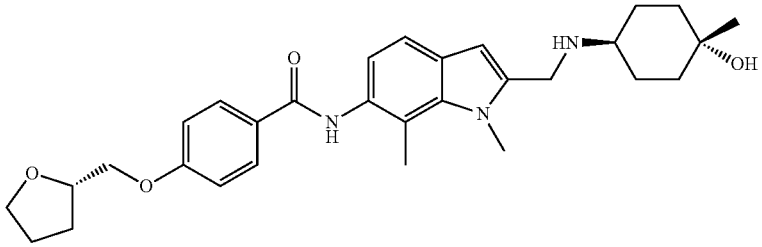 [SMILES: Cc1c(NC(=O)c2ccc(OC[C@@H]3CCCO3)cc2)ccc2cc(CN[C@H]3CC[C@](C)(O)CC3)n(C)c12]

N-(2-Formyl-1,7-dimethyl-1H-indol-6-yl)-4-[(2S)-tetrahydrofuran-2-ylmethoxy]benzamide (318 mg) obtained in Reference Example 66, trans-4-amino-1-methylcyclohexanol (210 mg) obtained in Reference Example 101 and acetic acid (1.6 mL) were added to N,N-dimethylacetamide (5.3 mL), and the mixture was stirred at room temperature for 1 hr. Sodium triacetoxyborohydride (344 mg) was added, and the mixture was stirred at room temperature for 18 hr. 8N Aqueous sodium hydroxide solution (4.05 mL) was added dropwise at 0° C. The mixture was extracted with ethyl acetate, washed with brine, dried over anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate and diisopropyl ether to give the title compound (323 mg, yield 79%) as a solid.

$^1$H NMR (300 MHz, DMSO-$d_6$) δ: 1.10 (3H, s), 1.18-1.39 (4H, m), 1.50-2.11 (8H, m), 2.54 (3H, s), 3.65-3.87 (2H, m), 3.83 (2H, s), 3.96-4.24 (7H, m), 6.28 (1H, s), 6.82 (1H, d, J=8.3 Hz), 7.05 (2H, d, J=8.7 Hz), 7.25 (1H, d, J=8.3 Hz), 7.98 (2H, d, J=8.7 Hz), 9.80 (1H, s).

melting point: 171-172° C.

elemental analysis ($C_{30}H_{39}N_3O_4 \cdot H_2O$)

Calculated: C, 68.81; H, 7.89; N, 8.02.

Found: C, 68.96; H, 7.82; N, 7.74.

Example 85

N-(1,7-dimethyl-2-{[(2-methylpropyl)amino]methyl}-1H-indol-6-yl)-4-[(2S)-tetrahydrofuran-2-ylmethoxy]benzamide

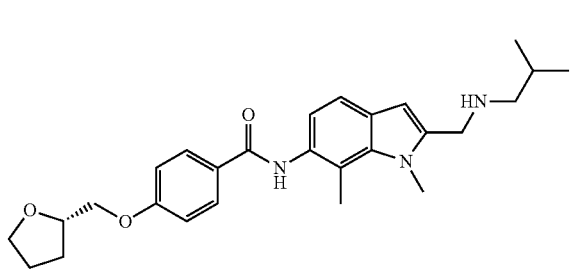 [SMILES: Cc1c(NC(=O)c2ccc(OC[C@@H]3CCCO3)cc2)ccc2cc(CNCC(C)C)n(C)c12]

N-(2-Formyl-1,7-dimethyl-1H-indol-6-yl)-4-[(2S)-tetrahydrofuran-2-ylmethoxy]benzamide (400 mg) obtained in Reference Example 66, 2-methylpropan-1-amine (152 μL) and acetic acid (2.04 mL) were added to N,N-dimethylacetamide (6.7 mL), and the mixture was stirred at room temperature for 1 hr. Sodium triacetoxyborohydride (432 mg) was added, and the mixture was stirred at room temperature for 12 hr. 8N Aqueous sodium hydroxide solution (5.05 mL) was added dropwise at 0° C. The mixture was extracted with ethyl acetate, washed with aqueous sodium hydrogen carbonate solution and brine, dried over anhydrous sodium sulfate, and concentrated under reduced pressure. The residue was purified by silica gel column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (394 mg, yield 87%) as a white solid.

$^1$H NMR (300 MHz, DMSO-$d_6$) δ: 0.87 (6H, d, J=6.8 Hz), 1.61-2.10 (5H, m), 2.38 (2H, d, J=6.8 Hz), 2.54 (3H, s), 3.65-3.75 (1H, m), 3.76-3.88 (3H, m), 3.97-4.11 (5H, m), 4.13-4.25 (1H, m), 6.28 (1H, s), 6.82 (1H, d, J=8.3 Hz), 7.05 (2H, d, J=9.1 Hz), 7.25 (1H, d, J=8.3 Hz), 7.98 (2H, d, J=8.7 Hz), 9.79 (1H, s).

melting point: 183° C.

elemental analysis ($C_{27}H_{35}N_3O_3$)

Calculated: C, 72.13; H, 7.85; N, 9.35.

Found: C, 71.83; H, 7.77; N, 9.14.

Example 86

N-{2-[(cyclopentylamino)methyl]-1,7-dimethyl-1H-indol-6-yl}-4-[(2S)-tetrahydrofuran-2-ylmethoxy]benzamide

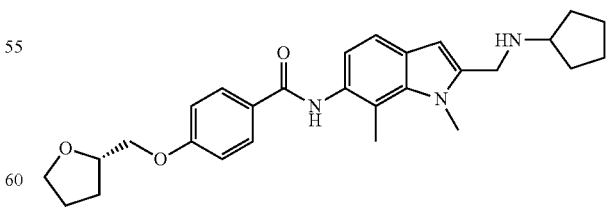

N-(2-Formyl-1,7-dimethyl-1H-indol-6-yl)-4-[(2S)-tetrahydrofuran-2-ylmethoxy]benzamide (90.3 mg) obtained in Reference Example 66, cyclopentylamine (45.4 μL) and acetic acid (0.46 mL) were added to N,N-dimethylacetamide (1.5 mL), and the mixture was stirred at room temperature for 2 hr. Sodium triacetoxyborohydride (97.4 mg) was added, and the mixture was stirred at room temperature for 1 week. 8N Aqueous sodium hydroxide solution (1.15 mL) was added dropwise at 0° C. The mixture was extracted with ethyl acetate, washed with aqueous sodium hydrogen carbonate solution and brine, dried over anhydrous sodium sulfate, purified by silica gel column chromatography [eluent; ethyl acetate:methanol=100:0 (volume ratio)→ethyl acetate:methanol=60:40 (volume ratio)] and crystallized from ethyl acetate and heptane to give the title compound (91.1 mg, yield 86%) as a white solid.

$^1$H NMR (300 MHz, DMSO-d$_6$) δ: 1.31-1.55 (4H, m), 1.58-2.09 (9H, m), 2.54 (3H, s), 3.01-3.12 (1H, m), 3.64-3.74 (1H, m), 3.75-3.85 (3H, m), 3.96-4.10 (5H, m), 4.12-4.24 (1H, m), 6.29 (1H, s), 6.82 (1H, d, J=8.3 Hz), 7.05 (2H, d, J=8.7 Hz), 7.25 (1H, d, J=8.3 Hz), 7.98 (2H, d, J=8.7 Hz), 9.80 (1H, s).

melting point: 190-192° C.

anhydrous sodium sulfate, purified by silica gel column chromatography [eluent; ethyl acetate:methanol=100:0 (volume ratio)→ethyl acetate:methanol=60:40 (volume ratio)], and crystallized from ethyl acetate and diisopropyl ether to give the title compound (62.4 mg, yield 17%) as a white solid.

$^1$H NMR (300 MHz, DMSO-d$_6$) δ: 1.10 (3H, s), 1.41-1.50 (4H, m), 1.60-2.10 (4H, m), 2.36-2.46 (2H, m), 2.54 (3H, brs), 3.56 (2H, s), 3.64-3.86 (2H, m), 3.96-4.26 (8H, m), 6.27 (1H, s), 6.81 (1H, d, J=7.7 Hz), 7.04 (2H, d, J=9.18 Hz), 7.24 (1H, d, J=8.5 Hz), 7.97 (2H, d, J=9.1 Hz), 9.79 (1H, s).

melting point: 140-141° C.

elemental analysis (C$_{29}$H$_{37}$N$_3$O$_4$.0.8H$_2$O)

Calculated: C, 68.83; H, 7.69; N, 8.30.

Found: C, 69.14; H, 7.58; N, 7.91.

Example 88

2-fluoro-N-(2-{[(trans-4-hydroxy-4-methylcyclohexyl)amino]methyl}-1,7-dimethyl-1H-indol-6-yl)-4-[(2S)-tetrahydrofuran-2-ylmethoxy]benzamide

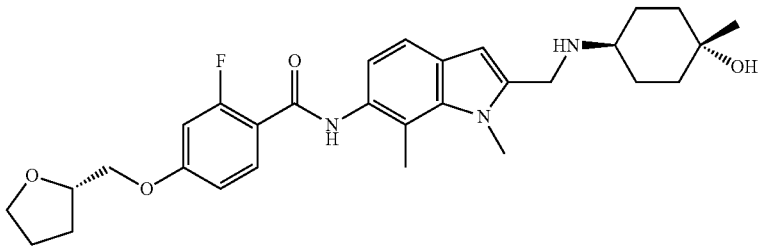

Example 87

N-{2-[(4-hydroxy-4-methylpiperidin-1-yl)methyl]-1,7-dimethyl-1H-indol-6-yl}-4-[(2S)-tetrahydrofuran-2-ylmethoxy]benzamide

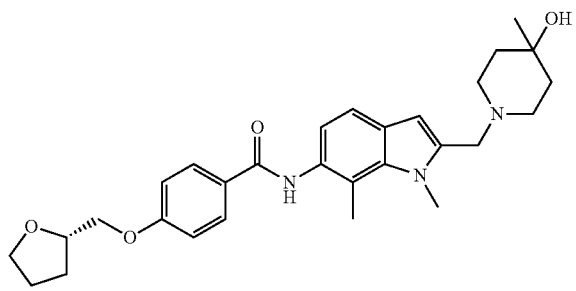 [SMILES: Cc1c(NC(=O)c2ccc(OC[C@@H]3CCCO3)cc2)ccc2cc(CN3CCC(C)(O)CC3)n(C)c12]

N-(2-Formyl-1,7-dimethyl-1H-indol-6-yl)-4-[(2S)-tetrahydrofuran-2-ylmethoxy]benzamide (300 mg) obtained in Reference Example 66, 4-methylpiperidin-4-ol hydrochloride (174 mg) and acetic acid (1.53 mL) were added to N,N-dimethylacetamide (20 mL), and the mixture was stirred at room temperature for 1 hr. Sodium triacetoxyborohydride (324 mg) was added, and the mixture was stirred at room temperature for 18 hr. 8N Aqueous sodium hydroxide solution (3.82 mL) was added dropwise at 0° C. The mixture was extracted with ethyl acetate, washed with brine, dried over 2-Fluoro-N-(2-formyl-1,7-dimethyl-1H-indol-6-yl)-4-[(2S)-tetrahydrofuran-2-ylmethoxy]benzamide (0.6 g) obtained in Reference Example 69 and trans-4-amino-1-methylcyclohexanol (340 mg) obtained in Reference Example 101 were suspended in NMP (20 mL) and acetic acid (7.0 mL), and the mixture was stirred at room temperature for 3 hr. Sodium triacetoxyborohydride (2.5 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (380 mg, yield 50%) as a colorless solid.

$^1$H NMR (300 MHz, DMSO-d$_6$) δ: 1.10 (3H, s), 1.28-1.35 (4H, m), 1.54-1.58 (2H, m), 1.66-1.72 (1H, m), 1.82-1.88 (5H, m), 1.96-2.00 (1H, m), 2.50 (3H, s), 2.58-2.60 (1H, m), 3.32 (1H, br), 3.69 (1H, q, J=6.9 Hz), 3.75-3.82 (3H, m), 3.99 (3H, s), 4.02-4.15 (3H, m), 6.27 (1H, s), 6.85-6.97 (3H, m), 7.23 (1H, d, J=8.4 Hz), 7.67 (1H, t, J=8.4 Hz), 9.62 (1H, s).

melting point: 131-132° C.

elemental analysis (C$_{30}$H$_{38}$N$_3$O$_4$F.0.5H$_2$O)

Calculated: C, 67.65; H, 7.38; N, 7.89.

Found: C, 67.74; H, 7.32; N, 7.99.

Example 89

2-fluoro-N-(2-{[(2-hydroxy-2-methylpropyl)amino]methyl}-1,7-dimethyl-1H-indol-6-yl)-4-[(2S)-tetrahydrofuran-2-ylmethoxy]benzamide

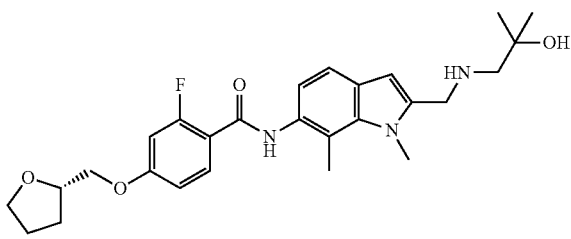 [SMILES: Cc1c(NC(=O)c2ccc(OC[C@@H]3CCCO3)cc2F)ccc2cc(CNCC(C)(C)O)n(C)c12]

2-Fluoro-N-(2-formyl-1,7-dimethyl-1H-indol-6-yl)-4-[(2S)-tetrahydrofuran-2-ylmethoxy]benzamide (0.60 g) obtained in Reference Example 69 and 1-amino-2-methylpropan-2-ol (446 mg) were suspended in NMP (20 mL) and acetic acid (7.0 mL), and the mixture was stirred at room temperature for 3 hr. Sodium triacetoxyborohydride (2.5 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (400 mg, yield 57%) as a colorless solid.

$^1$H NMR (300 MHz, DMSO-$d_6$) δ: 1.10 (6H, s), 1.64-1.72 (1H, m), 1.83-1.90 (2H, m), 1.95-2.07 (2H, m), 2.46 (2H, s), 2.59 (3H, s), 3.32 (1H, br), 3.69 (1H, q, J=6.3 Hz), 3.79 (1H, q, J=6.3 Hz), 3.87 (2H, s), 4.01 (3H, s), 4.02-4.09 (1H, m), 4.13-4.19 (1H, m), 4.23 (1H, s), 6.29 (1H, s), 6.86-6.98 (3H, m), 7.25 (1H, d, J=8.4 Hz), 7.68 (1H, t, J=8.4 Hz), 9.64 (1H, s).

melting point: 132-133° C.
elemental analysis ($C_{27}H_{34}N_3O_4F$)
Calculated: C, 67.06; H, 7.09; N, 8.69.
Found: C, 66.98; H, 7.09; N, 8.63.

Example 90

N-(1,7-dimethyl-2-{[(2-methylpropyl)amino]methyl}-1H-indol-6-yl)-4-[(1-hydroxycyclopropyl)ethynyl]benzamide

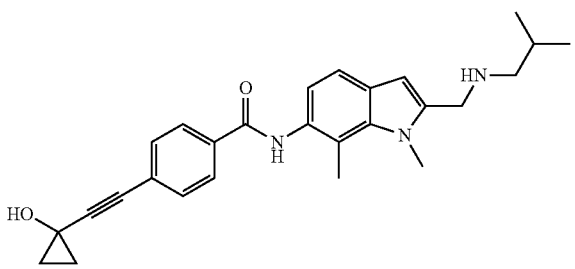 [SMILES: Cc1c(NC(=O)c2ccc(C#CC3(O)CC3)cc2)ccc2cc(CNCC(C)C)n(C)c12]

4-Bromo-N-(1,7-dimethyl-2-{[(2-methylpropyl)amino]methyl}-1H-indol-6-yl)benzamide (1.09 g) obtained in Reference Example 73, 1-ethynylcyclopropanol (266 mg), triphenylphosphine (80.2 mg), copper(I) iodide (21.1 mg) and bis(triphenylphosphine)palladium(II) dichloride (22.7 mg) were suspended in a mixed solvent of triethylamine (7.29 mL) and pyridine (7.29 mL), and the mixture was stirred under an argon atmosphere at 65° C. for 3 days. The mixture was cooled to room temperature, and the precipitate was filtered off. The filtrate was concentrated, purified by silica gel column chromatography [eluent; ethyl acetate:methanol=100:0 (volume ratio)→ethyl acetate:methanol=60:40 (volume ratio)] and NH silica gel column chromatography [eluent; hexane:ethyl acetate=40:60 (volume ratio)→hexane:ethyl acetate=0:100 (volume ratio)→ethyl acetate:methanol=100:0 (volume ratio)→ethyl acetate:methanol=80:20 (volume ratio)], and crystallized from ethyl acetate, diisopropyl ether and heptane to give the title compound (253 mg, yield 22%) as a pale-yellow solid.

$^1$H NMR (300 MHz, DMSO-$d_6$) δ: 0.87 (6H, d, J=6.6 Hz), 0.99-1.02 (4H, m), 1.62-1.73 (1H, m), 2.37 (2H, d, J=6.6 Hz), 2.55 (3H, s), 3.81 (2H, s), 4.00 (3H, s), 6.28 (1H, s), 6.35 (1H, s), 6.82 (1H, d, J=8.2 Hz), 7.25 (1H, d, J=8.2 Hz), 7.51 (2H, d, J=8.2 Hz), 7.98 (2H, d, J=8.2 Hz), 10.00 (1H, s).

melting point: 186° C.
elemental analysis ($C_{27}H_{31}N_3O_2 \cdot 0.9H_2O$)
Calculated: C, 72.75; H, 7.42; N, 9.43.
Found: C, 72.73; H, 7.20; N, 9.22.

Example 91

N-(2-{[(2,2-dimethylpropyl)amino]methyl}-1,7-dimethyl-1H-indol-6-yl)-4-[(1-hydroxycyclopropyl)ethynyl]benzamide

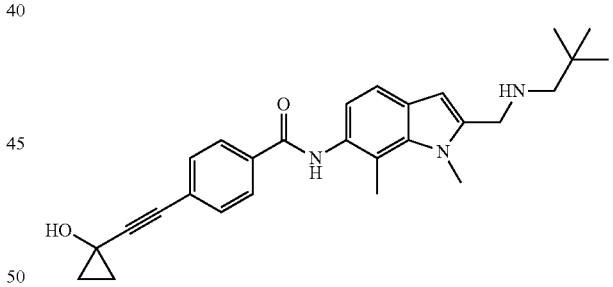

4-Bromo-N-(2-{[(2,2-dimethylpropyl)amino]methyl}-1,7-dimethyl-1H-indol-6-yl)benzamide (1.06 g) obtained in Reference Example 74, 1-ethynylcyclopropanol (266 mg), triphenylphosphine (80.2 mg), copper(I) iodide (21.1 mg) and bis(triphenylphosphine)palladium(II) dichloride (22.7 mg) were suspended in a mixed solvent of triethylamine (7.29 mL) and pyridine (7.29 mL), and the mixture was stirred under an argon atmosphere at 65° C. for 3 days. The mixture was cooled to room temperature, and the precipitate was filtered off. The filtrate was concentrated, purified by silica gel column chromatography [eluent; ethyl acetate:methanol=100:0 (volume ratio)→ethyl acetate:methanol=60:40 (volume ratio)] and NH silica gel column chromatography [eluent; hexane:ethyl acetate=40:60 (volume ratio)→hexane: ethyl acetate=0:100 (volume ratio)→ethyl acetate:methanol=100:0 (volume ratio)→ethyl acetate:methanol=80:20 (volume ratio)], and crystallized from ethyl acetate, diisopropyl ether and heptane to give the title compound (481 mg, yield 40%) as a pale-yellow solid.

$^1$H NMR (300 MHz, DMSO-$d_6$) δ: 0.87 (9H, s), 1.01 (4H, s), 2.33 (2H, s), 2.55 (3H, s), 3.85 (2H, s), 4.02 (3H, s), 6.29 (1H, s), 6.35 (1H, s), 6.82 (1H, d, J=8.0 Hz), 7.25 (1H, d, J=8.5 Hz), 7.51 (2H, d, J=8.2 Hz), 7.98 (2H, d, J=8.5 Hz), 10.00 (1H, s).

melting point: 182-183° C.

elemental analysis ($C_{28}H_{33}N_3O_2 \cdot 0.4H_2O$)

Calculated: C, 74.60; H, 7.56; N, 9.32.

Found: C, 74.82; H, 7.44; N, 9.08.

Example 92

4-[(1-hydroxycyclobutyl)ethynyl]-N-(2-{[(2-methylpropyl)amino]methyl}-1,7-dimethyl-1H-indol-6-yl)benzamide

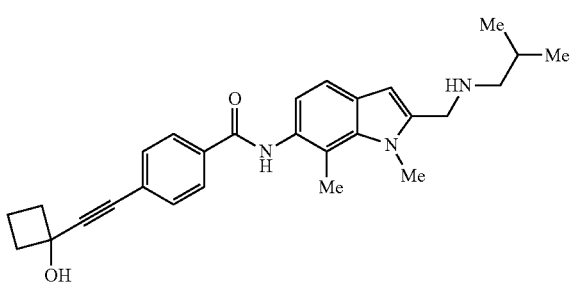 [SMILES: Cc1c(NC(=O)c2ccc(C#CC3(O)CCC3)cc2)ccc2cc(CNCC(C)C)n(C)c12]

Under an argon atmosphere, to a solution of 4-bromo-N-(1,7-dimethyl-2-{[(2-methylpropyl)amino]methyl}-1H-indol-6-yl)benzamide (1087 mg) obtained in Reference Example 73 in pyridine (7.07 mL) were added triphenylphosphine (76 mg), copper(I) iodide (20 mg), triethylamine (7.07 mL), 1-ethynylcyclobutanol (293 mg) and dichlorobis(triphenylphosphine)palladium(II) (21 mg), and the mixture was stirred at 65° C. for 2 days. The mixture was allowed to cool to room temperature, and the insoluble material was filtered off, and washed with a small amount of ethyl acetate. The filtrate was purified by silica gel column chromatography [eluent; hexane:ethyl acetate=1:4 (volume ratio)→ethyl acetate] and the obtained crude product was washed with ethyl acetate to give the title compound (451 mg, yield 40%) as pale-brown crystals.

$^1$H NMR (300 MHz, DMSO-$d_6$) δ: 0.87 (6H, d, J=6.4 Hz), 1.61-1.87 (3H, m), 2.17-2.30 (2H, m), 2.34-2.46 (4H, m), 2.56 (3H, s), 3.82 (2H, s), 4.01 (3H, s), 5.94 (1H, s), 6.29 (1H, s), 6.84 (1H, d, J=8.3 Hz), 7.26 (1H, d, J=8.0 Hz), 7.56 (2H, d, J=8.3 Hz), 8.01 (2H, d, J=8.3 Hz), 10.02 (1H, s).

melting point: 222-223° C.

elemental analysis ($C_{28}H_{33}N_3O_2$)

Calculated: C, 75.81; H, 7.50; N, 9.47.

Found: C, 75.20; H, 7.52; N, 9.14.

Example 93

N-(2-{[(2,2-dimethylpropyl)amino]methyl}-1,7-dimethyl-1H-indol-6-yl)-4-[(1-hydroxycyclobutyl)ethynyl]benzamide

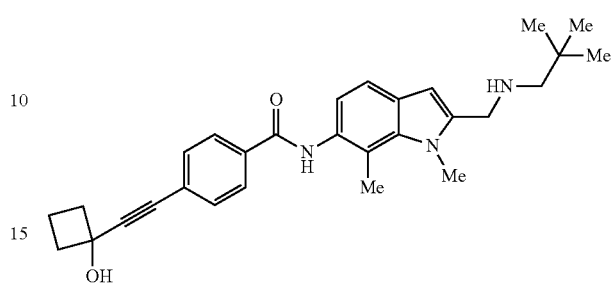

Under an argon atmosphere, to a solution of 4-bromo-N-(2-{[(2,2-dimethylpropyl)amino]methyl}-1,7-dimethyl-1H-indol-6-yl)benzamide (1083 mg) obtained in Reference Example 74 in pyridine (6.82 mL) were added triphenylphosphine (73 mg), copper(I) iodide (20 mg), triethylamine (6.82 mL), 1-ethynylcyclobutanol (282 mg) and dichlorobis(triphenylphosphine)palladium(II) (21 mg), and the mixture was stirred at 65° C. for 2 days. The mixture was allowed to cool to room temperature, and the insoluble material was filtered off, and washed with a small amount of ethyl acetate. The filtrate was purified by silica gel column chromatography [eluent; ethyl acetate→ethyl acetate:methanol=3:2 (volume ratio)] and NH-silica gel chromatography [eluent; hexane:ethyl acetate=3:7 (volume ratio)→ethyl acetate], and the obtained crude product was washed with diisopropyl ether-ethyl acetate to give the title compound (871 mg, yield 78%) as colorless crystals.

$^1$H NMR (300 MHz, DMSO-$d_6$) δ: 0.87 (9H, s), 1.73-1.87 (2H, m), 2.17-2.30 (2H, m), 2.33 (2H, s), 2.35-2.46 (2H, m), 2.55 (3H, s), 3.85 (2H, s), 4.02 (3H, s), 5.94 (1H, s), 6.29 (1H, s), 6.84 (1H, d, J=8.3 Hz), 7.26 (1H, d, J=8.0 Hz), 7.56 (2H, d, J=8.3 Hz), 8.01 (2H, d, J=8.3 Hz), 10.02 (1H, s).

melting point: 232-233° C.

elemental analysis ($C_{29}H_{35}N_3O_2$)

Calculated: C, 76.12; H, 7.71; N, 9.18.

Found: C, 75.90; H, 7.75; N, 8.94.

Example 94

N-(1,7-dimethyl-2-{[(tetrahydro-2H-pyran-4-ylmethyl)amino]methyl}-1H-indol-6-yl)-4-[(1-hydroxycyclobutyl)ethynyl]benzamide

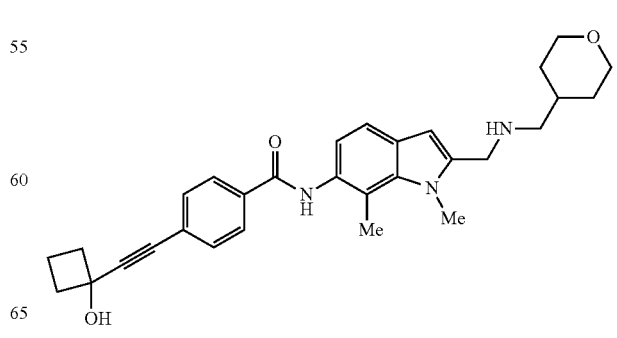

Under an argon atmosphere, to a solution of 4-bromo-N-(1,7-dimethyl-2-{[(tetrahydro-2H-pyran-4-ylmethyl)amino]methyl}-1H-indol-6-yl)benzamide (1123 mg) obtained in Reference Example 75 in pyridine (6.66 mL) were added triphenylphosphine (71 mg), copper(I) iodide (19 mg), triethylamine (6.66 mL), 1-ethynylcyclobutanol (275 mg) and dichlorobis(triphenylphosphine)palladium(II) (20 mg), and the mixture was stirred at 65° C. for 2 days. The mixture was allowed to cool to room temperature, and the insoluble material was filtered off, and washed with a small amount of ethyl acetate. The filtrate was purified by silica gel column chromatography [eluent; hexane:ethyl acetate=3:7→ethyl acetate (volume ratio)] and NH-silica gel chromatography [eluent; hexane:ethyl acetate=1:4 (volume ratio)→ethyl acetate], and the obtained crude product was washed with ethyl acetate to give the title compound (581 mg, yield 50%) as colorless crystals.

$^1$H NMR (300 MHz, DMSO-$d_6$) δ: 1.06-1.23 (2H, m), 1.58-1.88 (4H, m), 2.17-2.30 (2H, m), 2.35-2.48 (4H, m), 2.55 (3H, s), 3.21-3.31 (2H, m), 3.79-3.87 (4H, m), 4.00 (1H, s), 5.95 (1H, s), 6.30 (1H, s), 6.84 (1H, d, J=8.3 Hz), 7.27 (1H, d, J=8.3 Hz), 7.56 (2H, d, J=8.3 Hz), 8.01 (2H, d, J=8.3 Hz), 10.03 (1H, s).

melting point: 202-204° C.

elemental analysis ($C_{30}H_{35}N_3O_3$)

Calculated: C, 74.20; H, 7.26; N, 8.65.

Found: C, 72.32; H, 7.33; N, 8.24.

Example 95

N-(1,7-dimethyl-2-{[(tetrahydro-2H-pyran-4-ylmethyl)amino]methyl}-1H-indol-6-yl)-4-[(1-hydroxycyclopropyl)ethynyl]benzamide

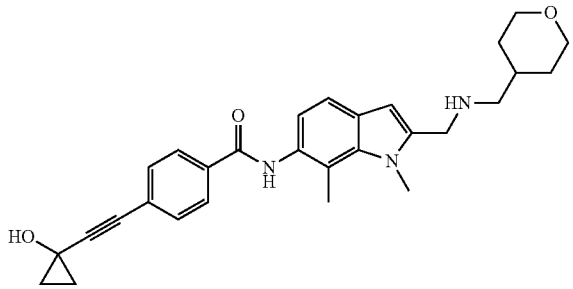 [SMILES: Cc1c(NC(=O)c2ccc(C#CC3(O)CC3)cc2)ccc2cc(CNCC3CCOCC3)n(C)c12]

4-Bromo-N-(1,7-dimethyl-2-{[(tetrahydro-2H-pyran-4-ylmethyl)amino]methyl}-1H-indol-6-yl)benzamide (1.12 g) obtained in Reference Example 75, 1-ethynylcyclopropanol (266 mg), triphenylphosphine (80.2 mg), copper(I) iodide (21.1 mg) and bis(triphenylphosphine)palladium(II) dichloride (22.7 mg) were suspended in a mixed solvent of triethylamine (7.29 mL) and pyridine (7.29 mL), and the mixture was stirred under an argon atmosphere at 65° C. for 3 days. The mixture was cooled to room temperature, and the precipitate was filtered off. The filtrate was concentrated, purified by silica gel column chromatography [eluent; ethyl acetate:methanol=100:0 (volume ratio)→Methyl acetate:methanol=60:40 (volume ratio)] and NH silica gel column chromatography [eluent; hexane:ethyl acetate=40:60 (volume ratio)→hexane:ethyl acetate=0:100 (volume ratio)→ethyl acetate:methanol=100:0 (volume ratio)→ethyl acetate:methanol=80:20 (volume ratio)], and crystallized from ethyl acetate, diisopropyl ether and heptane to give the title compound (180 mg, yield 14%) as a pale-yellow solid.

$^1$H NMR (300 MHz, DMSO-$d_6$) δ: 0.99-1.03 (4H, m), 1.09-1.26 (2H, m), 1.57-1.70 (3H, m), 2.44 (2H, d, J=6.6 Hz), 2.54 (3H, s), 3.20-3.30 (2H, m), 3.77-3.87 (4H, m), 3.99 (3H, s), 6.28 (1H, s), 6.35 (1H, s), 6.79-6.86 (1H, m), 7.25 (1H, d, J=7.7 Hz), 7.51 (2H, d, J=8.0 Hz), 7.98 (2H, d, J=9.1 Hz), 9.99 (1H, s).

elemental analysis ($C_{29}H_{33}N_3O_3 \cdot 1.4H_2O$)

Calculated: C, 70.11; H, 7.26; N, 8.46.

Found: C, 70.28; H, 7.47; N, 8.19.

Example 96

N-(2-{[(2-methylpropyl)amino]methyl}-3,7-dimethyl-1H-indol-6-yl)-4-[(2S)-tetrahydrofuran-2-ylmethoxy]benzamide

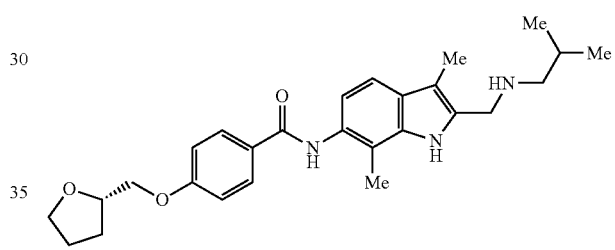

To a solution of N-(2-formyl-3,7-dimethyl-1H-indol-6-yl)-4-[(2S)-tetrahydrofuran-2-ylmethoxy]benzamide (220 mg) obtained in Reference Example 79 in N,N-dimethylacetamide (3.5 mL) were added isobutylamine (82 mg), sodium triacetoxyborohydride (238 mg) and acetic acid (1.12 mL), and the mixture was stirred at room temperature for 15 hr. Under ice-cooling, 8N aqueous sodium hydroxide solution (4.18 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=7:3 (volume ratio)] and NH-silica gel chromatography [eluent; ethyl acetate→ethyl acetate:methanol=9:1 (volume ratio)], and the obtained crude product was washed with diisopropyl ether-ethyl acetate to give the title compound (166 mg, yield 66%) as pale-brown crystals.

$^1$H NMR (300 MHz, DMSO-$d_6$) δ: 0.86 (6H, d, J=6.4 Hz), 1.59-2.08 (5H, m), 2.20 (3H, s), 2.27-2.33 (5H, m), 3.65-3.85 (4H, m), 3.96-4.09 (2H, m), 4.13-4.23 (1H, m), 6.86 (1H, d, J=8.3 Hz), 7.05 (2H, d, J=8.7 Hz), 7.21 (1H, d, J=8.3 Hz), 7.98 (2H, d, J=8.7 Hz), 9.75 (1H, s), 10.51 (1H, s).

melting point: 118-119° C.

elemental analysis ($C_{27}H_{35}N_3O_3$)

Calculated: C, 72.13; H, 7.85; N, 9.35.

Found: C, 69.33; H, 7.87; N, 8.90.

Example 97

N-(3,7-dimethyl-2-{[(tetrahydro-2H-pyran-4-ylmethyl)amino]methyl}-1H-indol-6-yl)-4-[(2S)-tetrahydrofuran-2-ylmethoxy]benzamide

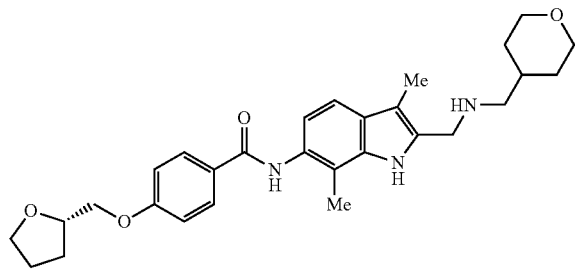 [SMILES: Cc1c(CNCC2CCOCC2)[nH]c2c(C)c(NC(=O)c3ccc(OC[C@@H]4CCCO4)cc3)ccc12]

To a solution of N-(2-formyl-3,7-dimethyl-1H-indol-6-yl)-4-[(2S)-tetrahydrofuran-2-ylmethoxy]benzamide (220 mg) obtained in Reference Example 79 in N,N-dimethylacetamide (3.5 mL) were added 4-aminomethyltetrahydropyran (129 mg), sodium triacetoxyborohydride (238 mg) and acetic acid (1.12 mL), and the mixture was stirred at room temperature for 15 hr. Under ice-cooling, 8N aqueous sodium hydroxide solution (4.18 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=1:1 (volume ratio)] and NH-silica gel chromatography [eluent; ethyl acetate→ethyl acetate:methanol=9:1 (volume ratio)], and the obtained crude product was washed with diisopropyl ether-ethyl acetate to give the title compound (162 mg, yield 59%) as colorless crystals.

$^1$H NMR (300 MHz, DMSO-$d_6$) δ: 1.05-1.21 (2H, m), 1.57-2.09 (7H, m), 2.20 (3H, s), 2.29 (3H, s), 2.37 (2H, d, J=6.1 Hz), 3.21-3.31 (2H, m), 3.65-3.87 (6H, m), 3.96-4.10 (2H, m), 4.14-4.23 (1H, m), 6.86 (1H, d, J=8.3 Hz), 7.05 (2H, d, J=9.1 Hz), 7.21 (1H, d, J=8.3 Hz), 7.98 (2H, d, J=8.7 Hz), 9.75 (1H, s), 10.49 (1H, s).

melting point: 184-185° C.
elemental analysis ($C_{29}H_{37}N_3O_4$)
Calculated: C, 70.85; H, 7.59; N, 8.55.
Found: C, 70.82; H, 7.67; N, 8.44.

Example 98

N-(2-{[(2,2-dimethylpropyl)amino]methyl}-3,7-dimethyl-1H-indol-6-yl)-4-[(2S)-tetrahydrofuran-2-ylmethoxy]benzamide

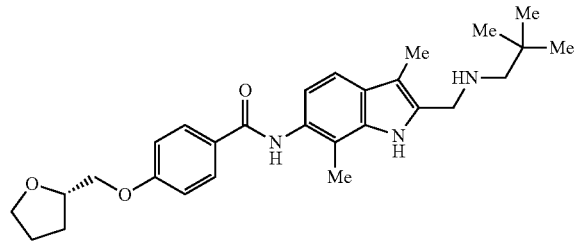 [SMILES: Cc1c(CNCC(C)(C)C)[nH]c2c(C)c(NC(=O)c3ccc(OC[C@@H]4CCCO4)cc3)ccc12]

To a solution of N-(2-formyl-3,7-dimethyl-1H-indol-6-yl)-4-[(2S)-tetrahydrofuran-2-ylmethoxy]benzamide (220 mg) obtained in Reference Example 79 in N,N-dimethylacetamide (3.5 mL) were added neopentylamine (98 mg), sodium triacetoxyborohydride (238 mg) and acetic acid (1.12 mL), and the mixture was stirred at room temperature for 15 hr. Under ice-cooling, 8N aqueous sodium hydroxide solution (4.18 mL) was added, and ethyl acetate and water were further added. The mixture was partitioned, and the aqueous layer was extracted with tetrahydrofuran. The combined organic layer was purified by silica gel column chromatography [hexane:ethyl acetate=3:7→ethyl acetate (volume ratio)] and NH-silica gel chromatography [eluent; ethyl acetate→ethyl acetate:methanol=95:5 (volume ratio)], and the obtained crude product was washed with diisopropyl ether-ethyl acetate to give the title compound (180 mg, yield 69%) as pale-yellow crystals.

$^1$H NMR (300 MHz, DMSO-$d_6$) δ: 0.86 (9H, s), 1.62-2.08 (5H, m), 2.19-2.25 (5H, m), 2.29 (3H, s), 3.65-3.85 (4H, m), 3.96-4.09 (2H, m), 4.13-4.23 (1H, m), 6.86 (1H, d, J=8.3 Hz), 7.05 (2H, d, J=9.0 Hz), 7.21 (1H, d, J=8.3 Hz), 7.98 (2H, d, J=8.7 Hz), 9.75 (1H, s), 10.50 (1H, s).

melting point: 178-179° C.
elemental analysis ($C_{28}H_{37}N_3O_3$)
Calculated: C, 72.54; H, 8.04; N, 9.06.
Found: C, 71.18; H, 8.11; N, 8.85.

Example 99

N-(2-{[(trans-4-hydroxy-4-methylcyclohexyl)amino]methyl}-3,7-dimethyl-1H-indol-6-yl)-4-[(2S)-tetrahydrofuran-2-ylmethoxy]benzamide

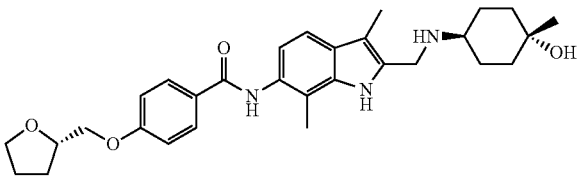 [SMILES: Cc1c(CN[C@H]2CC[C@](C)(O)CC2)[nH]c2c(C)c(NC(=O)c3ccc(OC[C@@H]4CCCO4)cc3)ccc12]

N-(2-Formyl-3,7-dimethyl-1H-indol-6-yl)-4-[(2S)-tetrahydrofuran-2-ylmethoxy]benzamide (261 mg) obtained in Reference Example 79, trans-4-amino-1-methylcyclohexanol (172 mg) obtained in Reference Example 101 and acetic acid (1.33 ml) were added to N,N-dimethylacetamide (4.1 mL), and the mixture was stirred at room temperature for 30 min. Sodium triacetoxyborohydride (282 mg) was added, and the mixture was stirred at room temperature for 17 hr. 8N Aqueous sodium hydroxide solution (3.3 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)] and crystallized from ethyl acetate and heptane to give the title compound (268 mg, yield 80%) as a white solid.

$^1$H NMR (300 MHz, DMSO-$d_6$) δ: 1.09 (3H, s), 1.14-1.38 (5H, m), 1.48-2.06 (7H, m), 2.19 (3H, s), 2.29 (3H, s), 3.62-3.85 (4H, m), 3.95-4.25 (5H, m), 6.82-6.88 (1H, m), 7.04 (2H, d, J=8.5 Hz), 7.19 (1H, d, J=8.0 Hz), 7.96 (2H, d, J=8.8 Hz), 9.74 (1H, s), 10.48 (1H, s).

melting point: 134-135° C.
elemental analysis ($C_{30}H_{39}N_3O_4 \cdot 1.4H_2O$)
Calculated: C, 67.87; H, 7.94; N, 7.92.
Found: C, 67.88; H, 7.97; N, 7.69.

Example 100

N-{2-[(cyclopentylamino)methyl]-3,7-dimethyl-1H-indol-6-yl}-4-[(2S)-tetrahydrofuran-2-ylmethoxy]benzamide

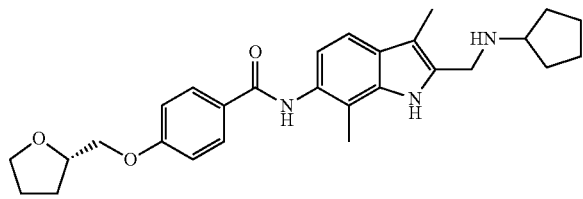 [SMILES: Cc1c(CNC2CCCC2)[nH]c2c(C)c(NC(=O)c3ccc(OC[C@@H]4CCCO4)cc3)ccc12]

N-(2-Formyl-3,7-dimethyl-1H-indol-6-yl)-4-[(2S)-tetrahydrofuran-2-ylmethoxy]benzamide (261 mg) obtained in Reference Example 79, cyclopentylamine (131 µl) and acetic acid (1.33 mL) were added to N,N-dimethylacetamide (4.1 mL), and the mixture was stirred at room temperature for 30 min. Sodium triacetoxyborohydride (282 mg) was added, and the mixture was stirred at room temperature for 17 hr. 8N Aqueous sodium hydroxide solution (3.3 mL) was added dropwise at 0° C. The mixture was extracted with ethyl acetate, washed with aqueous sodium hydrogen carbonate solution and brine, dried over anhydrous sodium sulfate, purified by silica gel-NH silica gel serial column chromatography [eluent; ethyl acetate:methanol=100:0 (volume ratio)→ethyl acetate:methanol=60:40 (volume ratio)], and crystallized from ethyl acetate, diisopropyl ether and heptane to give the title compound (250 mg, yield 82%) as a white solid.

$^1$H NMR (300 MHz, DMSO-$d_6$) δ: 1.25-1.97 (12H, m), 2.18 (3H, s), 2.28 (3H, s), 2.86-3.03 (1H, m), 3.61-3.83 (4H, m), 3.94-4.21 (3H, m), 6.84 (1H, d, J=8.5 Hz), 7.03 (2H, d, J=8.5 Hz), 7.19 (1H, d, J=8.2 Hz), 7.95 (2H, d, J=8.2 Hz), 9.72 (1H, s), 10.48 (1H, s).

melting point: 107-109° C.

elemental analysis ($C_{28}H_{35}N_3O_3 \cdot 0.9H_2O$)

Calculated: C, 70.38; H, 7.76; N, 8.79.

Found: C, 70.38; H, 7.79; N, 8.64.

Example 101

2-fluoro-N-(2-{[(2-hydroxy-2-methylpropyl)amino]methyl}-3,7-dimethyl-1H-indol-6-yl)-4-[(2S)-tetrahydrofuran-2-ylmethoxy]benzamide

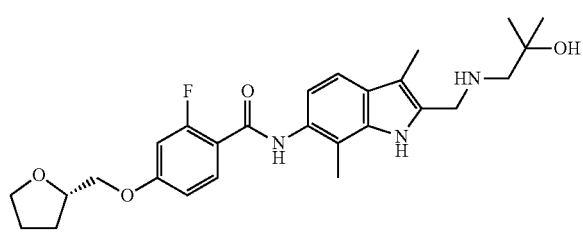 [SMILES: Cc1c(CNCC(C)(C)O)[nH]c2c(C)c(NC(=O)c3ccc(OC[C@@H]4CCCO4)cc3F)ccc12]

2-Fluoro-N-(2-formyl-3,7-dimethyl-1H-indol-6-yl)-4-[(2S)-tetrahydrofuran-2-ylmethoxy]benzamide (0.50 g) obtained in Reference Example 82 and 1-amino-2-methylpropan-2-ol (446 mg) were suspended in NMP (20 mL) and acetic acid (7.0 mL), and the mixture was stirred at room temperature for 3 hr. Sodium triacetoxyborohydride (2.5 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (348 ma, yield 59%) as a colorless solid.

$^1$H NMR (300 MHz, DMSO-$d_6$) δ: 1.09 (6H, s), 1.64-1.73 (1H, m), 1.81-1.90 (2H, m), 1.97-2.04 (1H, m), 2.21 (3H, s), 2.27 (3H, s), 2.40 (2H, s), 3.32 (1H, br), 3.69 (1H, q, J=6.9 Hz), 3.79 (1H, q, J=6.9 Hz), 3.86 (2H, s), 3.97-4.10 (2H, m), 4.16-4.19 (1H, m), 4.26 (1H, br), 6.87-6.97 (3H, m), 7.21 (1H, d, J=8.4 Hz), 7.69 (1H, t, J=8.7 Hz), 9.56 (1H, d, J=2.1 Hz), 10.58 (1H, s).

melting point: 151-152° C.

elemental analysis ($C_{27}H_{34}N_3O_4F \cdot 0.25H_2O$)

Calculated: C, 66.44; H, 7.12; N, 8.61.

Found: C, 66.37; H, 7.01; N, 8.51.

Example 102

2-fluoro-N-(2-{[(trans-4-hydroxy-4-methylcyclohexyl)amino]methyl}-3,7-dimethyl-1H-indol-6-yl)-4-[(2S)-tetrahydrofuran-2-ylmethoxy]benzamide

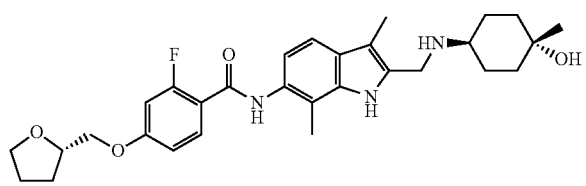 [SMILES: Cc1c(CN[C@H]2CC[C@](C)(O)CC2)[nH]c2c(C)c(NC(=O)c3ccc(OC[C@@H]4CCCO4)cc3F)ccc12]

2-Fluoro-N-(2-formyl-3,7-dimethyl-1H-indol-6-yl)-4-[(2S)-tetrahydrofuran-2-ylmethoxy]benzamide (0.6 g) obtained in Reference Example 82 and trans-4-amino-1-methylcyclohexanol (377 mg) obtained in Reference Example 101 were suspended in NMP (20 mL) and acetic acid (7.0 mL), and the mixture was stirred at room temperature for 3 hr. Sodium triacetoxyborohydride (2.5 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (183 mg, yield 25%) as a colorless solid.

$^1$H NMR (300 MHz, DMSO-$d_6$) δ: 1.09 (3H, s), 1.15-1.33 (4H, m), 1.53-1.64 (2H, m), 1.70-1.91 (6H, m), 1.97-2.04 (1H, m), 2.19 (3H, s), 2.33 (3H, s), 2.44 (1H, br), 3.69 (1H, q, J=6.9 Hz), 3.76-3.80 (3H, m), 3.97-4.06 (1H, m), 4.08 (2H, s), 4.15-4.18 (1H, m), 6.87-7.00 (3H, m), 7.20 (1H, d, J=8.4 Hz), 7.69 (1H, t, J=8.7 Hz), 9.55 (1H, s), 10.50 (1H, s).

melting point: 177-178° C.

elemental analysis ($C_{30}H_{38}N_3O_4F$)

Calculated: C, 68.81; H, 7.31; N, 8.02.

Found: C, 68.96; H, 7.54; N, 7.84.

Example 103

N-(2-{[(2,2-dimethylpropyl)amino]methyl}-7-fluoro-3-methyl-1H-indol-6-yl)-4-[(2S)-tetrahydrofuran-2-ylmethoxy]benzamide

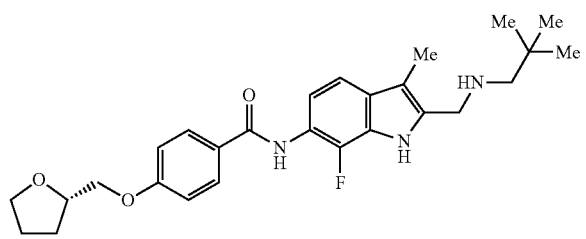 [SMILES: Cc1c(CNCC(C)(C)C)[nH]c2c(F)c(NC(=O)c3ccc(OC[C@@H]4CCCO4)cc3)ccc12]

To a solution of N-(7-fluoro-2-formyl-3-methyl-1H-indol-6-yl)-4-[(2S)-tetrahydrofuran-2-ylmethoxy]benzamide (280 mg) obtained in Reference Example 86 in N,N-dimethylacetamide (3.15 mL) were added neopentylamine (123 mg), sodium triacetoxyborohydride (299 mg) and acetic acid (1.41 mL), and the mixture was stirred at room temperature for 15 hr. Under ice-cooling, 8N aqueous sodium hydroxide solution (3.53 mL) was added, and ethyl acetate and water were further added. The mixture was partitioned, and the aqueous layer was extracted with ethyl acetate. The combined organic layer was washed with brine. The organic layer was purified by silica gel column chromatography [hexane:ethyl acetate=3:7→ethyl acetate (volume ratio)] and the obtained crude product was washed with isopropyl ether-ethyl acetate to give the title compound (134 mg, yield 40%) as pale-brown crystals.

$^1$H NMR (300 MHz, DMSO-$d_6$) δ: 0.85 (9H, s), 1.62-2.09 (5H, m), 2.21 (5H, s), 3.65-3.85 (4H, m), 3.97-4.10 (2H, m), 4.14-4.24 (1H, m), 6.96 (1H, dd, J=8.3, 6.8 Hz), 7.06 (2H, d, J=8.7 Hz), 7.19 (1H, d, J=8.3 Hz), 7.98 (2H, d, J=8.7 Hz), 9.86 (1H, s), 11.07 (1H, s).

melting point: 159-160° C.
elemental analysis ($C_{27}H_{34}N_3O_3F$)
Calculated: C, 69.36; H, 7.33; N, 8.99.
Found: C, 69.01; H, 7.35; N, 8.71.

Example 104

N-(7-fluoro-2-{[(2-methylpropyl)amino]methyl}-3-methyl-1H-indol-6-yl)-4-[(2S)-tetrahydrofuran-2-ylmethoxy]benzamide

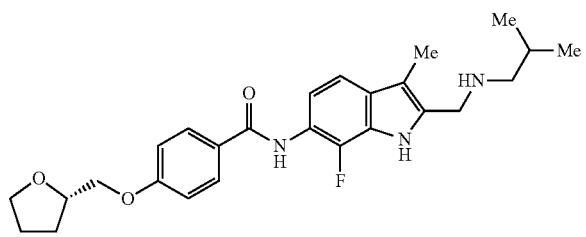 [SMILES: Cc1c(CNCC(C)C)[nH]c2c(F)c(NC(=O)c3ccc(OC[C@@H]4CCCO4)cc3)ccc12]

To a solution of N-(7-fluoro-2-formyl-3-methyl-1H-indol-6-yl)-4-[(2S)-tetrahydrofuran-2-ylmethoxy]benzamide (280 mg) obtained in Reference Example 86 in N,N-dimethylacetamide (3.15 mL) were added isobutylamine (103 mg) and acetic acid (1.41 mL), and the mixture was stirred at room temperature for 1 hr. Sodium triacetoxyborohydride (299 mg) was added, and the mixture was stirred at room temperature for 15 hr. Under ice-cooling, 8N aqueous sodium hydroxide solution (3.53 mL) was added, and ethyl acetate and water were further added. The mixture was partitioned, and the aqueous layer was extracted with ethyl acetate. The combined organic layer was washed with brine. The organic layer was purified by silica gel column chromatography [ethyl acetate→ethyl acetate:methanol=7:3 (volume ratio)] and the obtained crude product was washed with isopropyl ether-ethyl acetate to give the title compound (102 mg, yield 32%) as pale-yellow crystals.

$^1$H NMR (300 MHz, DMSO-$d_6$) δ: 0.86 (6H, d, J=6.4 Hz), 1.58-2.09 (6H, m), 2.21 (3H, s), 2.27 (2H, d, J=6.4 Hz), 3.65-3.85 (4H, m), 3.96-4.10 (2H, m), 4.14-4.24 (1H, m), 6.96 (1H, dd, J=8.3, 6.8 Hz), 7.06 (2H, d, J=9.1 Hz), 7.19 (1H, d, J=8.3 Hz), 7.98 (2H, d, J=8.7 Hz), 9.86 (1H, s), 11.08 (1H, s).

melting point: 134-135° C.
elemental analysis ($C_{26}H_{32}N_3O_3F$)
Calculated: C, 68.85; H, 7.11; N, 9.26.
Found: C, 69.04; H, 7.22; N, 9.15.

Example 105

N-(7-fluoro-3-methyl-2-{[(tetrahydro-2H-pyran-4-ylmethyl)amino]methyl}-1H-indol-6-yl)-4-[(2S)-tetrahydrofuran-2-ylmethoxy]benzamide To a solution of N-(7-fluoro-2-formyl-3-methyl-1H-indol-6-yl)-4-[(2S)-tetrahydrofuran-2-ylmethoxy]benzamide (280 mg) obtained in Reference Example 86 in N,N-dimethylacetamide (3.15 mL) were added 4-aminomethyltetrahydropyran (163 mg) and acetic acid (1.41 mL), and the mixture was stirred at room temperature for 1 hr. Sodium triacetoxyborohydride (299 mg) was added, and the mixture was stirred at room temperature for 15 hr. Under ice-cooling, 8N aqueous sodium hydroxide solution (3.53 mL) was added, and ethyl acetate and water were further added. The mixture was partitioned, and the aqueous layer was extracted with ethyl acetate. The combined organic layer was washed with brine. The organic layer was purified by silica gel column chromatography [ethyl acetate→ethyl acetate:methanol=7:3 (volume ratio)] and the obtained crude product was washed with isopropyl ether-ethyl acetate to give the title compound (143 mg, yield 41%) as a pale-yellow solid.

$^1$H NMR (300 MHz, DMSO-$d_6$) δ: 1.02-1.25 (2H, m), 1.56-2.10 (8H, m), 2.21 (3H, s), 2.35 (2H, d, J=6.1 Hz), 3.20-3.31 (2H, m), 3.65-3.86 (6H, m), 3.96-4.10 (2H, m), 4.14-4.24 (1H, m), 6.96 (1H, dd, J=8.3, 6.8 Hz), 7.06 (2H, d, J=8.7 Hz), 7.19 (1H, d, J=8.0 Hz), 7.98 (2H, d, J=8.7 Hz), 9.86 (1H, s), 11.07 (1H, s).

elemental analysis ($C_{28}H_{34}N_3O_4F$)
Calculated: C, 67.86; H, 6.92; N, 8.48.
Found: C, 67.57; H, 6.98; N, 8.26.

Example 106

N-(2-{[(2-methylpropyl)amino]methyl}-1,3,7-trimethyl-1H-indol-6-yl)-4-[(2S)-tetrahydrofuran-2-ylmethoxy]benzamide

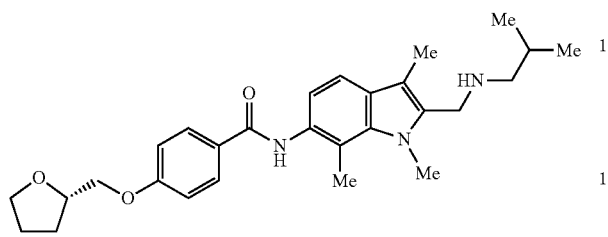

To a solution of N-(2-formyl-1,3,7-trimethyl-1H-indol-6-yl)-4-[(2S)-tetrahydrofuran-2-ylmethoxy]benzamide (340 mg) obtained in Reference Example 90 in N,N-dimethylacetamide (5 mL) were added isobutylamine (122 mg), sodium triacetoxyborohydride (355 mg) and acetic acid (1.67 mL), and the mixture was stirred at room temperature for 15 hr. Under ice-cooling, 8N aqueous sodium hydroxide solution (4.18 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=9:1 (volume ratio)] and the obtained crude product was washed with diisopropyl ether-ethyl acetate to give the title compound (288 mg, yield 74%) as colorless crystals.

$^1$H NMR (300 MHz, DMSO-$d_6$) δ: 0.86 (6H, d, J=6.8 Hz), 1.59-2.09 (6H, m), 2.21 (3H, s), 2.32-2.39 (2H, m), 2.53 (3H, s), 3.65-3.85 (4H, m), 3.96-4.09 (5H, m), 4.14-4.23 (1H, m), 6.84 (1H, d, J=8.3 Hz), 7.05 (2H, d, J=8.7 Hz), 7.23 (1H, d, J=8.0 Hz), 7.98 (2H, d, J=8.7 Hz), 9.80 (1H, s).

melting point: 171-172° C.
elemental analysis ($C_{28}H_{37}N_3O_3$)
Calculated: C, 72.54; H, 8.04; N, 9.06.
Found: C, 72.73; H, 8.15; N, 9.04.

Example 107

4-[(2S)-tetrahydrofuran-2-ylmethoxy]-N-(1,3,7-trimethyl-2-{[(tetrahydro-2H-pyran-4-ylmethyl)amino]methyl}-1H-indol-6-yl)benzamide

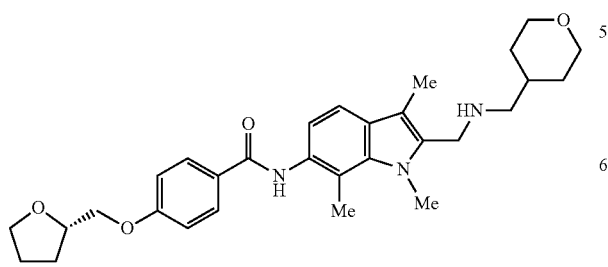

To a solution of N-(2-formyl-1,3,7-trimethyl-1H-indol-6-yl)-4-[(2S)-tetrahydrofuran-2-ylmethoxy]benzamide (340 mg) obtained in Reference Example 90 in N,N-dimethylacetamide (5 mL) were added 4-aminomethyltetrahydropyran (193 mg), sodium triacetoxyborohydride (355 mg) and acetic acid (1.67 mL), and the mixture was stirred at room temperature for 15 hr. Under ice-cooling, 8N aqueous sodium hydroxide solution (4.18 mL) was added, and ethyl acetate and water were further added. The mixture was partitioned, and the aqueous layer was extracted with ethyl acetate. The combined organic layer was washed with brine. The organic layer was purified by silica gel column chromatography [eluent; ethyl acetate→ethyl acetate:methanol=7:3 (volume ratio)] and the obtained crude product was washed with diisopropyl ether-ethyl acetate to give the title compound (352 mg, yield 83%) as colorless crystals.

$^1$H NMR (300 MHz, DMSO-$d_6$) δ: 1.04-1.22 (2H, m), 1.57-2.09 (7H, m), 2.21 (3H, s), 2.40-2.46 (2H, m), 2.53 (3H, s), 3.25 (2H, t, J=11.0 Hz), 3.65-3.88 (6H, m), 3.96-4.10 (5H, m), 4.13-4.24 (1H, m), 6.84 (1H, d, J=8.3 Hz), 7.05 (2H, d, J=8.7 Hz), 7.23 (1H, d, J=8.3 Hz), 7.98 (2H, d, J=8.3 Hz), 9.80 (1H, s).

melting point: 173-174° C.
elemental analysis ($C_{30}H_{39}N_3O_4$)
Calculated: C, 71.26; H, 7.77; N, 8.31.
Found: C, 71.31; H, 7.86; N, 8.25.

Example 108

N-(2-{[(2-hydroxy-2-methylpropyl)amino]methyl}-1,3,7-trimethyl-1H-indol-6-yl)-4-[(2S)-tetrahydrofuran-2-ylmethoxy]benzamide

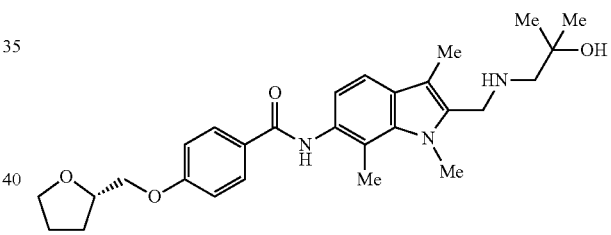

To a solution of N-(2-formyl-1,3,7-trimethyl-1H-indol-6-yl)-4-[(2S)-tetrahydrofuran-2-ylmethoxy]benzamide (340 mg) obtained in Reference Example 90 in N,N-dimethylacetamide (5 mL) were added 1-amino-4-methylpropan-2-ol (149 mg), sodium triacetoxyborohydride (355 mg) and acetic acid (1.67 mL), and the mixture was stirred at room temperature for 15 hr. Under ice-cooling, 8N aqueous sodium hydroxide solution (4.18 mL) was added, and ethyl acetate and water were further added. The mixture was partitioned, and the aqueous layer was extracted with tetrahydrofuran. The combined organic layer was purified by silica gel column chromatography [eluent; ethyl acetate→ethyl acetate:methanol=4:1 (volume ratio)] and the obtained crude product was washed with diisopropyl ether-ethyl acetate to give the title compound (325 mg, yield 81%) as colorless crystals.

$^1$H NMR (300 MHz, DMSO-$d_6$) δ: 1.08 (6H, s), 1.62-2.08 (5H, m), 2.21 (3H, s), 2.44 (2H, s), 2.53 (3H, s), 3.65-3.90 (4H, m), 3.99-4.08 (5H, m), 4.14-4.23 (2H, m), 6.84 (1H, d, J=8.3 Hz), 7.05 (2H, d, J=9.1 Hz), 7.24 (1H, d, J=8.0 Hz), 7.98 (2H, d, J=8.7 Hz), 9.81 (1H, s).

melting point: 186-188° C.
elemental analysis ($C_{28}H_{37}N_3O_4$)
Calculated: C, 70.12; H, 7.78; N, 8.76.
Found: C, 70.06; H, 7.87; N, 8.66.

Example 109

N-(2-{[(trans-4-hydroxy-4-methylcyclohexyl)amino]methyl}-1,3,7-trimethyl-1H-indol-6-yl)-4-[(2S)-tetrahydrofuran-2-ylmethoxy]benzamide

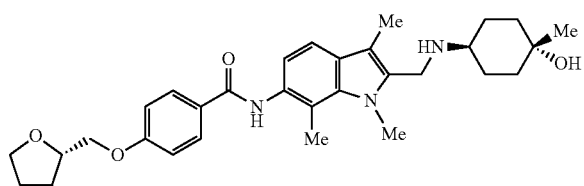 [SMILES: Cc1c(CN[C@H]2CC[C@](C)(O)CC2)n(C)c2c(C)c(NC(=O)c3ccc(OC[C@@H]4CCCO4)cc3)ccc12]

To a solution of N-(2-formyl-1,3,7-trimethyl-1H-indol-6-yl)-4-[(2S)-tetrahydrofuran-2-ylmethoxy]benzamide (340 mg) obtained in Reference Example 90 in N,N-dimethylacetamide (5 mL) were added trans-4-amino-1-methylcyclohexanol (324 mg) obtained in Reference Example 101, sodium triacetoxyborohydride (355 mg) and acetic acid (1.67 mL), and the mixture was stirred at room temperature for 20 hr. Under ice-cooling, 8N aqueous sodium hydroxide solution (4.18 mL) and ethyl acetate were added, and the mixture was successively washed with water and brine. The organic layer was purified by silica gel column chromatography [eluent; ethyl acetate→ethyl acetate:methanol=3:2 (volume ratio)] and the obtained crude product was washed with diisopropyl ether-ethyl acetate to give the title compound (200 mg, yield 46%) as colorless crystals.

$^1$H NMR (300 MHz, DMSO-$d_6$) δ: 1.10 (3H, s), 1.16-2.08 (13H, m), 2.20 (3H, s), 2.53 (3H, s), 3.65-3.85 (4H, m), 3.96-4.06 (5H, m), 4.11 (1H, s), 4.13-4.23 (1H, m), 6.84 (1H, d, J=8.3 Hz), 7.05 (2H, d, J=9.0 Hz), 7.23 (1H, d, J=7.9 Hz), 7.98 (2H, d, J=8.7 Hz), 9.81 (1H, s).

melting point: 183-184° C.
elemental analysis ($C_{31}H_{41}N_3O_4$)
Calculated: C, 71.65; H, 7.95; N, 8.09.
Found: C, 69.90; H, 7.85; N, 7.77.

Example 110

2-fluoro-N-(2-{[(trans-4-hydroxy-4-methylcyclohexyl)amino]methyl}-1,3,7-trimethyl-1H-indol-6-yl)-4-[(2S)-tetrahydrofuran-2-ylmethoxy]benzamide

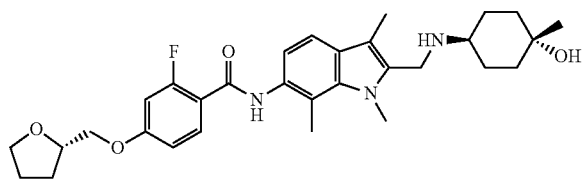 [SMILES: Cc1c(CN[C@H]2CC[C@](C)(O)CC2)n(C)c2c(C)c(NC(=O)c3ccc(OC[C@@H]4CCCO4)cc3F)ccc12]

2-Fluoro-N-(2-formyl-1,3,7-trimethyl-1H-indol-6-yl)-4-[(2S)-tetrahydrofuran-2-ylmethoxy]benzamide (1.1 g) obtained in Reference Example 93 and trans-4-amino-1-methylcyclohexanol (504 mg) obtained in Reference Example 101 were suspended in NMP (20 mL) and acetic acid (7.0 mL), and the mixture was stirred at room temperature for 3 hr. Sodium triacetoxyborohydride (3.0 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (470 mg, yield 34%) as a colorless solid.

$^1$H NMR (300 MHz, DMSO-$d_6$) δ: 1.09 (3H, s), 1.20-1.33 (4H, m), 1.50-1.60 (2H, m), 1.63-1.71 (1H, m), 1.80-1.90 (4H, m), 1.96-1.99 (2H, m), 2.19 (3H, s), 2.49 (1H, br), 2.57 (3H, s), 3.67-3.72 (1H, m), 3.75-3.82 (3H, m), 3.98 (3H, s), 3.99-4.15 (4H, m), 6.70-6.87 (3H, m), 7.22 (1H, d, J=8.4 Hz), 7.67 (1H, t, J=7.8 Hz), 9.62 (1H, s).

melting point: 162-163° C.
elemental analysis ($C_{32}H_{40}N_3O_4F.0.25H_2O$)
Calculated: C, 66.68; H, 7.53; N, 7.75.
Found: C, 68.69; H, 7.32; N, 7.64.

Example 111

2-fluoro-N-(2-{[(2-hydroxy-2-methylpropyl)amino]methyl}-1,3,7-trimethyl-1H-indol-6-yl)-4-[(2S)-tetrahydrofuran-2-ylmethoxy]benzamide

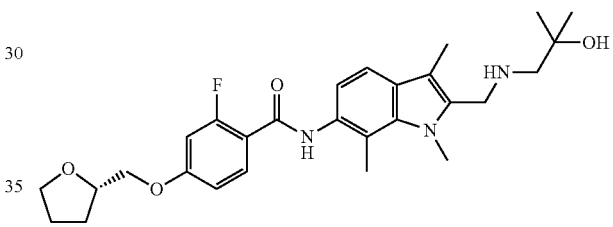

2-Fluoro-N-(2-formyl-1,3,7-trimethyl-1H-indol-6-yl)-4-[(2S)-tetrahydrofuran-2-ylmethoxy]benzamide (0.70 g) obtained in Reference Example 93 and 1-amino-2-methylpropan-2-ol (500 mg) were suspended in NMP (20 mL) and acetic acid (7.0 mL), and the mixture was stirred at room temperature for 3 hr. Sodium triacetoxyborohydride (3.0 g) was added and the mixture was stirred at room temperature for 3 hr. 1N Aqueous sodium hydroxide solution was added to discontinue the reaction and basify the mixture, and the mixture was partitioned and extracted with ethyl acetate. The organic layer was washed with saturated brine, and dried over anhydrous sodium sulfate, and the solvent was evaporated under reduced pressure. The residue was purified by silica gel column chromatography [eluent; methanol:ethyl acetate=0:100 (volume ratio)→methanol:ethyl acetate=20:80 (volume ratio)] to give the title compound (188 mg, yield 23%) as a colorless solid.

$^1$H NMR (300 MHz, DMSO-$d_6$) δ: 1.09 (6H, s), 1.64-1.72 (1H, m), 1.86-1.90 (2H, m), 1.97-2.00 (1H, m), 2.22 (3H, s), 2.48 (2H, s), 2.58 (3H, s), 3.37 (1H, br), 3.69 (1H, q, J=6.3 Hz), 3.79 (1H, q, J=6.3 Hz), 3.91 (2H, s), 4.01 (3H, s), 4.03-4.09 (2H, m), 4.16-4.19 (1H, m), 4.23-4.27 (1H, m), 6.89-6.97 (3H, m), 7.24 (1H, d, J=8.1 Hz), 7.68 (1H, t, J=8.4 Hz), 9.64 (1H, s).

melting point: 131-132° C.
elemental analysis ($C_{28}H_{36}N_3O_4F.0.5H_2O$)
Calculated: C, 66.38; H, 7.36; N, 8.29.
Found: C, 66.57; H, 7.16; N, 8.06.

Example 112

N-(7-fluoro-2-{[(trans-4-hydroxy-4-methylcyclohexyl)amino]methyl}-1,3-dimethyl-1H-indol-6-yl)-4-[(2S)-tetrahydrofuran-2-ylmethoxy]benzamide

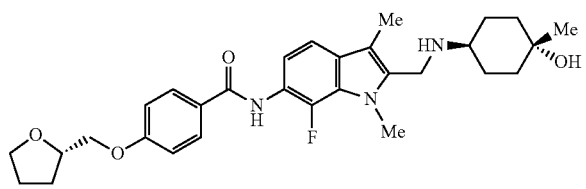 [SMILES: Cc1c(CN[C@H]2CC[C@](C)(O)CC2)n(C)c2c(F)c(NC(=O)c3ccc(OC[C@@H]4CCCO4)cc3)ccc12]

To a solution of N-(7-fluoro-2-formyl-1,3-dimethyl-1H-indol-6-yl)-4-[(2S)-tetrahydrofuran-2-ylmethoxy]benzamide (100 mg) obtained in Reference Example 95 in N,N-dimethylacetamide (2.0 mL) were added trans-4-amino-1-methylcyclohexanol (63 mg) obtained in Reference Example 101 and acetic acid (0.49 mL), and the mixture was stirred at room temperature for 1 hr. Sodium triacetoxyborohydride (100 mg) was added, and the mixture was stirred at room temperature for 15 hr. Under ice-cooling, 8N aqueous sodium hydroxide solution (1.2 mL) was added, and ethyl acetate and water were further added. The mixture was partitioned, and the aqueous layer was extracted twice with ethyl acetate. The combined organic layer was washed with brine. The organic layer was purified by silica gel column chromatography [ethyl acetate→ethyl acetate:methanol=7:3 (volume ratio)] to give the title compound (82 mg, yield 64%) as pale-yellow crystals.

$^1$H NMR (300 MHz, DMSO-$d_6$) δ: 1.09 (3H, s), 1.20-1.38 (5H, m), 1.50-2.14 (8H, m), 2.22 (3H, s), 3.65-3.85 (4H, m), 3.92 (3H, s), 3.96-4.24 (4H, m), 6.98 (1H, dd, J=8.3, 6.8 Hz), 7.06 (2H, d, J=9.0 Hz), 7.22 (1H, d, J=8.3 Hz), 7.98 (2H, d, J=8.7 Hz), 9.87 (1H, s).

melting point: 122-124° C.
elemental analysis ($C_{30}H_{38}N_3O_4F$)
Calculated: C, 68.81; H, 7.31; N, 8.02.
Found: C, 67.30; H, 7.45; N, 7.50.

Example 113

N-(7-fluoro-1,3-dimethyl-2-{[(tetrahydro-2H-pyran-4-ylmethyl)amino]methyl}-1H-indol-6-yl)-4-[(2S)-tetrahydrofuran-2-ylmethoxy]benzamide

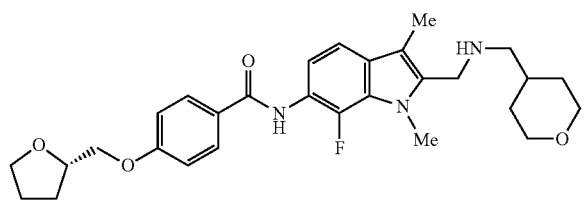 [SMILES: Cc1c(CNCC2CCOCC2)n(C)c2c(F)c(NC(=O)c3ccc(OC[C@@H]4CCCO4)cc3)ccc12]

To a solution of N-(7-fluoro-2-formyl-1,3-dimethyl-1H-indol-6-yl)-4-[(2S)-tetrahydrofuran-2-ylmethoxy]benzamide (100% mg) obtained in Reference Example 95 in N,N-dimethylacetamide (2.0 mL) were added 4-aminomethyltetrahydropyran (56 mg) and acetic acid (0.49 mL), and the mixture was stirred at room temperature for 1 hr. Sodium triacetoxyborohydride (100 mg) was added, and the mixture was stirred at room temperature for 15 hr. Under ice-cooling, 8N aqueous sodium hydroxide solution (1.2 mL) was added, and ethyl acetate and water were further added. The mixture was partitioned, and the aqueous layer was extracted twice with ethyl acetate. The combined organic layer was washed with brine. The organic layer was purified by silica gel column chromatography [ethyl acetate→ethyl acetate:methanol=7:3 (volume ratio)] to give the title compound (82 mg, yield 64%) as pale-yellow crystals.

$^1$H NMR (300 MHz, DMSO-$d_6$) δ: 1.03-1.20 (2H, m), 1.55-2.15 (7H, m), 2.23 (3H, s), 2.41 (2H, d, J=6.4 Hz), 3.25 (2H, t, J=10.9 Hz), 3.65-3.86 (6H, m), 3.92 (3H, s), 3.97-4.10 (2H, m), 4.13-4.24 (1H, m), 6.98 (1H, dd, J=8.5, 6.6 Hz), 7.06 (2H, d, J=8.7 Hz), 7.22 (1H, d, J=8.3 Hz), 7.97 (2H, d, J=9.0 Hz), 9.87 (1H, s).

melting point: 132-134° C.
elemental analysis ($C_{29}H_{36}N_3O_4F$)
Calculated: C, 68.35; H, 7.12; N, 8.25.
Found: C, 68.24; H, 7.33; N, 7.98.

Formulation Example 1

| | |
|---|---:|
| (1) Compound of Example 1 | 50 mg |
| (2) Lactose | 34 mg |
| (3) Cornstarch | 10.6 mg |
| (4) Cornstarch (paste) | 5 mg |
| (5) Magnesium stearate | 0.4 mg |
| (6) Calcium carboxymethylcellulose | 20 mg |
| total | 120 mg |

The above-mentioned (1) to (6) are mixed according to a conventional method and the mixture is tableted by a tableting machine to give a tablet.

Formulation Example 2

Production of Capsule

| | |
|---|---:|
| (1) Compound of Example 1 | 30 mg |
| (2) Microcrystalline cellulose | 10 mg |
| (3) Lactose | 19 mg |
| (4) Magnesium stearate | 1 mg |
| total | 60 mg |

(1), (2), (3) and (4) are mixed and filled in a gelatin capsule.

Experimental Example 1

Determination of Human MCH Receptor 1 (MCHR1) Competitive Inhibitory Activity of Test Compound Using Binding Assay Using human MCHR1(=SLC-1 receptor)-expressing CHO cell clone 57 and rat MCHR1-expressing CHO cell clone 44 described in WO01/82925, MCHR1-expressing CHO cellular membrane fractions were prepared by the following method. In phosphate buffered saline (pH 7.4) supplemented with 5 mM EDTA (ethylenediaminetetraacetic acid) were respectively suspended human and rat MCHR1-expressing CHO cells (1×10$^8$ cells) and centrifuged. Homogenate buffer (10 mL, 10 mM NaHCO$_3$, 5 mM EDTA, pH 7.5, 0.5 mM PMSF (phenylmethylsulfonyl fluoride), 20 mg/L leupeptin, 4 mg/L E-64, 1 mg/L pepstatin A) was added to the pellets of the cells and, using Polytron Homogenizer, the mixture was homogenated. The supernatant obtained after centrifugation at 400×g for 10 min was further centrifuged at 100,000×g for 1 hr to give precipitate of the membrane fraction. The precipitate were suspended in 2 mL of assay buffer [20 mM Tris-HCl (pH 7.5), 5 mM EDTA, 0.5 mM PMSF, 20 mg/L leupeptin, 4 mg/L E-64, 1 mg/L pepstatin A]. The membrane fractions were suspended in assay buffer to a protein concentration of 2 mg/mL, and after dispensing, preserved at −80° C. and used upon thawing each time when in use.

The MCHR1 ligand binding inhibitory activity of the test compound was determined as follows. An MCHR1-expressing CHO cellular membrane fraction (175 μL) diluted with an assay buffer was dispensed to a 96 well polypropylene plate (3363, Corning). DMSO solution (2 μL), 100 μm cold MCH (1-19) diluted with DMSO solution (2 μL), or a test compound solution diluted with DMSO solution to various concentrations (2 μL) was added, and lastly, [$^{125}$I]-MCH(4-19) diluted with assay buffer (25 μL) was added to each well. The reaction mixture was reacted at 25° C. for 1 hr with stirring, and the reaction mixture was filtered by suction using a glass filter plate (GF/C, PerkinElmer). The filter was washed 3 times with a wash solution (300 μL, 50 mM Tris-HCl buffer, pH 7.5). The glass filter plate was dried, a liquid scintillator was added at 25 μL/well, and the residual radioactivity was measured by TopCount (PerkinElmer). The binding inhibition rate of the test compound was calculated by the following formula.

Binding inhibition (%)=(radioactivity upon addition of test compound and hot MCH−radioactivity upon addition of cold MCH and hot MCH solution)/(radioactivity upon addition of DMSO solution and hot MCH−radioactivity upon addition of cold MCH and hot MCH solution)×100

The binding inhibition rates of test compounds (0.1 μM) as measured using human MCHR1-expressing CHO cell are shown in Table 1.

TABLE 1

| Compound No. | Binding inhibition rate (0.1 μM) |
| --- | --- |
| Example 6 | 82% |
| Example 12 | 98% |
| Example 15 | 96% |
| Example 17 | 97% |
| Example 20 | 91% |
| Example 50 | 97% |
| Example 51 | 92% |
| Example 53-2 | 97% |
| Example 55 | 98% |
| Example 60 | 98% |
| Example 63 | 98% |
| Example 67 | 101% |
| Example 70 | 95% |
| Example 74 | 91% |
| Example 75 | 94% |
| Example 78 | 91% |
| Example 83 | 99% |
| Example 84 | 101% |
| Example 88 | 95% |
| Example 103 | 100% |

As is clear from Table 1, the compound of the present invention has a superior MCH receptor 1 competitive inhibitory activity.

Experimental Example 2

Measurement of MCH Receptor 1 Antagonistic Activity of Test Compound Using $Ca^{2+}$ Mobilization Assay CHO cell (CHO dhfr−, clone #4) expressing a recombinant human MCHR1 gene for $Ca^{2+}$ mobilization assay was prepared by us. The cell was cultured in MEMα medium [445 mL of MEMα medium without nucleic acid and added with 5 mL of Penicillin-Streptomycin (Invitrogen) and 50 mL of dialyzed fetal bovine serum]. An integrated dispensing function fluorometer (CellLux, PerkinElmer) was used for $Ca^{2+}$ mobilization assay. CHO cells were sown in a 96 well plate (type 3904, Corning) with a black plate wall and clear well bottom at a density of 20000 cells/well, and cultured in an incubator for about 24 hr at 5% $CO_2$, 37° C. The medium was removed, and the cells were washed with phosphate buffered saline (PBS). A $Ca^{2+}$ indicator dye reagent (DOJINDO LABORATORIES, Ca screening no-wash kit Fluo4) was added at 90 μL/well, and the dye was allowed to penetrate into the cell for 30 min in an incubator at 5% $CO_2$, 37° C. The plate was set on a plate reader, a test compound solution diluted with an assay buffer [10 mM HEPES (pH 7.4), 1× assay buffer containing 0.1% BSA (DOJINDO LABORATORIES, attached to Ca screening no-wash kit Fluo4)] or DMSO solution was added at 10 μL/well, and ligand MCH (4-19) peptide (final concentration 20 nM) diluted with assay buffer or DMSO was added at 50 μL/well, during which changes in intracellular fluorescence were measured at 2 second intervals. The antagonistic activity of the test compound was calculated and shown as an inhibition rate (%) wherein the intracellular fluorescence activity resulting from the stimulation by the addition of ligand MCH (4-19) peptide was 100% and that of the well added with DMSO solution alone was 0%.

The inhibition rates (%) of test compounds (0.1 μM) as measured using human MCHR1-expressing CHO cell are shown in the following Table 2.

TABLE 2

| Compound No. | Inhibition rate (%) |
| --- | --- |
| Example 17 | 97 |
| Example 50 | 97 |
| Example 53-2 | 96 |
| Example 55 | 99 |
| Example 60 | 97 |
| Example 83 | 96 |
| Example 84 | 97 |
| Example 88 | 98 |

As is clear from Table 2, the compound of the present invention has a superior MCH receptor 1 antagonistic activity.

Experimental Example 3

Evaluation of Anorectic Effect Using Dietary Obese Male F344/Jcl Rats

Dietary obese male F344/Jcl rats (42-57-week-old) reared on a high-fat diet (Research Diets: D12451) from 5 weeks of age were used. From before the start of experiment, the rats were independently raised, a powder high-fat diet (Research Diets: D12451M) was given, tap water was orally administered for acclimation, and thereby the rats were habituated. The food intake from the evening of the day before the start of experiment to the next morning was measured, and the rats were grouped based on the food intake and the body weight of the previous day as indices. On the day of the start of experiment and in the evening of the next day, 0.5% methylcellulose solution was orally administered to the control group, and 0.5% methylcellulose suspension (5 mg/mL) of the test compound was orally administered to the compound administration group at 2 mL/kg (6 per group for both control group and compound administration group). The food intake from the initial administration to 2 days later was measured. The food intake inhibition rate of each compound administration group to the control group was calculated. The results are shown in Table 3.

TABLE 3

| Compound No. | Food intake inhibition rate (%) |
|---|---|
| Example 15 | 12.7* |
| Example 17 | 14.7** |
| Example 20 | 20.3** |
| Example 50 | 26.5*** |
| Example 55 | 22.7** |
| Example 60 | 19.9*** |
| Example 75 | 17.1* |
| Example 84 | 12.1* |
| Example 88 | 17.5** |

*, , *$p < 0.05, 0.01, 0.001$ (as compared with control group by Dunnett's multiple comparison test)

As is clear from Table 3, the compound of the present invention has a superior anorectic action.

INDUSTRIAL APPLICABILITY

Compound (I) has a melanin-concentrating hormone (MCH) receptor antagonistic action, and is low toxic. Therefore, the compound is highly useful as an anorexigenic agent and an agent for the prophylaxis or treatment of obesity and the like.

This application is based on a patent application No. 2010-001296 filed in Japan, the contents of which are incorporated by reference in full herein.

The invention claimed is:
1. A compound represented by the formula

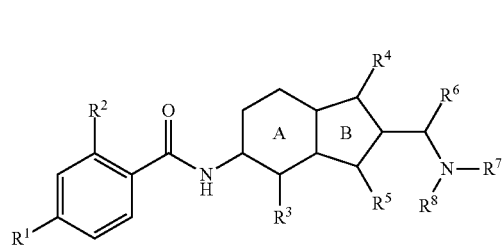

(I)

wherein
ring AB is an indole ring;
$R^1$ is
an optionally substituted $C_{1-6}$ alkoxy group,
an optionally substituted $C_{1-6}$ alkyl group,
an optionally substituted $C_{2-6}$ alkenyl group, or
an optionally substituted $C_{2-6}$ alkynyl group;
$R^2$ is a hydrogen atom or a fluorine atom;
$R^3$ is a hydrogen atom, a halogen atom or a $C_{1-6}$ alkyl group;
$R^4$ and $R^5$ are each independently a hydrogen atom or a methyl group;
$R^6$ is a hydrogen atom or a methyl group; and
(1) $R^7$ is a hydrogen atom or a $C_{1-6}$ alkyl group; and
$R^8$ is
an optionally substituted $C_{1-6}$ alkyl group,
an optionally substituted $C_{3-10}$ cycloalkyl group, or
an optionally substituted 4- to 7-membered saturated heterocyclic group; or
(2) $R^7$ and $R^8$ optionally form, together with the adjacent nitrogen atom, an optionally substituted 4- to 7-membered nitrogen-containing heterocycle,
or a salt thereof.
2. The compound according to claim 1, wherein $R^1$ is
(a) a $C_{1-6}$ alkoxy group optionally substituted by 1 to 3 substituents selected from the group consisting of a $C_{3-10}$ cycloalkyl group and a 5- or 6-membered oxygen-containing heterocyclic group, or
(b) a $C_{2-6}$ alkynyl group optionally substituted by 1 to 3 substituents selected from the group consisting of a $C_{3-10}$ cycloalkyl group optionally substituted by 1 to 3 hydroxy groups, or a salt thereof.
3. The compound according to claim 1, wherein $R^3$ is a hydrogen atom, a fluorine atom or a methyl group, or a salt thereof.
4. The compound according to claim 1, wherein $R^7$ is a hydrogen atom; and
$R^8$ is
(a) a $C_{1-6}$ alkyl group optionally substituted by 1 to 3 substituents selected from the group consisting of a hydroxy group, a $C_{1-6}$ alkoxy group and a 5- or 6-membered oxygen-containing heterocyclic group, or
(b) a $C_{3-10}$ cycloalkyl group optionally substituted by 1 to 3 substituents selected from the group consisting of a hydroxy group and a $C_{1-6}$ alkyl group,
or a salt thereof.
5. The compound according to claim 1, wherein $R^7$ and $R^8$ form, together with the adjacent nitrogen atom, a 4- to 6-membered nitrogen-containing heterocycle optionally substituted by 1 to 3 substituents selected from the group consisting of a hydroxy group and a $C_{1-6}$ alkyl group,
or a salt thereof.
6. The compound according to claim 1, wherein $R^1$ is
(a) a $C_{1-6}$ alkoxy group optionally substituted by 1 to 3 substituents selected from the group consisting of a $C_{3-10}$ cycloalkyl group and a 5- or 6-membered oxygen-containing heterocyclic group, or
(b) a $C_{2-6}$ alkynyl group optionally substituted by 1 to 3 substituents selected from the group consisting of a $C_{3-10}$ cycloalkyl group optionally substituted by 1 to 3 hydroxy groups;
$R^3$ is a hydrogen atom, a fluorine atom or a methyl group;
$R^7$ is a hydrogen atom; and
$R^8$ is
(a) a $C_{1-6}$ group optionally substituted by 1 to 3 substituents selected from the group consisting of a hydroxy group, a $C_{1-6}$ alkoxy group and a 5- or 6-membered oxygen-containing heterocyclic group, or
(b) a $C_{3-10}$ cycloalkyl group optionally substituted by 1 to 3 substituents selected from the group consisting of a hydroxy group and a $C_{1-6}$ alkyl group,
or a salt thereof.
7. The compound according to claim 1, wherein $R^1$ is
(a) a $C_{1-6}$ alkoxy group optionally substituted by 1 to 3 substituents selected from the group consisting of a $C_{3-10}$ cycloalkyl group and a 5- or 6-membered oxygen-containing heterocyclic group, or
(b) a $C_{2-6}$ alkynyl group optionally substituted by 1 to 3 substituents selected from the group consisting of a $C_{3-10}$ cycloalkyl group optionally substituted by 1 to 3 hydroxy groups;

$R^3$ is a hydrogen atom, a fluorine atom or a methyl group; and $R^7$ and $R^8$ form, together with the adjacent nitrogen atom, a 4- to 6-membered nitrogen-containing heterocycle optionally substituted by 1 to 3 substituents selected from the group consisting of a hydroxy group and a $C_{1-6}$ alkyl group, or a salt thereof.

8. N-(1-Methyl-2-{[(tetrahydro-2H-pyran-4-ylmethyl)amino]methyl}-1H-indol-5-yl)-4-[(2S)-tetrahydrofuran-2-ylmethoxy]benzamide or a salt thereof.

9. 4-(Cyclopropylmethoxy)-N-(2-{[(2-hydroxy-2-methylpropyl)amino]methyl}-1,4-dimethyl-1H-indol-5-yl)benzamide or a salt thereof.

10. N-(1,4-Dimethyl-2-{[(tetrahydro-2H-pyran-4-ylmethyl)amino]methyl}-1H-indol-5-yl)-4-[(2S)-tetrahydrofuran-2-ylmethoxy]benzamide or a salt thereof.

11. A medicament comprising the compound according to claim 1 or a salt thereof and a pharmacologically acceptable carrier.

12. The medicament according to claim 11, which is a melanin-concentrating hormone receptor antagonist.

13. The medicament according to claim 11, which is an anorexigenic agent.

14. The medicament according to claim 11, which is a prophylactic or therapeutic agent for obesity.

15. A method of treating obesity in a mammal in need thereof, comprising administering an effective amount of the compound according to claim 1 or a salt thereof to the mammal.

16. The medicament according to claim 11, which is a therapeutic agent for obesity.

* * * * *

UNITED STATES PATENT AND TRADEMARK OFFICE
CERTIFICATE OF CORRECTION

PATENT NO. : 8,642,770 B2
APPLICATION NO. : 13/520373
DATED : February 4, 2014
INVENTOR(S) : Shinichi Masada, Yoshito Terao and Toshiki Murata Page 1 of 1

It is certified that error appears in the above-identified patent and that said Letters Patent is hereby corrected as shown below:

In the Claims

Col. 158, claim 6, line 57, "a $C_{1-6}$group" should be --a $C_{1-6}$ alkyl group--.

Signed and Sealed this
Sixteenth Day of September, 2014

Michelle K. Lee
*Deputy Director of the United States Patent and Trademark Office*